US007214690B2

(12) United States Patent
Higuchi et al.

(10) Patent No.: US 7,214,690 B2
(45) Date of Patent: May 8, 2007

(54) TRICYCLIC QUINOLINONE AND TRICYCLIC QUINOLINE ANDROGEN RECEPTOR MODULATOR COMPOUNDS AND METHODS

(75) Inventors: Robert I. Higuchi, Solana Beach, CA (US); Lin Zhi, San Diego, CA (US); Donald S. Karanewsky, Escondido, CA (US); Anthony W. Thompson, San Diego, CA (US); Thomas R. Caferro, Holly Springs, NC (US); Neelakandha S. Mani, San Diego, CA (US); Jyun-Hung Chen, San Diego, CA (US); Marquis L. Cummings, Encinitas, CA (US); James P. Edwards, San Diego, CA (US); Mark E. Adams, San Diego, CA (US); Charlotte L. F. Deckhut, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 531 days.

(21) Appl. No.: 10/080,503

(22) Filed: Feb. 22, 2002

(65) Prior Publication Data
US 2002/0183314 A1    Dec. 5, 2002

Related U.S. Application Data

(60) Provisional application No. 60/271,115, filed on Feb. 23, 2001.

(51) Int. Cl.
*A61K 31/47* (2006.01)
*C07D 215/16* (2006.01)

(52) U.S. Cl. ...................... 514/314; 546/157
(58) Field of Classification Search ............... 514/314; 546/157
See application file for complete search history.

(56) References Cited

U.S. PATENT DOCUMENTS

| 3,919,238 | A |   | 11/1975 | Spencer et al. ........... 260/288 |
| 4,460,475 | A | * | 7/1984  | Hayatsu et al. ........... 210/674 |
| 4,623,638 | A | * | 11/1986 | Hayatsu et al. ........... 502/401 |
| 4,777,052 | A | * | 10/1988 | Weisberger et al. ........ 426/92 |
| 4,981,784 | A | * | 1/1991  | Evans et al. ............... 435/6 |
| 5,011,697 | A | * | 4/1991  | Jones et al. ............... 426/92 |
| 5,071,773 | A | * | 12/1991 | Evans et al. ............... 436/501 |
| 5,179,202 | A | * | 1/1993  | Gross ....................... 536/120 |
| 5,576,324 | A |   | 11/1996 | Kyotani et al. ............ 514/291 |
| 5,677,336 | A |   | 10/1997 | Jones et al. ............... 514/546 |
| 5,688,808 | A |   | 11/1997 | Jones et al. ............... 514/285 |
| 5,688,810 | A |   | 11/1997 | Jones et al. ............... 514/311 |
| 5,693,646 | A |   | 12/1997 | Jones et al. ............... 514/285 |
| 5,693,647 | A |   | 12/1997 | Jones et al. ............... 514/285 |
| 5,696,127 | A |   | 12/1997 | Jones et al. ............... 514/285 |
| 5,696,130 | A |   | 12/1997 | Jones et al. ............... 514/291 |
| 5,696,133 | A |   | 12/1997 | Jones et al. ............... 514/314 |
| 5,994,544 | A |   | 11/1999 | Jones et al. ............... 546/62 |
| 6,001,846 | A |   | 12/1999 | Edwards et al. ........... 514/285 |
| 6,017,924 | A |   | 1/2000  | Edwards et al. ........... 514/292 |
| 6,030,967 | A | * | 2/2000  | Mauri et al. ............... 514/215 |
| 6,093,821 | A |   | 7/2000  | Jones et al. ............... 544/333 |
| 6,093,826 | A |   | 7/2000  | Edwards et al. ........... 546/62 |
| 6,121,450 | A |   | 9/2000  | Jones et al. ............... 546/81 |
| 6,172,241 | B1 |  | 1/2001  | Edwards et al. ........... 549/280 |
| 6,180,794 | B1 |  | 1/2001  | Edwards et al. ........... 546/152 |
| 6,340,704 | B1 | * | 1/2002  | Mauri et al. ............... 514/463 |
| 6,448,405 | B1 |  | 9/2002  | Jones et al. ............... 546/62 |
| 6,462,038 | B1 |  | 10/2002 | Higuchi et al. ........... 514/224.5 |
| 6,534,516 | B1 |  | 3/2003  | Edwards et al. ........... 514/285 |
| 6,566,372 | B1 |  | 5/2003  | Zhi et al. .................. 514/312 |
| 6,667,313 | B1 |  | 12/2003 | Hamann et al. ........... 514/292 |
| 6,696,459 | B1 |  | 2/2004  | Jones et al. ............... 514/285 |
| 2002/0183346 | A1 | | 12/2002 | Zhi et al. .................. 514/291 |
| 2003/0130505 | A1 | | 7/2003  | Zhi et al. .................. 540/575 |
| 2003/0149268 | A1 | | 8/2003  | Hamann et al. ........... 546/81 |
| 2003/0186970 | A1 | | 10/2003 | Higuchi et al. ........... 514/224.2 |

FOREIGN PATENT DOCUMENTS

| DE | 24 27 409 | | 1/1975 |
| EP | 0 638 571 | | 4/1993 |
| JP | 50-25595 | | 3/1975 |
| JP | 03-282445 A2 | * | 12/1991 |
| JP | 07-013017 A2 | * | 1/1995 |
| JP | 3047434 B2 | * | 5/2000 |
| WO | 95/11215 | | 4/1995 |
| WO | 96/19458 | | 6/1996 |
| WO | WO 97/49709 A1 | | 12/1997 |

(Continued)

OTHER PUBLICATIONS

Simental et al., "Transcriptional Activation and Nuclear Targeting Signals of the Human Androgen Receptor," *Journal of Biological Chemistry*, 266(1), 510-518 (Jan. 5, 1991).*
Berger et al., "Interaction of Glucocorticoid Analogues with the Human Glucocorticoid Receptor," *J. of Steroid Biochem. and Molecular Biol.* 41(3-8), 733-738 (Mar. 1992).*
Rosen et al., "Intracellular Receptors and Signal Transducers and Activators of Transcription Superfamilies: Novel Targets for Small-Molecule Drug Discovery," Journal of Medicinal Chemistry, 38(25), 4855-4874 (Dec. 8, 1995).*
Gruber et al., "Topical Cyproterone Acetate Treatment in Women with Acne," Archives of Dermatology, 134, 459-463 (Apr. 1998)††.*

(Continued)

*Primary Examiner*—L. E. Crane
(74) *Attorney, Agent, or Firm*—Fish & Richardson P.C.; Stephanie Seidman; Frank J. Miskiel

(57) ABSTRACT

Novel non-steroidal tricyclic quinolinone and tricyclic quinoline compounds and compositions that are agonists, partial agonists and/or antagonists for androgen receptors (AR), their preparation and their uses are described.

58 Claims, No Drawings

FOREIGN PATENT DOCUMENTS

| | | |
|---|---|---|
| WO | 00/12502 | 3/2000 |
| WO | 01/16108 | 3/2001 |
| WO | 01/16133 | 3/2001 |
| WO | 01/16139 | 3/2001 |
| WO | 02/066475 | 8/2002 |
| WO | 02/068427 | 9/2002 |
| WO | 2005/018573 | 3/2005 |

OTHER PUBLICATIONS

Venturoli et al., "A Prospectiove Randomized Trial Comparing Low Dose Flutamide, Finasteride, Ketoconazole, and Cyproterone Acetate-Estrogen Regimens in the Treatment of Hirsutism," Journal Clinical Endocrinology & Metabolism, 84(4), 1304-1310 (1999)††.*

Rosen et al., "Intracellular Receptors and Signal Transducers and Activators of Transcription Superfamilies: Novel Targets for Small-Molecule Drug Discovery," *Journal of Medicinal Chemistry*, 38(25), 4855-4874 (Dec. 8, 1995)††.*

Evans, R., "The Steroid and Thyroid Hormone Receptor Superfamily," *Science*, 240:889-895 (May 13, 1988).

Hamann, L., et al., "Synthesis and Biological Activity of a Novel Series of Nonsteroidal, Peripherally Selective Androgen Receptor Antagonists Derived from 1,2-Dihydropyridono[5,6-g]quinolines," *J. Med. Chem.*, 41:623-639, (WEB publ. date: Jan. 22, 1998).

Edwards, J., et al., "New Nonsteroidal Androgen Receptor Modulators Based on 4-(Trifluoromethyl)-2(1H)-Pyrrolidino[3,2-g]Quinolinone," *Bioorganic & Medicinal Chemistry Letters*, 8:745-750 (1998).

Edwards, J., et al., "Nonsteroidal Androgen Receptor Agonists Based on 4-(Trifluoromethyl)-2H- Pyrano[3,2-g]Quinolin-2-One," *Bioorganic & Medicinal Chemistry Letters*, 9:1003-1008 (1999).

Higuchi, R., et al., "4-Alkyl- and 3,4-Dialkyl-1,2,3,4-Tetrahydro-8-Pyridono[5,6-g]Quinolines: Potent, Nonsteroidal Androgen Receptor Agonists," *Bioorganic & Medicinal Chemistry Letters*, 9:1335-1340 (1999).

Jones, G., *Comprehensive Heterocyclic Chemistry*, Katritzky, A.R.; Rees, C.W., eds. Pergamon, New York, 1984, vol. 2, Chap. 2.08, pp. 421-426.

Fujisaki, S., et al., "Halogenation Using N-Halogenocompounds. I. Effect of Amines on *ortho*- Bromination of Phenols with NBS," *Bull. Chem. Soc. Jpn.*, 66:1576-1579, (May 1993).

Wagaw, S., et al., "Palladium-Catalyzed Coupling of Optically Active Amines with Aryl Bromides," *J. Am. Chem. Soc.*, 119:8451-8458; Absr. Publ. Aug. 15, 1997.

Allegretto, E. A. and R.A. Heyman, "Intracellular receptor characterization and ligand screening by transactivation and hormone-binding assays," Methods in Molecular Genetics vol. 8: Human Molecular Genetics, pp. 405-420 (1996).

Croston et al., "Androgen receptor-mediated antagonism of estrogen-dependent low density lipoprotein receptor transcription in cultured hepatocytes," Endocrinology, 138(9):3779-3786 (1997).

Hamann, "Discovery of a potent, orally active, nonsteroidal androgen receptor agonist: 4-ethyl-1,2,3,4-tetrahydro-6-(trifluoromethyl)-8-pyridono[5,6-g]-quinoline (LG121071)," Journal of Medicinal Chemistry, 42(2):210-212 (1999).

Kong et al., "Effects of isosteric pyridone replacements in androgen receptor antagonists based on 1,2-dihydro- and 1,2,3,4-tetrahydro-2,2-dimethyl-6-trifluoromethyl-8-pyridono[5,6-g]quinolines," Bioorganic & Medicinal Chemistry Letters, 10(5)::411-414 (2000).

Lamb, P. and J. Rosen, "Drug discovery using receptors that modulate gene expression," Journal of Receptor & Signal Transduction Research, 17(1-3): 531-543 (1997).

Lawson et al., "Androgen responsiveness of the pituitary gonadotrope cell line LβT2," Journal of Endocrinology, 170(3):601-607 (2001).

McDonnell et al., "Definition of the cellular mechanisms which distinguish between hormone and antihormone activated steroid receptors," Seminars in Cancer Biology, 5(5):327-336 (1994).

Miner, J. N. and C. M. Tyree, "Drug discovery and the intracellular receptor family," Vitamins and Hormones, 62: 253-280 (2001).

Negro-Vilar, A., "Selective androgen receptor modulators (SARMs): A novel approach to androgen therapy for the new millennium," Journal of Clinical Endocrinology and Metabolism 84(10):3459-3462 (1999).

Rosen et al., "Intracellular receptors and signal transducers and activators of transcription superfamilies: Novel targets for small-molecule drug discovery," Journal of Medicinal Chemistry, 38(25):4855-4874 (1995).

Rosen, J. and A. Negro-Vilar, "Novel, non-steroidal, selective androgen receptor modulators (SARMs) with anabolic activity in bone and muscle and improved safety profile," Journal of Musculoskeltal and Neuronal Interactions, 2(3):222-224 (2002).

Santiso-Mere, D. and D.P. McDonnell, "Applied nuclear receptor research in the drug discovery process," Chimica*oggi*/Chemistry Today 12(5-6):29-36 (1994).

Zhi, L. and E. Martinborough, "Selective androgen receptor modulators (SARMs)," Chapter 17 in Annual Reports in Medicinal Chemistry 36:169-180 (2001).

Zhi et al., "Switching androgen receptor antagonists to agonists by modifying C-ring substituents on piperidino[3,2-g]quinolinone," Bioorganic & Medicinal Chemistry Letters, 9(7):1009-1012 (1999).

Bolognese et al., "Photochemistry of Ommochrome Pigments," J. Heterocyclic Chem. 25: 1243-1246 (1988).

Bolognese et al., "Oxidation of 3-Hydroxykynurenine. A Reexamination,", J. Heterocyclic Chem. 25: 1247-1250 (1988).

Bolognese et al., "Photochemistry of Ommochromes and Related Compounds," J. Heterocyclic Chem. 25: 979-983 (1988).

Boyer, M., "The management of prostate cancer," Aust. Prescr. 19:22-24 (1996) http://www.australianprescriber.com/magazines/vol19no1/ap19-1-11.htm (accessed on Jan. 28, 2005).

Bush et al., "Sample-distance Partial Least Squares: PLS optimized for many variables, with application to CoMFA," Journal of Computer-Aided Molecular Design 7(5): 587-619 (1993).

Castillo, P. and J.C. Rodriguez-Ubis, "A high-yield method for the methylenation of *o*-dihydroxyaromatic compounds: synthesis of methylenedioxycoumarins," Synthesis pp. 839-840 (1986).

Chemical Abstracts vol. 54, No. 8821, (1960) Mustafa et al., "Photochemical reaction in sunlight. Experiments with benzo[*k*]quinoline-5,6-quinone, monoamine and monoxmine derivatives in sunlight and in dark," J. A. Chem. Soc. 81:3409-3413 (1959).

Chemical Abstracts vol. 83, No. 179036, p. 577 (1975) JP 50-25595 published Mar. 18, 1975, entitled "9-Halothiazoloquinolines".

Claman et al., "SOGC clinical practice guidelines. Hirsutism: evaluation and treatment," J. Obstet Gynaecol Can. 24(1):62-7 (2002).

Debenedetti et al., "Isopurasol, a coumarin from *Pterocaulon virgatum*," Phytochemistry 51: 701-703 (1999).

Ishii et al., "Formation of Hydroxanthommatin-Derived Radical in the Oxidation of 3-Hydroxykynurenine," Archives of Biochemistry and Biophysics 294(2):616-622 (1992).

Kalinin et al., "Directed *ortho* Metalation—Cross Coupling Links. Carbamoyl Rendition of the Baker-Venkataraman Reaarangement. Reiospecific Route to Substituted 4-Hydroxycoumarins," Tetrahedron Letters 39:4995-4998 (1998).

Kawamori et al., "Effects of heterocyclic amines with mammary gland carcinogenic potential on estrogenic response of uterus in ovariectomized rats," Cancer Letters 162: 31-37 (2001).

Lancelot et al., "Pyrido[2,3-*h*]pyrrolo[1,2-α]quinoxalines," Chem. Pharm. Bull. 31:3160-3167 (1983) [Article in French, English abstract on first page of article].

LaMontagne et al., "Antimalarials. 13. 5-Alkoxy Analogues of 4-Methylprimaquine," J. Med. Chem. 25:964-968 (1982).

McIlroy et al., "Effects of proteinase inhibitors on adenylate cyclase," Biochem J. 188(2): 423-435 (1980).

Ohta et al., "Juvenile hormone antagonists," Kagaku to Seibutsu 17(2):92-94 (1979) [Article in Japanese].

Singh et al., "Androgen receptor antagonists (antiandrogens): structure-activity relationships," Curr. Med. Chem. 7(2):211-247 (2000).

Sperry et al., "Farnesol oxidation in insects: evidence that the biosynthesis of insect juvenile hormone is mediated by a specific alcohol oxidase," Insect Biochemistry and Molecular Biology 31(2): 171-178 (2001).

STN CAPLUS Abstract Database Accession No. 96:6616 Akhvlediani et al., "Chichibabin reaction in a series of angular pyrroloquinolines," Zhurnal Organicheskoi Khimii 17(7):1542-1546 (1981).

STN CAPLUS Abstract Database Accession No. 74:3531, Chapman et al., "Substitution reactions of thieno [3,2-f]quinoline," Journal of the Chemical Society, Section C: Organic (17): 2334-2339 (1970).

STN CAPLUS Abstract Database Accession No. 130:13934, El-Desoky et al., "Synthesis of pyrrolo-,thienopyrrolo-, and benzothienopyrroloquinolines as well as of triazoloindole derivatives," Zeitschrift fuer Naturforschung B: Chemical Sciences 53(10): 1216-1222 (1998).

STN CAPLUS Abstract Database Accession No. 133:171758, Ferlin et al., "Pyrrolo-quinoline derivatives as potential antineoplastic drugs," Bioorganic & Medicinal Chemistry 8(6): 1415-1422 (2000).

STN CAPLUS Abstract Database Accession No. 110:75273, Gryaznov et al., "Reactivity of 1H-pyrrolo [2-3-f-]-3H-pyrrolo[3.2-f]quinoline and their derivatives," Izvestiya Timiryazevskoi Sel/skokhozyaistvennoi Akademii (3): 185-190 (1988).

STN CAPLUS Abstract Database Accesion No. 128:3621, Majumdar et al., "Studies on amine oxide rearragements: regioselective synthesis of pyrrolo [3,2-f]quinolin-7-ones," Journal of Chemical Research, Synopses (9):310-311 (1997).

STN CAPLUS Abstract Database Accession No. 73:73505, Saksena et al., "Androgenic, antiandrogenic, and anabolic activity of azasteroids on immature castrated rats," Indian J. Med. Res. 58(4):513-518 (1970).

STN CAPLUS Abstract Database Accession No. 87:5939, SU 548608 published Feb. 28, 1977, entitled "Pyrroloquinoline derivatives".

STN CAPLUS Abstract Database Accession No. 71:81325, SU 241441 published Apr. 18, 1969, entitled "2-Methyl-3-(.beta.-aminoethyl-1H-pyrrolo [2,3-b]quinoline or 1-(beta.-aminoethyl)-2-methyl-3H-pyrrolo [3,2-f]quinoline,".

STN CAPLUS Abstract Database Accession No. 99:38395. Yamashkin et al., "Synthesis of pyrroloquinolones," Khimiya Geterotsiklicheskikh Soedinenii (4): 493-497 (1983).

STN CAPLUS Abstract Database Accession No. 131:213835, Yamashkin et al., "Reactivities of 5-, 6-, and 7-(enamino) indoles in the synthesis of pyrroloquinolines," Chemistry of Heterocyclic Compounds (New York) [Translation of Khimiya Geterotsiklicheskikh Soedinenii] 34(9): 1050-1065 (1998).

STN CAPLUS Abstract Database Accession No. 56:38406, Yoshikawa et al., "Synthesis of 4,6-diaminoquinoline derivatives. I. Synthesis of pyrrolo [f] quinoline derivatives," Yakugaku Zasshi 81: 1317-1322 (1961).

STN CAPLUS Abstract Database Accession No. 92:146650, Yudin et al., "Nitropyrroloquinolines," Khimiya Geterotsiklicheskikh Soedimenii (10): 1381-1385 (1979).

Willard et al., "Potential Diuretic-β-Adrenergic Blocking Agents: Synthesis of 3-[2-[1,1-Dimethylethyl)amino]-1-hydroxyethyl]-1,4-dioxino[2,3-g]quinolines," J.Org. Chem. 46: 3846-3852 (1981).

Certified English translation of Japanese Patent Application No. JP 50-25595 entitled "Production method for 9-halogeno thiozolo quinoline materials," Mar. 18, 1975: see ref. "A1" above.

* cited by examiner

TRICYCLIC QUINOLINONE AND TRICYCLIC QUINOLINE ANDROGEN RECEPTOR MODULATOR COMPOUNDS AND METHODS

RELATED APPLICATION

The present application claims the benefit of priority to U.S. Provisional Application No. 60/271,115, filed on Feb. 23, 2001 which is incorporated by reference in its entirety.

FIELD OF THE INVENTION

This invention relates to non-steroidal compounds that are modulators (i.e. agonists and antagonists) of androgen receptors and to methods for making and using such compounds.

BACKGROUND OF THE INVENTION

Intracellular receptors (IRs) form a class of structurally-related genetic regulators scientists have named "ligand dependent transcription factors." R.M. Evans, *Science,* 240: 889 (1988). Steroid receptors are a recognized subset of the IRs, including the progesterone receptor (PR) androgen receptor (AR), estrogen receptor (ER), glucocorticoid receptor (GR) and mineralocorticoid receptor (MR). Regulation of a gene by such factors requires both the IR itself and a corresponding ligand, which has the ability to selectively bind to the IR in a way that affects gene transcription.

A compound that binds an IR and mimics the effect of the native ligand is referred to as an "agonist", while a compound that inhibits the effect of the native ligand is called an "antagonist." The term "modulators" refers to compounds that are agonists, partial agonists or antagonists.

The effectiveness of known modulators of steroid receptors is often tempered by their undesired side-effect profile, particularly during long-term administration. For example, the effectiveness of progesterone and estrogen agonists, such as norgestrel and diethylstilbesterol, respectively, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a GR antagonist. Accordingly, identification of compounds that have good specificity for one or more steroid receptors, but have reduced or no cross-reactivity for other steroid or intracellular receptors, would be of significant value in the treatment of male and female hormone responsive diseases.

A group of quinolinone and coumarin analogs having a fused ring system of the aryl, piperidine, pyrrolidine, or indoline series have been described as androgen modulators. See U.S. Pat. No. 5,696,130; Int. Patent Appl. WO 97/49709; L.G. Hamann, et al. *J. Med. Chem.,* 41:623–639 (1998); J. P. Edwards, et al., *Bioorg. Med. Chem. Lett.,* 8:745–750 (1998); J. P. Edwards, et al, Bioorg. *Med. Chem. Lett.,* 9:1003–1008 (1999), R. I. Higuchi, et al., *Bioorg. Med. Chem. Lett.,* 9:1335–1340 (1999).

The entire disclosures of the publications and references referred to above and hereafter in this specification are incorporated herein by reference and are not admitted to be prior art.

SUMMARY OF THE INVENTION

The present invention is directed to androgen receptor modulator compounds. This invention is also directed to pharmaceutical compositions containing such compounds as well as methods of using such compounds and pharmaceutical compositions for modulating processes mediated by steroid receptors. More particularly, the invention relates to non-steroidal compounds that are high-affinity, high-specificity agonists, partial agonists (i.e., partial activators and/or tissue-specific activators) and antagonists for androgen receptors (AR). Also provided are methods of making such compounds and pharmaceutical compositions, as well as intermediates used in their synthesis.

Compounds of the present invention are represented by those having the formula:

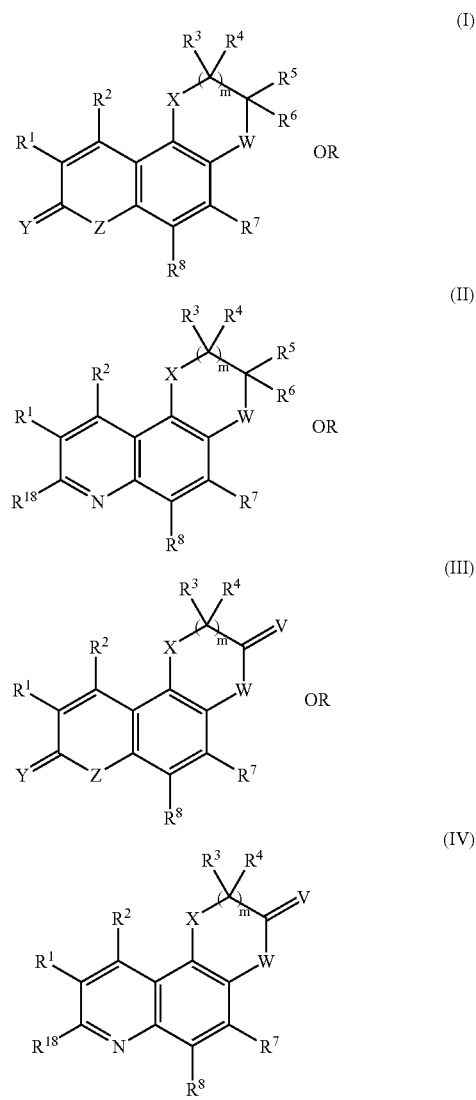

wherein:

$R^1$ is selected from the group of hydrogen, F, Cl, BR, I, $NO_2$, $OR^9$, $NR^{10}R^{11}$, $S(O)_nR^9$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted;

$R^2$ is selected from the group of hydrogen, F, Cl, BR, I, $CF_3$, $CF_2Cl$, $CF_2H$, $CFH_2$, $CF_2OR^9$, $CH_2OR^9$, $OR^9$, $S(O)_n$ $R^9$, $NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl aryl, arylalkyl, heteroaryl, alkynyl and alkenyl groups may be optionally substituted;

$R^3$ and $R^4$ each independently is selected from the group of hydrogen, $OR^9$, $S(O)_n R^9$, $NR^{10}R^{11}$, $C(Y)OR^{11}$, $C(Y)NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted; or $R^3$ and $R^4$ taken together form a three to eight membered saturated or unsaturated carbocyclic or heterocyclic ring; or $R^3$ and $R^5$ taken together form a three to eight membered saturated or unsaturated carbocyclic ring; or $R^3$ and $R^6$ taken together form a three to eight membered saturated or unsaturated carbocyclic ring; or $R^3$ and $R^{13}$ taken together form a three to eight membered saturated or unsaturated heterocyclic ring;

$R^5$ and $R^6$ each independently are selected from the group of hydrogen, $CF_3$, $CF_2Cl$, $CF_2H$, $CFH_2$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted; or $R^5$ and $R^6$ taken together form a three to eight membered saturated or unsaturated carbocyclic ring; or $R^5$ and $R^{13}$ taken together form a three to eight membered saturated or unsaturated heterocyclic ring; or $R^6$ and $R^{13}$ taken together form a three to eight membered saturated or unsaturated heterocyclic ring;

$R^7$ is selected from the group of hydrogen, F, Cl, BR, I, $C_1$–$C_8$ alkyl, $C_1$–$C_8$ haloalkyl, $C_1$–$C_8$ heteroalkyl, aryl, heteroaryl, $OR^9$, $S(O)_n R^9$, $NR^{10}R^{11}$, $C(Y)OR^{11}$ and $C(Y)NR^{10}R^{11}$, wherein the alkyl, haloalkyl, heteroalkyl, aryl and heteroaryl groups may be optionally substituted;

$R^8$ is selected from the group of hydrogen, F, Cl, BR, I, $C_1$–$C_8$ alkyl, $C_1$–$C_8$ haloalkyl, $C_1$–$C_8$ heteroalkyl, aryl, heteroaryl, $OR^9$, $S(O)_n R^9$, $NR^{10}R^{11}$, $C(Y)OR^{11}$ and $C(Y)NR^{10}R^{11}$, wherein the alkyl, haloalkyl, heteroalkyl, aryl and heteroaryl groups may be optionally substituted;

$R^9$ is selected from the group of hydrogen, $C_1$–$C_8$ alkyl, $C_1$–$C_8$ haloalkyl, $C_1$–$C_8$ heteroalkyl, aryl, heteroaryl and arylalkyl, wherein the alkyl, haloalkyl, heteroalkyl, aryl, heteroaryl and arylalkyl groups may be optionally substituted;

$R^{10}$ is selected from the group of hydrogen, $C_1$–$C_8$ alkyl, $C_1$–$C_8$ haloalkyl, $C_1$–$C_8$ heteroalkyl, aryl, heteroaryl, arylalkyl, $CO_2R^{12}$, $C(O)R^{12}$, $SO_2R^{12}$ and $S(O)R^{12}$, wherein the alkyl, haloalkyl, heteroalkyl, aryl, heteroaryl and arylalkyl groups may be optionally substituted;

$R^{11}$ and $R^{12}$ each independently is selected from the group of hydrogen, $C_1$–$C_8$ alkyl, $C_1$–$C_8$ haloalkyl, $C_1$–$C_8$ heteroalkyl, aryl, heteroaryl and arylalkyl, wherein the alkyl, haloalkyl, heteroalkyl, aryl, heteroaryl and arylalkyl groups may be optionally substituted;

$R^{13}$ is selected from the group of $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl, wherein the alkyl, haloalkyl, heteroalkyl, alkenyl, alkynyl, cycloalkyl, aryl, heteroaryl, arylalkyl and heteroarylalkyl groups may be optionally substituted;

$R^{16}$ is selected from the group of hydrogen, $C_1$–$C_8$ alkyl, $C_1$–$C_8$ haloalkyl, $C_1$–$C_8$ heteroalkyl, $COR^{17}$, $CO_2R^{17}$ and $CONR^{12}R^{17}$, wherein the alkyl, haloalkyl and heteroalkyl groups may be optionally substituted;

$R^{17}$ is selected from the group of hydrogen, $C_1$–$C_8$ alkyl, $C_1$–$C_8$ haloalkyl and $C_1$–$C_8$ heteroalkyl, wherein the alkyl, haloalkyl and heteroalkyl groups may be optionally substituted;

$R^{18}$ is selected from the group of hydrogen, F, BR, Cl, I, CN, $C_1$–$C_8$ alkyl, $C_1$–$C_8$ haloalkyl, $C_1$–$C_8$ heteroalkyl, $OR^{16}$, $NR^{16}R^{17}$, $SR^{16}$, $CH_2R^{16}$, $COR^{17}$, $CO_2R^{17}$, $CONR^{16}R^{17}$, $SOR^{17}$ and $SO_2R^{17}$, wherein the alkyl, haloalkyl and heteroalkyl groups may be optionally substituted;

$R^{19}$ is selected from the group of hydrogen, $C_1$–$C_8$ alkyl, $C_1$–$C_{18}$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl, wherein the alkyl, haloalkyl, heteroalkyl, alkenyl, alkynyl, cycloalkyl, aryl, heteroaryl, arylalkyl and heteroarylalkyl groups may be optionally substituted;

m is selected from the group of 0, 1 and 2;

n is selected from the group of 0, 1 and 2;

V is selected from the group of O and S;

W is selected from the group of O, $S(O)_n$, NH, $N\{R^{13}\}$, $N\{C(Y)R^{11}\}$ and $N\{SO_2R^{11}\}$;

X and Z each independently is selected from the group of O, $S(O)_n$, NH, $N\{R^{11}\}$, $N\{C(Y)R^{11}\}$, $N\{SO_2R^{12}\}$ and $N\{S(O)R^{12}\}$; and Y is selected from the group of O, S, $N\{R^{19}\}$ and $N\{OR^{19}\}$;

and pharmaceutically acceptable salts thereof.

DETAILED DESCRIPTION OF THE INVENTION

In accordance with the present invention, we have developed novel compounds, compositions and methods of preparing non-steroidal compounds that are AR modulators. Specifically, we have developed agonists, partial agonists (i.e., partial activators and/or tissue-specific activators) and antagonists for androgen receptors and methods of preparing these compounds and compositions. Compounds of the present invention may be high affinity, high specificity agonists, partial agonists, or antagonists for androgen receptors.

In accordance with the present invention and as used herein, the following structure definitions are provided for nomenclature purposes. Furthermore, in an effort to maintain consistency in the naming of compounds of similar structure but differing substituents, the compounds described herein are named according to the following general guidelines. The numbering system for the location of substituents on such compounds is also provided.

A 2H-[1,4]oxazino[2,3-f]quinoline is represented by the following structure:

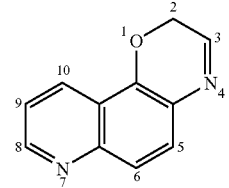

An 8H-[1,4]oxazino[2,3-f]quinoline is represented by the following structure:

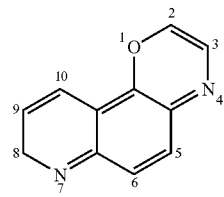

A 1H,6H-pyrrolo[1',2':4,5][1,4]oxazino[2,3-f]quinolin-2-one is represented by the following structure:

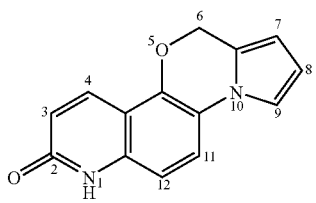

In accordance with the present invention and as used herein, the following terms are defined with the following meanings, unless explicitly stated otherwise.

The term "alkyl," alone or in combination, refers to an optionally substituted straight-chain or branched-chain alkyl radical having from 1 to about 12 carbon atoms. The term also includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain alkyl radicals having one or more carbon-carbon double bonds and having from 2 to about 6 carbon atoms as well as those having from 2 to about 4 carbon atoms. Examples of alkenyl radicals include ethenyl, propenyl, 1,4-butadienyl and the like.

The term "alkynyl," alone or in combination, refers to an optionally substituted straight-chain or branched-chain hydrocarbon radical having one or more carbon-carbon triple-bonds and having from 2 to about 12 carbon atoms. The term also includes substituted straight-chain or branched-chain alkyl radicals having one or more carbon-carbon tyriple bonds and having from 2 to about 6 carbon atoms as well as those having from 2 to about 4 carbon atoms. Examples of alkynyl radicals include ethynyl, propynyl, butynyl and the like.

The term "heteroalkyl" refers to alkyl groups, as described above, in which one or more skeletal atoms are oxygen, nitrogen, sulfur or combinations thereof. The term heteroalkyl also includes alkyl groups in which one 1 to about 6 skeletal atoms are oxygen, nitrogen, sulfur or combinations thereof as well as those in which 1 to 4 skeletal atoms are oxygen, nitrogen, sulfur or combinations thereof and those in which 1 to 2 skeletal atoms are oxygen, nitrogen, sulfur or combinations thereof.

The term "alkoxy," alone or in combination, refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as below. Examples of aryloxy radicals include phenoxy, benzyloxy and the like.

The term "alkylthio," alone or in combination, refers to an alkyl thio radical wherein the term alkyl is defined as above.

The term "arylthio," alone or in combination, refers to an aryl thio radical wherein the term aryl is defined as below.

The term "oxo" refers to =O.

The term "aryl," alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen and sulfur. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "heteroarylalkyl" refers to a $C_1$–$C_4$ alkyl group containing a heteroaryl group, each of which may be optionally substituted.

The term "heteroarylthio" refers to the group —S-heteroaryl.

The term "acyloxy" refers to the ester group —OC(O)—R, where R is hydrogen, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

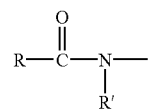

where R and R' each independently is selected from the group of hydrogen, alkyl, aryl and arylalkyl, wherein the alkyl, aryl and arylalkyl groups may be optionally substituted.

The term "cycloalkyl", alone or in combination, refers to a monocyclic, bicyclic or tricyclic alkyl radical wherein each cyclic moiety has from 3 to about 8 carbon atoms. Examples of cycloalkyl radicals include cyclopropyl, cyclobutyl, cyclopentyl, cyclohexyl and the like.

The term "arylalkyl," alone or in combination, refers to an alkyl radical as defined above in which one hydrogen atom is replaced by an aryl radical as defined above, such as, for example, benzyl, 2-phenylethyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, or combinations thereof.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

"Optionally substituted" groups may be substituted or unsubstituted. The substituents of an "optionally substituted" group may include, without limitation, one or more substituents independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, hydrogen, F, Cl, BR, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$ and $NR^{10}R^{11}$. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstututed (e.g., —$CH_2CF_3$).

The term "halogen" includes F, Cl, Br and I.

The term "mediate" means affect or influence. Thus, for example, conditions mediated by an androgen receptor are those in which an androgen receptor plays a role. Androgen receptors are known to play a role in conditions including, for example, acne, male-pattern baldness, sexual dysfunction, impotence, wasting diseases, hirsutism, hypogonadism, prostatic hyperplasia, osteoporosis, cancer cachexia, and hormone-dependent cancers.

The term "selective" refers to compounds that display reactivity towards a particular receptor (e.g., an androgen receptor) without displaying cross-reactivity towards another receptor (e.g., glucocorticoid receptor). Thus, for example, selective compounds of the present invention may display reactivity towards androgen receptors without displaying cross-reactivity towards glucocorticoid receptors.

Compounds of the present invention are represented by those having the formula:

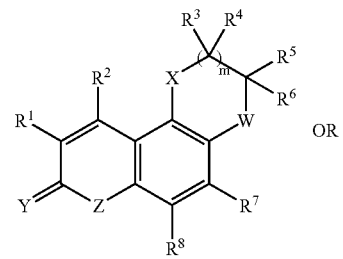

(I)

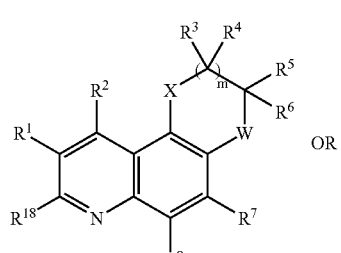

(II)

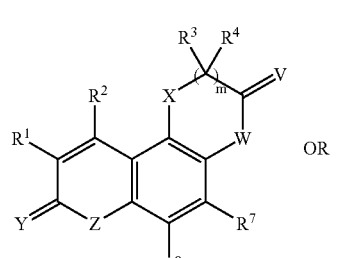

(III)

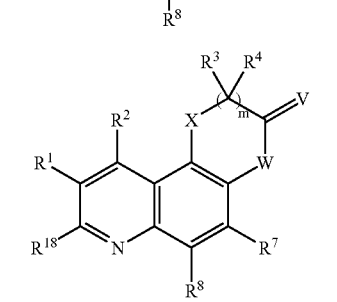

(IV)

wherein:

$R^1$ is selected from the group of hydrogen, F, Cl, BR, I, $NO_2$, $OR^9$, $NR^{10}R^{11}$, $S(O)_nR^9$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted;

$R^2$ is selected from the group of hydrogen, F, Cl, BR, I, $CF_3$, $CF_2Cl$, $CF_2H$, $CFH_2$, $CF_2OR^9$, $CH_2OR^9$, $OR^9$, $S(O)_n R^9$, $NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl aryl, arylalkyl, heteroaryl, alkynyl and alkenyl groups may be optionally substituted;

$R^3$ and $R^4$ each independently is selected from the group of hydrogen, $OR^9$, $S(O)_nR^9$, $NR^{10}R^{11}$, $C(Y)OR^{11}$, $C(Y)NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted; or $R^3$ and $R^4$ taken together form a three to eight membered saturated or unsaturated carbocyclic or heterocyclic ring; or $R^3$ and $R^5$ taken together form a three to eight membered saturated or unsaturated carbocyclic ring; or $R^3$ and $R^6$ taken together form a three to eight membered saturated or unsaturated carbocyclic ring; or $R^3$ and $R^{13}$ taken together form a three to eight membered saturated or unsaturated heterocyclic ring;

$R^5$ and $R^6$ each independently are selected from the group of hydrogen, $CF_3$, $CF_2Cl$, $CF_2H$, $CFH_2$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl, wherein the alkyl, haloalkyl, heteroalkyl, cycloalkyl, aryl, arylalkyl, heteroaryl, alkynyl and alkenyl groups may be optionally substituted; or $R^5$ and $R^6$ taken together form a three to eight membered saturated or unsaturated carbocyclic ring; or $R^5$ and $R^{13}$ taken together form a three to eight membered saturated or unsaturated heterocyclic ring; or $R^6$ and $R^{13}$ taken together form a three to eight membered saturated or unsaturated heterocyclic ring;

$R^7$ is selected from the group of hydrogen, F, Cl, BR, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$, wherein the alkyl, haloalkyl, heteroalkyl, aryl and heteroaryl groups may be optionally substituted;

$R^8$ is selected from the group of hydrogen, F, Cl, BR, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$, wherein the alkyl, haloalkyl, heteroalkyl, aryl and heteroaryl groups may be optionally substituted;

A $R^9$ is selected from the group of hydrogen, $C_1$–$C_8$ alkyl, $C_1$–$C_8$ haloalkyl, $C_1$–$C_8$heteroalkyl, aryl, heteroaryl and arylalkyl, wherein the alkyl, haloalkyl, heteroalkyl, aryl, heteroaryl and arylalkyl groups may be optionally substituted;

$R^{10}$ is selected from the group of hydrogen, $C_1$–$C_8$ alkyl, $C_1$–$C_8$ haloalkyl, $C_1$–$C_8$heteroalkyl, aryl, heteroaryl, arylalkyl, $CO_2R^{12}$, $C(O)R^{12}$, $SO_2R^{12}$ and $S(O)R^{12}$, wherein the alkyl, haloalkyl, heteroalkyl, aryl, heteroaryl and arylalkyl groups may be optionally substituted;

$R^{11}$ and $R^{12}$ each independently is selected from the group of hydrogen, $C_1$–$C_8$ alkyl, $C_1$–$C_8$ haloalkyl, $C_1$–$C_8$ heteroalkyl, aryl, heteroaryl and arylalkyl, wherein the alkyl, haloalkyl, heteroalkyl, aryl, heteroaryl and arylalkyl groups may be optionally substituted;

$R^{13}$ is selected from the group of $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl, wherein the alkyl, haloalkyl, heteroalkyl, alkenyl, alkynyl, cycloalkyl, aryl, heteroaryl, arylalkyl and heteroarylalkyl groups may be optionally substituted;

$R^{16}$ is selected from the group of hydrogen, $C_1$–$C_8$ alkyl, $C_1$–$C_8$ haloalkyl, $C_1$–$C_8$heteroalkyl, $COR^{17}$, $CO_2R^{17}$ and $CONR^{12}R^{17}$, wherein the alkyl, haloalkyl and heteroalkyl groups may be optionally substituted;

$R^{17}$ is selected from the group of hydrogen, $C_1$–$C_8$ alkyl, $C_1$–$C_8$ haloalkyl and $C_1$–$C_8$ heteroalkyl, wherein the alkyl, haloalkyl and heteroalkyl groups may be optionally substituted;

$R^{18}$ is selected from the group of hydrogen, F, BR, Cl, I, CN, $C_1$–$C_8$ alkyl, $C_1$–$C_8$ haloalkyl, $C_1$–$C_8$ heteroalkyl, $OR^{16}$, $NR^{16}R^{17}$, $SR^{16}$, $CH_2R^{16}$, $COR^{17}$, $CO_2R^{17}$, $CONR^{16}R^{17}$, $SOR^{17}$ and $SO_2R^{17}$, wherein the alkyl, haloalkyl and heteroalkyl groups may be optionally substituted;

$R^{19}$ is selected from the group of hydrogen, $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl, wherein the alkyl, haloalkyl, heteroalkyl, alkenyl, alkynyl, cycloalkyl, aryl, heteroaryl, arylalkyl and heteroarylalkyl groups may be optionally substituted;

m is selected from the group of 0, 1 and 2;

n is selected from the group of 0, 1 and 2;

V is selected from the group of O and S;

W is selected from the group of O, $S(O)_n$, NH, $N\{R^{13}\}$, $N\{C(Y)R^{11}\}$ and $N\{SO_2R^{11}\}$;

X and Z each independently is selected from the group of O, $S(O)_n$, NH, $N\{R^{11}\}$, $N\{C(Y)R^{11}\}$, $N\{SO_2R^{12}\}$ and $N\{S(O)R^{12}\}$; and Y is selected from the group of O, S, $N\{R^{19}\}$ and $N\{OR^{19}\}$;

and pharmaceutically acceptable salts thereof.

In one aspect, the present the invention provides compounds represented by formula I through IV. In another aspect, the present invention provides a pharmaceutical composition comprising an effective amount of an AR modulating compound of formula I through IV shown above, wherein $R^1$ through $R^{13}$, $R^{16}$ through $R^{19}$, m, n, V, W, X, Y, and Z are as described above.

In another aspect, the present invention provides a method of modulating processes mediated by ARs by administering to a patient an effective amount of a compound of formula I through IV shown above, wherein $R^1$ through $R^{13}$, $R^{16}$ through $R^{19}$, m, n, V, W, X, Y, and Z are as described above. In one aspect, the modulation is activation, while in another aspect, the modulation is inhibition. In each case, the method involves administering to a patient a pharmaceutically effective amount of a compound of formula I through IV shown above, wherein $R^1$ through $R^{13}$, $R^{16}$ through $R^{19}$, m, n, V, W, X, Y, and Z are as described above.

With regard to the foregoing variables, the inventors contemplate any combination of the Markush groups as set forth above and as described in the following table.

TABLE A

Table of Markush Groups by Variable

|  | Markush Group A | Markush Group B | Markush Group C | Markush Group D |
|---|---|---|---|---|
| $R^1$ | hydrogen, F, Cl $OR^9$, $NR^{10}R^{11}$, $S(O)_nR^9$, $C_1$–$C_4$ alkyl, $C_1$–$C_4$ | hydrogen, F, Cl, $C_1$– $C_4$ alkyl, $C_1$–$C_4$ haloalkyl and $C_1$–$C_4$ | hydrogen, F and optionally substituted $C_1$–$C_4$ alkyl. | hydrogen and optionally substituted $C_1$–$C_4$ alkyl |

TABLE A-continued

Table of Markush Groups by Variable

| | Markush Group A | Markush Group B | Markush Group C | Markush Group D |
|---|---|---|---|---|
| | haloalkyl and $C_1$–$C_4$ heteroalkyl, wherein the alkyl, haloalkyl and heteroalkyl groups may be optionally substituted | heteroalkyl, wherein the alkyl, haloalkyl and heteroalkyl may be optionally substituted. | | |
| $R^2$ | hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $C_1$–$C_6$ alkyl, $C_1$–$C_6$ haloalkyl, $C_1$–$C_6$ heteroalkyl, $C_2$–$C_6$ alkynyl and $C_2$–$C_6$ alkenyl, wherein the alkyl, haloalkyl, heteroalkyl, alkynyl and alkenyl groups may be optionally substituted | hydrogen, F, Cl, $CF_3$, $CF_2Cl$, $CF_2H$, $CFH_2$, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted. | hydrogen, $C_1$–$C_2$ alkyl, $C_1$–$C_2$ haloalkyl and $C_1$–$C_2$ heteroalkyl, wherein the alkyl, haloalkyl and heteroalkyl groups may be optionally substituted. | $CF_3$ |
| $R^3$ | hydrogen, $C_1$–$C_6$ alkyl, $C_1$–$C_6$ haloalkyl, $C_1$–$C_6$ heteroalkyl, $C(Y)OR^{11}$ and $C(Y)NR^{10}R^{11}$, wherein the alkyl, haloalkyl and heteroalkyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen, $C(Y)OR^{11}$ and $C(Y)NR^{10}R^{11}$ | hydrogen |
| | $R^3$ and $R^6$ taken together form a three to eight membered saturated or unsaturated carbocyclic ring | $R^3$ and $R^6$ taken together form a four to six membered saturated or unsaturated carbocyclic ring | | |
| $R^4$ | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and optionally substituted $C_1$–$C_2$ alkyl | hydrogen and methyl | hydrogen |
| $R^5$ | hydrogen, $CF_3$, $CF_2Cl$, $CF_2H$, $CFH_2$, $C_1$–$C_6$ alkyl, $C_1$–$C_6$ haloalkyl, $C_1$–$C_6$ heteroalkyl, $C_2$–$C_6$ alkynyl, $C_2$–$C_6$ alkenyl, wherein the alkyl, haloalkyl, heteroalkyl, alkynyl and alkenyl groups may be optionally substituted | hydrogen, $CF_3$, $CF_2Cl$, $CF_2H$, $CFH_2$, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, $CF_3$, $CF_2Cl$, $CF_2H$, $CFH_2$, $C_1$–$C_4$ alkyl, $C_1$–$C_4$ haloalkyl and $C_1$–$C_4$ heteroalkyl, wherein said alkyl, haloalkyl and heteroalkyl groups may be optionally substituted | hydrogen and $CF_3$ |
| $R^6$ | hydrogen, $CF_3$, $CF_2Cl$, $CF_2H$, $CFH_2$, $C_1$–$C_6$ alkyl, $C_1$–$C_6$ haloalkyl, $C_1$–$C_6$ heteroalkyl, aryl, | hydrogen, $CF_3$, $CF_2Cl$, $CF_2H$, $CFH_2$, $C_1$–$C_4$ alkyl, $C_1$–$C_4$ haloalkyl, $C_1$–$C_4$ heteroalkyl, $C_2$– | hydrogen, $CF_3$, $CF_2Cl$, $CF_2H$, $CFH_2$, $C_1$–$C_4$ alkyl, $C_1$–$C_4$ haloalkyl and $C_1$–$C_4$ heteroalkyl, | hydrogen and optionally substituted $C_1$–$C_4$ alkyl |

TABLE A-continued

Table of Markush Groups by Variable

| | Markush Group A | Markush Group B | Markush Group C | Markush Group D |
|---|---|---|---|---|
| | arylalkyl, heteroaryl, $C_2$–$C_6$ alkynyl and $C_2$–$C_6$ alkenyl, wherein the alkyl, heteroalkyl, haloalkyl, aryl, arylalkyl, heteroaryl, alkynyl and alkenyl groups may be optionally substituted | $C_4$ alkynyl and $C_2$–$C_4$ alkenyl, wherein the alkyl, heteroalkyl, haloalkyl, alkynyl and alkenyl groups may be optionally substituted | wherein the alkyl, haloalkyl and heteroalkyl groups may be optionally substituted | |
| | $R^3$ and $R^6$ taken together form a three to eight membered saturated or unsaturated carbocyclic ring | aryl, arylalkyl and heteroaryl, wherein the aryl, arylalkyl and heteroaryl groups may be optionally substituted | $R^3$ and $R^6$ taken together form a four to six membered saturated or unsaturated carbocyclic ring | |
| | $R^6$ and $R^{13}$ taken together form a five to seven membered saturated or unsaturated heterocyclic ring | | $R^6$ and $R^{13}$ taken together form a five to six membered saturated or unsaturated heterocyclic ring | $R^6$ and $R^{13}$ taken together form a five membered saturated or unsaturated heterocyclic ring |
| $R^7$ | hydrogen, F, Cl, Br, I, $C_1$–$C_6$ alkyl, $C_1$–$C_6$ haloalkyl and $C_1$–$C_6$ heteroalkyl, wherein the alkyl, haloalkyl and heteroalkyl, groups may be optionally substituted $OR^9$, $S(O)_nR^9$, $NR^{10}R^{11}$, $C(Y)OR^{11}$ and $C(Y)NR^{10}R^{11}$ | hydrogen, F, Cl, $C_1$–$C_4$ alkyl, $C_1$–$C_4$ haloalkyl and $C_1$–$C_4$ heteroalkyl, wherein the alkyl, haloalkyl and heteroalkyl, groups may be optionally substituted | hydrogen and optionally substituted $C_1$–$C_2$ alkyl | hydrogen and methyl |
| $R^8$ | hydrogen, F, Cl, Br, I, $C_1$–$C_6$ alkyl, $C_1$–$C_6$ haloalkyl and $C_1$–$C_6$ heteroalkyl, wherein the alkyl, haloalkyl and heteroalkyl, groups may be optionally substituted $OR^9$, $S(O)_nR^9$, $NR^{10}R^{11}$, $C(Y)OR^{11}$ and $C(Y)NR^{10}R^{11}$ | hydrogen F, Cl, $C_1$–$C_4$ alkyl, $C_1$–$C_4$ haloalkyl and $C_1$–$C_4$ heteroalkyl, wherein the alkyl, haloalkyl and heteroalkyl, groups may be optionally substituted | hydrogen and optionally substituted $C_1$–$C_2$ alkyl | hydrogen and methyl |
| $R^9$ | hydrogen, $C_1$–$C_6$ alkyl, $C_1$–$C_6$ haloalkyl, $C_1$–$C_6$ heteroalkyl, aryl, heteroaryl and arylalkyl, wherein the alkyl, haloalkyl, heteroalkyl, aryl, heteroaryl and arylalkyl groups may be optionally substituted | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen and optionally substituted $C_1$–$C_4$ alkyl | hydrogen and methyl |
| $R^{10}$ | hydrogen, $CO_2R^{12}$, $C(O)R^{12}$, $SO_2R^{12}$, $S(O)R^{12}$, $C_1$–$C_6$ alkyl, $C_1$–$C_6$ haloalkyl and | hydrogen, $C_1$–$C_4$ alkyl, $C_1$–$C_4$ haloalkyl and $C_1$–$C_4$ heteroalkyl, | hydrogen, $S(O)R^{12}$, $SO_2R^{12}$, $C(O)R^{12}$ and $CO_2R^{12}$ | hydrogen and methyl |

TABLE A-continued

Table of Markush Groups by Variable

| | Markush Group A | Markush Group B | Markush Group C | Markush Group D |
|---|---|---|---|---|
| | $C_1$–$C_6$ heteroalkyl, wherein the alkyl, haloalkyl and heteroalkyl groups may be optionally substituted | wherein the alkyl, haloalkyl and heteroalkyl groups may be optionally substituted | | |
| $R^{11}$ | hydrogen, $C_1$–$C_6$ alkyl, $C_1$–$C_6$ haloalkyl, $C_1$–$C_6$ heteroalkyl, aryl, heteroaryl and arylalkyl, wherein the alkyl, haloalkyl, heteroalkyl, aryl, heteroaryl and arylalkyl groups may be optionally substituted | hydrogen, $C_1$–$C_4$ alkyl, $C_1$–$C_4$ haloalkyl, $C_1$–$C_4$ heteroalkyl, aryl, heteroaryl and arylalkyl, wherein the alkyl, haloalkyl, heteroalkyl, aryl, heteroaryl and arylalkyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and methyl |
| $R^{12}$ | hydrogen, $C_1$–$C_6$ alkyl, $C_1$–$C_6$ haloalkyl, $C_1$–$C_6$ heteroalkyl, aryl, heteroaryl and arylalkyl, wherein the alkyl, haloalkyl, heteroalkyl, aryl, heteroaryl and arylalkyl groups may be optionally substituted | hydrogen, $C_1$–$C_4$ alkyl, $C_1$–$C_4$ haloalkyl, $C_1$–$C_4$ heteroalkyl, aryl, heteroaryl and arylalkyl, wherein the alkyl, haloalkyl, heteroalkyl, aryl, heteroaryl and arylalkyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl, and heteroalkyl groups may be optionally substituted | hydrogen and methyl |
| $R^{13}$ | $CF_3$, $CF_2Cl$, $CF_2H$, $CFH_2$, $CH_2CF_3$, $CH_2CF_2Cl$, $CH_2CCl_2F$, $C_1$–$C_6$ alkyl, $C_1$–$C_6$ haloalkyl, $C_1$–$C_6$ heteroalkyl, $C_2$–$C_6$ alkenyl, $C_2$–$C_6$ alkynyl, $C_3$–$C_6$ cycloalkyl, aryl, heteroaryl, arylalkyl and heteroarylalkyl, wherein the alkyl, haloalkyl, heteroalkyl, alkenyl, alkynyl, cycloalkyl, aryl, heteroaryl, arylalkyl and heteroarylalkyl groups may be optionally substituted | $CF_3$, $CF_2Cl$, $CF_2H$, $CFH_2$, $CH_2CF_3$, $CH_2CF_2Cl$, $CH_2CCl_2F$, $C_1$–$C_4$ alkyl, $C_1$–$C_4$ haloalkyl, $C_1$–$C_4$ heteroalkyl, $C_2$–$C_4$ alkenyl and aryl wherein the alkyl, haloalkyl, heteroalkyl, alkenyl and aryl groups may be optionally substituted | $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | $CF_3$, $CF_2Cl$, $CF_2H$, $CFH_2$, $CH_2CF_3$, $CH_2CF_2Cl$, $CH_2CCl_2F$, methyl, ethyl, propyl, isopropyl, isobutyl, cyclopropyl-methyl and allyl |
| | $R^6$ and $R^{13}$ taken together form a five to seven membered saturated or unsaturated heterocyclic ring | $R^6$ and $R^{13}$ taken together form a five to six membered saturated or unsaturated heterocyclic ring | $R^6$ and $R^{13}$ taken together form a five to six membered saturated or unsaturated heterocyclic ring | $R^6$ and $R^{13}$ taken together form a five membered saturated or unsaturated heterocyclic ring |
| $R^{16}$ | hydrogen, $C_1$–$C_6$ alkyl, $C_1$–$C_6$ haloalkyl, $C_1$–$C_6$ heteroalkyl, $COR^{17}$, $CO_2R^{17}$ and $CONR^{12}R^{17}$, wherein the alkyl, haloalkyl and | hydrogen, $C_1$–$C_4$ alkyl, $C_1$–$C_4$ haloalkyl and $C_1$–$C_4$ heteroalkyl and wherein the alkyl, haloalkyl and heteroalkyl groups may be | hydrogen and optionally substituted $C_1$–$C_4$ alkyl | hydrogen and methyl |

TABLE A-continued

Table of Markush Groups by Variable

| | Markush Group A | Markush Group B | Markush Group C | Markush Group D |
|---|---|---|---|---|
| | heteroalkyl groups may be optionally substituted | optionally substituted | | |
| $R^{17}$ | hydrogen, $C_1$–$C_6$ alkyl, $C_1$–$C_6$ haloalkyl and $C_1$–$C_6$ heteroalkyl, wherein the alkyl, haloalkyl and heteroalkyl groups may be optionally substituted | hydrogen, $C_1$–$C_4$ alkyl, $C_1$–$C_4$ haloalkyl and $C_1$–$C_4$ heteroalkyl and wherein the alkyl, haloalkyl and heteroalkyl groups may be optionally substituted | hydrogen and optionally substituted $C_1$–$C_4$ alkyl | hydrogen and methyl |
| $R^{18}$ | hydrogen, F, Cl, CN, $C_1$–$C_6$ alkyl, $C_1$–$C_6$ haloalkyl, $C_1$–$C_6$ heteroalkyl, $OR^{16}$, $NR^{16}R^{17}$, $SR^{16}$, $CH_2R^{16}$, $COR^{17}$, $CO_2R^{17}$, $CONR^{17}R^{17}$, $SOR^{17}$ and $SO_2R^{17}$, wherein the alkyl, haloalkyl and heteroalkyl groups may be optionally substituted | hydrogen, F, Cl, $OR^{16}$, $SR^{16}$, $NR^{16}R^{17}$, $C_1$–$C_4$ alkyl, $C_1$–$C_4$ haloalkyl and $C_1$–$C_4$ heteroalkyl and wherein the alkyl, haloalkyl and heteroalkyl groups maybe optionally substituted | hydrogen, F, Cl, $OR^{16}$, $SR^{16}$ and $NR^{16}R^{17}$ | H, F, Cl and $OR^{16}$ |
| $R^{19}$ | hydrogen, $C_1$–$C_6$ alkyl, $C_1$–$C_6$ haloalkyl, $C_1$–$C_6$ heteroalkyl, $C_2$–$C_6$ alkenyl and $C_2$–$C_6$ alkynyl, wherein the alkyl, haloalkyl, heteroalkyl, alkenyl and alkynyl groups may be optionally substituted | hydrogen, $C_1$–$C_4$ alkyl, $C_1$–$C_4$ haloalkyl and $C_1$–$C_4$ heteroalkyl, wherein the alkyl, haloalkyl and heteroalkyl groups may be optionally substituted | hydrogen and optionally substituted $C_1$–$C_4$ atkyl | hydrogen and methyl |
| m | 0 and 1 | 1 | 0 | |
| V | S | 0 | | |
| W | NH, N{$R^{13}$}, N{C(Y)$R^{11}$} and N{$SO_2R^{11}$} | NH and N{$R^{13}$} | | |
| X | O, S, NH and N{$R^{11}$} | O and S | O | S |
| Y | O and S | O | S | |
| Z | NH, N{$R^{11}$} and O | NH and N{$R^{11}$} | | |

The compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, tris (hydroxymethyl)aminomethane and the like and suitable combinations of any two or more thereof. Additional pharmaceutically acceptable salts are known to those skilled in the art.

AR agonist, partial agonist and antagonist compounds (including compounds with tissue-selective AR modulator activity) of the present invention may be useful in the treatment of process(es) mediated by androgen receptor(s), including acne (antagonist), male-pattern baldness (antagonist), male hormone replacement therapy (agonist), sexual dysfunction (agonist), wasting diseases (agonist), hirsutism (antagonist), stimulation of hematopoiesis (agonist), hypogonadism (agonist), prostatic hyperplasia (antagonist), osteoporosis (agonist), male contraception (agonist), impotence (agonist), cancer cachexia (agonist), various hormone-dependent cancers (e.g., prostate cancer (antagonist), breast cancer and the like), process(es) requiring anabolic agents (agonist) and the like. It is understood by those of skill in the art that a partial agonist may be used where agonist activity is desired, or where antagonist activity is desired, depending upon the AR modulator profile of the particular partial agonist.

It is understood by those skilled in the art that while the compounds of the present invention will typically be employed as selective agonists, partial agonists or antagonists, that there may be instances where a compound with a mixed steroid receptor profile is desirable. For example, use of a PR agonist (i.e., progestin) in female contraception often leads to the undesired effects of increased water retention and acne flare-ups. In this instance, a compound that is primarily a PR agonist, but also displays some AR and MR modulating activity, may prove useful. Specifically, the mixed MR effects would be useful to control water balance in the body, while the AR effects would help to control any acne flare-ups that occur.

Furthermore, it is understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists and antagonists) according to the present invention include: (3R)-2,3,4,7-Tetrahydro-3-methyl-10-(trifluoromethyl)-8H-[1,4]oxazino[2,3-f]quinolin-8-one (Compound 101); (3R)-2,3,4,7-Tetrahydro-3,4-dimethyl-10-(trifluoromethyl)-8H-[1,4]oxazino[2,3-f]quinolin-8-one (Compound 102); (3R)-4-Ethyl-2,3,4,7-tetrahydro-3-methyl-10-(trifluoromethyl)-8H-[1,4]oxazino[2,3-f]quinolin-8-one (Compound 103); (3R)-2,3,4,7-Tetrahydro-3-methyl-4-(2,2,2-trifluoroethyl)-10-(trifluoromethyl)-8H-[1,4]oxazino[2,3-f]quinolin-8-one (Compound 104); (3R)-2,3,4,7-Tetrahydro-3-methyl-4-propyl-10-(trifluoromethyl)-8H-[1,4]oxazino[2,3-f]quinolin-8-one (Compound 105); (3R)-4-Allyl-2,3,4,7-tetrahydro-3-methyl-10-(trifluoromethyl)-8H-[1,4]oxazino[2,3-f]quinolin-8-one (Compound 106); (3R)-3-Ethyl-2,3,4,7-tetrahydro-10-(trifluoromethyl)-8H-[1,4]oxazino[2,3-f]quinolin-8-one (Compound 107); (3R)-3-Ethyl-2,3,4,7-tetrahydro-4-methyl-10-(trifluoromethyl)-8H-[1,4]oxazino[2,3-f]quinolin-8-one (Compound 108); (3R)-3,4-Diethyl-2,3,4,7-tetrahydro-10-(trifluoromethyl)-8H-[1,4]oxazino[2,3-f]quinolin-8-one (Compound 109); (3R)-3-Ethyl-2,3,4,7-tetrahydro-4-(2,2,2-trifluoroethyl)-10-(trifluoromethyl)-8H-[1,4]oxazino[2,3-f]quinolin-8-one (Compound 110); (3R)-4-(2-Chloro-2,2-difluoroethyl)-3-ethyl-2,3,4,7-tetrahydro-10-(trifluoromethyl)-8H-[1,4]oxazino[2,3-f]quinolin-8-one (Compound 111); (3R)-4-(2,2-Difluoroethyl)-3-ethyl-2,3,4,7-tetrahydro-10-(trifluoromethyl)-8H-[1,4]oxazino[2,3-f]quinolin-8-one (Compound 112); (3R)-3-Ethyl-2,3,4,7-tetrahydro-4-propyl-10-(trifluoromethyl)-8H-[1,4]oxazino[2,3-f]quinolin-8-one (Compound 113); (3R)-4-Allyl-3-ethyl-2,3,4,7-tetrahydro-10-(trifluoromethyl)-8H-[1,4]oxazino[2,3-f]quinolin-8-one (Compound 114); (3R)-3-Ethyl-2,3,4,7-tetrahydro-4-isobutyl-10-(trifluoromethyl)-8H-[1,4]oxazino[2,3-f]quinolin-8-one (Compound 115); (3R/S)-2,3,4,7-Tetrahydro-3-propyl-10-(trifluoromethyl)-8H-[1,4]oxazino[2,3-f]quinolin-8-one (Coumpound 116); (3R/S)-2,3,4,7-Tetrahydro-4-methyl-3-propyl-10-(trifluoromethyl)-8H-[1,4]oxazino[2,3-f]quinolin-8-one (Coumpound 117); (3R/S)-4-Ethyl-2,3,4,7-tetrahydro-3-propyl-4-(2,2,2-trifluoroethyl)-10-(trifluoromethyl)-8H-[1,4]oxazino[2,3-f]quinolin-8-one (Coumpound 118); (3R/S)-2,3,4,7-Tetrahydro-3-propyl-4-(2,2,2-trifluoroethyl)-10-(trifluoromethyl)-8H-[1,4]oxazino[2,3-f]quinolin-8-one (Compound 119); (3R)-2,3,4,7-Tetrahydro-3-isopropyl-10-(trifluoromethyl)-8H-[1,4]oxazino[2,3-f]quinolin-8-one (Coumpound 120); (3R)-2,3,4,7-Tetrahydro-3-isopropyl-4-methyl-10-(trifluoromethyl)-8H-[1,4]oxazino[2,3-f]quinolin-8-one (Coumpound 121); (3R)-4-Ethyl-2,3,4,7-tetrahydro-3-isopropyl-10-(trifluoromethyl)-8H-[1,4]oxazino[2,3-f]quinolin-8-one (Coumpound 122); (3R)-2,3,4,7-Tetrahydro-3-isopropyl-4-(2,2,2-trifluoroethyl)-10-(trifluoromethyl)-8H-[1,4]oxazino[2,3-f]quinolin-8-one (Coumpound 123); (3R)-4-(2-Chloro-2,2-difluoroethyl)-2,3,4,7-tetrahydro-3-isopropyl-10-(trifluoromethyl)-8H-[1,4]oxazino[2,3-f]quinolin-8-one (Coumpound 124; (3R)-4-(2,2-Difluoroethyl)-2,3,4,7-tetrahydro-3-isopropyl-10-(trifluoromethyl)-8H-[1,4]oxazino[2,3-f]quinolin-8-one (Coumpound 125); (3R)-4-Allyl-2,3,4,7-tetrahydro-3-isopropyl-10-(trifluoromethyl)-8H-[1,4]oxazino[2,3-f]quinolin-8-one (Coumpound 126); (3R)-2,3,4,7-Tetrahydro-3-phenyl-10-(trifluoromethyl)-8H-[1,4]oxazino[2,3-f]quinolin-8-one (Coumpound 127); (3R)-2,3,4,7-Tetrahydro-3-phenyl-4-(2,2,2-trifluoroethyl)-10-(trifluoromethyl)-8H-[1,4]oxazino[2,3-f]quinolin-8-one (Compound 128); (3R)-4-Cyclopropylmethyl-2,3,4,7-tetrahydro-3-phenyl-10-(trifluoromethyl)-8H-[1,4]oxazino[2,3-f]quinolin-8-one (Coumpound 129); (3R)-3-Benzyl-2,3,4,7-tetrahydro-4-(2,2,2-trifluoroethyl)-10-(trifluoromethyl)-8H-[1,4]oxazino[2,3-f]quinolin-8-one (Compound 130); 2,3,4,7-Tetrahydro-10-(trifluoromethyl)-8H-[1,4]oxazino[2,3-f]quinolin-8-one (Coumpound 131); 2,3,4,7-tetrahydro-4-(2,2,2-trifluoroethyl)-10-(trifluoromethyl)-8H-[1,4]oxazino[2,3-f]quinolin-8-one (Coumpound 132); (7aR,10aS)-7,7a,8,9,10,10a-Hexahydro-1-(trifluoromethyl)-7-(2,2,2-trifluoroethyl)-4H-cyclopenta[5,6][1,4]oxazino[2,3-f]quinolin-3-one (Coumpound 133); (7aR,10aS)-7-Ethyl-7,7a,8,9,10,10a-hexahydro-1-(trifluoromethyl)-4H-cyclopenta[5,6][1,4]oxazino[2,3-f]quinolin-3-one (Coumpound 134); (7aR,10aS)-7,7a,8,9,10,10a-Hexahydro-3-isopropoxy-1-(trifluoromethyl)-7-(2,2,2-trifluoroethyl)-4H-cyclopenta[5,6][1,4]oxazino[2,3-f]quinolin-3-one (Coumpound 135); (±)-(2S,3R)-2,3,4,7-Tetrahydro-2,3-dimethyl-4-(2,2,2-trifluoroethyl)-10-(trifluoromethyl)-8H-[1,4]oxazino[2,3-f]quinolin-8-one (Coumpound 136); (7R)-6,6a,7,8,9,10-Hexahydro-4-(trifluoromethyl)-1H-pyrrolo[1',2':4,5][1,4]oxazino[2,3-f]quinolin-2-one (Coumpound 137); 2,3,4,7-Tetrahydro-2,2,4-trimethyl-10-(trifluoromethyl)-8H-[1,4]oxazino[2,3-f]quinolin-8-one (Coumpound 138); (3R)-8-Chloro-3-ethyl-3,4-dihydro-8-isopropoxy-4-(2,2,2-trifluoroethyl)-10-(trifluoromethyl)-2H-[1,4]oxazino[2,3-f]quinoline (Coumpound 139); (3R)-3-Ethyl-3,4-dihydro-8-isopropoxy-8-methoxy-4-(2,2,2-trifluoroethyl)-10-(trifluoromethyl)-2H-[1,4]oxazino[2,3-f]quinoline (Coumpound 140); (±)-2,3,4,7-Tetrahydro-4-(2,2,2-trifluoroethyl)-3,10-bis(trifluoromethyl)-8H-[1,4]oxazino[2,3-f]quinolin-8-one (Compound 141); (−)-2,3,4,7-Tetrahydro-4-(2,2,2-trifluoroethyl)-3,10-bis(trifluoromethyl)-8H-[1,4]oxazino[2,3-f]quinolin-8-one (Coumpound 142); (+)-2,3,4,7-Tetrahydro-4-(2,2,2-trifluoroethyl)-3,10-bis(trifluoromethyl)-8H-[1,4]oxazino[2,3-f]quinolin-8-one (Compound 143).

Within such group, representative compounds include: 3R)-2,3,4,7-Tetrahydro-3-methyl-4-(2,2,2-trifluoroethyl)-10-(trifluoromethyl)-8H-[1,4]oxazino[2,3-f]quinolin-8-one (Coumpound 104); (3R)-3-Ethyl-2,3,4,7-tetrahydro-4-(2,2,2-trifluoroethyl)-10-(trifluoromethyl)-8H-[1,4]oxazino[2,3-f]quinolin-8-one (Coumpound 110); (3R)-4-(2-Chloro-2,2-difluoroethyl)-3-ethyl-2,3,4,7-tetrahydro-10-(trifluoromethyl)-8H-[1,4]oxazino[2,3-f]quinolin-8-one (Coumpound 111); (3R)-4-(2,2-Difluoroethyl)-3-ethyl-2,3,4,7-tetrahydro-10-(trifluoromethyl)-8H-[1,4]oxazino[2,3-f]quinolin-8-one (Coumpound 112); (3R)-2,3,4,7-Tetrahydro-3-isopropyl-4-(2,2,2-trifluoroethyl)-10-(trifluoromethyl)-8H-[1,4]oxazino[2,3-f]quinolin-8-one (Coumpound 123); (3R)-4-(2-Chloro-2,2-difluoroethyl)-2,3,4,7-tetrahydro-3-isopropyl-10-(trifluoromethyl)-8H-[1,4]oxazino[2,3-f]quinolin-8-one (Coumpound 124); (3R)-4-(2,2-Difluoroethyl)-2,3,4,7-tetrahydro-3-isopropyl-10-(trifluoromethyl)-8H-[1,4]oxazino[2,3-f]quinolin-8-one (Coumpound 125); (7aR,10aS)-7-Ethyl-7,7a,8,9,10,10a-hexahrydro-1-(trifluoromethyl)-4H-cyclopenta[5,6][1,4]oxazino[2,3-f]quinolin-3-one (Coumpound 134); (7aR,10aS)-7,7a,8,9,10,10a-Hexahydro-1-(trifluoromethyl)-7-(2,2,2-trifluoroethyl)-4H-cyclopenta[5,6][1,4]oxazino[2,3-f]quinolin-3-one (Coumpound 133); (±)-(2S,3R)-2,3,4,7-Tetrahydro-2,3-dimethyl-4-(2,2,2-trifluoroethyl)-10-(trifluoromethyl)-8H-[1,4]oxazino[2,3-f]quinolin-8-one (Coumpound 136); (±)-2,3,4,7-Tetrahydro-4-(2,2,2-trifluoroethyl)-3,10-bis(trifluoromethyl)-8H-[1,4]oxazino[2,3-f]quinolin-8-one (Compound 141); (−)-2,3,4,7-Tetrahydro-4-(2,2,2-trifluoroethyl)-3,10-bis(trifluoromethyl)-8H-[1,4]oxazino[2,3-f]quinolin-8-one (Coumpound 142); (+)-2,3,4,7-Tetrahydro-4-(2,2,2-trifluoroethyl)-3,10-bis(trifluoromethyl)-8H-[1,4]oxazino[2,3-f]quinolin-8-one (Compound 143); (±)-2,3,4,7-Tetrahydro-3-(2,2,2-trifluoroethyl)-10-(trifluoromethyl)-8H-[1,4]oxazino[2,3-f]quinolin-8-one (Coumpound 144); (±)-2,3,4,7-Tetrahydro-4-methyl-3-(2,2,2-trifluoroethyl)-10-(trifluoromethyl)-8H-[1,4]oxazino[2,3-f]quinolin-8-one (Compound 145); (±)-4-Ethyl-2,3,4,7-tetrahydro-3-(2,2,2-trifluoroethyl)-10-(trifluoromethyl)-8H-[1,4]oxazino[2,3-f]quinolin-8-one (Coumpound 146); (±)-2,3,4,7-Tetrahydro-3,4-bis(2,2,2-trifluoroethyl)-10-(trifluoromethyl)-8H-[1,4]oxazino[2,3-f]quinolin-8-one (Coumpound 147); (−)-2,3,4,7-Tetrahydro-3,4-bis(2,2,2-trifluoroethyl)-10-(trifluoromethyl)-8H-[1,4]oxazino[2,3-f]quinolin-8-one (Coumpound 148); (+)-2,3,4,7-Tetrahydro-3,4-bis(2,2,2-trifluoroethyl)-10-(trifluoromethyl)-8H-[1,4]oxazino[2,3-f]quinolin-8-one (Coumpound 149); (±)-4-Cyclopropylmethyl-2,3,4,7-tetrahydro-3-(2,2,2-trifluoroethyl)-10-(trifluoromethyl)-8H-[1,4]oxazino[2,3-f]quinolin-8-one (Coumpound 150); (3R)-4-Cyclopropylmethyl-3-ethyl-2,3,4,7-tetrahydro-10-(trifluoromethyl)-8H-[1,4]oxazino[2,3-f]quinolin-8-one (Compound 151); (3R)-4-(2-Chloroethyl)-2,3,4,7-tetrahydro-3-isopropyl-10-(trifluoromethyl)-8H-[1,4]oxazino[2,3-f]quinolin-8-one (Coumpound 152); (±)-2,3,4,7-Tetrahydro-2-methyl-4-(2,2,2-trifluoroethyl)-10-(trifluoromethyl)-8H-[1,4]oxazino[2,3-f]quinolin-8-one (Compound 153); (3R)-3-Ethyl-4-(2-hydroxy-2-methylpropyl)-2,3,4,7-tetrahydro-10-(trifluoromethyl)-8H-[1,4]oxazino[2,3-f]quinolin-8-one (Coumpound 1); (3R)-2,3,4,7-Tetrahydro-3-isobutyl-[4-(2,2,2-trifluoroethyl)-10-(trifluoromethyl)-8H-[1,4]oxazino[2,3-f]quinolin-8-one (Coumpound 155).

Compounds of the present invention, comprising classes of heterocyclic nitrogen compounds and their derivatives, can be obtained by routine chemical synthesis, e.g., by modification of the heterocyclic nitrogen compounds disclosed or by a total synthesis approach.

The sequences of steps for several general schemes to synthesize the compounds of the present invention are shown below. In each of the schemes the R groups (e.g., $R^1$, $R^2$, etc.) correspond to the specific substitution patterns noted in the Examples. HoweveR¹, it will be understood by those skilled in the art that other functionalities disclosed herein at the indicated positions of compounds of formulas I through IV also comprise potential substituents for the analogous positions on the structures within the schemes.

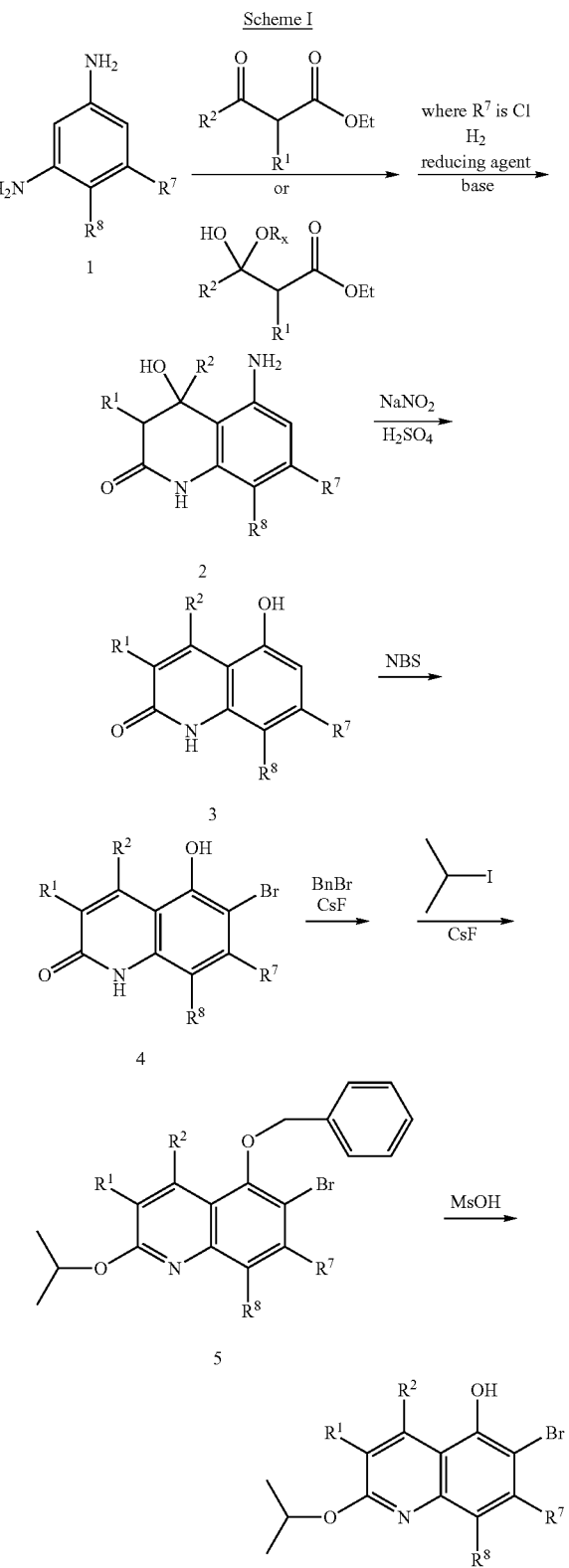

Scheme I

A synthesis of an 8H-[1,4]oxazino[2,3-f]quinolin-8-one compound (e.g., structures 9 and 11), is depicted in Schemes I and II. The process of Scheme I begins with the Knorr cyclization of a phenylenediamine derivative, for example, 5-chloro-1,3-phenylenediamine (structure 1), with a β-ketoester, or its corresponding hydrate or hemiacetal, for example ethyl 4,4,4-trifluoroacetoacetate, to afford the corresponding (1H)-quinolin-2-one. See G. Jones, *Comprehensive Heterocyclic Chemistry*, Katritzky, A. R.; Rees, C. W., eds. Pergamon, New York, 1984. Vol. 2, chap. 2.08, pp 421–426, the disclosure of which is herein incorporated by reference. Reduction of the halide group could be achieved by chemical reduction, with, for example, a metal catalyst, for example, 10% Pd—C, in a hydrogen atmosphere, to afford a compound of structure 2. Conversion of the aniline to a phenol could be effected by treatment of structure 2 with a diazotizing agent, for example, sodium nitrite in sulfuric acid, to afford a compound of structure 3. Bromination of the phenol with a brominating reagent, for example, N-bromosuccinimide, in the presence of a base, for example, diisopropylamine, affords a compound of structure 4. See S. Fujisaki, et. al, *Bull. Chem. Soc. Jpn.* 1993, 66, 1576–1579, the disclosure of which is herein incorporated by reference.

Selective protection of the phenolic oxygen could be achieved by treatment of structure 4 with an alkyl halide, for example, benzyl bromide, in the presence of a base, for example, cesium fluoride, to afford the corresponding ether. Protection of the pyridone ring, with, for example isopropyl iodide, mediated by a base, for example, cesium fluoride, affords the corresponding imino ether (structure 5). Selective hydrolysis of the phenolic ether could be accomplished by acidic hydrolysis, with, for example, a 1:1 mixture of methanesulfonic acid and acetic acid, to afford a phenol of structure 6.

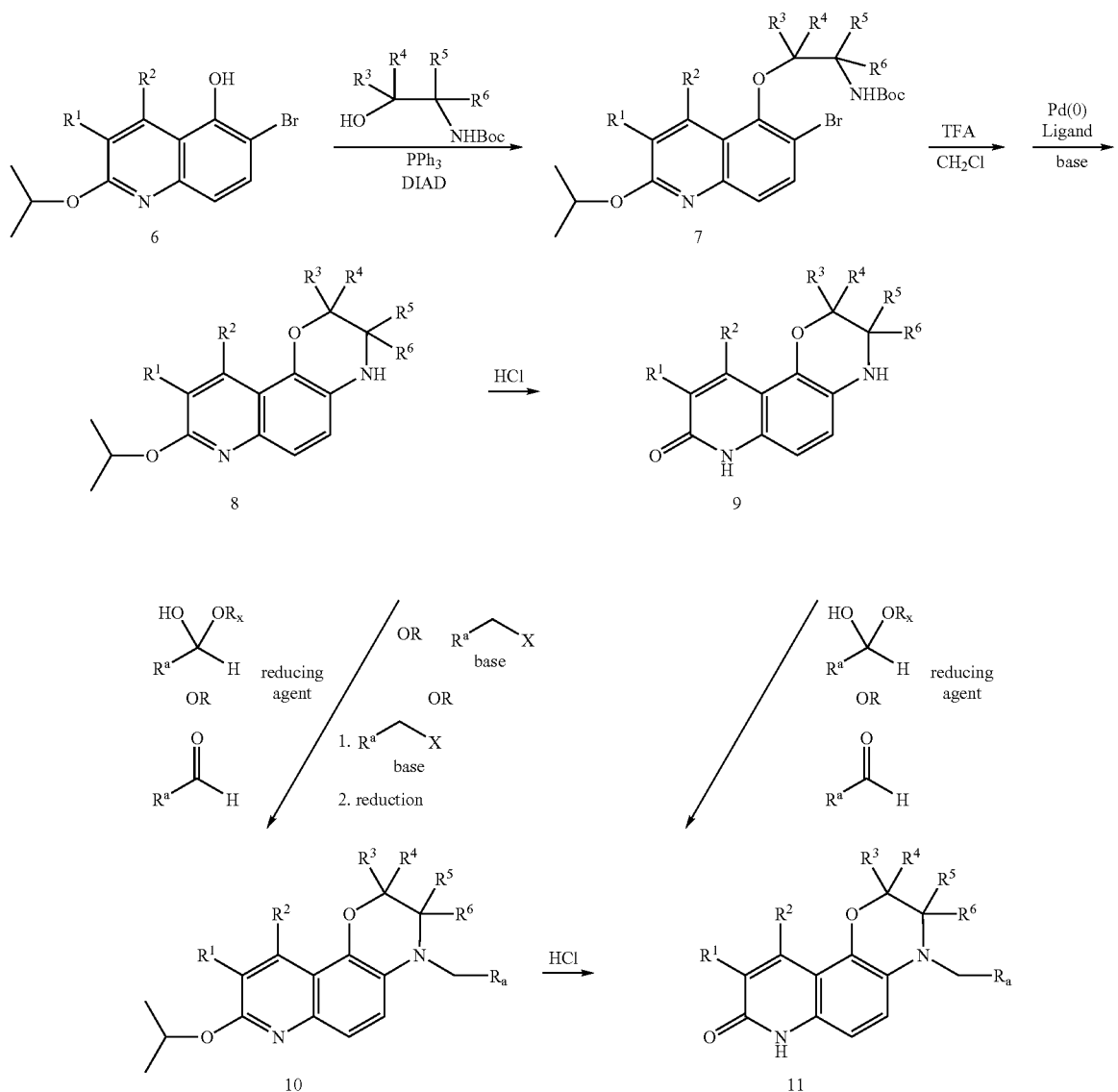

The following transformations are illustrated in Scheme II. Alkylation of the phenolic oxygen was accomplished by treatment of the phenol with a protected amino alcohol, for example, (R)-N-t-boc-alinol, under Mitsunobu conditions, for example, triphenylphosphine and disopropyl azodicarboxylate, in the presence of a base, for example, N-methylmorpholine, to afford the corresponding Mitsunobu product. Removal of the t-butoxycarbonyl protecting group can be accomplished by acidic hydrolysis, with, for example, trifluoroacetic acid, to afford a compound of structure 7 (Scheme II). Closure of the amine to the aromatic halide can be achieved by treatment of compound with a transition metal, for example $Pd_2(dba)_3$ in the presence of a ligand, for example, BINAP, and a base, for example, sodium t-butoxide, to afford a compound of structure 8. See S. Wagaw, et. al., *J. Am. Chem. Soc.* 1997, 119, 8451–8458, the disclosure of which is herein incorporated by reference. Treatment of a compound of structure 8 with an acid, for example hydrochloric acid in acetic acid, at elevated temperatures, affords an 8H-[1,4]oxazino[2,3-f]quinolin-8-one of structure 9. Alternatively, treatment of a compound of structure 8 with an aldehyde or its corresponding hydrate or hemiacetal, for example, trifluoroacetaldehyde hemiacetal, in the presence of a reducing agent, for example, sodium cyanoborohydride, in a carboxylic acid, for example, trifluoroacetic acid, affords a compound of structure 10. Alternatively, alkylation could be achieve by alkylation of structure 8 with an alkyl halide, for example, allyl bromide, mediated by a base, for example potassium carbonate, to afford a compound of structure 10. Treatment of a compound of structure 10 with an acid, for example hydrochloric acid in acetic acid, affords an 8H-[1,4]oxazino[2,3-f]quinolin-8-one, a compound of structure 11. Alternatively, treatment of a compound of structure 9 with an aldehyde or its corresponding hydrate or hemiacetal, for example, cyclopropylmethylcarboxaldehyde, in the presence of a reducing agent, for example, sodium cyanoborohydride, in a carboxylic acid, for example, acetic acid, affords a compound of structure 11.

An enantiomer of structures 9 or 11, or a racemic mixture may be obtained by the synthetic route as described in Scheme II, by starting with the enantiomer of the β-aminoalcohol as shown (e.g., an (S)-β-amino alcohol), or a racemic mixture of the β-aminoalcohol shown (e.g., a (±)-β-amino alcohol. Accordingly, an (S)-β-amino alcohol, employed in Scheme II, produces an (S)-quinolinone; an (R)-β-amino alcohol, employed in Scheme II, produces an (R)-quinolinone; and a racemic mixture of the β-amino alcohol, employed in Scheme II, produces a racemic mixture of the corresponding quinolinone. A racemic mixture of quinolinones could be separated into its corresponding enantiomers by separation on chiral HPLC with, for example, a chirapak AS column eluted with hexanes:ethanol.

Scheme III

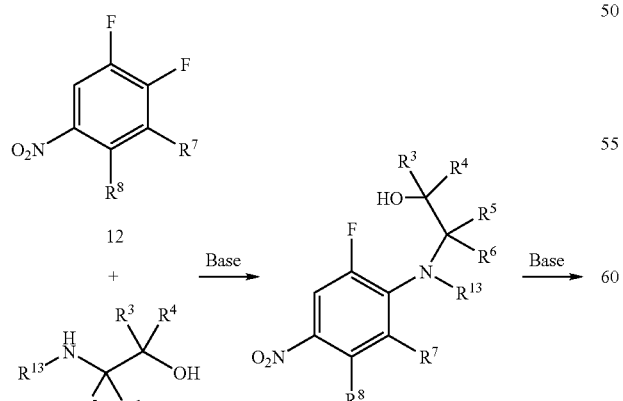

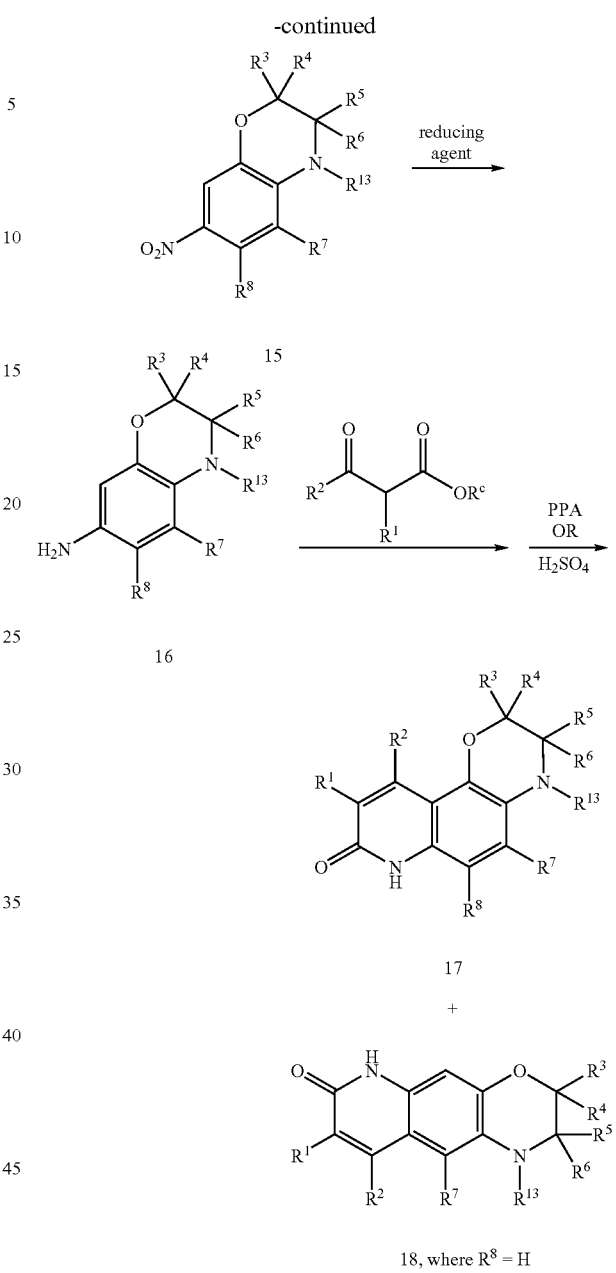

18, where $R^8$ = H

The asymmetric synthesis in Scheme III begins with the chemo- and regioselective N-alkylation of a β-aminoalcohol, either as a single enantiomer (R or S) or its racemate, for example, (R)-prolinol, onto a 3,4-dihalonitrobenzene, for example, 3,4-difluoronitrobenzene, mediated by a base, for example, sodium bicarbonate, to afford an optically pure arylamino alcohol (e.g., structure 14). Benzoxazine compounds (e.g., structure 15), may then be formed by cyclization of the N-alkyl substituted amino alcohol compounds (e.g., structure 14) by treatment with a base such as sodium hydride. Reduction of nitro benzoxazine compounds (e.g., structure 15) with a reducing agent, for example, zinc and calcium chloride affords an amino benzoxazine compound (e.g., structure 16). Treatment of an amino benzoxazine with a β-ketoester or its corresponding hydrate, for example ethyl 4,4,4-trifluoroacetoacetate, at elevated temperatures, affords the corresponding acetanilide. Treatment of the acetanilide with an acid, for example, sulfuric acid, affords an optically pure quinolinone compound (e.g., structures 17 and 18). An enantiomer of structure 17, or a racemic mixture may be obtained by the synthetic route as described in Scheme III, by starting with the enantiomer of the β-aminoalcohol as shown (e.g., an (S)-β-amino alcohol), or a racemic mixture of the β-aminoalcohol shown (e.g., a (±)-β-amino alcohol. Accordingly, an (R)-β-amino alcohol, employed in Scheme III, produces an (S)-quinolinone; an (R)-β-amino alcohol, employed in Scheme III, produces an (R)-quinolinone; and a racemic mixture of the β-amino alcohol, employed in Scheme III, produces a racemic mixture of the corresponding quinolinone.

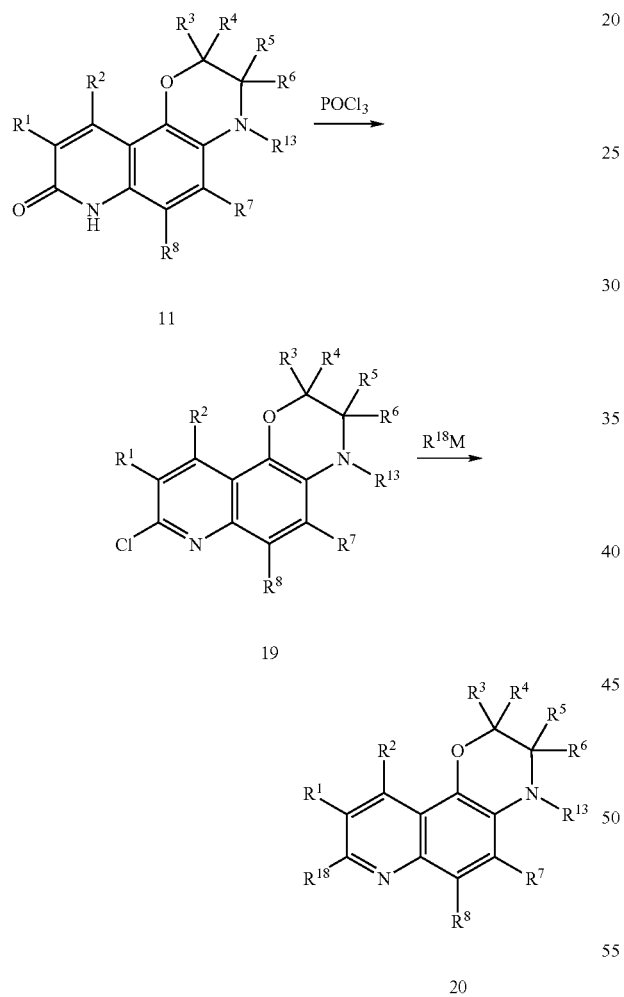

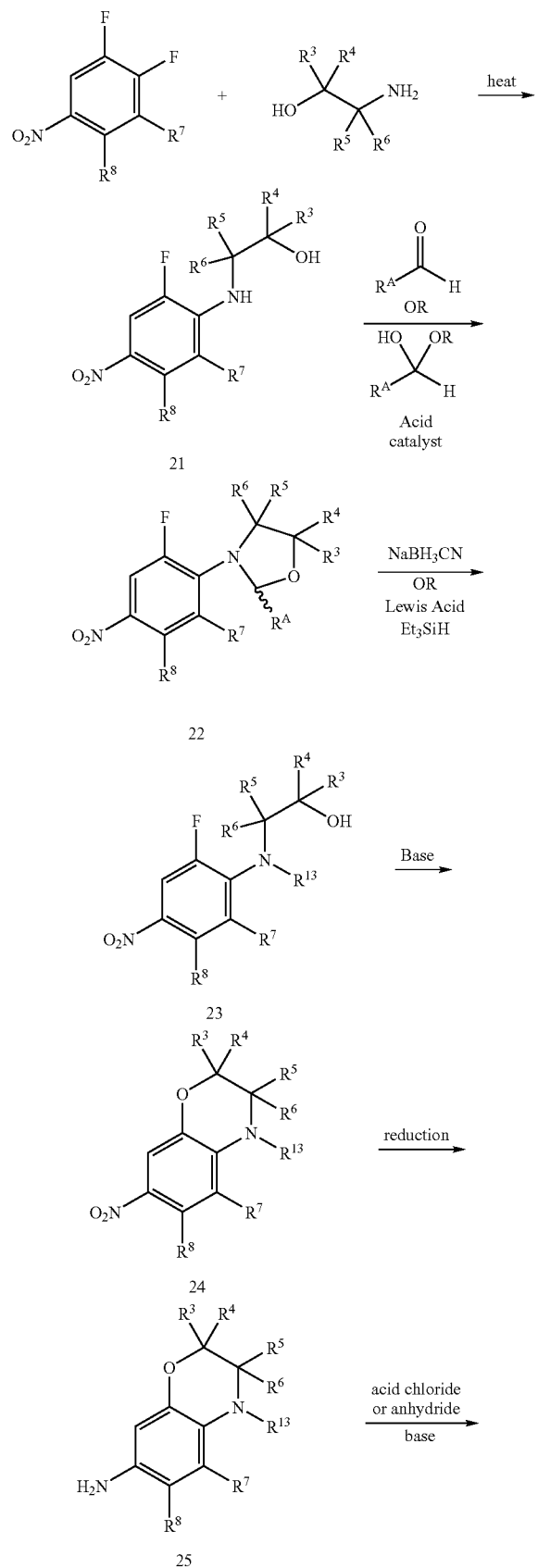

A synthesis of an 8H-[1,4]oxazino[2,3-f]quinoline (e.g., structures 19 and 20), is depicted in Scheme IV. The process of Scheme IV begins by treatment of a quinolinone with a halogenating agent, for example, phosphorus oxychloride, to afford a compound of structure 19. Substitution of the halide can be accomplished by treatment with a nucleophile, for example, sodium methoxide in methanol, to afford a compound of structure 20.

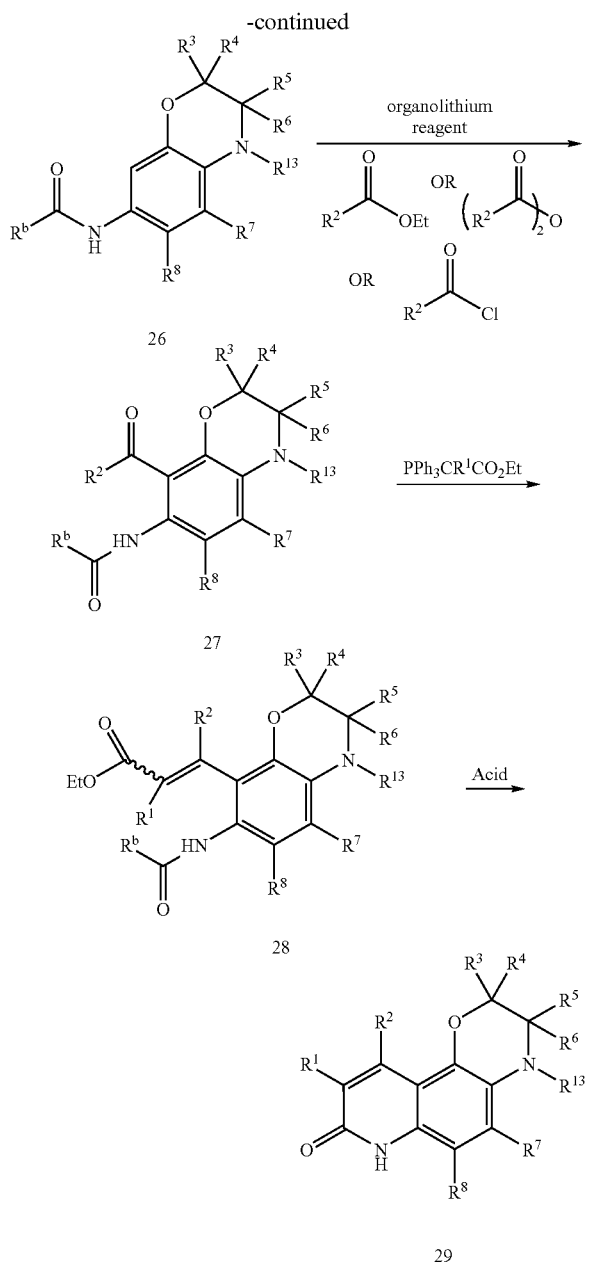

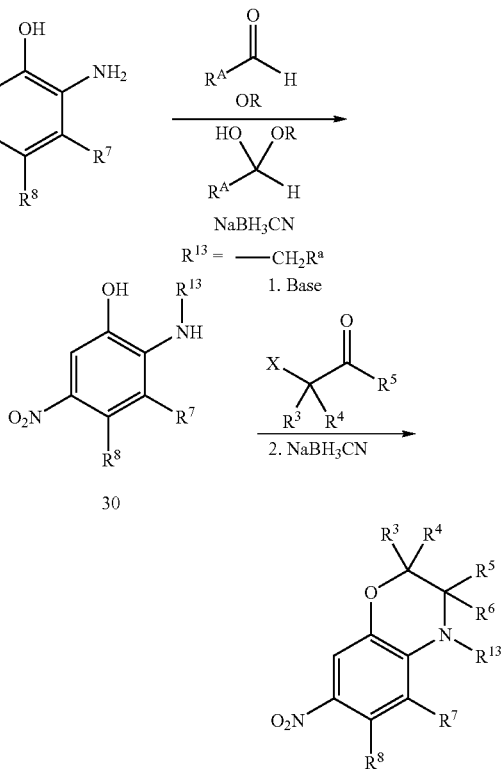

ture 23) by treatment with a base such as sodium hydride. Reduction of nitro benzoxazine compounds (e.g., structure 24) with a reducing agent, for example, palladium on carbon under a hydrogen atmosphere, affords an aminobenzoxazine compound (e.g., structure 25). Treatment of a compound of structure 25 with an acylating agent, for example trimethylacetyl chloride, in the presence of a base, for example, pyridine, affords a compound of structure 26. $R^b$ may be, in addition to t-butyl, an aryl or a sterically hindered alkyl substituent. Alternatively, it may be t-butoxy, aryloxy, or a sterically hindered alkoxy substituent. Regioselective lithiation of a compound of structure 26 with a strong base, for example, t-butyllithium followed by quenching with an acylating agent, for example, ethyl trifluoroacetate, affords a compound of structure 27. The base may be an alternative organolithium reagent, for example, sec-butyllithium or n-butyllithium. Treatment of a compound of structure 27 with a Homer-Emmons reagent, for example, (carbethoxymethylene)triphenylphosphorane produces a compound of structure 28. Annulation of a compound of structure 28 to the pyridone ring may be accomplished by treatment of a compound of structure 28 with an acid, for example hydrochloric acid in acetic acid, to afford a compound of structure 29.

An enantiomer of structure 29, or a racemic mixture, may be obtained by the synthetic route as described in Scheme V, by starting with the enantiomer of the β-aminoalcohol as shown (e.g., an (S)-β-amino alcohol), or a racemic mixture of the β-aminoalcohol shown (e.g., a (+)-β-amino alcohol. Accordingly, an (S)-β-amino alcohol, employed in Scheme V, produces an (S)-quinolinone; an (R)-β-amino alcohol, employed in Scheme V, produces an (R)-quinolinone; and a racemic mixture of the β-amino alcohol, employed in Scheme V, produces a racemic mixture of the corresponding quinolinone.

The asymmetric synthesis of Scheme V begins with the chemo- and regioselective N-alkylation of a β-aminoalcohol, either as a single enantiomer (R or S) or its racemate, for example, (R)-2-amino-1-butanol, onto a 3,4-dihalonitrobenzene, for example, 3,4-difluoronitrobenzene, to afford an optically pure arylamino alcohol (e.g., Structure 21). Treatment of amino alcohol compounds such as Structure 21 with an aldehyde or the corresponding hydrate or hemiacetal, for example, trifluoroacetaldehyde ethyl hemiacetal, in the presence of an acid catalyst, for example p-toluenesulfonic acid, affords an optically pure oxazolidine compound (e.g., structure 22). Treatment of an oxazolidine compound such as structure 22 with a reducing agent, for example, triethylsilane, in the presence of an acid, for example, titanium tetrachloride, affords an N-alkyl substituted amino alcohol compound (e.g., structure 23). Benzoxazine compounds (e.g., structure 24), may then be formed by cyclization of the N-alkyl substituted amino alcohol compounds (e.g., struc- An alternative racemic route to nitrobenzoxazine compounds of structure 24 (Scheme VI) begins with the N-alkylation of a 2-amino-5-nitrophenol nitrogen by treatment with an aldehyde, its corresponding hydrate or hemiacetal, with for example, trifluoroacetaldehyde hydrate in the presence of a reducing agent, for example, sodium cyanoborohydride, in an acid, for example trifluoroacetic acid. This procedure affords an N-alkylated compound of structure 30. This can be further transformed by alkylation with a haloketone, for example, 2-bromobutanone, mediated by a base, for example, potassium carbonate, followed by treatment with a reducing agent, for example, sodium cyanoborohydride, in an acid, for example acetic acid, to afford a benzoxazine compound (e.g., structure 24).

Scheme VII describes a route to compounds of structure 34. A compound of structure 5 is treated with an amine, amide, or carbamate, for example butylamine, and a transition metal, for example $Pd_2(dba)_3$, in the presence of a ligand, for example BINAP, and a base, for example, cesium carbonate, to afford a compound of structure 31. Removal of the benzyl group with a reducing agent, for example palladium on carbon under a hydrogen atmosphere, affords a compound of structure 32. A compound of structure 32 is treated with an alpha-haloester, for example, ethyl bromoacetate, in the presence of a base, for example potassium carbonate, to afford a compound of structure 33. A compound of structure 33 is hydrolyzed with an acid, for example, concentrated HCl in acetic acid, to afford a compound of structure 34.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, the steroid modulator compounds of the present invention can be combined in a mixture with a pharmaceutically acceptable carrier to provide pharmaceutical compositions useful for treating the biological conditions or disorders noted herein in mammalian and, more particularly, in human patients. The particular carrier employed in these pharmaceutical compositions may take a wide variety of forms depending upon the type of administration desired. Suitable administration routes include enteral (e.g., oral), topical, suppository and parenteral (e.g., intravenous, intramuscular and subcutaneous).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like may be employed. Due to their ease of administration, tablets and capsules represent a desirable oral dosage form for the pharmaceutical compositions of the present invention.

For parenteral administration, the carrier will typically include sterile water, although other ingredients that aid in solubility or serve as preservatives may also be included. Furthermore, injectable suspensions may also be prepared, in which case appropriate liquid carriers, suspending agents and the like may be employed.

For topical administration, the compounds of the present invention may be formulated using bland, moisturizing bases, such as ointments or creams. Examples of suitable ointment bases are petrolatum, petrolatum plus volatile silicones, lanolin and water in oil emulsions such as Eucerin™, available from Beiersdorf (Cincinnati, Ohio). Examples of suitable cream bases are Nivea™, available from Beiersdorf (Cincinnati, Ohio), cold cream (USP), Purpose Cream™, available from Johnson & Johnson (New Brunswick, N.J.), hydrophilic ointment (USP) and Lubriderm™, available from Warner-Lambert (Morris Plains, N.J.).

The pharmaceutical compositions and compounds of the present invention will generally be administered in the form of a dosage unit (e.g., tablet, capsule, etc.). The compounds of the present invention generally are administered in a daily dosage of from about 1 µg/kg of body weight to about 500 mg/kg of body weight. Typically, the compounds of the

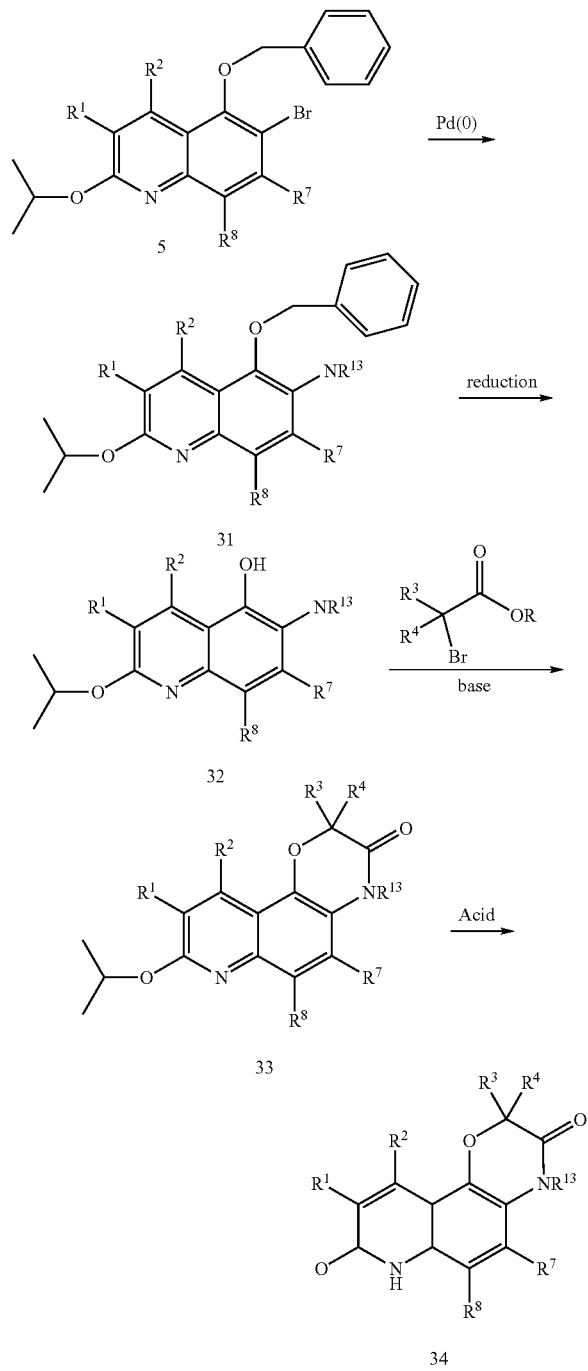

Scheme VII present invention are administered in a daily dosage of from about 10 µg/kg to about 250 mg/kg of body weight. Most often, the compounds of the present invention are administered in a daily dosage of from about 20 µg/kg to about 100 mg/kg body weight. As recognized by those skilled in the art, the particular quantity of pharmaceutical composition according to the present invention administered to a patient will depend upon a number of factors, including, without limitation, the biological activity desired, the condition of the patient and the patient's tolerance for the drug.

The compounds of this invention also have utility when labeled (e.g., radio-labeled, isotopically-labeled and the like) as ligands for use in assays to determine the presence of AR in a cell background or extract. They are particularly useful due to their ability to selectively activate androgen receptors and can therefore be used to determine the presence of such receptors in the presence of other steroid receptors or related intracellular receptors. Thus, the invention provides methods of determining the presence of androgen receptors (AR) in a cell or cell extract.

These invention methods comprise contacting the cell or cell extract with the compounds of the present invention which have been labeled and testing the contacted cell or cell extract to determine the presence of AR. Testing can be accomplished via testing for activation of androgen receptor(s) (e.g., via elevated presence of the product of androgen mediated process(es)), via separation of the bound compound/receptor combination and the like, which techniques are known to those of skill in the art.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice and then isolating the bound ligand/receptor combination by separation techniques which are known to those of skill in the art. These techniques include column separation, filtration, centrifugation, tagging and physical separation and antibody complexing, among others. Thus, the invention also provides methods for purifying samples of steroid receptors in vitro. Invention methods comprise contacting a sample containing steroid receptors with one or more of the compounds of the present invention so that the compounds bind to the steroid receptors to form a bound compound/receptor combination and separating out the bound compound/receptor combination.

The compounds and pharmaceutical compositions of the present invention can be used in the treatment of the diseases and conditions described herein. In this regard, the compounds and compositions of the present invention may prove particularly useful as modulators of male sex steroid-dependent diseases and conditions (e.g., process(es) mediated by androgen receptors) such as the treatment of acne, male-pattern baldness, sexual dysfunction, wasting diseases, hirsutism, hypogonadism, prostatic hyperplasia, osteoporosis, impotence, cancer cachexia and various hormone-dependent cancers, including prostate and breast cancer. The compounds of the present invention may also prove useful in male hormone replacement therapy, stimulation of hematopoiesis, male contraception and as anabolic agents.

As utilized herein, the term "modulate" includes the ability of a modulator for a member of the androgen receptor family to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control. Thus, both inhibitory effects on androgen receptors and activating effects on androgen receptors are contemplated within the scope of modulation.

The compounds of the present invention may be extremely potent activators of AR, displaying 50% maximal activation of AR (e.g., activation of AR, determined by measurement of luciferase production levels compared to levels achieved by dihydrotestosterone (DHT)) at a concentration of less than 100 nM (Cotransfection assay concentration), at a concentration of less than 50 nM, at a concentration of less than 20 nM, or even at a concentration of 10 nM or less. (See, for example, Biological Examples.)

In addition, selected compounds of the present invention may be extremely potent antagonists of AR, displaying 50% maximal inhibition of AR (e.g., inhibition of AR, determined by measurement of luciferase production levels compared to levels achieved by dihydrotestosterone (DHT)) at a concentration of less than 100 nM (Cotransfection assay concentration), at a concentration of less than 50 nM, at a concentration of less than 20 nM, or even at a concentration of 10 nM or less. (See, for example, Biological Examples.)

Selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration.

The invention will be further illustrated by reference to the following non-limiting Examples.

EXAMPLE 1

(3R)-2,3,4,7-Tetrahydro-3-methyl-10-(trifluoromethyl-8H-[1,4]oxazino[2,3-f]quinolin-8-one (Compound 101, Structure 9 of Scheme II, where $R^1$, $R^3$, $R^4$, $R^5$,=H, $R^2$=trifluoromethyl, $R^6$=Me)

5-Amino-7-chloro-3,4-dihydro-4-hydroxy-4-(trifluoromethyl)-1H-quinolin-2-one: To a solution of 5-chloro-1,3-phenylenediamine (15.0 g, 0.105 mol) in 70 mL ethanol was added ethyl 4,4,4-trifluoroacetoacetate (20.4 g, 0.111 mol), then the mixture was heated at reflux for 18 h. The solvent was removed under reduced pressure until the product began to precipitate. The material was allowed to crystallize for 2 h, whereupon it was filtered and rinsed with cold ether to afford 10.9 g (37%) of 5-amino-7-chloro-3,4-dihydro-4-hydroxy-4-(trifluoromethyl)-1H-quinolin-2-one, a tan solid. The filtrate was concentrated until solid began to precipitate and afforded an additional 3.0 g (10%). $^1$H NMR (400 MHz, acetone-$d_6$) δ 11.0 (broad s, 1H), 9.64 (s, 1H), 7.42 (t, 1H, J=8.1), 6.99 (d, 1H, J=8.1), 6.90 (s, 1H), 6.79 (d, 1H, J=8.1).

5-Amino-3,4-dihydro-4-hydroxy-4-(trifluoromethyl)-1H-quinolin-2-one (Structure 2 of Scheme I, where $R^1$, $R^7$, $R^8$=H, $R^2$=trifluoromethyl): A mixture of 5-amino-7-chloro-3,4-dihydro-4-hydroxy-4-(trifluoromethyl)-1H-quinolin-2-one (8.0 g, 28 mmol), KOAc (5.6 g, 57 mmol) and 10% Pd—C (4.0 g) in 200 mL ethanol was stirred under an atmosphere of hydrogen for 2 h. The mixture was filtered through Celite and concentrated under reduced pressure. The resultant solid was dissolved in EtOAc (250 mL) and washed sequentially with saturated NaHCO$_3$ (200 mL) and brine (200 mL), dried over MgSO$_4$, filtered and concentrated to afford 7.0 g (100%) of 5-amino-3,4-dihydro-4-hydroxy-4-(trifluoromethyl)-1H-quinolin-2-one, a foamy tan solid. $^1$H NMR (400 MHz, acetone-$d_6$) δ 9.16 (broad s, 1H), 6.99

(t, 1H, J=8.0), 6.44 (broad s, 1H), 6.39 (d, 1H, J=7.9), 6.26 (d, 1H, J=7.9), 5.44 (broad s, 2H), 3.09 (d, AB, J=17.0), 2.93 (d, AB, J=17.0).

5-Hydroxy-4-(trifluoromethyl)-1H-quinolin-2-one (Structure 3 of Scheme I. where $R^1$, $R^7$, $R^8$=H, $R^2$=trifluoromethyl): To a solution of 5-amino-3,4-dihydro-4-hydroxy-4-(trifluoromethyl)-1H-quinolin-2-one (6.0 g, 24 mmol) in 100 mL 4.8 M $H_2SO_4$ was added a solution of $NaNO_2$ (1.85 g, 26.8 mmol) in 6 mL water at 0° C. The reaction mixture became deep red. This solution was transferred to 120 mL 10M $H_2SO_4$ preheated to 145° C. The mixture was heated at 145° C. for 0.5 h, then poured into 400 g of ice water. The crude solid was adsorbed onto silica gel and eluted with 9:1 $CH_2Cl_2$:MeOH to afford 4.6 g (82%) of 5-hydroxy-4-(trifluoromethyl)-1H-quinolin-2-one, an off-white solid. $^1$H NMR (400 MHz, acetone-$d_6$) δ 11.0 (broad s, 1H), 9.64 (s, 1H), 7.42 (t, 1H, J=8.1), 6.99 (d, 1H, J=8.1), 6.90 (s, 1H), 6.79 (d, 1H, J=8.1).

6-Bromo-5-hydroxy-4-(trifluoromethyl)-1H-quinolin-2-one (Structure 4 of Scheme I, where $R^1$, $R^7$, $R^8$=H, $R^2$=trifluoromethyl): To a solution of 5-hydroxy-4-(trifluoromethyl)-1H-quinolin-2-one (4.38 g, 19.1 mmol) and diisopropylamine (14 mL, 100 mmol) in 100 mL EtOAc was added a solution of N-bromosuccinimide (3.74 g, 21.0 mmol) in 70 mL EtOAc at −10° C. over 30 min. The reaction mixture was stirred for 1 h, then acidified to pH 1 by the addition of 6M HCl. The mixture was extracted with EtOAc (3×150 mL) and the combined organic layers were washed with brine (200 mL), dried over $MgSO_4$, filtered and concentrated under reduced pressure. Recrystallization from chloroform:hexanes afforded 4.5 g (77%) of 6-bromo-5-hydroxy-4-(trifluoromethyl)-1H-quinolin-2-one, an off-white solid. $R_f$0.4 (1:1 EtOAc:hexanes); $^1$H NMR (400 MHz, acetone-$d_6$) δ 11.1 (broad s, 1H), 8.75 (broad s, 1H), 7.76 (d, 1H, J=8.8), 7.04 (d, 1H, J=8.8), 6.98 (s, 1H).

5-Benzyloxy-6-bromo-4-(trifluoromethyl)-1H-quinolin-2-one: To a suspension of 6-bromo-5-hydroxy-4-(trifluoromethyl)-1H-quinolin-2-one (9.42 g, 30.6 mmol) and CsF (13.9 g, 91.7 mmol) in 102 mL DMF was added benzyl bromide (6.54 g, 38.2 mmol) dropwise. After 24 h, the mixture was poured into 0.1 M $NaHSO_4$ (500 mL) and extracted with EtOAc (1:1). The aqueous layer was reextracted with EtOAc (500 mL) and the combined organic layers were washed sequentially with water (500 mL), brine (300 mL), dried over $MgSO_4$, filtered and concentrated to a slurry. The mixture was cooled to 0° C., filtered and the resultant solids washed with cold EtOAc to afford 7.26 g (60%) of 5-benzyloxy-6-bromo-4-(trifluoromethyl)-1H-quinolin-2-one, a tan solid. Rf 0.26 (7:3 hexanes:acetone); $^1$H NMR (400 MHz, acetone-$d_6$) δ 11.3 (broad s, 1H), 7.91 (d, 1H, J=9.0, 1H), 7.61 (d, 2H, J=7.3), 7.43 (t, 2H, J=7.2), 7.25–7.35 (m, 1H), 7.32 (d, 1H, J=9.0), 7.06 (s, 1H), 5.10 (s, 1H).

5-Benzyloxy-6-bromo-2-isopropoxy-4-(trifluoromethyl) quinoline (Structure 5 of Scheme I. where $R^1$, $R^7$, $R^8$=H, $R^2$=trifluoromethyl): To a suspension of 5-benzyloxy-6-bromo-4-(trifluoromethyl)-1H-quinolin-2-one (11.7 g, 29.4 mmol) and CsF (17.8 g, 117 mmol) in 150 mL DMF was added isopropyl iodide (19.9 g, 117 mmol). After 28 h, the mixture was partitioned between EtOAc (500 mL) and water (250 mL) and the aqueous layer was extracted with EtOAc. The combined organic layers were washed with water (200 mL), brine (100 mL), dried over $MgSO_4$, filtered and concentrated to afford 13 g (100%) of 5-benzyloxy-6-bromo-2-isopropoxy-4-(trifluoromethyl)quinoline. $^1$H NMR (400 MHz, $CDCl_3$) δ 7.85 (d, 1H, J=9.0), 7.55–7.65 (m, 3H), 7.38–7.48 (m, 2H), 7.32–7.38 (m, 1H), 7.31 (s, 1H), 5.54 (sept, 1H, J=6.2), 5.06 (s, 2H), 1.42 (d, 6H, J=6.2).

6-Bromo-5-hydroxy-2-isopropoxy-4-(trifluoromethyl) quinoline (Structure 6 of Scheme L, where $R^1$, $R^7$, $R^8$=H, $R^2$=trifluoromethyl): A solution of 5-benzyloxy-6-bromo-2-isopropoxy-4-(trifluoromethyl)quinoline (13.5 g, 30.8 mmol) in 31 mL methanesulfonic acid and 31 mL acetic acid was stirred at rt for 10 h, whereupon it was poured in water (500 mL), neutralized with $K_2CO_3$ (ca. 75 g) and extracted with EtOAc (3×200 mL). The combined organic layers were washed with brine (200 mL), dried over $MgSO_4$, filtered and concentrated. Flash chromatography (2%–5% EtOAc:hexanes, gradient elution) afforded 9.9 g (92%) of 6-bromo-5-hydroxy-2-isopropoxy-4-(trifluoromethyl)quinoline, a yellow-brown oil. $^1$H NMR (400 MHz, $CDCl_3$) δ 7.71 (d, 1H, J=9.1), 7.38 (d, 1H, J=9.1), 6.23 (s, 1H), 5.53 (sept, 1H, J=6.2), 1.41 (d, 6H, J=6.2).

General Method 1: Mitsunobu reaction of a phenol with a protected aminoalcohol. To a solution of the bromophenol substrate (1 equiv), the N-Boc-protected aminoalcohol (1.6 equiv), triphenylphosphine (1.6 equiv) and N-methylmorpholine (10 equiv) in dry THF (0.1–0.2 M) was added diisopropyl azodicarboxylate (1.6 equiv) dropwise, producing an orange color. After 5 min, the ice bath was removed and the reaction was stirred at rt for 2–16 h. The reaction mixture was poured into water (40 mL/mmol), neutralized with 1.0 M HCl and extracted with EtOAc (2×25 mL/mmol). The combined extracts were washed with of 0.1 M HCl (20 mL/mmol) and brine (20 mL/mmol), dried over $MgSO_4$, filtered, concentrated. Column chromatography (hexane:EtOAc) afforded the desired aryl ether.

(2'R)-6-Bromo-5-[(2'-t-butoxycarbonylamino)-1'-propoxy]-2-isopropoxy-4-(trifluoromethyl)quinoline (Structure 7 of Scheme II, where $R^1$, $R^3$, $R^4$, $R^5$,=H, $R^2$=trifluoromethyl, $R^6$=Me): The compound was prepared according to General Method 1 (EXAMPLE 1) from 6-bromo-5-hydroxy-2-isopropoxy-4-(trifluoromethyl) quinoline (0.50 g, 1.43 mmol), (R)-N-Boc-alinol (400 mg, 2.28 mmol), triphenylphosphine (600 mg, 2.28 mmol) and diisopropyl azodicarboxylate (0.45 ml, 2.28 mmol) in 0.6 mL N-methylmorpholine in 14 mL dry THF to afford 484 mg (67%) of (2'R)-6-bromo-5-[(2'-t-butoxycarbonylamino)-1'-propoxy]-2-isopropoxy-4-(trifluoromethyl)quinoline after flash chromatography (100% hexanes to 6:1 hexanes/EtOAc, gradient elution). $^1$H NMR (500 MHz, $CDCl_3$)δ 7.80 (d, J=9.3, 1H), 7.56 (d, J=8.8, 1H), 7.30 (s, 1H), 5.53 (sept, J=6.4, 1H), 4.95 (bs, 1H), 4.18 (m, 1H), 3.98 (m, 1H), 3.94 (m, 1H), 1.46 (s, 9H), 1.41 (d, J=6.4, 6H), 1.37 (d, J=6.8, 3H).

General Method 2: Hydrolysis of a t-butoxycarbonyl protected amine. To a solution of the carbamate substrate in $CH_2Cl_2$ (0.2 M) was added an equal volume of TFA and the solution was stirred at rt for 1 h. The mixture was poured into water (100 mL/mmol), neutralized with 6 M NaOH and extracted with EtOAc (2×50 mL/mmol). The combined extracts were washed sequentially with saturated $NaHCO_3$ (50 mL/mmol) and brine (50 mL/mmol), dried over $MgSO_4$, filtered and concentrated. Column chromatography ($CH_2Cl_2$/MeOH) afforded the desired free amine.

(2'R)-6-Bromo-5-(2'-amino-1'-propoxy)-2-isopropoxy-4-(trifluoromethyl)quinoline: This compound was prepared according to General Method 2 (EXAMPLE 1) from (2'R)-6-bromo-5-[(2'-t-butoxycarbonylamino)-1'-propoxy]-2-isopropoxy-4-(trifluoromethyl)quinoline (480 mg, 0.95 mmol) in 5 mL $CH_2Cl_2$ and 5 mL TFA to afford 346 mg (90%) of (2'R)-6-bromo-5-(2'-amino-1'-propoxy)-2-isopropoxy-4-(trifluoromethyl)quinoline. $^1$H NMR (500 Es: MHz, $CDCl_3$)

δ 7.81 (d, J=8.8, 1H), 7.57 (d, J=9.3, 1H), 7.30 (s, 1H), 5.53 (m, 1H), 3.93 (m, 1H), 3.84 (m, 1H), 3.66 (m, 1H), 2.33 (bs, 2H), 1.41 (d, J=6.4, 3H), 1.40 (d, J=6.4, 3H), 1.22 (d, J=6.4, 3H).

General Method 3: Palladium catalyzed coupling of an amine with an aryl bromide. To a mixture of (±)-2,2'-bis (diphenylphosphino)-1,1'-binaphthyl (4–10 mol %), $Pd_2(dba)_3$ (2–5 mol%), sodium t-butoxide (1.4 equiv) was added a solution of the amino aryl bromide (1 equiv) in toluene (0.1–0.2 M). The reddish solution was heated at 90–100° C. for 6–24 h, whereupon it was poured into cold saturated $NH_4Cl$ (20 mL/mmol). The mixture was extracted with EtOAc (2×40 mL/mmol) and the combined organic layers were washed with brine, dried over $MgSO_4$, filtered and concentrated. Flash chromatography (hexanes:EtOAc) afforded the desired 2H-[1,4]oxazino[2,3-f]quinoline.

(3R)-3,4-Dihydro-8-isopropoxy-3-methyl-10-(trifluoromethyl)-2H-[1,4]oxazino[2,3-f]guinoline (Structure 8 of Scheme II, where $R^1$, $R^3$, $R^4$, $R^5$,=H, $R^2$=trifluoromethyl, $R^6$=Me): This compound was prepared according to General Method 3 (EXAMPLE 1) from (2'R)-6-bromo-5-(2'-amino-1'-propoxy)-2-isopropoxy-4-(trifluoromethyl)quinoline (346 mg, 0.85 mmol), (±)-2,2'-bis(diphenylphosphino)-1,1'-binaphthyl (21 mg, 4 mol%), $Pd_2(dba)_3$ (15.6 mg, 2 mol%), sodium t-butoxide (114 mg, 1.19 mmol) to afford 190 mg (70%) of (3R)-3,4-dihydro-8-isopropoxy-3-methyl-10-(trifluoromethyl)-2H-[1,4]oxazino[2,3-f]quinoline after purification by flash chromatography (100% hexanes to 4:1 hexanes:EtOAc, gradient elution). $^1$H NMR (500 MHz, $CDCl_3$) δ 7.36 (d, J=8.8, 1H), 7.18 (s, 1H), 7.03 (d, J=8.8, 1H), 5.47 (m, 1H), 4.33 (dd, J=10.7, 2.9, 1H), 3.78 (dd, J=10.7, 8.1, 1H), 3.74 (bs, 1H), 3.66 (m, 1H), 1.38 (d, J=5.9, 3H), 1.37 (d, J=6.4, 3H), 1.24 (d, J=6.4, 3H).

General Method 4: Acid mediated hydrolysis of an isopropyl imino ether to a pyridone. A solution of the imino ether in a 3:1 acetic acid:concentrated HCl (0.1–0.2 M) solution was heated 60–100° C. for 4–16 h. The solution was poured into saturated $NaHCO_3$ (80 mL/mmol), extracted with EtOAc (2×80 mL), dried over $MgSO_4$, filtered and concentrated and purified as indicated.

(3R)-2,3,4,7-Tetrahydro-3-methyl-10-(trifluoromethyl)-8H-[1,4]oxazino[2,3-f]quinolin-8-one (Compound 101, Structure 9 of Scheme II, where $R^1$, $R^3$, $R^4$, $R^5$, H, R=trifluoromethyl, $R^6$=Me): Compound 101 was prepared by General Method 4 (EXAMPLE 1) from (R)-3,4-dihydro-8-isopropoxy-3-methyl-10-(trifluoromethyl)-2H-[1,4]oxazino[2,3-f]quinoline (14 mg, 0.043 mmol) in 1:1 acetic acid:concentrated HCl (0.01M) heated at 90° C. for 4 h to afford 7 mg (58%) of Compound 101, a yellow solid, after column chromatography (3:1 hexanes:EtOAc to 1:1 hexanes:EtOAc, gradient elution). $^1$H NMR (500 MHz, $CDCl_3$) δ12.37 (bs, 1H), 7.13 (s, 1H), 6.94 (d, J=8.79, 1H), 6.92 (d, J=8.79, 1H), 4.34 (dd, J=10.74, 2.93, 1H), 3.79 (dd, J=10.74, 8.10, 1H), 3.69 (bs, 1H), 3.62 (m, 1H), 1.24 (d, J=6.35, 3H).

EXAMPLE 2

(3R)-2,3,4,7-Tetrahydro-3,4-dimethyl-10-(trifluoromethyl)-8H-[4]oxazino[2,3-f]quinolin-8-one (Compound 102, Structure 11 of Scheme II, where $R^1$, $R^3$, $R^4$, $R^5$,=H, $R^2$ trifluoromethyl, $R^6$=Me, $R^{13}$=$CH_3$)

General Method 5: Reductive amination of a 2H-[1,4] oxazino[2,3-f]quinoline or an 8H-[1,4]oxazino[2,3-f]quinolin-8-one derivative with sodium cyanoborohydride and an aldehyde, its hydrate, or its hemiacetal. A solution of the 2H-[1,4]oxazino[2,3-f]quinoline or 8H-[1,4]oxazino[2,3-f]quinolin-8-one (1 equiv) and the aldehyde, its hydrate or hemiacetal (10 equiv) in acetic acid or trifluoroacetic acid, was stirred at room temperature for 2 h, whereupon sodium cyanoborohydride (5 equiv) was added portionwise. The solution was stirred for 12–24 h at rt, then poured into cold saturated $NaHCO_3$ (pH 8–10). The aqueous layer was extracted with EtOAc (2×40 mL/mmol) and the combined organic layers were washed with brine, dried over $MgSO_4$, filtered, concentrated and purified as indicated, or used directly in the next step.

(3R)-2,3,4,7-Tetrahydro-3,4-dimethyl-10-(trifluoromethyl)-8H-[1,4]oxazino[2,3-f]quinolin-8-one (Compound 102, Structure 11 of Scheme II, where $R^1$, $R^3$, $R^4$, $R^5$,=H, $R^2$=trifluoromethyl, $R^6$=Me, $R^{13}$=$CH_3$): Compound 102 was prepared according to General Method 5 (EXAMPLE 2) from (3R)-3,4-dihydro-8-isopropoxy-3-methyl-10-(trifluoromethyl)-2H-[1,4]oxazino[2,3-f]quinoline (12 mg, 0.04 mmol), 37% formaldehyde solution (0.010 mL, 0.2 mmol, 5 equiv) and $NaCNBH_3$ (10 mg, 0.2 mmol, 5 equiv) in 1 mL AcOH (0.04 M) to afford 9 mg (ca. 70%) of (R)-3,4-dihydro-8-isopropoxy-3,4-dimethyl-10-(trifluoromethyl)-2H-[1,4]oxazino[2,3-f]quinoline. This material (9 mg, 0.03 mmol) was taken on directly according to General Method 4 (EXAMPLE 1) by treatment with 3 mL acetic acid and 3 mL concentrated HCl and heated at 90° C. for 4 h to afford 7 mg (89%) of Compound 102 after flash chromatography (3:1 hexanes:EtOAc to 1:1 hexanes:EtOAc, gradient elution). $^1$H NMR (500 MHz, $CDCl_3$) δ 11.90 (bs, 1H), 7.12 (s, 1H), 7.01 (d, J=9.3, 1H), 6.96 (d, J=9.3, 1H), 4.19 (dd, J=10.7, 2.9, 1H), 4.11 (dd, J=10.7, 3.7, 1H), 3.43 (m, 1H), 2.93 (s, 3H), 1.21 (d, J=6.8, 3H)

EXAMPLE 3

(3R)-4-Ethyl-2,3,4,7-tetrahydro-3-methyl-10-(trifluoromethyl)-8H-[1,4]oxazino[2,3-f]quinolin-8-one (Compound 103, Structure 11 of Scheme II, where $R^1$, $R^3$, $R^4$, $R^5$,=H, R=trifluoromethyl, $R^6$=Me, $R^{13}$ $CH_2CH_3$)

General Method 6: Reductive amination of a 2H-[1,4] oxazino[2,3-]quinoline or an 8H-[1,4]oxazino[2,3-f]quinolin-2-one with sodium borohydride with acetic acid or a substituted acetic acid. To a solution of the 2H-[1,4]oxazino[2,3-f]quinoline or 8H-[1,4]oxazino[2,3-f]quinolin-2-one in a substituted acetic acid was added $NaBH_4$ pellets (5–10 equiv). After 12–24 h, the reaction was carefully poured into cold saturated $NaHCO_3$. The aqueous layer was extracted with EtOAc (2×40 mL/mmol) and the combined organic layers were washed with brine, dried over $MgSO_4$, filtered, concentrated and the compound was purified as indicated.

(3R)-4-Ethyl-2,3,4,7-tetrahydro-3-methyl-10-(trifluoromethyl)-8H-[1,4]oxazino[2,3-f]quinolin-8-one (Compound 103, Structure 11 of Scheme II, where $R^1$, $R^3$, $R^4$, $R^5$,=H, $R^2$=trifluoromethyl, $R^6$=Me, $R^{13}$=$CH_2CH_3$): This compound was prepared according to General Method 6 (EXAMPLE 3) from (3R)-3,4-dihydro-8-isopropoxy-3-methyl-10-(trifluoromethyl)-2H-[1,4]oxazino[2,3-f]quinoline (16 mg, 0.049 mmol) and $NaBH_4$ pellets (large excess, >10 equiv) in 5 mL acetic acid (0.01 M stirred at rt for 12 h, to afford 18 mg (100%) of (3R)-4-ethyl-3,4-dihydro-8-isopropoxy-3-methyl-10-(trifluoromethyl)-2H-[1,4]oxazino[2,3-f] quinoline. This material (18 mg, 0.050 mmol) was carried on according to General Method 4 (EXAMPLE 1) by treatment with 2.5 mL acetic acid and 2.5 mL concentrated HCl and heated at 90° C. for 4 h to afford 9 mg (57%) of Compound 103, after purification by column chromatography (3:1 hexanes: EtOAc to 1:1 hexanes:EtOAc, gradient elution). $^1$H NMR (500 MHz, $CDCl_3$) δ 12.02 (bs, 1H), 7.12 (s, 1H), 7.04 (d, J=8.8, 1H), 6.97 (d, J=9.3, 1H), 4.10 (dd, J=10.2, 3.4, 1H), 4.02 (dd, J=10.3, 2.9, 1H), 3.53 (m, 1H), 3.43 (m, 1H), 3.32 (m, 1H), 1.22 (d, J=6.9, 3H), 1.18 (t, J=7.1, 3H).

EXAMPLE 4

(3R)-2,3,4,7-Tetrahydro-3-methyl-4-(2,2,2-trifluoroethyl)-10-(trifluoromethyl)-8H-[1,4]oxazino[2,3-f]quinolin-8-one (Compound 104, Structure 11 of Scheme II, where $R^1$, $R^3$, $R^4$, $R^5$,=H, $R^2$=trifluoromethyl, $R^6$=Me, $R^{13}$ $CH_2CF_3$)

This compound was prepared according to General Method 6 (EXAMPLE 3) from (3R)-3,4-dihydro-8-isopropoxy-3-methyl-10-(trifluoromethyl)-2H-[1,4]oxazino[2,3-f]quinoline (4 mg, 0.01 mmol) and NaBH$_4$ pellets (large excess, >10 equiv) in 2.5 mL trifluoroacetic acid (0.005 M) stirred at rt for 12 h, to afford 4 mg (80%) of (R)-3,4-dihydro-8-isopropoxy-3-methyl-4-(2,2,2-trifluoroethyl)-10-(trifluoromethyl)-2H-[1,4]oxazino[2,3-f]quinoline. This material (4 mg, 0.01 mmol) was carried on according to General Method 4 (EXAMPLE 1) by treatment with 2 mL acetic acid and 2 mL concentrated HCl (0.003 M) and heated at 90° C. for 4 h to afford 3.2 mg (71%) of Compound 104, after purification by column chromatography (3:1 hexanes:EtOAc to 1:1 hexanes:EtOAc, gradient elution). $^1$H NMR (500 MHz, CDCl$_3$) δ 12.00 (bs, 1H), 7.16 (s, 1H), 7.11 (d, J=9.3, 1H), 7.00 (d, J=8.8, 1H), 4.20 (d, J=10.7, 2.9, 1H), 4.09 (dd, J=10.7, 2.4, 1H), 3.82 (m, 2H), 3.60 (m, 1H), 1.26 (d, J=6.8, 3H).

EXAMPLE 5

(3R)-2,3,4,7-Tetrahydro-3-methyl-4-propyl-10-(trifluoromethyl)-8H-[1,4]oxazino[2,3-f]quinolin-8-one (Compound 105, Structure 11 of Scheme II, where $R^1$, $R^3$, $R^4$, $R^5$,=H, $R^2$=trifluoromethyl, $R^6$=Me, $R^{13}$$CH_2CH_2CH_3$)

This compound was prepared according General Method 6 (EXAMPLE 3) from (3R)-3,4-dihydro-8-isopropoxy-3-methyl-10-(trifluoromethyl)-2H-[1,4]oxazino[2,3-f]quinoline (11 mg, 0.03 mmol), propionaldehyde (0.3 mmol, 10 eq) and NaCNBH$_3$ (10 equiv) in 4 mL TFA (0.03 M) stirred at rt for 12 h to afford 12 mg (100%) of (R)-3,4-dihydro-8-isopropoxy-3-methyl-4-propyl-10-(trifluoromethyl)-2H-[1,4]oxazino[2,3-f]quinoline. This material (12 mg, 0.030 mmol) was carried on according to General Method 4 (EXAMPLE 1) by treatment with 3 mL acetic acid and 3 mL concentrated HCl and heated at 90° C. for 4 h to afford 8 mg (75%) of Compound 105 after purification by silica gel chromatography (3:1 hexanes:EtOAc to 1:1 hexanes:EtOAc, gradient elution). $^1$H NMR (500 MHz, CDCl$_3$) δ11.15 (bs, 1H), 7.10 (s, 1H), 6.99 (d, J=8.8, 1H), 6.88 (d, J=8.8, 1H), 4.11 (dd, J=10.7, 3.2, 1H), 4.03 (dd, J=10.7, 2.4, 1H), 3.51 (m, 1H), 3.30 (m, 1H), 3.14 (m, 1H), 1.64 (m, 2H), 1.21 (d, J=6.4, 3H), 0.97 (t, J=7.3, 3H).

EXAMPLE 6

(3R)-4-Allyl-2,3,4,7-tetrahydro-3-methyl-10-(trifluoromethyl)-8H-[1,4]oxazino[2,3-f]quinolin-8-one (Compound 106, Structure 11 of Scheme II, where $R^1$, $R^3$, $R^4$, $R^5$,=H, $R^2$=trifluoromethyl, $R^6$=Me, $R^3$=—$CH_2CH$=$CH_2$)

To a suspension of (R)-3,4-dihydro-8-isopropoxy-3-methyl-10-(trifluoromethyl)-2H-[1,4]oxazino[2,3-f]quinoline (13 mg, 0.04 mimol) and K$_2$CO$_3$ (28 mg, 0.2 mmol, 5 eq) in 1 ml DMF (0.04 M) was added allylbromide (0.03 mL, 0.4 mmol, 10 eq). The reaction was heated to 50° C. and allowed to stir for 12 h, whereupon the reaction was poured into 10 mL water and neutralized with 1N HCl. The aqueous layer was extracted with EtOAc (2 ×40 mL/mmol) and the combined organic layers were washed with brine, dried over Na$_2$SO$_4$, filtered, concentrated to afford 10 mg (75%) of (R)-4-allyl-3,4-dihydro-8-isopropoxy-3-methyl-10-(trifluoromethyl)-2H-[1,4]oxazino[2,3-f]quinoline. This material (10 mg, 0.03 mmol) was carried on directly according to General Method 4 (EXAMPLE 1) by treatment with 2 mL concentrated HCl (001.M) and heated at 50° C. for 6 h to afford 6 mg (67%) of Compound 106 after silica gel column chromatography (gradient 3:1 hexanes:EtOAc to 1:1 hexanes:EtOAc, gradient elution) $^1$H NMR (500 MHz, CDCl$_3$) δ 11.89 (bs, 1H), 7.11 (s, 1H), 7.00 (d, J=8.8, 1H), 6.93 (d, J=8.8, 1H), 5.86 (m, 1H), 5.24 (m, 2H), 4.10 (m, 2H), 3.90 (m, 2H), 3.55 (m, 1H), 1.22 (d, J=6.8, 3H).

EXAMPLE 7

(3R)-3-Ethyl-2,3,4,7-tetrahydro-10-(trifluoromethyl)-8H-[1,4]Oxazino[2,3-f]quinolin-8-one (Compound 107, Structure 9 of Scheme II, where $R^1$, $R^3$, $R^4$, $R^5$,=H, $R^2$=trifluoromethyl, $R^6$=Et)

(2'R)-6-Bromo-5-[(2'-t-butoxycarbonylamino)-1'-butoxy]-2-isopropoxy-4-(trifluoromethyl)quinoline (Structure 7 of Scheme II, where $R^1$, $R^3$, $R^4$, $R^5$, H, $R^2$=trifluoromethyl, $R^6$=Et): This compound was prepared according to General Method 1 (EXAMPLE 1) from 6-bromo-5-hydroxy-2-isopropoxy-4-(trifluoromethyl)quinoline (1.5 g, 4.4 mmol), (2R)-2-N-t-butoxycarbonylamino-1-butanol (1.5 g, 7.8 mmol), triphenylphosphine (2.0 g, 7.8 mmol), DIAD (1.5 mL, 7.8 mmol) and N-methylmorpholine (2.0 mL) in THF (40 mL) to afford 1.7 g (74%) of 6-bromo-5-[(2'-t-butoxycarbonylamino)-1'-butoxy]-2-isopropoxy-4-(trifluoromethyl)quinoline as a tan solid. R 0.4 (9:1 hexane:EtOAc); $^1$H NMR (400 MHz, CDCl$_3$) δ 7.80 (d, 1H, J=8.9), 7.55 (d, 1H, J=8.9), 7.29 (s, 1H), 5.52 (septet, 1H, J=6.3), 4.80 (broad s, 1H), 4.06–3.90 (m, 3H), 1.91–1.81 (m, 1H), 1.71–1.59 (m, 1H), 1.46 (s, 9H), 1.41 (d, 6H, J=6.2), 1.01 (t, 3H, J=7.4).

(3R)-3-Ethyl-3,4-dihydro-8-isopropoxy-10-(trifluoromethyl)-2H-[1,4]oxazino[2,3-f]quinoline (Structure 8 of Scheme II, where $R^1$ $R^3$ $R^4$, $R^5$=H, $R^2$=trifluoromethyl, $R^6$=Et): This compound was prepared according to General Method 2 (EXAMPLE 1) from 6-bromo-5-[(2'-t-butoxycarbonylamino)-1'-butoxy]-2-isopropoxy-4-(trifluoromethyl)quinoline (1.3 g, 2.5 mmol) in CH$_2$Cl$_2$(10 mL) and TFA (10 mL) to afford 1.0 g (95%) of (2'R)-6-bromo-5-(2'-amino-1'-butoxy)-2-isopropoxy-4-(trifluoromethyl)quinoline. This material (1.0 g, 2.4 mmol) was carried on according to General Method 3 (EXAMPLE 1) by treatment with Pd$_2$(dba)$_3$ (0.043 g, 2 mol %), BINAP (0.059 g, 4 mol%) and t-BuONa (0.32 g, 3.3 mmol) in toluene (10 mL) heated at reflux to afford 0.51 g (63%) of (3R)-3-ethyl-3,4-dihydro-8-isopropoxy-10-(trifluoromethyl)-2H-[1,4]oxazino[2,3-f]quinoline, a yellow solid. R$_f$ 0.4 (9:1 hexane:EtOAc); $^1$H NMR (400 MHz, CDCl$_3$) δ 7.36 (d, 1H, J=8.8), 7.18 (s, 1H), 7.03 (d, 1H, J=8.8), 5.47 (septet, 1H, J=6.2), 4.36 (dd, ABX, 1H, J=10.6, 2.9), 3.87 (dd, ABX, 1H, J=10.4, 7.5), 3.83 (broad s, 1H), 3.48–3.40 (m, 1H), 1.63–1.53 (m, 2H), 1.38 (d, 6H, J=6.2), 1.06 (t, 3H, J=7.4).

(3R)-3-Ethyl-2,3,4,7-tetrahydro-10-(trifluoromethyl)-8H-[1,4]oxazino[2,3-f]quinolin-8-one (Compound 107, Structure 9 of Scheme II, where $R^1$, $R^3$, $R^4$, $R^5$,=H, $R^2$ trifluoromethyl, $R^6$=Et): Compound 107 was prepared according to General Method 4 (EXAMPLE 1) from (3R)-3-ethyl-3,4-dihydro-8-isopropoxy-10-(trifluoromethyl)-2H-[1,4]oxazino[2,3-f]quinoline (0.220 g, 0.646 mmol) in conc. HCl (1.0 mL) in AcOH (2.0 mL) heated at 90° C. to afford 0.190 g (98%) of Compound 107, a yellow solid. $R_f$ 0.4 (9:1 $CH_2Cl_2$:MeOH); $^1$H NMR (400 MHz, $CDCl_3$) δ 12.63 (broad s, 1H), 7.12 (s, 1H), 6.96 (d, 1H, J=8.6), 6.92 (d, 1H, J=8.6), 4.36 (dd, ABX, 1H, J=10.3, 2.8), 3.86 (dd, ABX, 1H, J=10.6, 7.8), 3.77 (broad s, 1H), 3.43–3.33 (m, 1H), 1.62–1.50 (m, 2H), 1.05 (t, 3H, J=7.5).

EXAMPLE 8

(3R)-3-Ethyl-2,3,4,7-tetrahydro-4-methyl-10-(trifluoromethyl-8H-[1,4]oxazino[2,3-f]quinolin-8-one (Compound 108, Structure 11 of Scheme II, where $R^1$, $R^3$, $R^5$,=H, $R^2$=trifluoromethyl, $R^6$=Et, $R^{13}$=$CH_3$)

(3R)-3-Ethyl-3,4-dihydro-8-isopropoxy-4-methyl-10-(trifluoromethyl)-2H-[1,4]oxazino[2,3-f]quinoline (Structure 10 of Scheme II, where $R^1$, $R^3$, $R^4$, $R^5$,=H, $R^2$=trifluoromethyl, $R^6$=Et, $R^{13}$=$CH_3$): This compound was prepared by General Method 5 (EXAMPLE 1) from (3R)-3-ethyl-3,4-dihydro-8-isopropoxy-10-(trifluoromethyl)-2H-[1,4]oxazino[2,3-f]quinoline (0.015 g, 0.044 mmol), paraformaldehyde (0.013 g, 0.44 mmol) and $NaCNBH_3$ (0.014 g, 0.22 mmol) in 1 mL glacial acetic acid to afford 0.014 g (93%) of (3R)-3-ethyl-3,4-dihydro-8-isopropoxy-4-methyl-10-(trifluoromethyl)-2H-[1,4]oxazino[2,3-f]quinoline, of sufficient purity as to be used directly in the next reaction. $R_f$ 0.5 (9:1 hexane:EtOAc); $^1$H NMR (400 MHz, $CDCl_3$) δ 7.44 (d, 1H, J=9.0), 7.20 (d, 1H, J=9.0), 7.18 (s, 1H), 5.48 (septet, 1H, J=6.2), 4.29 (dd, ABX, 1H, J=10.7, 2.5), 4.02 (dd, ABX, 1H, J=10.7, 2.7), 3.21–3.16 (m, 1H), 3.03 (s, 3H), 1.74–1.56 (m, 2H), 1.39 (d, 3H, J=6.2), 1.37 (d, 3H, J=6.2), 0.99 (t, 3H, J=7.5).

(3R)-3-Ethyl-2,3,4,7-tetrahydro-4-methyl-10-(trifluoromethyl)-8H-[1,4]oxazino[2,3-f]quinolin-8-one (Compound 108, Structure 11 of Scheme II, where $R^1$, $R^3$, $R^4$, $R^5$, H, R=trifluoromethyl, $R^6$=Et, $R^{13}$=$CH_3$): Compound 108 was prepared according to General Method 4 (EXAMPLE 1) from (3R)-3-ethyl-3,4-dihydro-8-isopropoxy-4-methyl-10-(trifluoromethyl)-2H-[1,4]oxazino[2,3-f]quinoline (0.014 g, 0.039 mmol) in conc. HCl (0.5 mL) in AcOH (1.0 mL) heated at 90° C. to afford 10 mg (83%) of Compound 108, a yellow solid. $R_f$ 0.6 (9:1 $CH_2Cl_2$:MeOH); 1H NMR (400 MHz, $CDCl_3$) δ 12.53 (broad s, 1H), 7.13 (s, 1H), 7.01 (s, 2H), 4.29 (dd, ABX, 1H, J=10.7, 2.5), 4.05 (dd, ABX, 1H, J=10.7, 2.7), 3.20–3.14 (m, 1H), 2.98 (s, 3H), 1.74–1.52 (m, 2H), 0.98 (t, 3H, J=7.5).

EXAMPLE 9

(3R)-3,4-Diethyl-2,3,4,7-tetrahydro-10-(trifluoromethyl)-8H-[1,4]oxazino[2,3-f]quinolin-8-one (Compound 109, Structure 11 of Scheme II, where $R^1$, $R^3$, $R^4$, $R^5$,=H, R=trifluoromethyl, $R^6$ Et, $R^{13}$ $CH_2CH_3$)

(3R)-3,4-Diethyl-3,4-dihydro-8-isopropoxy-10-(trifluoromethyl)-2H-[1,4]oxazino[2,3-f]quinoline (Structure 10 of Scheme II, where $R^1$, $R^3$, $R^4$, $R^5$,=H, $R^2$=trifluoromethyl, $R^6$=Et, $R^3CH_{23}$): A solution of (3R)-3-ethyl-3,4-dihydro-8-isopropoxy-10-(trifluoromethyl)-2H-[1,4]oxazino[2,3-f]quinoline (0.020 g, 0.059 mmol), excess acetic anhydride (ca. 0.5 mL) and excess triethylamine (ca. 0.5 mL) in THF was heated at 50° C. for 24 h. The reaction mixture was poured into 25 mL water and extracted with EtOAc (2×25 mL). The extracts were washed sequentially with 25 mL portions of saturated $NaHCO_3$, 0.1 N HCl and brine, dried over $MgSO_4$, filtered and concentrated to afford 0.018 g of a yellow oil. This crude material was dissolved in 1.5 mL MTBE, transferred to a slurry of LAH (0.003 g) in 1.5 mL MTBE and heated to reflux for 20 h. The reaction mixture was poured into water (25 mL) and extracted with diethyl ether (2×25 mL). The extracts were washed with brine (25 mL), dried over $MgSO_4$, filtered and concentrated to 0.013 g yellow oil. Column chromatography (5–10% EtOAc in hexane gradient) afforded 4 mg (18%) of (3R)-3,4-diethyl-3,4-dihydro-8-isopropoxy-10-(trifluoromethyl)-2H-[1,4]oxazino[2,3-f]quinoline as a yellow oil. $R_f$ 0.7 (9:1 hexane: EtOAc); $^1$H NMR (400 MHz, $CDCl_3$) δ 7.43 (d, 1H, J=9.0), 7.26 (d, 1H, J=9.0), 7.17 (s, 1H), 5.47 (septet, 1H, J=6.2), 4.30 (dd, ABX, 1H, J=10.4, 2.1), 3.83 (dd, ABX, 1H, J=10.5, 2.6), 3.56–3.48 (m, 1H), 3.37–3.28 (m, 1H), 3.25–3.19 (m, 1H), 1.65–1.55 (m, 2H), 1.39 (d, 3H, J=6.2), 1.37 (d, 3H, J=6.2), 1.20 (t, 3H, J=7.1), 0.98 (t, 3H, J=7.4).

(3R)-3,4-Diethyl-2,3,4,7-tetrahydro-10-(trifluoromethyl)-8H-[1,4]oxazino[2,3-f]quinolin-8-one (Compound 109, Structure 11 of Scheme II, where $R^5$, $R^3$, $R^4$, $R^5$,=H, $R^2$=trifluoromethyl, $R^6$=E , $R^3$ 3CHCH ): Compound 109 was prepared according to General Method 4 (EXAMPLE 1) from (3R)-3,4-diethyl-3,4-dihydro-8-isopropoxy-10-(trifluoromethyl)-2H-[1,4]oxazino[2,3-f]quinoline (0.008 g, 0.022 mmol) in conc. HCl (0.5 mL) and AcOH (1.0 mL) heated at 90° C. to afford 6 mg (86%) of Compound 109, a yellow solid. Rf 0.6 (9:1 $CH_2Cl_2$;MeOH); $^1$H NMR (400 MHz, $CDCl_3$) δ 12.43 (broad s, 1H), 7.13 (s, 1H), 7.08 (d, 1H, J=9.0), 7.01 (d, 1H, J=9.0), 4.29 (dd, ABX, 1H, J=10.5, 1.9), 3.85 (dd, ABX, 1H, J=10.6, 2.6), 3.50–3.41 (m, 1H), 3.32–3.23 (m, 1H), 3.25–3.16 (m, 1H), 1.65–1.51 (m, 2H), 1.18 (t, 3H, J=7.1), 0.97 (t, 3H, J=7.5).

EXAMPLE 10

(3R)-3-Ethyl-2,3,4,7-tetrahydro-4-(2,2,2-trifluoroethyl)-10-(trifluoromethyl)-8H-[1,4]oxazino[2,3-f] quinolin-8-one (Compound 110, Structure 11 of Scheme 1, where $R^1$, $R^3$, $R^4$, $R^5$,=H, $R^2$=trifluoromethyl, R=Et, $R^{13}$=$CH_2CF_3$)

This compound was prepared according to General Method 5 (EXAMPLE 2) from (3R)-3-ethyl-3,4-dihydro-8-isopropoxy-10-(trifluoromethyl)-2H-[1,4]oxazino[2,3-f] quinoline (0.008 g, 0.024 mmol), $NaCNBH_3$ (0.007 g, 0.118 mmol) and trifluoroacetaldehyde ethyl hemiacetal (0.028 mL, 0.235 mmol) in TFA (0.8 mL) to afford 0.017 g of (3R)-3-ethyl-3,4-dihydro-8-isopropoxy-4-(2,2,2-trifluoroethyl)-10-(trifluoromethyl)-2H-[1,4]oxazino[2,3-f]quinoline, a brown-red solid. This material (0.017 g) was carried on according to General Method 4 (EXAMPLE 1) by treatment with conc. HCl (0.3 mL) in AcOH (0.6 mL) and heated at 95° C. for 2 h to afford 0.006 g (67% for the 2 steps) of Compound 110, a yellow solid. $R_f$ 0.4 (9:1 $CH_2Cl_2$;MeOH); $^1$H NMR (400 MHz, $CDCl_3$) δ 12.47 (broad s, 1H), 7.15 (s, 1H), 7.14 (d, 1H, J=8.9), 7.02 (d, 1H, J=8.9), 4.38 (d, 1H, J=10.9), 3.98 (dd, 1H, J=10.8, 2.4) 3.93–3.65 (m, 2H), 3.27–3.22 (m, 1H), 1.68–1.51 (m, 2H), 0.98 (t, 3H, J=7.5).

EXAMPLE 11

(3R)-4-(2-Chloro-2,2-difluoroethyl)-3-ethyl-2,3,4,7-tetrahydro-10-(trifluoromethyl)-8H-[1,4]oxazino[2, 3-f]quinolin-8-one (Compound 111, Structure 11 of Scheme II, where $R^1$, $R^3$ $R^4$, $R^1$,=H, $R^1$=trifluoromethyl, $R^6$=Et, $R^{13}$=$CH_2CClF_2$)

(3R)-4-(2-Chloro-2,2-difluoroethyl)-3-ethyl-3,4-dihydro-8-isopropoxy-10-(trifluoromethyl)-2H-[1,4]oxazino[2,3-f] quinoline (Structure 10 of Scheme II, where $R^1$, $R^3$, $R^4$, $R^5$, $R^7$, $R^8$=H, $R^2$=trifluoromethyl, $R^6$=Et, $R^{13}$=$CH_2CClF_2$):

This compound was prepared according to General Method 6 (EXAMPLE 3) from (3R)-3-ethyl-3,4-dihydro-8-isopropoxy-10-(trifluoromethyl)-2H-[1,4]oxazino[2,3-f]quinoline (22 mg, 0.06 mmol) and NaBH$_4$ pellets (large excess, >10 equiv) in 4 mL chlorodifluoroacetic acid (0.02 M) stirred at rt for 12 h, to afford 17 mg (61%) of (3R)-4-(2-chloro-2,2-difluoroethyl)-3-ethyl-3,4-dihydro-8-isopropoxy-10-(trifluoromethyl)-2H-[1,4]oxazino[2,3-f]quinoline. $^1$H NMR (500 MHz, CDCl$_3$) 7.44 (d, 1H, J=9.3), 7.32 (d, J=1H, 9.3), 7.21 (s, 1H), 5.50 (m, 1H), 4.39 (dd, 1H, J=10.7, 1.5), 4.09 (m, 1H), 3.99 (dd, 1H, J=10.7, 2.4), 3.92 (m, 1H), 3.33 (m, 1H), 1.6 (m, 2H), 1.39 (d, 3H, J=6.3), 1.38 (d, 3H, J=6.3), 0.99 (t, 3H, J=7.3).

(3R)-4-(2-Chloro-2,2-difluoroethyl)-3-ethyl-2,3,4,7-tetrahydro-10-(trifluoromethyl)-8H-[1,4]oxazino[2,3-f]quinolin-8-one (Compound 111, Structure 11 of Scheme II, where R$^1$, R$^3$, R$^4$, R$^5$,=H, R$^2$=trifluoromethyl, R$^6$=Et, R$^{13}$=CH$_2$CClF$_2$): Compound 111 was prepared according to General Method 4 (EXAMPLE 1) from (3R)-4-(2-chloro-2,2-difluoroethyl)-3-ethyl-3,4-dihydro-8-isopropoxy-10-(trifluoromethyl)-2H-[1,4]oxazino[2,3-f]quinoline (17 mg. 0.03 mmol) in 1 mL acetic acid and 1 mL concentrated HCl heated at 90° C. for 4 h to afford 8 mg (53%) of Compound 111, after purification by flash chromatography (3:1 hexanes:EtOAc to 1:1 hexanes:EtOAc, gradient elution). $^1$H NMR (500 MHz, CDCl$_3$) 12.54 (bs, 1H), 7.19 (d, 1H, J=8.8), 7.15 (s, 1H), 7.03 (d, 1H, J=8.8), 4.39 (d, 1H, J=10.7), 4.06 (m, 1H), 4.01 (dd, 1H, J=10.3, 2.0), 3.86 (m, 1H), 3.31 (m, 1H), 1.59 (m, 2H), 0.98 (t, 3H, J=7.3).

EXAMPLE 12

(3R)-4-(2,2-Difluoroethyl)-3-ethyl-2,3,4,7-tetrahydro-10-(trifluoromethyl)-8H-[1,4]oxazino[2,3-f] quinolin-8-one (Compound 112, Structure 11 of Scheme II, where R$^1$, R$^3$, R$^4$, R$^5$,=H, R$^2$=trifluoromethyl, R$^6$=Et, R$^3$=CH$_2$CHF$_2$)

Compound 112 was prepared according to General Method 6 (EXAMPLE 3) from (3R)-3-ethyl-3,4-dihydro-8-isopropoxy-10-(trifluoromethyl)-2H-[1,4]oxazino[2,3-f] quinoline (13 mg, 0.04 mmol) and NaBH$_4$ pellets (large excess, >10 equiv) in 3 mL difluoroacetic acid (0.01 M) stirred at rt for 12 h, to afford 8 mg (53%) of (3R)-4-(2,2-difluoroethyl)-3-ethyl-3,4-dihydro-8-isopropoxy-10-(trifluoromethyl)-2H-[1,4]oxazino[2,3-f]quinoline. This material (8 mg, 0.02 mmol) was carried on according to General Method 4 (EXAMPLE 1) by treatment with 1.5 mL acetic acid and 1.5 mL concentrated HCl and heated at 90° C. for 4 h to afford 4 mg (57%) of Compound 112, after purification by column chromatography (3:1 hexanes: EtOAc to 1:1 hexanes:EtOAc, gradient elution). $^1$H NMR (500 MHz, CDCl$_3$) 12.19 (bs, 1H), 7.14 (s, 1H), 7.09 (d, 1H, J=8.8), 6.99 (d, 1H, J=9.3), 5.95 (m, 1H), 4.34 (dd, 1H, J=10.7, 1.5), 3.98 (dd, 1H, J=10.7, 2.4), 3.70 (m, 1H), 3.58 (m, 1H), 3.25 (m, 1H), 1.58 (m, 2H), 0.98 (t, 3H, J=7.3).

EXAMPLE 13

(3R)-3-Ethyl-2,3,4,7-tetrahydro-4-propyl-10-(trifluoromethyl)-8H-[1,4]oxazino[2,3-f]quinolin-8-one (Compound 113, Structure 11 of Scheme II, where R$^1$, R$^3$, R$^4$, R$^5$,=H, R$^2$=trifluoromethyl, R$^6$=Et, R=CH$_2$CH$_2$CH$_3$)

(3R)-4-Allyl-3-ethyl-3,4-dihydro-8-isprolpoxy-10-(trifluoromethyl)-2H-[1,4]oxazino[2,3-f]quinoline: To a suspension of (3R)-3-ethyl-3,4-dihydro-8-isopropoxy-10-(trifluoromethyl)-2H-[1,4]oxazino[2,3-f]quinoline (0.250 g, 0.734 mmol) and K$_2$CO$_3$ (0.507 g, 3.67 mmol) in 3 mL DMF was added allyl bromide (0.636 mL, 7.34 mmol) and the reaction mixture was heated to 50° C. for 4 h. The reaction mixture was poured into 40 mL water and extracted with EtOAc (2×30 mL). The extracts were washed with 40 mL each water and brine, dried over MgSO$_4$, filtered and concentrated to a yellow oil. Column chromatography (5–10% EtOAc in hexane gradient) afforded 0.24 g (86% yield) of (3R)-4-allyl-3-ethyl-3,4-dihydro-8-isopropoxy-10-(trifluoromethyl)-2H-[1,4]oxazino[2,3-f]quinoline, a yellow oil. R$_f$0.6 (9:1 hexane:EtOAc); $^1$H NMR (400 MHz, CDCl$_3$) δ7.41 (d, 1H, J=9.0), 7.21 (d, 1H, J=9.0), 7.18 (s, 1H), 5.96–5.85 (m, 1H), 5.47 (septet, 1H, J=6.1), 5.25 (dd, ABX, 1H, J=17.1, 1.1), 5.20 (d, 1H, J=10.1), 4.31 (dd, ABX, 1H, J=10.7, 2.2), 4.03 (dd, ABX, 1H, J=16.8, 5.0), 3.95–3.89 (m, 2H), 3.27–3.22 (m, 1H), 1.69–1.59 (m, 2H), 1.38 (d, 3H, J=6.1), 1.37 (d, 3H, J=6.1), 0.97 (t, 3H, J=7.5).

(3R)-3-Ethyl-3,4-dihydro-8-isopropoxy-4-propyl-10-(trifluoromethyl)-2H-[1,4]oxazino[2,3-f]quinoline: To a solution of (3R)-4-allyl-3-ethyl-3,4-dihydro-8-isopropoxy-10-(trifluoromethyl)-2H-[1,4]oxazino[2,3-f]quinoline (0.24 g, 0.63 mmol) and 0.1 mL Et$_3$N in 3 mL EtOAc was added 10% Pd on carbon (0.08 g) and the mixture was vigorously stirred under H$_2$ atmosphere for 1 h. The reaction mixture was filtered through Celite and concentrated to give 0.23 g (96% yield) of (3R)-3-ethyl-3,4-dihydro-8-isopropoxy-4-propyl-10-(trifluoromethyl)-2H-[1,4]oxazino[2,3-f]quinoline, a yellow oil. R$_f$0.7 (9:1 hexane:EtOAc); $^1$H NMR (400 MHz, CDCl$_3$) δ 7.41 (d, 1H, J=9.1), 7.22 (d, 1H, J=9.1), 7.17 (s, 1H), 5.47 (septet, 1H, J=6.2), 4.30 (dd, ABX, 1H, J=10.5, 1.6), 3.86 (dd, ABX, 1H, J=10.5, 2.5), 3.47–3.35 (m, 1H), 3.23–3.11 (m, 2H), 1.70–1.55 (m, 4H), 1.38 (d, 3H, J=6.2), 1.37 (d, 3H, J=6.2), 1.02–0.91 (m, 6H).

(3R)-3-Ethyl-2,3,4,7-tetrahydro-4-propyl-10-(trifluoromethyl)-8H-[1.4]oxazino[2,3-f]quinolin-8-one (Compound 113, Structure 11 of Scheme I, where R$^1$, R$^3$, R$^4$, R$^5$,=H, R=trifluoromethyl, R$^6$=Et, R$^{13}$=CH$_2$CH$_2$CH$_3$): Compound 113 was prepared according to General Method 4 (EXAMPLE 1) from (3R)-3-ethyl-3,4-dihydro-8-isopropoxy-4-propyl-10-(trifluoromethyl)-2H-[1,4]oxazino[2,3-f]quinoline (0.23 g, 0.60 mmol) in conc. HCl (2.0 mL) and AcOH (4.0 mL) heated at 95° C. to afford 0.18 g (88%) of Compound 113, a yellow solid. R$_f$0.6 (9:1 CH$_2$Cl$_2$:MeOH); $^1$H NMR (400 MHz, CDCl$_3$) δ 11.79 (broad s, 1H), 7.11 (s, 1H), 7.03 (d, 1H, J=8.9), 6.93 (d, 1H, J=8.8), 4.30 (dd, ABX, 1H, J=10.8, 2.0), 3.89 (dd, ABX, 1H, J=10.6, 2.7), 3.39–3.29 (m, 1H), 3.21–3.16 (m, 1H), 3.16–3.06 (m, 1H), 1.69–1.51 (m, 4H), 1.01–0.93 (m, 6H).

EXAMPLE 14

(3R)-4-Allyl-3-ethyl-2,3,4,7-tetrahydro-10-(trifluoromethyl)-8H-[1,4]oxazino[2,3-f]quinolin-8-one (Compound 114, Structure 11 of Scheme II, where R$^1$, R$^3$, R$^4$, R$^5$,=H, R$^2$=trifluoromethyl, R$^6$=Et, R$^{13}$=—CH$_2$CH=CH$_2$)

Compound 114 was prepared by General Method 4 (EXAMPLE 1) from (3R)-4-allyl-3-ethyl-3,4-dihydro-8-isopropoxy-10-(trifluoromethyl)-2H-[1,4]oxazino[2,3-f]quinoline (EXAMPLE 13) (0.016 g, 0.041 mmol) in conc. HCl (1 mL) heated at 75° C. to afford 13 mg (93%) of Compound 114, a yellow solid. R$_f$0.5 (9:1 CH$_2$Cl$_2$:MeOH); $^1$H NMR (400 MHz, CDCl$_3$) δ 12.52 (broad s, 1H), 7.12 (s, 1H), 7.04 (d, 1H, J=8.9), 6.99 (d, 1H, J=8.9), 5.91–5.81 (m, 1H), 5.26–5.18 (m, 2H), 4.31 (dd, ABX, 1H, J=10.6, 2.2), 4.00–3.92 (m, 2H), 3.87 (dd, ABX, 1H, J=16.8, 5.1), 3.25–3.20 (m, 1H), 1.65–1.51 (m, 2H), 0.96 (t, 3H, J=7.4).

EXAMPLE 15

(3R)-3-Ethyl-2,3,4,7-tetrahydro-4-isobutyl-10-(trifluoromethyl)-8H-[1,4]oxazino[2,3-f]quinolin-8-one (Compound 115, Structure 11 of Scheme II, where $R^1$, $R^3$, $R^4$, $R^5$, $R^7$, $R^8$=H, $R^2$=trifluoromethyl, $R^6$=Et, $R^{13}$=CH$_2$CH(CH$_3$)$_2$)

(3R)-3-Ethyl-3,4-dihydro-8-isopropoxy-4-methallyl-10-(trifluoromethyl)-2H-[1,4]oxazino[2,3-f]quinoline: To a suspension of (R)-3-ethyl-3,4-dihydro-8-isopropoxy-10-(trifluoromethyl)-2H-[1,4]oxazino[2,3-f]quinoline (0.020 g, 0.059 mmol) and K$_2$CO$_3$ (0.041 g, 0.295 mmol) in 1 mL DMF was added methallyl bromide (0.077 mL, 0.767 mmol) and the reaction mixture was heated to 50° C. for 16 h. The reaction mixture was poured into 25 mL water and extracted with EtOAc (2×25 mL). The extracts were washed with 25 mL each water and brine, dried over MgSO$_4$, filtered and concentrated to a yellow oil. Column chromatography (5–10% EtOAc in hexane gradient) gave 0.020 g (87%) of (R)-3-ethyl-3,4-dihydro-8-isopropoxy-4-methallyl-10-(trifluoromethyl)-2H-[1,4]oxazino[2,3-f]quinoline, a yellow oil. R$_f$0.7 (9:1 hexane:EtOAc); $^1$H NMR (400 MHz, CDCl$_3$) δ 7.39 (d, 1H, J=9.0), 7.18 (s, 1H), 7.12 (d, 1H, J=9.0), 5.47 (septet, 1H, J=6.2), 4.91 (s, 2H), 4.33 (dd, ABX, 1H, J=10.6, 2.0), 3.96 (dd, ABX, 1H, J=10.7, 2.6), 3.86 (d, 1H, J=17.0), 3.80 (d, 1H, J=17.0), 3.25–3.20 (m, 1H), 1.79 (s, 3H), 1.65–1.59 (m, 2H), 1.38 (d, 3H, J=6.1), 1.37 (d, 3H, J=6.1), 0.97 (t, 3H, J=7.5).

(3R)-3-Ethyl-2,3,4,7-tetrahydro-4-isobutyl-10-(trifluoromethyl)-8H-[1,4]oxazino[2,3-f]quinolin-8-one (Compound 115, Structure 11 of Scheme II, where $R^1$, $R^3$, $R^4$, $R^5$,=H, $R^2$=trifluoromethyl, $R^6$=Et, $R^{13}$=CH$_2$CH(CH$_3$)$_2$): To a solution of (R)-3-ethyl-3,4-dihydro-8-isopropoxy-4-methallyl-10-(trifluoromethyl)-2H-[1,4]oxazino[2,3-f]quinoline (0.010 g, 0.025 mmol in 1.5 mL EtOAc and 0.1 mL Et$_3$N was added 10% Pd on carbon (0.006 g) and the mixture was vigorously stirred under H$_2$ atmosphere for 1 h. The reaction mixture was filtered through Celite and concentrated to afford 0.010 g (100% yield) of (R)-3-ethyl-3,4-dihydro-4-isobutyl-8-isopropoxy-10-(trifluoromethyl)-2H-[1,4]oxazino[2,3-f]quinoline, a yellow oil. This material (0.010 g, 0.025 mmol) was carried on according to General Method 4 (EXAMPLE 1) by treatment with conc. HCl (0.5 mL) in AcOH (1.0 mL) and heated at 95° C. to afford Compound 115 (0.008 g, 89% yield) as a yellow solid. Rf 0.5 (9:1 CH$_2$Cl$_2$:MeOH); $^1$H NMR (400 MHz, CDCl$_3$) δ 11.81 (broad s, 1H), 7.11 (s, 1H), 7.00 (d, 1H, J=9.0), 6.92 (d, 1H, J=9.0), 4.33 (dd, ABX, 1H, J=10.4, 1.2), 3.98 (dd, ABX, 1H, J=10.4, 2.3), 3.23 (dd, ABX, 1H, J=14.5, 4.8), 3.15–3.10 (m, 1H), 2.80 (dd, ABX, 1H, J=14.5, 9.8), 2.07–1.97 (m, 1H), 1.62–1.49 (m, 2H), 1.01 (d, 3H, J=6.5), 0.98–0.92 (m, 6H).

EXAMPLE 16

(±)-2,3,4,7-Tetrahydro-3-propyl-10-(trifluoromethyl)-8H-1,4]oxazino[2,3-f]quinolin-8-one (Compound 116, Structure 9 of Scheme II, where $R^1$, $R^3$, $R^4$, $R^5$, $R^7$, $R^8$=H, $R^2$=trifluoromethyl, $R^6$=n-Pr)

(±)-6-Bromo-5-[(2'-t-butoxycarbonylamino)-1'pentoxy]-2-isopropoxy-4-(trifluoromethyl)quinoline (Structure 7 of Scheme II, where $R^1$, $R^3$, $R^4$, $R^5$, $R^7$, $R^8$=H, $R^2$=trifluoromethyl, $R^6$=n-Pr): This compounds was prepared according to General Method 1 (EXAMPLE 1) from 6-bromo-5-hydroxy-2-isopropoxy-4-(trifluoromethyl) quinoline (0.5 g, 1.43 mmol, 1 equiv), (±)-2-(N-t-butoxycarbonylamino)-1-pentanol (470 mg, 2.28 mol, 1.6 equiv), triphenylphosphine (600 mg, 2.28 mol, 1.6 equiv), diisopropyl azodicarboxylate (0.45 ml, 2.28 mol, 1.6 equiv) and N-methylmorpholine (0.6 ml, 10 equiv) in dry THF (14 ml, 0.1 M) to afford 483 mg (63%) of (±)-6-bromo-5-[(2'-t-butoxycarbonylamino)-1'-pentoxy]-2-isopropoxy-4-(trifluoromethyl)quinoline, a white foam, after column chromatography (100% hexanes to 9:1 hexanes:EtOAc, gradient elution). $^1$H NMR (500 MHz, CDCl$_3$) δ 7.8 (d, J=8.8, 1H), 7.55 (d, J=8.8, 1H), 7.3 (s, 1H), 5.52 (m, 1H), 4.79 (bs, 1H), 4.12 (m, 1H), 3.99 (m, 2H), 1.7 (m, 1H), 1.63 (m, 1H), 1.46 (s, 9H), 1.41 (d, J=5.9, 6H), 0.98 (t, J=7.3, 3H).

(±-6-Bromo-5-(2'-amino-1'-pentoxy)-2-isopropoxy-4-(trifluoromethyl)quinoline: This compound was prepared according to General Method 2 (EXAMPLE 1) from (±)-6-bromo-5-[(2'-t-butoxycarbonylamino)-1'-pentoxy]-2-isopropoxy-4-(trifluoromethyl)quinoline (480 mg, 0.9 mmol) in 5 mL CH$_2$Cl$_2$ and 5 mL TFA (0.09 M) stirred at rt for 2 h to afford 280 mg (72%) of (±)-6-bromo-5-(2'-amino-1'-pentoxy)-2-isopropoxy-4-(trifluoromethyl)quinoline after column chromatography (9:1 hexanes:ethyl acetate to 1:1 hexanes:ethyl acetate, gradient elution). $^1$H NMR (500 MHz, CDCl$_3$) δ 7.81 (d, J=8.8, 1H), 7.55 (d, J=8.8, 1H), 7.30 (s, 1H), 5.53 (m, 1H), 3.86 (m, 2H), 3.45 (m, 1H), 1.42 (d, J=5.9, 3H), 1.41 (d, J=5.9, 3H), 1.39 (m, 4H), 0.95 (t, J=6.8, 3H).

(±)-3,4-Dihydro-8-isopropoxy-3-propyl-10-(trifluoromethyl)-2H-[1,4]oxazino[23-f]quinoline (Structure 8 of Scheme II, where $R^1$, $R^3$, $R^4$, $R^5$,=H, $R^2$=trifluoromethyl, $R^6$=n-Pr): This compound was prepared according to General Method 3 (EXAMPLE 1) from (±)-6-bromo-5-(2'-amino-1'-pentoxy)-2-isopropoxy-4-(trifluoromethyl)quinoline (280 mg, 0.64 mol, 1 equiv), (±)-2,2'-bis (diphenylphosphino)-1,1'-binaphthyl (16 mg, 4 mol %), Pd$_2$(dba)$_3$ (11.8 mg, 2 mol %), sodium t-butoxide (87 mg, 0.9 mmol, 1.4 equiv) in 5 mL toluene (0.2 M) heated at 90° C. for 12 h to afford 172 mg (75%) of (+)-3,4-dihydro-8-isopropoxy-3-propyl-10-(trifluoromethyl)-2H-[1,4]oxazino [2,3-f]quinoline after flash chromatography (100% hexanes to 4:1 hexanes:EtOAc). $^1$H NMR (500 MHz, CDCl$_3$) δ 7.36 (d, J=8.8, 1H), 7.18 (s, 1H), 7.03 (d, J=8.8, 1H), 5.47 (m, 1H), 4.35 (dd, J=10.7, 2.9, 1H), 3.85 (dd, J=10.7, 7.6, 1H), 3.81 (s, 1H), 3.52 (m, 1H), 1.51 (m, 4H), 1.38 (d, J=5.9, 6H), 1.00 (t, J=6.6, 3H).

(±)-2,3,4,7-Tetrahydro-3-propyl-10-(trifluoromethyl)-8H-[1,4]oxazino[2,3-f]quinolin-8-one (Compound 116, Structure 9 of Scheme II, where $R^1$, $R^3$, $R^4$,=H, $R^2$=trifluoromethyl, $R^6$=n-Pr): Compound 116 was prepared according to General Method 4 (EXAMPLE 1) from (±)-3,4-dihydro-8-isopropoxy-3-propyl-10-(trifluoromethyl)-2H-[1,4]oxazino[2,3-f]quinoline (10 mg, 0.03 mmol) in 1 mL 1:1 acetic acid:concentrated HCl (0.03 M) heated at 90° C. for 3 h to afford 8 mg (97%) of Compound 116. $^1$H NMR (500 MHz, CDCl$_3$) δ 11.55 (bs, 1H), 7.11 (s, 1H), 6.91 (d, J=8.8, 1H), 6.86 (d, J=8.8, 1H), 4.35 (dd, J=10.25, 2.93, 1H), 3.85 (dd, J=10.7, 7.8, 1H), 3.73 (bs, 1H), 3.47 (m, 1H), 1.47 (m, 4H), 1.00 (t, J=6.6, 3H).

EXAMPLE 17

(±)-2,3,4,7-Tetrahydro-4-methyl-3-propyl-10-(trifluoromethyl)-8H-[1,4]oxazino[2,3-f]quinolin-8-one (Compound 117, Structure 11 of Scheme II, where $R^1$, $R^3$, $R^4$, $R^5$,=H, R=trifluoromethyl, $R^6$=n–PR, $R^{13}$=CH$_3$)

Compound 117 was prepared according to General Method 5 (EXAMPLE 2) from (±)-3,4-dihydro-8-isopropoxy-3-propyl-10-(trifluoromethyl)-2H-[1,4]oxazino[2,3-f]quinoline (18 mg, 0.05 mmol), 37% aqueous formaldehyde (0.01 mL, 0.3 mmol, 5 eq), sodium cyanoborohydride (16 mg, 0.3 mmol, 5 eq) in 1 mL acetic acid (0.05 M) stirred at rt for 12 h to afford 7 mg of (3R/S)-3,4-dihydro-8-isopropoxy-4-methyl-3-propyl-10-(trifluoromethyl)-2H-[1,4]oxazino[2,3-f]quinoline. This material (7 mg, 0.02 mmol) was carried on according to General Method 4 (EXAMPLE 1) by treatment with 4 mL of a 1:1 acetic acid:concentrated HCl (5 mM) and heated at 90° C. for 6 h to afford 5 mg (83%) of Compound 117 after column chromatography (3:1 hexanes:EtOAc to 1:1 hexanes:EtOAc, gradient elution). $^1$H NMR (500 MHz, CDCl$_3$) δ 10.83 (bs, 1H), 7.11 (s, 1H), 6.99 (d, J=8.8, 1H), 6.87 (d, J=8.8, 1H), 4.28 (dd, J=10.7, 2.2, 1H), 4.07 (dd, J=10.7, 2.4, 1H), 3.24 (m, 1H), 2.97 (s, 3H), 1.48 (m, 4H), 0.96 (t, J=7.3, 3H).

EXAMPLE 18

(±)-4-Ethyl-2,3,4,7-Tetrahydro-3-propyl-10-(trifluoromethyl)-8H-[1,4]oxazino[2,3-f]quinolin-8-one (Compound 118, Structure 11 of Scheme II, where $R^1$, $R^3$, $R^4$, $R^5$,=H, R=trifluoromethyl, $R^6$=n-Pr, $R^{13}$=CH$_3$CH$_3$)

Compound 118 was prepared according to General Method 6 (EXAMPLE 3) from (±)-3,4-dihydro-8-isopropoxy-3-propyl-10-(trifluoromethyl)-2H-[1,4]oxazino[2,3-f]quinoline (11 mg, 0.03 mmol) and NaBH$_4$ pellets (>10 equiv) in 1 mL acetic acid (0.03 M) stirred at rt for 12 h to afford 9 mg of (±)-4-ethyl-3,4-dihydro-8-isopropoxy-3-propyl-10-(trifluoromethyl)-2H-[1,4]oxazino[2,3-f]quinoline. This material (9 mg, 0.02 mmol) was carried on according to General Method 4 (EXAMPLE 1) by treatment with 4 mL of 1:1 acetic acid:concentrated HCl (5.9 mM) and heated at 90° C. for 6 h to afford 6 mg (75%) of Compound 118 after flash chromatography (3:1 hexanes:EtOAc to 1:1 hexanes:EtOAc, gradient elution). $^1$H NMR (500 MHz, CDCl$_3$) δ 11.91 (bs, 1H), 7.12 (s, 1H), 7.07 (d, J=8.8, 1H), 6.96 (d, J=8.8, 1H), 4.27 (dd, J=10.3, 2.0, 1H), 3.90 (dd, J=10.3, 2.7, 1H), 3.44 (m, 1H), 3.27 (m, 1H), 3.26 (m, 1H), 1.52 (m, 2H), 1.41 (m, 2H), 1.18 (t, J=7.1, 3H) 0.94 (t, J=7.3, 3H).

EXAMPLE 19

(±)-2,3,4,7-Tetrahydro-3-propyl-4-(2,2,2-trifluoroethyl)-10-(trifluoromethyl)-8H-[1,4]oxazino[2,3-f]quinolin-8-one (Compound 119, Structure 11 of Scheme II, where $R^1$, $R^3$, $R^4$, $R^5$,=H, $R^2$=trifluoromethyl, $R^6$=n-Pr $R^{13}$=CH$_2$CF$_3$)

Compound 119 was prepared according to General Method 6 (EXAMPLE 3) from (±)-3,4-dihydro-8-isopropoxy-3-propyl-10-(trifluoromethyl)-2H-[1,4]oxazino[2,3-f]quinoline (16 mg, 0.05 mmol) and NaBH$_4$ pellets (>10 equiv) in 11 mL trifluoroacetic acid (0.04 M) stirred at rt for 12 h to afford 27 mg of (+)-3,4-dihydro-3-propyl-4-(2,2,2-trifluoroethyl)-10-(trifluoromethyl)-8H-[1,4]oxazino[2,3-f]quinoline. This material (27 mg, 0.06 mmol) was carried on according to General Method 4 (EXAMPLE 1) by treatment with 1:1 acetic acid:concentrated HCl (0.03M) and heated at 90° C. for 6 h to afford 11 mg (50% for the 2 steps) of Compound 119 after flash chromatography (3:1 hexanes: EtOAc to 1:1 hexanes:EtOAc, gradient elution). $^1$H NMR (500 MHz, CDCl$_3$) δ 11.78 (bs, 1H), 7.14 (s, 1H), 7.07 (d, J=8.8, 1H), 6.95 (d, J=8.8, 1H), 4.35 (dd, J=10.7, 1.5, 1H), 3.99 (dd, J=10.7, 2.4, 1H), 3.83 (m, 1H), 3.72 (m, 1H), 3.32 (m, 1H), 1.51 (m, 2H), 1.42 (m, 2H), 0.93 (t, J=7.3, 3H).

EXAMPLE 20

(3R)-2,3,4,7-Tetrahydro-3-isopropyl-10-(trifluoromethyl)-8H-[1,4]oxazino[2,3-f]quinolin-8-one (Compound 120, Structure 9 of Scheme II, where $R^1$, $R^3$, $R^4$, $R^5$,=H, $R^2$=trifluoromethl, $R^6$=i–Pr)

(2'R)-6-Bromo-5-[(2'-t-butoxycarbonylamino)-3'-methyl-1'-pentoxy]-2-isopropoxy-4-(trifluoromethyl)guinoline (Structure 7 of Scheme II, where $R^1$, $R^3$, $R^4$, $R^5$,=H, R=trifluoromethyl, $R^6$=i–Pr): This compound was prepared according to General Method 1 (EXAMPLE 1) from 6-bromo-5-hydroxy-2-isopropoxy-4-(trifluoromethyl)quinoline (0.755 g, 2.16 mmol), (R)-N-t-Boc valinol (0.701 g, 3.45 mmol), triphenylphosphine (0.905 g, 3.45 mmol), DLAD (0.679 mL, 3.45 mmol) and N-methylmorpholine (1.5 mL) in THF (20 mL) to afford 0.79 g (68%) of (2'R)-6-bromo-5-[(2'-t-butoxycarbonylamino)-3'-methyl-1'-pentoxy]-2-isopropoxy-4-(trifluoromethyl)quinoline, a tan solid. R$_f$0.4 (9:1 hexane:EtOAc); $^1$H NMR (400 MHz, CDCl$_3$) δ 7.79 (d, 1H, J=9.0), 7.55 (d, 1H, J=9.0), 7.30 (s, 1H), 5.52 (septet, 1H, J=6.2), 4.81–4.75 (m, 1H), 4.14–3.90 (m, 3H), 2.15–2.01 (m, 1H), 1.46 (s, 9H), 1.41 (d, 6H, J=6.2), 0.99–0.96 (m, 6H).

(3R)-3,4-Dihydro-8-isopropoxy-3-isopropyl-10-(trifluoromethyl)-2H-[1,4]oxazino[2,3-f]guinoline: This compound was prepared according to General Method 2 (EXAMPLE 1) from (2'R)-6-bromo-5-[(2'-t-butoxycarbonylamino)-3'-methyl-1'-pentoxy]-2-isopropoxy-4-(trifluoromethyl)quinoline (0.79 g, 1.5 mmol) in CH$_2$Cl$_2$ (10 mL) and TFA (10 mL) to afford (2'R)-6-bromo-5-(2'-amino-3'-methyl-1'-pentoxy)-2-isopropoxy-4-(trifluoromethyl)quinoline (0.52 g, 80% yield). This material (0.52 g, 1.2 nmmol) was carried on according to General Method 3 (EXAMPLE 1) by treatment with Pd$_2$(dba)$_3$ (0.021 g, 2 mol %), (±)-BINAP (0.030 g, 4 mol %) and t-BuONa (0.158 g, 1.64 mmol) in toluene (7 mL) to afford 0.320 g (77%) of (3R)-3,4-dihydro-8-isopropoxy-3-isopropyl-10-(trifluoromethyl)-2H-[1,4]oxazino[2,3-f]quinoline, a yellow solid. R$_f$0.4 (9:1 hexane:EtOAc); $^1$H NMR (400 MHz, CDCl$_3$) δ 7.36 (d, 1H, J=8.7), 7.18 (s, 1H), 7.04 (d, 1H, J=8.7), 5.47 (septet, 1H, J=6.1), 4.36 (dd, ABX, 1H, J=10.6, 2.8), 3.97 (dd, ABX, 1H, J=10.6, 7.5), 3.87 (broad s, 1H), 3.29–3.21 (m, 1H), 1.83–1.74 (m, 1H), 1.38 (d, 6H, J=6.2), 1.06 (d, 3H, J=6.8), 1.03 (d, 3H, J=6.8).

(3R)-2,3,4,7-TetrahAdro-3-isopropyl-10-(trikluoromethyl)-8H-[1,4]oxazino[2,3-f]quinoline-8-one (Compound 120, Structure 9 of Scheme II, where $R^1$, $R^3$, $R^4$, $R^5$, H, R=trifluoromethyl, $R^6$=i–Pr):

Compound 120 was prepared according to General Method 4 (EXAMPLE 1) from (3R)-3,4-dihydro-8-isopropoxy-3-isopropyl-10-(trifluoromethyl)-2H-[1,4]oxazino[2,3-f]quinoline (0.006 g, 0.017 mmol) in conc. HCl (0.5 mL) and AcOH (1.0 mL) to afford Compound 120 (0.005 g, 100% yield), a yellow solid. R$_f$0.4 (9:1 CH$_2$Cl$_2$:MeOH); $^1$H NMR (400 MHz, CDCl$_3$) δ 12.48 (broad s, 1H), 7.12 (s, 1H), 6.93 (s, 2H), 4.37 (dd, ABX, 1H, J=10.6, 2.8), 3.97 (dd, ABX, 1H, J=10.4, 7.5), 3.81 (broad s, 1H), 3.26–3.16 (m, 1H), 1.83–1.71 (m, 1H), 1.06 (d, 3H, J=6.7), 1.03 (d, 3H, J=6.7).

EXAMPLE 21

(3R)-2,3,4,7-Tetrahydro-3-isopropyl-4-methyl-10-(trifluoromethyl)-8H-[1,4]oxazino[2,3-f]quinolin-8-one (Compound 121, Structure 11 of Scheme II, where $R^1$, $R^3$ $R^4$, $R^5$,=H, $R^2$=trifluoromethyl, $R^6$=i-PR, $R^{13}$=$CH_3$)

Compound 121 was prepared according to General Method 5 (EXAMPLE 2) from (3R)-3,4-dihydro-8-isopropoxy-3-isopropyl-10-(trifluoromethyl)-2H-[1,4]oxazino[2,3-f]quinoline (0.010 g, 0.028 mmol) with paraformaldehyde (0.008 g, 0.280 mmol) and $NaCNBH_3$ (0.009 g, 0.140 mmol) in AcOH (1 mL) to afford 0.009 g (90%) of (3R)-3,4-dihydro-8-isopropoxy-3-isopropyl-4-methyl-10-(trifluoromethyl)-2H-[1,4]oxazino[2,3-f]quinoline, a yellow oil. This material (0.009 g, 0.025 mmol) was carried on according to General Method 4 (EXAMPLE 1) by treatment with conc. HCl (0.5 mL) and AcOH (1 mL) to afford 0.006 g (86%) of Compound 121 as a yellow solid. Rf 0.6 (9:1 $CH_2Cl_2$:MeOH); $^1H$ NMR (400 MHz, $CDCl_3$) δ 12.49 (broad s, 1H), 7.13 (s, 1H), 7.06 (d, 1H, J=8.9), 7.02 (d, 1H, J=8.9), 4.43 (dd, ABX, 1H, J=10.9, 1.8), 3.86 (dd, ABX, 1H, J=10.9, 2.9), 3.03 (s, 3H), 2.93–2.88 (m, 1H), 2.02–1.91 (m, 1H), 0.99 (d, 3H, J=6.9), 0.95 (d, 3H, J=6.9).

EXAMPLE 22

(3R)-4-Ethyl-2,3,4,7-tetrahydro-3-isopropyl-10-(trifluoromethyl)-8H-[1,4]oxazino[2,3-f]quinolin-8-one (Compound 122, Structure 11 of Scheme II, where $R^1$, $R^3$, $R^4$, $R^5$,=H, R=trifluoromethyL $R^6$=i-PR, $R^{13}$=$CH_2CH_3$)

Compound 122 was prepared according to General Method 5 (EXAMPLE 2) from (3R)-3,4-dihydro-8-isopropoxy-3-isopropyl-10-(trifluoromethyl)-2H-[1,4]oxazino[2,3-f]quinoline (50 mg, 0.14 mmol) and $NaBH_4$ pellets (>10 equiv) in 2 mL acetic acid to afford 30 mg (ca. 60%) of (3R)-4-ethyl-3,4-dihydro-8-isopropoxy-3-isopropyl-10-(trifluoromethyl)-2H-[1,4]oxazino[2,3-f]quinoline. This material (30 mg, 0.08 mmol) was carried on according to General Method 4 (EXAMPLE 1) by treatment with 4 mL of 1:1 acetic acid:concentrated HCl (0.02M) heated at 90° C. for 4 h to afford 15 mg (57%) of Compound 122, a yellow solid, after column chromatography (3:1 hexanes:EtOAc to 1:1 hexanes:EtOAc, gradient elution). $^1H$ NMR (500 MHz, $CDCl_3$) δ 11.87 (bs, 1H), 7.13 (d, J=9.3, 1H), 7.12 (s, 1H), 6.96 (d, J=8.9, 1H), 4.49 (d, J=10.8, 1H), 3.69 (dd, J=10.7, 2.7, 1H), 3.49 (m, 1H), 3.24 (m, 1H), 2.88 (bd, J=7.9, 1H) 1.83 (m, 1H), 1.64 (t, J=7.1, 3H), 0.98 (d, J=10.6, 3H), 0.96 (d, J=10.6, 3H).

EXAMPLE 23

(3R)-2,3,4,7-Tetrahydro-3-isopropyl-4-(2,2,2-trifluoroethyl)-10-(trifluoromethyl)-8H-[1,4]oxazino[2,3-f]quinolin-8-one (Compound 123, Structure 11 of Scheme II, where $R^1$, $R^3$, $R^4$, $R^5$,=H, $R^2$=trifluoromethyl, $R^6$=i-PR, $R^{13}$=$CH_2CF_3$)

Compound 123 was prepared according to General Method 3 (EXAMPLE 1) from (3R)-3,4-dihydro-8-isopropoxy-3-isopropyl-10-(trifluoromethyl)-2H-[1,4]oxazino[2, 3f]quinoline (0.32 g, 0.90 mmol) with $NaBH_4$ (0.52 g, 14 mmol) in TFA (10 mL) to afford 0.39 g (100%) of (3R)-3,4-dihydro-8-isopropoxy-3-isopropyl-4-(2,2,2-trifluoroethyl)-10-(trifluoromethyl)-2H-[1,4]oxazino[2,3-f]quinoline, a yellow oil. This material (0.39 g, 0.90 mmol) was carried on according to General Method 4 (EXAMPLE 1) by treatment with conc. HCl (3 mL) in AcOH (6 mL) to afford 0.31 g (88%) of Compound 123, a yellow solid. $R_f$ 0.3 (19:1 $CH_2Cl_2$:MeOH); $^1H$ NMR (400 MHz, $CDCl_3$) δ 12.87 (broad s, 1H), 7.20 (d, 1H, J=8.9), 7.15 (s, 1H), 7.01 (d, 1H, J=8.9), 4.58 (d, 1H, J=10.8), 3.93–3.82 (m, 2H), 3.72–3.61 (m, 1H), 2.88 (d, 1H, J=9.2), 1.81–1.74 (m, 1H), 1.00 (d, 3H, J=6.2), 0.98 (d, 3H, J=6.2).

EXAMPLE 24

(3R)-4-(2-Chloro-2,2-difluoroethyl)-2,3,4,7-tetrahydro-3-isopropyl-10-(trifluoromethyl)-8H-[1,4]oxazino[2,3-f]quinolin-8-one (Compound 124, Structure 11 of Scheme II, where $R^1$, $R^3$, $R^4$, $R^5$,=H, $R^2$=trifluoromethyl, $R^6$=i-PR, $R^{13}$=$CH_2CClF_2$)

(3R)-4-(2-Chloro-2,2-difluoroethyl)-3,4-dihydro-8-isopropoxy-3-isopropyl-10-(trifluoromethyl)-2H-[1,4]oxazino [2,3-f]quinoline (Structure 10 of Scheme II, where $R^1$, $R^3$, $R^4$, $R^5$=H, $R^2$=trifluoromethyl, $R^6$=i-PR, $R^{13}$=$CH_2CClF_2$): This compound was prepared according to General Method 6 (EXAMPLE 3) from (3R)-4-(2-chloro-2,2-difluoroethyl)-3,4-dihydro-8-isopropoxy-3-isopropyl-10-(trifluoromethyl)-2H-[1,4]oxazino[2,3-f]quinoline (30 mg, 0.1 mmol) and $NaBH_4$ pellets (large excess, >10 equiv) in 3 mL chlorodifluoroacetic acid (0.03 M) stirred at rt for 12 h, to afford 22 mg (57%) of (3R)-4-ethyl-3,4-dihydro-8-isopropoxy-3-methyl-10-(trifluoromethyl)-2H-[1,4]oxazino[2,3-f]quinoline. $^1H$ NMR (500 MHz, $CDCl_3$) δ 7.44 (d, J=9.3, 1H), 7.30 (d, J=9.3, 1H), 7.21 (s, 1H), 5.98 (m, 1H), 5.49 (m, 1H), 4.55 (dd, J=10.7, 2.4, 1H), 3.84 (dd, J=10.7, 2.4, 1H), 3.79 (m, 1H), 3.54 (m, 1H), 2.93 (m, 1H), 1.84 (m, 1H), 1.39 (d, J=6.3, 3H), 1.38 (d, J=6.3, 3H), 1.00 (d, J=9.8, 3H), 0.99 (d, J=9.8, 3H).

(3R)-4-(2-Chloro-2,2-difluoroethyl)-2,3,4,7-tetrahydro-3-isopropyl-10-(trifluoromethyl)-8H-[1,4]oxazino[2,3-f] quinolin-8-one (Compound 124, Structure 11 of Scheme II, where $R^1$, $R^3$, $R^4$, $R^5$,=H, $R^2$=trifluoromethyl, $R^6$=i-PR, $R^{13}$=$CH_2CClF_2$):

Compound 124 was prepared according to General Method 4 (EXAMPLE 1) from (3R)-4-ethyl-3,4-dihydro-8-isopropoxy-3-methyl-10-(trifluoromethyl)-2H-[1,4]oxazino [2,3-f]quinoline (22 mg, 0.02 mmol) in 2 mL acetic acid and 2 mL concentrated HCl and heated at 90° C. for 4 h to afford 14 mg (72%) of Compound 124, after purification by column chromatography (3:1 hexanes: EtOAc to 1:1 hexanes:EtOAc, gradient elution). $^1H$ NMR (500 MHz, $CDCl_3$) δ 12.10 (bs, 1H), 7.25 (d, J=9.3, 1H), 7.14 (s, 1H), 6.98 (d, J=9.3, 1H), 4.58 (dd, J=10.7, 1.3, 1H), 4.10 (m, 1H), 3.94 (dd, J=10.7, 2.4, 1H), 3.78 (m, 1H), 2.96 (bd, J=9.8, 1H), 1.81 (m, 1H), 1.00 (d, J=6.8, 3H), 0.98 (d, J=6.8, 3H).

EXAMPLE 25

(3R)-4-(2,2-Difluoroethyl)-2,3,4,7-tetrahydro-3-isopropyl-10-(trifluoromethyl)-8H-[1,4]oxazino[2,3-f]quinolin-8-one (Compound 125, Structure 11 of Scheme II, where $R^1$, $R^3$, $R^4$, $R^5$,=H, $R^2$=trifluoromethyl, $R^6$=i-Pr, $R^{13}$=$CH_2CHF_2$)

Compound 125 was prepared according to General Method 6 (EXAMPLE 3) from (3R)-3,4-dihydro-8-isopropoxy-3-isopropyl-10-(trifluoromethyl)-2H-[1,4]oxazino[2, 3-f]quinoline (30 mg, 0.1 mmol) and NaBH₄ pellets (large excess, >10 equiv) in 5 mL difluoroacetic acid (0.02 M) stirred at rt for 12 h, to afford 28 mg (79%) of (3R)-4-ethyl-3,4-dihydro-8-isopropoxy-3-isopropyl-10-(trifluoromethyl)-2H-[1,4]oxazino[2,3-f]quinoline. $^1$H NMR (500 MHz, CDCl₃) 7.44 (d, J=9.3, 1H), 7.30 (d, J=9.3, 1H), 7.21 (s, 1H), 5.98 (m, 1H), 5.49 (m, 1H), 4.55 (dd, J=10.7, 2.4, 1H), 3.84 (dd, J=10.7, 2.4, 1H), 3.79 (m, 1H), 3.54 (m, 1H), 2.93 (m, 1H), 1.84 (m, 1H), 1.39 (d, J=6.3, 3H), 1.38 (d, J=6.3, 3H), 1.00 (d, J=9.8, 3H), 0.99 (d, J=9.8, 3H). This material (13 mg, 0.03 mmol) was carried on according to General Method 4 (EXAMPLE 1) by treatment with 3 mL acetic acid and 3 mL concentrated HCl heated at 90° C. for 4 h to afford 8 mg (70%) of Compound 125, after purification by column chromatography (3:1 hexanes: EtOAc to 1:1 hexanes:EtOAc, gradient elution). $^1$H NMR (500 MHz, CDCl₃) δ 11.59 (bs, 1H), 7.15 (d, J=8.8, 1H), 7.13 (s, 1H), 6.94 (d, J=8.8, 1H), 5.96 (m, 1H), 4.55 (dd, J=10.7, 1.3, 1H), 3.87 (dd, J=10.7, 2.4, 1H), 3.74 (m, 1H), 3.50 (m, 1H), 2.91 (bd, J=8.8, 1H), 1.80 (m, 1H), 1.00 (d, J=11.7, 3H), 0.97 (d, J=11.7, 3H).

EXAMPLE 26

(3R)-4-Allyl-2,3,4,7-tetrahydro-3-isopropyl-10-(trifluoromethyl)-8H-[1,4]oxazino[2,3-f]quinolin-8-one (Compound 126, Structure 11 of Scheme II, where R¹, R³, R⁴, R⁵,=H, R²=trifluoromethyl, R⁶=i-PR, R¹³=CH₂CHCH₂)

A suspension of (3R)-3,4-dihydro-8-isopropoxy-3-isopropyl-10-(trifluoromethyl)-2H-[1,4]oxazino[2,3-f]quinoline (0.010 g, 0.028 mmol) and K₂CO₃ (0.019 g, 0.140 mmol) in DMF (1.0 mL) was treated with allyl bromide (0.024 mL, 0.280 mmol) and heated at 50° C. for 16 h. The reaction mixture was poured into 25 mL water and extracted with EtOAc (2×25 mL). The extracts were washed with 25 mL each water and brine, dried over MgSO₄, filtered and concentrated to a yellow oil. Column chromatography (5–10% EtOAc in hexane gradient) gave 0.010 g (91%) of (3R)-4-allyl-3,4-dihydro-8-isopropoxy-3-isopropyl-10-(trifluoromethyl)-2H-[1,4]oxazino[2,3-f]quinoline, a yellow oil. This material (0.006 g, 0.015 mmol) was carried on according to General Method 4 (EXAMPLE 1) by treatment with conc. HCl (1.0 mL) heated at 70° C. for 1 h to afford 0.004 g (80%) of Compound 126, a yellow solid. R_f 0.6 (9:1 CH₂Cl₂:MeOH); $^1$H NMR (400 MHz, CDCl₃) δ 11.82 (broad s, 1H), 7.12 (d, 1H, J=8.9), 7.11 (s, 1H), 6.93 (d, 1H, J=8.9), 5.92–5.81 (m, 1H), 5.27–5.17 (m, 2H), 4.48 (d, 1H, J=10.9), 3.99 (dd, ABX, 1H, J=16.4, 5.8), 3.84 (dd, ABX, 1H, J=16.4, 5.8), 3.77 (dd, ABX, 1H, J=10.9, 2.8), 2.96–2.93 (m, 1H), 1.94–1.84 (m, 1H), 0.98 (d, 3H, J=6.7), 0.96 (d, 3H, J=6.7).

EXAMPLE 27

(3R)-2,3,4,7-Tetrahydro-3-phenyl-10-(trifluoromethyl)-8H-[1,4]oxazino[2,3-f]quinolin-8-one (Compound 127, Structure 9 of Scheme II, where R¹, R³, R⁴, R⁵,=H, R²=trifluoromethyl, R⁶=Ph)

(2'R)-6-Bromo-5-[(2'-t-butoxycarbonylamino)-2'-phenylethoxy]-2-isopropoxy-4-(trifluoromethyl)quinoline (Structure 7 of Scheme II, where R¹, R³, R⁴, R⁵,=H, R²=trifluoromethyl, R⁶=Ph): This compound was prepared according to General Method 1 (EXAMPLE 1) from 6-bromo-5-hydroxy-2-isopropoxy-4-(trifluoromethyl)quinoline (500 mg, 1.43 mmol), (2R)-(−)-N-t-butoxycarbonyl-2-phenylglycinol (542 mg, 2.28 mmol), triphenylphosphine (615 mg, 2.28 mmol), diisopropyl azodicarboxylate (462 mg, 2.28 mmol) and 4-methylmorpholine (570 mg, 5.64 mmol) in 15 mL THF to afford 295 mg (36%) of (2'R)-6-bromo-5-[(2'-t-butoxycarbonylamino)-2'-phenylethoxy]-2-isopropoxy-4-(trifluoromethyl)quinoline, a colorless oil, after column chromatography (1:1 EtOAc: hexanes). $^1$H NMR (400 MHz, CDCl₃) δ 7.78 (d, 1H, J=9.0), 7.55 (d, 1H, J=9.0), 7.39–7.24 (m, 6H), 5.52 (septet, 1H, J=6.2), 5.23 (s, 1H), 4.11 (m, 2H), 4.02 (m, 1H), 1.45–1.20 (m, 15H).

(3R)-3,4-Dihydro-8-isopropoxy-3-phenyl-10-(trifluoromethyl)-2H-[1,4]oxazino[2,3-f]quinoline (Structure 8 of Scheme II. where R¹, R³, R⁴R⁵,=H, R²=trifluoromethyl R⁶=Ph): This compound was prepared according to General Method 2 (EXAMPLE 1) from (2'R)-6-bromo-5-[(2'-t-butoxycarbonylamino)-2'-phenylethoxy]-2-isopropoxy-4-(trifluoromethyl)quinoline (295 mg, 0.52 mmol) in CH₂Cl₂ (5 mL) and TFA (5 mL) to give 243 mg (100%) of (2'R)-6-bromo-5-(2'-amino-2'-phenylethoxy)-2-isopropoxy-4-(trifluoromethyl)quinoline, an amber oil. This material (243 mg, 0.52 mmol) was carried on according to General Method 3 (EXAMPLE 1), by treatment with Pd₂(dba)₃ (24 mg, 0.026 mmol), BINAP (32.2 mg, 0.052 mmol) and sodium t-butoxide (70 mg, 0.73 mmol) in 8 mL toluene to afford 123 mg (61%) of (3R)-3,4-dihydro-8-isopropoxy-3-phenyl-10-(trifluoromethyl)-2H-[1,4]oxazino[2,3-f]quinoline, a yellow solid, after column chromatography (9:1 hexanes:EtOAc). $^1$H NMR (400 MHz, CDCl₃) δ 7.63–7.02 (m, 8H), 5.49 (septet, 1H, J=6.2), 4.62 (dd, 1H, J=8.3, 3.2), 4.45 (dd, 1H, J=10.6, 3.2), 4.12 (s, 1H), 4.02 (dd, 1H, J=10.6, 8.3), 1.40 (d, 3H, J=6.2), 1.39 (d, 3H, J=6.2).

(3R)-2,3,4,7-Tetrahydro-3-phenyl-10-(trifluoromethyl)-8H-[1,4]oxazino[2,3f]quinolin-8-one (Compound 127, Structure 9 of Scheme II, where R¹ R¹, R³, R⁴, R⁵, =H, R²=trifluoromethyl, R⁶=Ph):

Compound 127 was prepared according to General Method 4 (EXAMPLE 1) from (3R)-3,4-dihydro-8-isopropoxy-3-phenyl-10-(trifluoromethyl)-2H-[1,4]oxazino[2,3-f]quinoline (33.3 mg, 0.086 mmol) in 4 mL AcOH and 4 mL conc. HCl to afford 15.5 mg (52%) of the Compound 127, a yellow solid, after column chromatography (1:1 EtOAc: hexanes). $^1$H NMR (400 MHz, CDCl₃) δ 11.6 (s, 1H), 7.40 (m, 5H), 7.14 (s, 1H), 7.00 (d, 1H, J=8.6), 6.95 (d, 1H, J=8.6), 4.58 (m, 1H), 4.44 (m, 1H), 4.03 (m, 2H).

EXAMPLE 28

(3R)-2,3,4,7-Tetrahydro-3-phenyl-4-(2,2,2-trifluoroethyl)-10-(trifluoromethyl)-8H-[1,4]oxazino[2,3-f]quinolin-8-one (Compound 128, Structure 11 of Scheme II, where R¹, R³, R⁴, R⁵,=H, R²=trifluoromethyl, R⁶=Ph, R¹³=CH₂CF₃)

(3R)-3,4-Dihydro-8-isopropoxy-3-phenyl-4-(2,2,2-trifluoroethyl)-10-(trifluoromethyl)-2H-[1,4]oxazino[2,3-f]quinoline (Structure 10 of Scheme II, where R¹, R³, R⁴, R⁵,=H, R²=trifluoromethyl, R⁶=Ph, R¹³=CH₉CF₃): This compound was prepared according to General Method 6 (EXAMPLE 3) from (3R)-3,4-dihydro-8-isopropoxy-3-phenyl-10-(trifluoromethyl)-2H-[1,4]oxazino[2,3-f]quinoline (49.5 mg, 0.127 mmol) and NaBH₄ (300 mg, 7.9 mmol) in 5 mL TFA, to afford 50.7 mg (85%) of (3R)-3,4-dihydro-8-isopropoxy-3-phenyl-4-(2,2,2-trifluoroethyl)-10-(trifluoromethyl)-2H-[1,4]oxazino[2,3-f]quinoline, a yellow solid, after column chromatography (1:3 CH₂Cl₂:hexanes). $^1$H NMR (400 MHz, CDCl₃) δ 7.55–7.10 (m, 8H), 5.50 (septet, 1H, J=6.2), 4,77 (dd, 1H, J=4.4, 3.4), 4.39 (dd, 1H, J=11.0, 3.4), 4.29 (dd, 1H, J=11.0, 4.4), 4.10 (m, 1H), 3.66 (m, 1H), 1.40 (d, 6H, J=6.2).

(3R)-2,3,4,7-Tetrahydro-3-phenyl-4-(2,2,2-trifluoroethyl)-10-(trifluoromethyl)-8H-[1,4]oxazino[2,3-f]guinolin-8-one (Compound 128, Structure 11 of Scheme II, where $R^1$, $R^3$, $R^4$, $R^5$,=H, $R^2$=trifluoromethyl, $R^6$=Ph, $R^{13}$=CH$_2$CF$_3$):

Compound 128 was prepared according to General Method 4 (EXAMPLE 1) from (3R)-3,4-dihydro-8-isopropoxy-3-phenyl-4-(2,2,2-trifluoroethyl)-10-(trifluoromethyl)-2H-[1,4]oxazino[2,3-f]quinoline (50.7 mg, 0.11 mmol) in 2 mL AcOH and 2 mL conc. HCl to afford 32.4 mg (70%) of the Compound 128, a yellow solid, after column chromatography (1:1 EtOAc:hexane). $^1$H NMR (400 MHz, CDCl$_3$) δ 11.0 (s, 1H), 7.40–7.05 (m, 8H), 4.74 (dd, 1H, J=4.6, 3.2), 4.39 (dd, 1H, J=11.0, 3.2), 4.29 (dd, 1H, J=11.0, 4.6), 4.04 (m, 1H), 3.63 (m, 1H).

EXAMPLE 29

(3R)-4-Cyclopropylmethyl-2,3,4,7-tetrahydro-3-phenyl-10-(trifluoromethyl)-8H-[1,4]oxazino[2,3-f] quinolin-8-one (Compound 129, Structure 11 of Scheme II, where $R^1$, $R^3$ $R^4$, $R^5$,=H, $R^2$=trifluoromethyl, $R^6$=Ph, $R^{13}$=CH$_2$-cyclopropyl)

Compound 129 was prepared according to General Method 5 (EXAMPLE 2) from Compound 128 (EXAMPLE 28) (11.6 mg, 0.034 mmol), cyclopropanecarboxaldehyde (282 mg, 4.0 mmol), AcOH (104 mg, 1.75 mmol) and NaCNBH$_3$ (150 mg, 2.39 mmol) in 3 mL MeOH to afford 8.4 mg (63%) of Compound 129, a yellow solid, after column chromatography (1:1 EtOAc:hexane). $^1$H NMR (400 MHz, CDCl$_3$) δ 11.2 (s, 1H), 7.40–7.25 (m, 6H), 7.14 (s, 1H), 7.07 (d, 1H, J=9.0), 4.77 (dd, 1H, J=6.6, 3.6), 4.33 (dd, 1H, J=10.9, 3.6), 4.15 (dd, 1H, J=10.9, 6.6), 3.62 (dd, 1H, J=15.3, 4.6), 2.65 (dd, 1H, J=15.3, 7.9), 0.94 (m, 1H), 0.51 (m, 1H), 0.40 (m, 1H), 0.13 (m, 1H), –0.06 (m, 1H).

EXAMPLE 30

(3R)-3-Benzyl-2,3,4,7-tetrahydro-4-(2,2,2-trifluoroethyl)-10-(trifluoromethyl)-8H-[1,4]oxazino[2,3-f] quinolin-8-one (Compound 130, Structure 11 of Scheme II, where $R^1$, $R^3$, $R^4$, $R^5$,=H, $R^2$=trifluoromethyl, $R^6$=benzyl, $R^{13}$=CH$_2$CF$_3$)

(2'R)-6-Bromo-5-[(2'-t-butoxycarbonylamino)-3'-phenyl-1'-propoxy]-2-isopropoxy-4-(trifluoromethyl)quinoline (Structure 7 of Scheme II, where $R^1$, $R^3$, $R^4$, $R^5$,=H, R=trifluoromethyl, $R^6$=benzyl): This compound was prepared according to General Method 1 (EXAMPLE 1) from the bromophenol (525 mg, 1.5 mmol), (R)-(+)-N-t-butoxycarbonyl-2-amino-3-phenyl-1-propanol (603 mg, 2.4 mmol), triphenylphosphine (646 mg, 2.4 mmol), diisopropyl azodicarboxylate (514 mg, 2.5 mmol) and N-methylmorpholine (607 mg, 6.0 mmol) in 15 mL THF to afford 212 mg (24%) of (2'R)-6-bromo-5-[(2'-t-butoxycarbonylamino)-3'-phenyl-1'-propoxy]-2-isopropoxy-4-(trifluoromethyl)quinoline, a colorless oil, after column chromatography (1:9 EtOAc:hexane). $^1$H NMR (400 MHz, CDCl$_3$) δ 7.78 (d, 1H, J=9.0), 7.54 (d, 1H, J=9.0), 7.32–7.18 (m, 6H), 5.52 (septet, 1H, J=6.2), 4.87 (s, 1H), 4.36 (m, 1H), 4.03 (m, 2H), 3.09 (m, 1H), 1.45–1.20 (m, 15H).

(3R)-3-Benzyl-3,4-dihydro-8-isopropoxy-10-(trifluoromethyl)-2H-[1,4]oxazino[2,3-f]quinoline (Structure 8 of Scheme II, where $R^1$, $R^3$, $R^4$, $R^5$,=H, $R^2$=trifluoromethyl $R^6$=benzyl): This compound was prepared according to General Method 2 (EXAMPLE 1) from (2'R)-6-bromo-5-[(2'-t-butoxycarbonylamino)-3'-phenyl-1'-propoxy]-2-isopropoxy-4-(trifluoromethyl)quinoline (212 mg, 0.365 mmol) in CH$_2$Cl$_2$ (5 mL) and TFA (5 mL) to give 176 mg (100%) of (2'R)-6-bromo-5-(2'-amino-3'-phenyl-1'-propoxy)-2-isopropoxy-4-(trifluoromethyl)quinoline, an amber oil. This material (176 mg, 0.365 mmol) was carried on according to General Method 3 (EXAMPLE 1) by treatment with Pd$_2$(dba)$_3$ (16.7 mg. 0.018 mmol), BINAP (22.7 mg, 0.036 mmol) and sodium t-butoxide (52.6 mg, 0.55 mmol) in 10 mL toluene to afford 26.2 mg (18%) of (R)-3-benzyl-3,4-dihydro-8-isopropoxy-10-(trifluoromethyl)-2H-[1,4]oxazino[2,3-f]quinoline, a yellow solid, after column chromatography (1:9 EtOAc:hexane). $^1$H NMR (400 MHz, CDCl$_3$) δ 7.42–7.15 (m, 7H), 6.96 (d, 1H, J=9.0), 5.47 (septet, 1H, J=6.2), 4.35 (dd, 1H, J=2.8, 10.5), 4.02 (dd, 1H, J=10.5, 6.6), 3.82 (s, 1H), 3.75 (m, 1H), 2.91 (dd, 1H, J=5.6, 13.3), 2.75 (dd, 1H, J=8,6, 13.3), 1.38 (d, 3H, J=6.2), 1.37 (d, 3H, J=6.2).

(3R)-3-Benzyl-3,4-dihydro-8-isopropoxy-4-(2,2,2-trifluoroethyl)-10-(trifluoromethyl)-2H-[1,4]oxazino[2,3-f] quinoline (Structure 10 of Scheme II, where $R^1$, $R^3$, $R^4$, $R^5$, =H, $R^2$=trifluoromethyl, $R^6$=benzyl, $R^{13}$=CH$_2$CF$_3$): This compound was prepared according to General Method 6 (EXAMPLE 3) from (3R)-3-benzyl-3,4-dihydro-8-isopropoxy-10-(trifluoromethyl)-2H-[1,4]oxazino[2,3-f]quinoline (25.8 mg, 0.064 mmol) and NaBH$_4$ (300 mg, 7.9 mmol) in 3 mL TFA, to afford 29.6 mg (95%) of (3R)-3-benzyl-3,4-dihydro-8-isopropoxy-4-(2,2,2-trifluoroethyl)-10-(trifluoromethyl)-2H-[1,4]oxazino[2,3-f]quinoline, a yellow solid, after column chromatography (1:9 EtOAc:hexane). $^1$H NMR (400 MHz, CDCl$_3$) δ 7.51–7.10 (m, 8H), 5.51 (septet, 1H, J=6.2), 4,29 (d, 1H, J=10.5), 3.91 (m, 2H), 3.70–3.50 (m, 2H), 2.90 (dd, 1H, J=6.3, 13.3), 2.80 (dd, 1H, J=9.2, 13.3), 1.39 (d, 6H, J=6.2).

(3R)-3-Benzyl-2,3,4,7-tetrahvdro-4-(2,2,2-trifluoroethyl)-10-(trifluoromethyl)-8H-[1,4]oxazino[2,3-f]quinolin-8-one (Compound 130, Structure 11 of Scheme II, where $R^1$, $R^3$, $R^4$, $R^5$,=H, $R^2$=trifluoromethyl, $R^6$=benzyl, $R^{13}$=CH$_2$CF$_3$):

Compound 130 was prepared according to General Method 4 (EXAMPLE 1) from (3R)-3-benzyl-3,4-dihydro-8-isopropoxy-4-(2,2,2-trifluoroethyl)-10-(trifluoromethyl)-2H-[1,4]oxazino[2,3-f]quinoline (29.6 mg, 0.061 mmol) in AcOH (3 mL) and conc. HCl (3 mL) to afford 20.2 mg (75%) of the Compound 130, a yellow solid, after column chromatography (1:1 EtOAc:hexane). $^1$HNMR (400 MHz, CDCl$_3$) δ 11.0 (s, 1H), 7.37–7.04 (m, 8H), 4.29 (d, 1H, J=10.6), 3.93–3.80 (m, 2H), 3.65–3.48 (m, 2H), 2.90 (dd, 1H, J=6.2, 13.3), 2.78 (dd, 1H, J=9.2, 13.3).

EXAMPLE 31

2,3,4,7-Tetrahydro-10-(trifluoromethyl)-8H-[1,4] oxazino[2,3-f]quinolin-8-one (Compound 131, Structure 9 of Scheme II, where $R^1$, $R^3$, $R^4$, $R^5$, $R^6$, $R^7$, $R^8$=H, $R^2$=trifluoromethyl)

(2'R)-6-Bromo-5-[(2'-t-butoxycarbonylamino)ethoxy]-2-isopropoxy-4-(trifluoromethyl)quinoline (Structure 7 of Scheme II, where $R^1$, $R^3$, $R^4$, $R^5$, $R^6$,=H, $R^2$=trifluoromethyl): This compound was prepared according to General Method 1 (EXAMPLE 1) from 6-bromo-5-hydroxy-2-isopropoxy-4-(trifluoromethyl)quinoline (533 mg, 1.52 mmol), N-butoxycarbonyl ethanolamine (270 mg, 1.67 mmol), triphenylphosphine (438 mg, 1.67 mmol) and DIAD (0.33 mL, 1.67 mmol) in 15 mL THF to afford 317 mg (42%) of 6-bromo-5-[(2'-t-butoxycarbonylamino)ethoxy]-2-isopropoxy-4-(trifluoromethyl)quinoline after purification by flash chromatography (silica gel, 100% hexanes to 10% ethyl acetate/hexanes, gradient elution). $^1$H NMR (CDCl$_3$) δ 7.80 (d, J=9.0, 1H), 7.56 (d, J=9.0, 1H), 7.30 (s, 1H), 5.53 (m, 1H), 5.19 (br s, 1H), 4.08 (m, 2H), 3.60 (m, 2H), 1.48 (s, 9H), 1.41 (d, J=6.1, 6H).

3,4-Dihydro-8-isopropoxy-10-(trifluoromethyl)-2H-[1,4]oxazino[2,3-f]quinoline (Structure 8 of Scheme II, where $R^1$, $R^3$, $R^4$, $R^5$, $R^6$,=H, $R^2$=trifluoromethyl): This compound was prepared according to General Method 2 (EXAMPLE 1) from 6-bromo-5-[(2'-t-butoxycarbonylamino)ethoxy]-2-isopropoxy-4-(trifluoromethyl)quinoline (208 mg, 0.42 mmol) in 5 mL of methylene chloride and 5 mL of tnrfluoroacetic acid to afford 78 mg (47%) of 6-bromo-5-(2'-aminoethoxy)-2-isopropoxy-4-(trifluoromethyl)quinoline. This material (78 mg) was carried on according to General Method 3 (EXAMPLE 1) by treatment with sodium tert-butoxide (26.9 mg, 0.28 mmol), BINAP (5.0 mg, 0.008 mmol), Pd$_2$(dba)$_3$ (3.7 mg, 0.004 mmol) and toluene (1.3 mL) heated at reflux overnight to afford 52.5 mg (84%) of 3,4-dihydro-8-isopropoxy-10-(trifluoromethyl)-2H-[1,4]oxazino[2,3-f]quinoline, a yellow oil, after flash chromatography (2% ethyl acetate/hexanes to 50% ethyl acetate/hexanes, gradient elution). $^1$H NMR (400 MHz, CDCl$_3$) δ 7.36 (d, J=8.8, 1H), 7.18 (s, 1H), 7.03 (d, J=8.8, 1H), 5.47 (m, 1H), 4.67 (br s, 1H), 4.31 (dd, J=4.5, 4.3, 2H), 3.54 (dd, J=4.4, 4.3, 2H), 1.38 (d, J=6.2, 6H).

2,3,4,7-Tetrahydro-10-(trifluoromethyl-8H-[1,4]oxazino[2,3-f]quinolin-8-one (Compound 131, Structure 9 of Scheme II, where $R^1$, $R^3$, $R^4$, $R^5$, $R^6$,=H, $R^2$=trifluoromethyl):

Compound 131 was prepared according to General Method 4 (EXAMPLE 1) from 3,4-dihydro-8-isopropoxy-10-(trifluoromethyl)-2H-[1,4]oxazino[2,3-f]quinoline (10 mg, 0.032 mmol) in 0.64 mL glacial acetic acid and 0.32 mL conc. HCl heated at 70° C. for 90 minutes to afford 5 mg of Coumpound 131 after flash chromatography (4:1 hexanes:EtOAc). $^1$H NMR (400 MHz, acetone-d$_6$) δ 10.85 (br s, 1H), 7.01 (d, J=8.62, 1H), 6.91 (d, J=8.64, 1H), 6.86 (s, 1H), 4.26 (m, 2H), 3.46 (m, 2H).

EXAMPLE 32

2,3,4,7-Tetrahydro-4-(2,2,2-trifluoroethyl)-10-(trifluoromethyl)-8H-[1,4]oxazino[2,3-f]quinolin-8-one (Compound 132, Structure 11 of Scheme II, where $R^1$, $R^3$, $R^4$, $R^5$, $R^6$,=H, $R^2$=trifluoromethyl, $R^{13}$=CH$_2$CF$_3$)

Compound 132 was prepared according to General Method 3 (EXAMPLE 1) from 3,4-dihydro-8-isopropoxy-10-(trifluoromethyl)-2H-[1,4]oxazino[2,3-f]quinoline (20.0 mg, 0.064 mmol) and sodium borohydride (excess of 20 mg) in 3 mL trifluoroacetic acid to afford 25 mg (ca. 100%) of 3,4-dihydro-8-isopropoxy-4-(2,2,2-trifluoroethyl)-10-(trifluoromethyl)-2H-[1,4]oxazino[2,3-f]quinoline, a red oil. No further purification was performed and the material was directly transformed according to General Method 4 (EXAMPLE 1) from 3,4-dihydro-8-isopropoxy-4-(2,2,2-trifluoroethyl)-10-(trifluoromethyl)-2H-[1,4]oxazino[2,3-f]quinoline (25 mg) in 0.32 mL conc. HCl and 0.64 mL glacial acetic acid heated at 70° C. for 90 minutes to afford 11 mg (49%) of Compound 132 after purification by flash chromatography (9:1 hexanes:EtOAc to 1:1 hexanes:EtOAc, gradient elution). $^1$H NMR (400 MHz, acetone-d$_6$) δ 11.05 (br s, 1H), 7.31 (d, J=9.0, 1H), 7.04 (d, J=8.8, 1H), 6.92 (s, 1H), 4.32 (t, J=4.3, 2H), 4.14 (q, J=9.5, 2H), 3.61 (t, J=4.4, 2H).

EXAMPLE 33

(7aR,10aS)-7,7a,8,9,10,10a-Hexahydro-7-methyl-1-(trifluoromethyl)-4H-cyclopenta[5,6][1,4]oxazino[2,3-f]quinolin-3-one (Compound 133, Structure 11 of Scheme II, where $R^1$, $R^4$, $R^5$,=H, $R^2$=trifluoromethyl, $R^3$, $R^6$=—CH$_2$CH$_2$CH$_2$—, $R^{13}$=CH$_3$)

(2'R)-6-Bromo-5-[(2'-t-butoxycarbonylamino)-1'-cyclopentoxy]-2-isopropoxy-4-(trifluoromethyl)quinoline (Structure 7 of Scheme II, where $R^1$, $R^4$, $R^5$,=H, $R^2$=trifluoromethyl, $R^3$, $R^6$=—CH$_2$CH$_2$CH$_2$—): The compound was prepared according to General Method 1 (EXAMPLE 1) from 6-bromo-5-hydroxy-2-isopropoxy-4-(trifluoromethyl)quinoline (0.50 g, 1.43 mmol), (1R, 2R)-2-N-t-butoxycarbonylamino-1-cyclopentanol (460 mg, 2.28 mmol), triphenylphosphine (600 mg, 2.28 mmol) and diisopropyl azodicarboxylate (0.45 ml, 2.28 mmol) in 0.6 mL N-methylmorpholine in 14 mL dry THF to afford 190 mg (25%) of (2'R)-6-bromo-5-[(2'-t-butoxycarbonylamino)-1'-cyclopentoxy]-2-isopropoxy-4-(trifluoromethyl)quinoline after flash chromatography (100% hexanes to 6:1 hexanes/EtOAc, gradient elution). $^1$H NMR (500 MHz, CDCl$_3$) δ 7.78 (d, J=8.8, 1H), 7.49 (d, J=8.8, 1H), 7.24 (s, 1H), 5.52 (m, 1H), 5.28 (d, J=9.3, 1H), 4.96 (m, 1H), 4.11 (m, 1H), 2.04 (m, 2H), 1.82 (m, 2H), 1.59 (m, 2H), 1.45 (s, 9H), 1.42 (d, J=7.8, 3H), 1.41 (d, J=7.8, 3H).

(2'R)-6-Bromo-5-(2'-amino-1'-cyclopentoxy)-2-isopropoxy-4-(trifluoromethyl)quinoline: This compound was prepared according to General Method 2 (EXAMPLE 1) from (2'R)-6-bromo-5-[(2'-t-butoxycarbonylamino)-1'-cyclopentoxy]-2-isopropoxy-4-(trifluoromethyl)quinoline (190 mg, 0.35 mmol) in 3 mL CH$_2$Cl$_2$ and 3 mL TFA to afford 133 mg (86%) of (2'R)-6-bromo-5-(2'-amino-1'-cyclopentoxy)-2-isopropoxy-4-(trifluoromethyl)quinoline.

(7aR,10aS)-3-Isopropoxy-1-(trifluoromethyl)-7,7a,8,9,10,10a-hexahydrocyclopenta[5,6][1,4]oxazino[2,3-f]quinoline (Structure 8 of Scheme II, where $R^1$, $R^4$, $R^5$,=H, $R^2$=trifluoromethyl, $R^3$, $R^6$=—CH$_2$CH$_2$CH$_2$—): This compound was prepared according to General Method 3 (EXAMPLE 1) from (2'R)-6-bromo-5-(2'-amino-1'-cyclopentoxy)-2-isopropoxy-4-(trifluoromethyl)quinoline (133 mg, 0.37 mmol), (±)-2,2'-bis(diphenylphosphino)-1,1'-binaphthyl (7.6 mg, 4 mol %), Pd$_2$(dba)$_3$ (5.6 mg, 2 mol %), sodium t-butoxide (41 mg, 1.19 mmol) to afford 73 mg (68%) of (7aR,10aS)-7,7a,8,9,10,10a-hexahydro-3-isopropoxy-1-(trifluoromethyl)-cyclopenta[5,6][1,4]oxazino[2,3-f]quinoline after purification by flash chromatography (100% hexanes to 4:1 hexanes:EtOAc, gradient elution). $^1$H NMR (500 MHz, CDCl$_3$) δ 7.38 (d, J=8.8, 1H), 7.18 (s, 1H), 7.04 (d, J=8.8, 1H), 5.47 (m, 1H), 4.13 (m, 1H), 4.06 (s, 1H), 3.78 (m, 1H), 2.06 (m, 2H), 1.96 (m, 2H), 1.65 (m, 2H), 1.38 (d, J=5.9, 3H), 1.37 (d, J=6.4, 3H)

(7aR,10aS)-7,7a,8,9,10,10a-Hexahydro-7-methyl-1-(trifluoromethyl)-4H-cyclopenta[5,6][1,4]oxazino[2,3-f]quinolin-3-one (Compound 133, Structure 11 of Scheme II, where $R^1$, $R^4$, $R^5$,=H, $R^2$=trifluoromethyl, $R^3$, $R^6$=—CH$_2$CH$_2$CH$_2$—, $R^{13}$=CH$_3$):

Compound 133 was prepared according to General Method 5 (EXAMPLE 2) from (7aR,10aS)-7,7a,8,9,10,10a-hexahydro-3-isopropoxy-1-(trifluoromethyl)-cyclopenta[5,6][1,4]oxazino[2,3-f]quinoline (5 mg, 0.014 mmol), 37% aqueous formaldehyde solution (0.01 mL, 0.14 mmol) and NaBH$_3$CN (9 mg, 0.14 mmol) in 1 mL acetic acid to afford 5 mg of (7aR,10aS)-7,7a,8,9,10,10a-hexahydro-3-isopropoxy-7-methyl-1-(trifluoromethyl)-cyclopenta[5,6][1,4]oxazino[2,3-f]quinoline. This material (5 mg, 0.01 mmol) carried on according to General Method 4 (EXAMPLE 1) by treatment with 4 mL of 1:1 acetic acid:concentrated HCl (3 mM) heated at 90° C. for 4 h to afford 3.9 mg (90%) of Compound 133, a yellow solid, after column chromatography (3:1 hexanes:EtOAc to 1:1 hexanes:EtOAc, gradient elution). $^1$H NMR (500 MHz, CDCl$_3$) δ 10.58 (bs, 1H), 7.10 (s, 1H), 7.00 (d, J=8.8, 1H), 6.87 (d, J=8.8, 1H), 4.15 (m, 1H), 3.53 (m, 1H), 2.98 (s, 3H), 2.02 (m, 4H), 1.64 (m, 2H), 0.88 (t, J=6.8, 3H).

EXAMPLE 34

(7aR,10aS)-7-Ethyl-7,7a,8,9,10,10a-hexahydro-1-(trifluoromethyl)-4H-cyclopenta[5,6][1,4]oxazino[2,3-f]quinolin-3-one (Compound 134, Structure 11 of Scheme II, where R$^1$, R$^4$, R$^5$,=H, R$^2$=trifluoromethyl, R$^3$, R$^6$=—CH$_2$CH$_2$CH$_2$—, R$^{13}$=CH$_2$CH$_3$)

Compound 134 was prepared according to General Method 5 (EXAMPLE 2) from (7aR,10aS)-7,7a,8,9,10,10a-hexahydro-3-isopropoxy-1-(trifluoromethyl)-cyclopenta[5,6][1,4]oxazino[2,3-f]quinoline (5 mg, 0.014 mmol) and NaBH$_4$ pellets (>10 equiv) in 5 mL acetic acid to afford 5 mg of (7aR,10aS)-7-ethyl-7,7a,8,9,10,10a-hexahydro-3-isopropoxy-1-(trifluoromethyl)-cyclopenta[5,6][1,4]oxazino[2,3-f]quinoline. This material (5 mg, 0.01 mmol) was carried on according to General Method 4 (EXAMPLE 1) by treatment with 4 mL of 1:1 acetic acid:concentrated HCl (3 mM) and heated at 90° C. for 4 h to afford 4 mg (89%) of Compound 134, a yellow solid, after column chromatography (3:1 hexanes:EtOAc to 1:1 hexanes:EtOAc, gradient elution). $^1$H NMR (500 MHz, CDCl$_3$)δ11.01 (bs, 1H), 7.10 (s, 1H), 7.01 (d, J=8.8, 1H), 6.90 (d, J=8.8, 1H), 4.00 (m, 1H), 3.59 (ddd, J=10.0, 7.1, 3.4 1H), 3.44 (m, 2H), 2.03 (m, 4H), 1.61 (m, 2H), 1.20 (t, J=7.1, 3H).

EXAMPLE 35

7,7a,8,9,10,10a-Hexahydro-7-(2,2,2-trifluoroethyl)1-(trifluoromethyl)-4H-cyclopenta[5,6][1,4]oxazino[2,3-f]quinolin-8-one (Compound 135, Structure 11 of Scheme II, Where R$^1$, R$^4$, R$^5$,=H, R$^2$=trifluoromethyl, R$^3$, R$^6$=—CH$_2$CH$_2$CH$_2$—, R$^{13}$=CH$_2$CF$_3$)

Compound 135 was prepared according to General Method 6 (EXAMPLE 3) from (7aR,10aS)-7,7a,8,9,10,10a-hexahydro-3-isopropoxy-1-(trifluoromethyl)-cyclopenta[5,6][1,4]oxazino[2,3-f]quinoline (20 mg, 0.057 mmol) and NaBH$_4$ pellets (excess) in 7 mL TFA to afford 20 mg of (7aR,10aS)-7,7a,8,9,10,10a-hexahydro-3-isopropoxy-1-(trifluoromethyl)-7-(2,2,2-trifluoroethyl)-cyclopenta[5,6][1,4]oxazino[2,3-f]quinoline. This material (20 mg, 0.046 mmol) was carried on according to General Method 4 (EXAMPLE 1) by treatment with 6 mL of 1:1 acetic acid:concentrated HCl (0.01 M) heated at 90° C. for 4 h to afford 15 mg (83%) of Compound 135, a yellow solid, after column chromatography (3:1 hexanes:EtOAc to 1:1 hexanes:EtOAc, gradient elution). $^1$H NMR (500 MHz, CDCl$_3$) δ12.10 (bs, 1H), 7.15 (s, 1H), 7.10 (d, J=8.8, 1H), 7.01 (d, J=8.8, 1H), 4.14 (m, 1H), 3.94 (m, 2H), 3.72 (ddd, J=10.5, 7.6, 3.4, 1H), 2.18 (m, 2H), 2.01 (m, 2H), 1.68 (m, 2H).

EXAMPLE 36

(±)-(2'S,3'R,)-2,3,4,7-Tetrahydro-2,3-dimethyl-4-(2,2,2-trifluoroethl)-10-(trifluoromethyl)-8H-[1,4]oxazino[2,3-f]quinolin-8-one (Compound 136, Structure 11 of Scheme II, where R$^1$, R$^4$, R$^5$,=H, R$^2$=trifluoromethyl, R$^3$, R$^6$=Me, R$^{13}$=CH$_2$CF$_3$)

(±)-(2'S,3'R,)-6-Bromo-5-[(3'-t-butoxycarbonylamino)-2'-butoxy]-2-isopropoxy-4-(trifluoromethyl)quinoline (Structure 7 of Scheme II, where R$^1$, R$^4$, R$^5$, R$^7$, R$^8$=H, R$^2$=trifluoromethyl, R$^3$, R$^6$=Me). The compound was prepared according to General Method 1 (EXAMPLE 1) from 6-bromo-5-hydroxy-2-isopropoxy-4-(trifluoromethyl)quinoline (0.30 g, 0.8 mmol), (±)-(2R,3R)-3-N-t-butoxycarbonyl-2-butanol (405 mg, 2.14 mmol), triphenylphosphine (562 mg, 2.14 mmol) and diisopropyl azodicarboxylate (0.42 ml, 2.14 mmol) in 0.24 mL N-methylmorpholine in 15 mL dry THF to afford 124 mg (28%) of (±)-(2'S,3'R,)-6-bromo-5-[(3'-t-butoxycarbonylamino)-2'-butoxy]-2-isopropoxy-4-(trifluoromethyl)quinoline after flash chromatography (100% hexanes to 6:1 hexanes/EtOAc, gradient elution). $^1$H NMR (500 MHz, CDCl$_3$) δ 7.75 (d, J=8.8, 1H), 7.49 (d, J=8.8, 1H), 7.25 (s, 1H), 5.52 (m, 1H), 4.93 (m, 1H), 4.84 (m, 1H), 3.97 (m, 1H), 1.45 (s, 9H), 1.43 (d, J=5.9, 3H), 1.40 (d, J=6.4, 3H), 1.21 (d, J=5.4, 3H), 0.87 (d, J=6.4, 3H).

(±)-(2'S,3'R, )-6-Bromo-5-(3'-amino-2'-butoxy)-2-isopropoxy-4-(trifluoromethyl)quinoline. This compound was prepared according to General Method 2 (EXAMPLE 1) from (±)-(2'S,3'R,)-6-bromo-5-[(3'-t-butoxycarbonylamino)-2'-butoxy]-2-isopropoxy-4-(trifluoromethyl)quinoline (124 mg, 0.24 mmol) in 4 mL CH$_2$Cl$_2$ and 4 mL TFA to afford 82 mg (82%) of (±)-(2'S,3'R,)-6-bromo-5-(3'-amino-2'-butoxy)-2-isopropoxy-4-(trifluoromethyl)quinoline.

(±)-(2S,3R)-3,4-Dihydro-8-isopropoxy-2,3-dimethyl-10-(trifluoromethyl)-2H-[1,4]oxazino[2,3-f]quinoline (Structure 8 of Scheme II, where R$^1$, R$^4$, R$^5$=H, R$^2$=trifluoromethyl R$^3$, R$^6$=Me): This compound was prepared according to General Method 3 (EXAMPLE 1) from (±)-(2'S,3'R,)-6-bromo-5-(3'-amino-2'-butoxy)-2-isopropoxy-4-(trifluoromethyl)quinoline (82 mg, 0.19 mmol), (+)-2,2'-bis(diphenylphosphino)-1,1'-binaphthyl (5 mg, 4 mol%), Pd$_2$(dba)$_3$ (3.5 mg, 2 mol %), sodium t-butoxide (26 mg, 0.27 mmol) to afford 31 mg (47%) of (±)-(2S,3R)-3,4-dihydro-8-isopropoxy-2,3-dimethyl-10-(trifluoromethyl)-2H-[1,4]oxazino[2,3-f]quinoline, after purification by flash chromatography (100% hexanes to 4:1 hexanes:EtOAc, gradient elution). $^1$H NMR (500 MHz, CDCl$_3$) δ 7.35 (d, J=8.8, 1H), 7.18 (s, 1H), 7.02 (d, J=8.8, 1H), 5.47 (m, 1H), 4.36 (m, 1H), 3.79 (bs, 1H), 3.57 (m, 1H), 1.38 (d, J=6.3, 3H), 1.37 (d, J=6.3, 3H), 1.30 (d, J=6.8, 3H), 1.19 (d, J=6.3, 3H).

(±)-(2S,3R)-3,4-Dihydro-8-isopropoxy-2,3-dimethyl-4-(2,2,2-trifluoroethyl)-10-(trifluoromethyl)-2H-[1,4]oxazino[2,3-f]quinoline (Structure 10 of Scheme II, where R$^1$, R$^4$, R$^5$,=H, R$^2$=trifluoromethyl, R$^3$, R$^6$=Me, R$^{13}$ CH$_2$CF$_3$): This compound was prepared according to General Method 6 (EXAMPLE 3) from (±)-(2S,3R)-3,4-dihydro-8-isopropoxy-2,3-dimethyl-10-(trifluoromethyl)-2H-[1,4]oxazino[2,3-f]quinoline (17 mg, 0.05 mmol) and NaBH$_4$ pellets (>10 equiv) in 4 mL trifluoroacetic acid (0.01 M) to afford 12 mg (ca. 60%) of (±)-(2S,3R)-3,4-dihydro-8-isopropoxy-2,3-dimethyl-10-(trifluoromethyl)-2H-[1,4]oxazino[2,3-f]quinoline, which was carried on without purification.

(±)-(2S,3R)-2,3,4,7-Tetrahydro-2,3-dimethyl-4-(2,2,2-trifluoroethyl)-10-(trifluoromethyl)-8H-[1,4]oxazino[2,3-f]

quinolin-8-one (Compound 136, Structure 11 of Scheme II, where $R^1$, $R^4$, $R^5$,=H, $R^2$=trifluoromethyl, $R^3$, $R^6$=Me, $R^{13}$=CH$_2$CF$_3$):

Compound 136 was prepared by General Method 4 (EXAMPLE 1) from (±)-(2S,3R)-3,4-dihydro-8-isopropoxy-2,3-dimethyl-10-(trifluoromethyl)-2H-[1,4]oxazino[2,3-f]quinoline (12 mg, 0.03 mmol) in 4 mL of a 1:1 acetic acid:concentrated HCl (0.01 M) heated at 90° C. for 4 h to afford 8 mg (75%) of Compound 136, a yellow solid, after column chromatography (3:1 hexanes:EtOAc to 1:1 hexanes:EtOAc, gradient elution). $^1$H NMR (500 MHz, CDCl$_3$) δ 11.96 (bs, 1H), 7.14 (s, 1H), 7.08 (d, J=9.3, 1H), 6.97 (d, J=9.3, 1H), 4.20 (m, 1H), 3.77 (m, 2H), 3.34 (m, 1H), 1.41 (d, J=6.3, 3H), 1.09 (d, J=6.8, 3H).

EXAMPLE 37

(6aR)-6a,7,8,9-Tetrahydro-4-(trifluoromethyl)-1H,6H-pyrrolo[1',2':4,5][1,4]oxazino-[2,3-f]quinolin-2-one (Compound 137, Structure 17 of Scheme III, where $R^1$, $R^3$, $R^4$, $R^5$, $R^7$, $R^8$=H, $R^2$=trifluoromethyl, $R^6$, $R^{13}$=—CH$_2$CH$_2$CH$_2$—)

(R)-[1-(2-Fluoro-4-nitrophenyl)-2-pyrrolidinyl]-methanol (Structure 14 of Scheme III, where $R^3$, $R^4$, $R^5$, $R^7$, $R^8$=H, $R^6$, $R^{13}$=—CH$_2$CH$_2$CH$_2$—: A suspension of 3,4-difluoronitrobenzene (1.57 g, 9.8 mmol), (R)-2-pyrrolidinemethanol (1.0 g, 9.8 mmol) and K$_2$CO$_3$ (1.36 g, 9.8 mmol) in 30 mL DMF was heated at 75° C. for 20 h, whereupon the mixture was partitioned between water (100 mL) and EtOAc (100 mL). The aqueous layer was extracted with EtOAc (100 mL) and the combined organic layers washed with brine, dried over Na$_2$SO$_4$, filtered and concentrated. Flash chromatography (19:1 CH$_2$Cl$_2$:MeOH) afforded 2.27 g (96%) of (R)-[1-(2-fluoro-4-nitrophenyl)-2-pyrrolidinyl]-methanol, an orange solid. R$_f$0.17 (7:3 hexanes:EtOAc); $^1$H NMR (400 MHz, CDCl$_3$) δ 7.94 (dd, 1H, J=9.1, 2.6), 7.89 (dd, 1H, J=14.4, 2.6), 6.68 (t, 1H, J=9.0), 4.25–4.32 (m, 1H), 3.60–3.75 (m, 3H), 3.40–3.50 (m, 1H), 1.95–2.15 (m, 4H), 1.43 (t, 1H, J=5.8).

(3aR)-2,3,3a,4-Tetrahydro-7-nitro-1H-pyrrolo[2,1-c][1,4]benzoxazine (Structure 15 of Scheme III, where $R^3$, $R^4$, $R^5$, $R^7$, $R^8$=H, $R^6$, $R^{13}$=—CH$_2$CH$_2$CH$_2$—: A suspension of (R)-[1-(2-fluoro-4-nitrophenyl)-2-pyrrolidinyl]-methanol (2.27 g, 9.4 mmol) and NaH (60% mineral oil suspension, 0.737 g, 18.9 mmol) in 35 mL THF was heated at reflux for 1 h. The reaction was quenched with phosphate buffer and the aqueous layer was extracted with EtOAc. The solution was filtered through Celite and the organic layer was washed with brine, dried over MgSO$_4$, filtered and concentrated. Flash chromatography (3:2 EtOAc:hexanes) afforded 476 mg (22%) of (3aR)-2,3,3a,4-tetrahydro-7-nitro-1H-pyrrolo[2,1-c][1,4]benzoxazine, an orange solid. R$_f$0.55 (3:2 hexanes:EtOAc); $^1$H NMR (400 MHz, CDCl$_3$) δ 7.87 (dd, 1H, J=9.2, 2.4), 7.74 (d, 1H, J=2.4), 6.44 (d, 1H, J=8.8), 4.56 (dd, 1H, J=10.3, 3.4), 3.65–3.72 (m, 3H), 3.60 (broad t, 1H, J=8.6), 3.44 (t, 1H, J=10.0), 3.36 (td, 1H, J=9.8, 7.3), 2.15–2.25 (m, 2H), 2.05–2.15 (m, 1H), 1.45–1.55 (m, 1H).

(3aR)-7-Amino-2,3,3a,4-tetrahydro-1H-pyrrolo[2,1-c][1,4]benzoxazine (Structure 16 of Scheme III, where $R^3$, $R^4$, $R^5$, $R^7$, $R^8$=H, $R^6$, $R^{13}$=—CH$_2$CH$_2$CH$_2$—): A suspension of (3aR)-2,3,3a,4-tetrahydro-7-nitro-1H-pyrrolo[2,1-c][1,4]benzoxazine (0.470 g, 2.10 mmol) and 10% Pd—C (28 mg) in 15 mL EtOAc and 15 mL EtOH was stirred under a hydrogen atmosphere overnight. The mixture was filtered through Celite and concentrated to afford 0.39 g (98%) of (3aR)-7-amino-2,3,3a,4-tetrahydro-1H-pyrrolo[2,1-c][1,4] benzoxazine. R$_f$0.55 (3:2 hexanes:EtOAc); $^1$H NMR (400 MHz, CDCl$_3$) δ 6.50 (d, 1H, J=8.3), 6.32 (d, 1H, J=2.4), 6.29 (dd, 1H, J=8.3, 2.4), 4.31 (dd, 1H, J=8.3, 1.5), 3.37–3.50 (m, 3H), 3.31 (broad s, 2H), 3.13 (broad q, 1H, J=8.3), 2.07–2.15 (m, 1H), 1.90–2.05 (m, 2H), 1.40–1.50 (m, 1H).

(6aR)-6a,7,8,9-Tetrahydro-4-(trifluoromethyl)-1H,6H-pyrrolo[1',2':4,5][1,4]-oxazino-[2,3-f]quinolin-2-one (Compound 137, Structure 17 of Scheme III, where $R^1$, $R^3$, $R^4$, $R^5$, $R^7$, $R^8$=H, $R^2$=trifluoromethyl, $R^6$, $R^{13}$=—CH$_2$CH$_2$CH$_2$—): A solution of (3aR)-7-amino-2,3,3a,4-tetrahydro-1H-pyrrolo[2,1-c][1,4]benzoxazine (0.390 g, 2.05 mmol) and ethyl 4,4,4-trifluoroacetoacetate (0.378 g, 2.05 mmol) in 14 mL benzene was heated at reflux for 16 h, whereupon the solvent was removed in vacuo. The resultant solid was treated with 7 mL concentrated sulfuric acid and heated to 100° C. for several hours. The solution was poured into ice and neutralized with 6N NaOH and extracted with EtOAc (3×40 mL). The combined organic layers were washed with brine, dried over MgSO$_4$, filtered and concentrated. Flash chromatography (92:8 CH$_2$Cl$_2$:MeOH) afforded 120 mg of an impure yellow solid. Further purification was performed by reverse phase HPLC (ODS, 5 micron, 10×250 mm, 3 mL/min) to afford 5 mg (ca. 1%) of Compound 137. $^1$H NMR (500 MHz, acetone-d$_6$) δ 10.8 (v. broad s, 1H), 7.07 (d, AB, 1H, J=8.6), 7.04 (d, AB, 1H, J=8.6), 6.88 (s, 1H), 4.59 (dd, 1H, J=10.0, 3.8), 3.38–3.45 (m, 2H), 3.34 (t, 1H, J=10.0), 3.16–3.22 (m, 1H), 2.12–2.22 (m, 2H), 2.00–2.10 (m, 2H), 1.50–1.60 (m, 2H).

EXAMPLE 38

2,3,4,7-Tetrahydro-2,2,4-trimethyl-10-(trifluoromethyl)-8H-[1,4]oxazino[2,3-f]quinolin-8-one (Compound 138, Structure 17 of Scheme III, where $R^1$, $R^5$, $R^6$, $R^7$, $R^8$=H, $R^2$=trifluoromethyl, $R^3$, $R^4$, $R^{13}$=Me)

To a solution of 7-amino-3,4-dihydro-2,2,4-trimethyl-2H-1,4-benzoxazine (0.16 g, 0.83 mmol) in 6 mL toluene was added ethyl 4,4,4-trifluoroacetoacetate (0.18 mL, 1.25 mmol), then the mixture was heated at reflux for 3 h. The solvent was removed under reduced pressure to an oil. This oil was dissolved in 4 mL conc. H$_2$SO$_4$ and heated at reflux for 2 h and neutralized by pouring into cold NaOH solution. Flash chromatography afforded Compound 138, a by-product of the reaction. $^1$H NMR (400 MHz, CDCl$_3$) δ 10.81 (bs, 1H), 7.12 (s, 1H), 7.06 (d, J=7.5, 1H), 7.01 (d, J=7.5, 1H), 3.02 (s, 2H), 2.98 (s, 3H) and 1.36 (s, 6H).

EXAMPLE 39

(3R)-8-Chloro-3-ethyl-3,4-dihydro-4-(2,2,2-trifluoroethyl)-10-(trifluoromethyl)-2H-[1,4]oxazino[2,3-f]quinoline (Compound 139, Structure 19 of Scheme IV, where $R^1$, $R^3$, $R^4$, $R^5$, $R^7$, $R^8$=H, $R^2$=trifluoromethyl, $R^6$=Et, $R^{13}$=CH$_2$CF$_3$)

A solution of Compound 110 (EXAMPLE 10) (48 mg, 0.13 mmol) in 1.3 mL phosphorus oxychloride was heated at 80° C. for 4 h. The mixture was poured into cold water (20 mL) and saturated NaHCO$_3$ (10 mL) and extracted with EtOAc (2×30 mL). The combined organic layers were washed with brine (20 mL), dried over MgSO$_4$, filtered and concentrated. Flash chromatography (hexanes:EtOAc 4:1) afforded 28 mg (56%) of Compound 139, a yellow oil. $^1$H NMR (400 MHz, CDCl$_3$) δ 7.68 (d, J=9.2, 1H), 7.67 (s, 1H), 7.42 (d, J=9.2, 1H), 4.45 (d, J=10.8, 1H), 4.00–4.15 (m, 1H), 3.99 (dd, J=10.8, 2.2, 1H), 3.77–3.90 (m, 1H), 3.35–3.45 (m, 1H), 1.45–1.65 (m, 2H), 1.01 (t, J=7.4, 3H).

EXAMPLE 40

(3R)-3-Ethyl-3,4-dihydro-8-methoxy-4-(2,2,2-trifluoroethyl)-10-(trifluoromethyl)-2H-[1,4]oxazino[2,3-f]quinoline (Compound 140, Structure 20 of Scheme IV, where $R^1$, $R^3$, $R^4$, $R^5$, $R^7$, $R^8$=H, $R^2$=trifluoromethyl, $R^6$=Et, $R^{13}$=CH$_2$CF$_3$, $R^{18}$=OMe)

A solution of Compound 139 (EXAMPLE 139) (10 mg, 0.025 mmol) and NaOMe (16 mg, 0.30 mmol) in 2 mL MeOH was heated at reflux for 18 h. The mixture was partitioned between saturated NH$_4$Cl (10 mL) and EtOAc (20 mL). The organic layer was washed with brine (10 mL), dried over MgSO$_4$, filtered and concentrated. Flash chromatography (hexanes:EtOAc 4:1) afforded 6 mg (60%) of Compound 140, an off-white solid. $^1$H NMR (400 MHz, CDCl$_3$) δ 7.49 (d, J=9.1, 1H), 7.29 (d, J=9.1, 1H), 7.26 (s, 1H), 4.49 (dd, J=10.7, 1.5, 1H), 4.04 (s, 3H), 3.97 (dd, J=10.7, 2.4, 1H), 3.85–3.95 (m, 1H), 3.75–3.85 (m, 1H), 3.22–3.32 (m, 1H), 1.55–1.65 (m, 2H), 0.99 (t, J=7.4, 3H).

EXAMPLE 41

(3R)-3-Ethyl-2,3,4,7-tetrahydro-4-(2,2,2-trifluoroethyl)-10-(trifluoromethyl)-8-H-[1,4]oxazino[2,3-f]quinoline-8-one (Compound 110, Structure 29 of Scheme V, where $R^1$, $R^3$, $R^4$, $R^5$, $R^7$, $R^8$=H, R=trifluoromethyl, $R^6$=Et, $R^1$=CH$_2$CF (2R)-(+)-2-(2-Fluoro-4-nitrophenyl)amino-1-butanol (Structure 21 of Scheme V, where $R^3$, $R^4$, $R^5$, $R^7$, $R^8$=H, $R^6$=Et): A mixture of 118 g (0.74 mole) of 3,4-difluoronitrobenzene and 85 g (0.95 mole) of R-(+)-2-amino-1-butanol was dissolved in 400 mL of absolute ethanol. To this solution was then added 62.2 g (0.74 mole) of sodium bicarbonate. The suspension was stirred and heated at reflux temperature for 12 h when TLC indicated complete conversion of the 3,4-difluoronitrobenzene. After cooling to room temperature, the reaction mixture was filtered with the aid of additional ethanol and the ethanol was then evaporated. The crude product thus obtained was distilled under reduced pressure (10–112° C., 2 mm Hg) to afford (2R)-(+)-2-(2-fluoro-4-nitrophenyl)amino-1-butanol as a red solid. Yield, 162 g (96%). [α]$_D$=+95.4 (CHCl$_3$, c 22.7); $^1$H NMR (CDCl$_3$) δ7.88 (1H, dd, J=2.4, 8.9), 7.76 (1H dd J=2.4, 11.7), 6.66 (1H, dd, J=8.7), 4.88 (1H, m), 3.76 (1H dd J=4.2, 11.2), 3.68 (1H, dd J=4.2, 11.2), 3.52 (1H, m), 2.63 (1H, bs), 1.70 (1H, m), 1.59 (1H, m), 0.97 (3H, t, J=7.5). $^{13}$C NMR: ppm 150.1, 147.7, 142.8, 142.7, 136.1, 122.3, 110.9, 110.7, 109.5, 63.6, 55.8, 24.4, 10.4.

(2S,4R)-(−)-3-(2-Fluoro-4-nitrophenyl)-4-ethyl-2-(trifluoromethyl)-1,3-oxazolidine (Structure 22 of Scheme V, where $R^3$, $R^4$, $R^5$, $R^7$, $R^8$=H, $R^6$=Et, RA=trifluoromethyl) and (2R,4R)-(+)-3-(2-Fluoro-4-nitrophenyl)-4-ethyl-2-(trifluoromethyl)-1,3-oxazolidine (Structure 22 of Scheme V, where $R^1$, $R^4$, $R^5$, $R^7$, R=H, $R^2$=Et, R=trifluoromethyl): A 2-L three-necked necked RB flask equipped with a Dean-Stark condenser was charged sequentially with 172 g (0.75 mole) of (2R)-(+)-2-(2-fluoro-4-nitrophenyl)amino-1-butanol, 750 mL of toluene, 543 g (3.77 mole) of trifluoroacetaldehyde ethyl hemiacetal and 34.4 g of p-toluenesulfonic acid. The reaction mixture was refluxed with azeotropic removal of water for 10–12 h. After cooling to room temperature the reaction mixture was concentrated under reduced pressure.

The residue was dissolved in ethyl acetate and washed with aqueous sodium bicarbonate, brine and dried over anhydrous MgSO$_4$. After filtration, the solvents were removed under reduced pressure to afford a mixture of the desired oxazolidines (2S,4R)-(−)-3-(2-fluoro-4-nitrophenyl)-4-ethyl-2-(trifluoromethyl)-1,3-oxazolidine (cis-isomer) and (2R,4R)-(+)-3-(2-fluoro-4-nitrophenyl)-4-ethyl-2-(trifluoromethyl)-1,3-oxazolidine (trans-isomer) as a low melting solid. The product was found to be a mixture of two diastereoisomers (cis/trans, 4:3). Total yield 230 g (100%). (2S,4R)-(−)-3-(2-fluoro-4-nitrophenyl)-4-ethyl-2-(trifluoromethyl)-1,3-oxazolidine (cis-isomer): $^1$H NMR (CDCl$_3$) δ 8.01 (1H, dd, J=2.5, 8.9), 7.95 (1H, dd J=2.5, 13.1), 6.95 (1H, t, J=8.7), 5.82 (1H, q, J=4.6), 4.42 (1H, bt, J=7.46), 4.27 (1H, m), 4.08 (1H, d, J=8.5), 1.65 (1H, m), 1.49 (1H, m), 0.87 (3H, t, J=7.4). $^{13}$C-NMR: ppm 153.2, 150.7, 140.9, 136.8, 128.0, 125.1, 122.2, 121.2, 119.3, 118.5, 113.5, 113.2, 85.4, 71.4, 59.2, 26.1, 9.3.

(2R)-2-[2-Fluoro-4-nitro(2,2,2-trifluoroethyl)anilino]-1-butanol (Structure 23 of Scheme V, where $R^3$, $R^4$, $R^5$, $R^7$, $R^8$=H. $R^6$=Et, $R^{13}$=CH$_2$CF$_3$): A 2-L three-necked RB flask equipped with an addition funnel and mechanical stirrer was charged sequentially with 230 g (0.75 mole) of the mixture of (−)-(2S,4R)- and (+)-(2R,4R)-3-(2-fluoro-4-nitrophenyl) 4-ethyl-2-(trifluoromethyl)-1,3-oxazolidine, 1.0 Liter of dry chloroform and 290 g (2.5 mole) of triethylsilane. The solution stirred under an atmosphere of nitrogen and cooled to −78° C. 161 g (0.85 mole) of TiCl$_4$ was added in drops through the addition funnel. After the addition was complete, the reaction mixture was allowed to warm to room temperature and stirred for another 24 h. The reaction mixture was quenched with ice and then neutralized with aq. Na$_2$CO$_3$. The organic layers were washed with water, brine and dried over MgSO$_4$. After filtration, the solvents were evaporated under reduced pressure and the residue was purified by silica gel column chromatography (ethyl acetate: hexanes 1:9) to afford (2R)-2-[2-fluoro-4-nitro(2,2,2-trifluoroethyl)anilino]-1-butanol as a glassy solid. Yield 190 g (82%). $^1$H NMR (500 MHz, CDCl$_3$) δ 7.98 (dd, J=8.8, 2.4, 1H), 7.94 (dd, J=13.2, 2.9, 1H), 7.37 (dd, J=8.8, 8.8, 1H), 4.12 (m, 1H), 3.87 (m, 1H), 3.77 (m, 1H), 3.70 (m, 1H), 3.57 (m, 1H), 1.78 (dd, J=6.8, 4.4, 1H), 1.58 (dq, J=7.8, 2.9, 2H), 0.95 (t, J=7.3, 1H).

(+)-(3R)-3-Ethyl-3,4-dihydro-7-nitro-4-(2,2,2-trifluoroethyl)-2H-1,4-benzoxazine (Structure 24 of Scheme V where $R^3$,$R^4$,$R^5$, $R^7$, $R^8$=H. $R^6$=Et, R=CH$_2$CF$_3$): A solution of 190 g (0.612 mole) of the crude (2R)-2-[2-fluoro-4-nitro (2,2,2-trifluoroethyl)anilino]-1-butanol in 1 Liter of dry THF was added dropwise to a stirred suspension of 36.77 g (0.919 mole, 1.5 eq) of sodium hydride in 1.5 L of dry THF under nitrogen atmosphere. After complete addition, the reaction mixture was refluxed for 3 h when TLC of the reaction mixture indicated complete conversion. After cooling to room temperature, 400 mL of methanol was added to destroy excess sodium hydride. The reaction mixture was poured into ice-cold water and extracted with ethyl acetate. The organic portions were combined, washed with brine and dried over MgSO$_4$. After filtration, the solvents were evaporated under reduced pressure. The crude product thus obtained was purified by silica gel column chromatography (ethyl acetate:hexanes 1:9) to obtain (+)-(3R)-3-ethyl-3,4-dihydro-7-nitro-4-(2,2,2-trifluoroethyl)-2H-1,4-benzoxazine as a yellow crystalline solid. Yield 71 g (40%). [α]$_D$=+56.6 (CHCl$_3$, c 7.8); $^1$H NMR (CDCl$_3$) δ 7.80 (1H, dd, J=2.56, 8.98), 7.71 (1H, d, J=2.57), 6.72 (1H, d, J=9.07), 4.34 (1H, dd, J=1.44, 11.02), 4.12 (1H, m), 4.06 (1H, dd, J=2.12, 11.04), 3.79 (1H, m), 3.37 (1H, m), 1.68 (2H, m), 1.00 (3H, t, J=7.54). $^{13}$C NMR: ppm 142.6, 139.1, 138.6, 126.1, 118.6, 112.6, 110.8, 64.9, 58.9, 50.6, 22.5 and 10.3.

(3R)-3-Ethyl-3,4-dihydro-4-(2,2,2-trifluoroethyl)-7-(trimethylacetamido)-2H-1,4-benzoxazine (Structure 26 of Scheme V, where $R^3$, $R^4$, $R^5$, $R^7$, $R^8$=H, $R^6$=Et, $R^{13}$=CH$_2$CF$_3$, $R^b$=t-butyl): A solution of 35 g (0.121 mole) 7-nitrobenzoxazine in 700 mL of ethyl acetate containing 3.5 g of 10% palladium on carbon was hydrogenated under ambient pressure. The reaction mixture was stirred for 12 h at room temperature. When TLC of the reaction mixture indicated complete conversion, 14.2 g (0.18 mol) of pyridine was added to the solution. After stirring for an hour, 17.4 g of trimethylacetyl chloride was added dropwise to the reaction mixture and it was stirred for another 2 hours until TLC indicated the complete conversion. The reaction mixture was quenched with ice and the organic layers were washed with sodium bicarbonate solution, 0.5 N HCl and brine. The crude product thus obtained was subject to silica gel column chromatography (ethyl acetate:hexanes 1:9) to afford the desired (3R)-3-ethyl-3,4-dihydro-4-(2,2,2-trifluoroethyl)-7-(trimethylacetamido)-2H-1,4-benzoxazine as a white solid. Yield 35 g (84%). $[\alpha]_D$=−24.0 (CHCl$_3$, c 1.5); $^1$H NMR (CDCl$_3$) δ 7.04 (1H, d, J=2.45), 6.97 (1H, dd, J=2.46, 6.2), 6.69 (1H, d, J=8.66), 4.20 (1H, dd, J=1.78, 10.77), 3.96 (1H, dd, J=2.22, 10.68), 3.81 (1H, m), 3.68 (1H, m), 3.14 (1H, m), 1.57 (2H, m), 0.95 (3H, t, J=7.48). $^{13}$C NMR: ppm 176.5, 144.3, 130.4, 129.7, 115.0, 114.3, 109.8, 65.0, 59.1, 53.8, 39.6, 27.9, 22.7, 10.7.

(3R)-(−)-3-Ethyl-3,4-dihdro-8-(trifluoroacetyl)-4-(2,2,2-trifluoroethyl)-7-(trimethylacetamido)-2H-1,4-benzoxazine (Structure 27 of Scheme V, where $R^3$, $R^4$, $R^5$, $R^7$, $R^8$=H, $R^6$=Et, $R^{13}$=CH$_2$CF$_3$, $R^b$=t-butyl): A solution of 35 g (0.102 mol) of (3R)-3-ethyl-3,4-dihydro-4-(2,2,2-trifluoroethyl)-7-(trimethylacetamido)-2H-1,4-benzoxazine was dissolved in 800 mL of dry ether under nitrogen atmosphere. The solution was then cooled to −30° C. and 150 mL (1.7M in pentane, 0.255 mol) of n-BuLi was added dropwise. The reaction mixture was stirred at −30° C. for one hour before it was allowed to warm to −8° C. The temperature of the reaction mixture was then maintained at −8° C. to −5° C. for 5 hours after which it was cooled down to −30° C. 57.9 g of ethyl trifluoroacetate (0.408 mol) was then added to the reaction mixture and the solution was allowed to warm up to room temperature overnight. The reaction mixture was poured in to aqueous ammonium chloride and extracted with ether. The organic portions were combined, washed with brine, dried over MgSO$_4$ and evaporated under reduced pressure. The crude product thus obtained was purified by silica gel column chromatography (ethyl acetate:hexanes 1:9) to provide 25 g (56%) of (3R)-(−)-3-ethyl-3,4-dthydro-8-(trifluoroacetyl)-4-(2,2,2-trifluoroethyl)-7-(methylacetamido)-2H-1,4-benzoxazine.

(3R)-8-[2-1-Carbethoxyprop-1-enyl)]-3-ethyl-3,4-dihydro-4-(2,2,2-trifluoroethyl)-7-(trimethylacetamido)-2H-1,4-benzoxazine (Structure 28 of Scheme V, where $R^3$, $R^4$, $R^5$, $R^7$, $R^8$=H, $R^6$=Et, $R^{13}$=CH$_2$CF$_3$, $R^b$=t-butyl): A 1-L round bottom flask was charged with 25 g (57 mmol) of (3R)-(−)-3-ethyl-3,4-dihydro-8-(trifluoroacetyl)-4-(2,2,2-trifluoroethyl)-7-(trimethylacetamido)-2H-1,4-benzoxazine, 23.8 g (68.4 mmol) of (carbethoxymethylene)-triphenyl phosphorane and 500 mL of toluene. The solution was heated to reflux for 4–5 hours until TLC indicated that the starting material was gone. The toluene was evaporated and 500 mL of ether/hexane (1:1) was added to the crude product. The solution was then cooled down to −5° C. for several hours and filtered. The filtrate was concentrated under reduced pressure and subject to silica gel column (ethyl acetate: hexane, 1:4) to afford 28.5 g (93%) (3R)-8-[2-(1-carbethoxyprop-1-enyl)]-3-ethyl-3,4-dihydro-4-(2,2,2-trifluoroethyl)-7-(trimethylacetamido)-2H-1,4-benzoxazine as a brown oil. $[\alpha]_D$=−24.4 (CHCl$_3$, c 20.1); $^1$H NMR (CDCl$_3$) δ 8.83 (1H, b), 7.67 (1H, d, J=9.01), 6.94 (1H, d, J=8.99), 4.30 (1H, dd, J=1.64, 10.80), 4.05 (1H, dd, J=2.38, 10.82), 3.92 (1H, m), 3.69 (1H, m), 3.24 (1H, m), 1.59 (2H, m), 1.27 (6H, s), 0.96 (3H, t, J=7.38). $^{13}$C NMR: ppm 186.4, 177.4, 144.3, 129.9, 129.4, 129.3, 126.6, 123.8, 121.0, 120.3, 119.7, 117.4, 116.4, 114.6, 113.5, 111.7, 65.6, 58.6, 52.7, 39.9, 27.7, 22.8, 10.4.

(3R)-3-Ethyl-2,3,4,7-tetrahydro-4-(2,2,2-trifluoroethyl)-10-(trifluoromethyl)-8-H-[1,4]oxazino[2,3-f]guinoline-8-one (Compound 110, Structure 29 of Scheme V, where $R^1$, $R^3$, $R^4$, $R^5$, $R^7$, $R^8$=H, $R^2$=trifluoromethyl, $R^6$=Et, $R^{13}$=CH$_2$CF$_3$): 36 g (70.6 mmol) of (3R)-8-[2-(1-carbethoxyprop-1-enyl)]-3-ethyl-3,4-dihydro-4-(2,2,2-trifluoroethyl)-7-(trimethylacetamido)-2H-1,4-benzoxazine was dissolved in 761 mL of acetic acid and 507 mL of concentrated hydrochloric acid. The solution was heated to reflux for 12 hours until TLC indicated the complete conversion of the starting material. The reaction mixture was then allowed to cool to room temperature. The reaction was neutralized with cold aqueous NaOH solution to pH 6–7 and extracted with EtOAc. The combined organic solution was evaporated and purified by silica gel column. (Ethyl acetate:hexane 1:1) chromatography and subsequent recrystallization from methanol to obtain 23 g of Compound 110 as a yellow solid. Yield: 86%. $[\alpha]_D$=42.0 (EtOH, c 63.5); $^1$H NMR (CDCl$_3$) δ 12.9 (1H, b), 7.15 (1H, s), 7.13 (1H, d, J=8.9), 7.05 (1H, d, J=8.96), 4.37 (1H, d, J=10.76), 3.97 (1H, dd, J=2.04, 10.7), 3.84 (1H, m), 3.74 (1H, m), 3.23 (1H, m), 1.58 (2H, m), 0.97 (3H, t, J=7.52). $^{13}$C NMR: ppm 162.2, 139.5, 137.8, 133.9, 127.8, 125.2, 123.7, 121.9, 121.0, 109.7, 106.5, 64.2, 58.4, 55.1, 22.9, 10.3.

EXAMPLE 42

(±)-2,3,4,7-Tetrahydro-4-(2,2,2-trifluoroethyl)-3,10-bis(trifluoromethyl)-8H-[1,4]oxazino[2,3-f]quinolin-8-one (Compound 141, Structure 29 of Scheme V, where $R^1$, $R^3$, $R^4$, $R^5$, $R^7$, $R^8$=H, $R^2$, $R^6$=trifluoromethyl, $R^{13}$=—CH$_2$, CF$_3$)

2-(2,2,2-Trifluoroethyl)amino-5-nitrophenol (Structure 30 of Scheme VI, where $R^7$, $R^8$=H, $R^{13}$=CH$_2$CF$_3$): To a solution of 2-amino-5-nitrophenol (250 mg, 1.62 mmol) in 3 mL of trifluoroacetic acid stirred at 0° C., was added sodium borohydride (pellets, 375 mg, 9.91 mmol). The orange solution was allowed to slowly warm to rt and stirred for 12 h. The solution was diluted with 50 mL of water and cooled to 0° C. Solid potassium carbonate was then slowly added until the pH reached 7.The solution was extracted with ethyl acetate (2×100 mL) and the combined organic layers were washed with brine (25 mL), dried with anhydrous magnesium sulfate, filtered and concentrated to give an orange solid. Flash chromatography (7:3 hexanes:EtOAc) afforded 0.32 g (83%) of 2-(2,2,2-trifluoroethyl)amino-5-nitrophenol, a yellow solid. $^1$H NMR (400 MHz, acetone-d$_6$) 9.48 (broad s, 1H), 7.79 (dd, 1H, J=9.1, 2.4), 7.67 (d, 1H, J=2.4), 6.96 (d, 1H, J=8.8), 6.20 (broad s, 1H), 4.26–4.18 (m, 2H).

(±)-3,4-Dihydro-3-hydroxy-7-nitro-4-(2,2,2-trifluoroethyl)-3-(trifluoromethyl)-2H-1,4-benzoxazine (Structure 24 of Scheme VI, where $R^3$, $R^4$, $R^7$, $R^8$=H, $R^5$=OH, $R^6$=trifluoromethyl, $R^{13}$=CH$_2$CF$_3$): To solution of 2-(trifluoroethyl)amino-5-nitrophenol (100 mg, 0.45 mmol) and potassium carbonate (250 mg, 1.81 mmol) in 0.5 mL of dry dimethyformamide pre-heated to 65–75° C. was added 1-bromo-3,3,3-trifluoroacetone (0.28 mL, 2.70 mmol) via a syringe pump over 2 h. The crimson solution was then allowed to stir for 2–3 hours at 65–75° C., then the solution was allowed to cool to room temperature, extracted with ethyl acetate (2×50 mL) and washed with brine (25 mL). The organic layer was dried with anhydrous magnesium sulfate, filtered and concentrated under reduced pressure to give a brown oil. The crude oil was purified via flash chromatography (4:1 hexanes:EtOAc) to afford 97 mg (63%) of (+)-3,4-dihydro-3-hydroxy-7-nitro-4-(2,2,2-trifluoroethyl)-3-(trifluoromethyl)-2H-1,4-benzoxazine. $^1$H NMR (400 MHz, CDCl$_3$) d 7.89 (dd, 1H, J=7.8, 2.5), 7.80 (d, 1H, J=2.5), 6.94 (d, 1H, J=9.1), 4.71 (d, 1H, J=11.5), 4.51–4.63 (s, 1H), 4.08–4.12 (m, 1H), 4.00–4.06 (m, 2H).

(±)-3,4-Dihydro-7-nitro-4-(2,2,2-trifluoroethyl)-3-(trifluoromethyl)-2H-1,4-benzoxazine (Structure 24 of Scheme VI, where R$^3$, R$^4$, R$^5$, R$^7$, R$^8$=H, R$^6$=trifluoromethyl, R$^{13}$=CH$_2$CF$_3$): To a solution of (±)-3,4-dihydro-3-hydroxy-7-nitro-4-(2,2,2-trifluoroethyl)-3-(trifluoromethyl)-2H-1,4-benzoxazine (0.10 g, 0.29 mmol) in 3 mL of trifluoroacetic acid and then sodium cyanoborohydride (3.0 g, 47.4 rmmol) was slowly added via an solid addition funnel under nitrogen at 0° C. over the course of 30 minutes the reaction was allowed to warm to rt and stirred for 12 hours. The reaction mixture was then diluted with water and cooled to 0° C. Solid potassium carbonate was then added slowly to pH 7.The solution was extracted with ethyl acetate (2×100 mL) and the combined organic layers were washed with brine (50 mL), dried over magnesium sulfate, filtered and evaporated under reduced pressure to give an oil. The oil was purified via flash chromatography (7:3 hexanes:EtOAc) to afford 51 mg (52%) of (±)-3,4-dihydro-7-nitro-4-(2,2,2-trifluoroethyl)-3-(trifluoromethyl)-2H-1,4-benzoxazine. $^1$H NMR (400 MHz, CDCl$_3$) d 7.87 (dd, 1H, J=9.1, 2.8), 7.81 (d, 1H, J=2.5), 6.92 (d, 1H, J=9.1), 4.73 (d, 1H, J=12.1), 4.48–4.39 (m, 1H), 4.13–4.06 (m, 2H), 3.99–3.88 (mn, 1H).

(±)-7-Amino-3,4-dihydro-4-(2,2,2-trifluoroethyl)-3-(trifluoromethyl)-2H-1,4-benzoxazine (Structure 25 of Scheme V, where R$^3$, R$^4$, R$^5$, R$^7$, R$^8$=H, R$^6$=trifluoromethyl, R$^{13}$=CH$_2$CF$_3$): To a solution of (±)-3,4-dihydro-7-nitro-4-(2,2,2-trifluoroethyl)-3-(trifluoromethyl)-2H-1,4-benzoxazine (100 mg, 0.30 mmol) in 1.5 mL ethyl acetate was added 10% Pd—C (42 mg). The reaction mixture was then purged with nitrogen and then purged with hydrogen. A hydrogen balloon was then inserted through a septum into the reaction mixture and allowed to stir for 3 hours at room temperature. The solution was then filtered through a pad of celite and rinsed with ethyl acetate. The solvent was evaporated under reduced pressure to give a crude brown oil which was purified via flash chromatography (2:1 hexanes:EtOAc) to afford 85 mg (93%) (±)-7-amino-3,4-dihydro-4-(2,2,2-trifluoroethyl)-3-(trifluoromethyl)-2H-1,4-benzoxazine. $^1$H NMR (400 MHz, CDCl$_3$) 6.68 (d, 1H, J=8.4), 6.32–6.28 (m, 2H), 4.56 (dd, 1H, J=12.0, 0.96), 4.16–4.00 (m, 2H), 3.84–3.69 (m, 2H), 3.60–3.32 (m, 2H).

(±)-3,4-Dihydro-4-(2,2,2-trifluoroethyl)-3-(trifluoromethyl)-7-(trimethylacetamido)-2H-1,4-benzoxazine (Structure 26 of Scheme V, where R$^3$, R$^4$, R$^5$, R$^7$, R$^8$=H, R$^6$=trifluoromethyl, R$^{13}$=CH$_3$, R$^b$=t-butyl): To a solution of (±)-7-amino-3,4-dihydro-4-(2,2,2-trifluoroethyl)-3-(trifluoromethyl)-2H-1,4-benzoxazine (140 mg, 0.47 mmol) in 5 mL EtOAc was added trimethylacetyl chloride (0.085 mL, 0.70 mmol) and anhydrous pyridine (0.056 mL, 0.70 mmol). The solution was allowed to stir at rt for 12 h. The solution was then washed sequentially with saturated sodium bisulfate (2×10 mL), copper sulfate (10 mL) and brine (10 mL). The organic phase was dried with anhydrous magnesium sulfate, filtered and the solvent was evaporated under reduced pressure to yield an oil. The oil was purified via flash chromatography (7:3 hexanes:EtOAc) to afford 160 mg (89%) of (±)-3,4-dihydro-4-(2,2,2-trifluoroethyl)-3-(trifluoromethyl)-7-(trimethylpropionamido)-2H-1,4-benzoxazine. $^1$H NMR (CDCl$_3$, 400 MHz) d 1.25 (s, 9H), 3.78 (sext, J=8.0 Hz, 1H), 3.88 (m, 1H), 4.02 (m, 1H), 4.22 (sext. J=8.3 Hz, 1H), 4.59 (d, J=11.6 Hz, 1H), 6.77 (d, J=8.8 Hz, 1H), 7.05 (dd, J=2.4 Hz, 8.8 Hz, 1H), 7.11 (d, J=2.44 Hz, 1H), 7.15 (s, 1H).

(±)-3,4-Dihydro-8-(trifluoroacetyl)-4-(2,2,2-trifluoroethyl)-3-(trifluoromethyl)-7-(trimethylacetamido)-2H-1,4-benzoxazine (Structure 27 of Scheme V, where R$^3$, R$^4$, R$^5$, R$^7$, R$^8$=H, R$^2$, R$^6$=trifluoromethyl, =CH$_2$CF$_3$, R$^b$=t-butyl): To a solution of (±)-7-(2,2-dimethylpropionamido)-3,4-dihydro-4-(2,2,2-trifluoroethyl)-3-(trifluoromethyl)-2H-1,4-benzoxazine (200 mg, 0.52 mmol) in 3 mL of dry diethyl ether at −30° C. was added t-butyllithium (1.7M/pentane, 0.80 mL, 1.35 mmol) was added dropwise over of 30 min and then stirred at −10° C. The deep yellow solution was allowed to stir at −10° C. for 5–6 hours and then recooled to −30° C. and trifluoroethyl acetate (0.186 mL, 1.56 mmol) was slowly added. The reaction was allowed to gradually warm to room temperature over the course of 12 hours. The reaction was quenched with saturated ammonium chloride (2 mL) and extracted with ethyl acetate (2×10 mL). The combined organic layers were washed with brine (5 mL), dried over anhydrous magnesium sulfate, filtered and evaporated under reduced pressure to give a brown oil. The substrate was purified via flash chromatography (4:1 hexanes:EtOAc) to afford 40 mg (15%) of (±)-3,4-dihydro-8-(trifluoroacetyl)-4-(2,2,2-trifluoroethyl)-3-(trifluoromethyl)-7-(trimethylacetamido)-2H-1,4-benzoxazine. $^1$H NMR (400 MHz, CDCl$_3$) d 8.92 (s, 1H), 7.81 (d, 1H), 7.06 (d, 1H), 4.68 (d, 1H, J=12), 4.22–4.38 (m, 1H), 4.05–4.12 (m, 1H), 3.93–4.20 (m, 1H), 3.78–3.91 (m, 1H), 1.28 (s, 9H).

(±)-8-[2-(1-Carbethoxyprop-1-enyl)]-3,4-dihydro-4-(2,2,2-trifluoroethyl)-3-(trifluoromethyl)-7-(trimethylacetamido)-2H-1,4-benzoxazine (Structure 28 of Scheme V, where R$^1$, R$^3$, R$^4$, R$^5$, R$^7$, R$^8$=H, R$^2$, R$^6$=trifluoromethyl, R$^{13}$=CH$_2$CF$_3$, R$^b$=t-butyl): A solution of (±)-3,4-dihydro-8-(trifluoroacetyl)-4-(2,2,2-trifluoroethyl)-3-(trifluoromethyl)-7-(trimethylacetamido)-2H-1,4-benzoxazine (40 mg, 0.08 mmol) and (carboxymethylene)triphenyl phosphorane (35 mg, 0.10 nmmol) in 1 mL of dry toluene was heated at reflux for 5 h, whereupon the solvent was removed under reduced pressure to afford an oil. Flash chromatography (7:3 hexanes:EtOAc) afforded 18 mg (40%) of (±)-8-[2-(1-carbethoxyprop-1-enyl)]-3,4-dihydro-4-(2,2,2-trifluoroethyl)-3-(trifluoromethyl)-7-(trimethylacetamido)-2H-1,4-benzoxazine. $^1$H NMR (400 MHz, CDCl$_3$) d 7.61 (d, 1H), 7.22 (s, 1H), 6.92 (d, 1H), 6.30 (s, 1H), 4.62–4.71 (m, 1H), 4.25–4.34 (m, 1H), 4.05–4.10 (m, 1H), 3.92–4.05 (m, 1H), 3.79–3.91 (m, 1H), 1.38 (t, 3H), 1.29 (s, 9H), 1.23 (q, 2H).

(±)-2,3,4,7-Tetrahydro-4-(2,2,2-trifluoroethyl)-3,10-bis(trifluoromethyl)-8H-[1,4]oxazino[2,3-f]quinolin-8-one (Compound 141, Structure 29 of Scheme V, where R$^1$, R$^3$, R$^4$, R$^5$, R$^7$, R$^8$=H, R$^2$=trifluoromethyl, R$^6$=trifluoromethyl, R$^{13}$=—CH$_2$C$_3$): A solution of (±)-8-[2-(1-carbethoxyprop-1-enyl)]-3,4-dihydro-4-(2,2,2-trifluoroethyl)-3-(trifluoromethyl)-7-(trimethylacetamido)-2H-1,4-benzoxazine (18 mg, 0.030 mmol) in 0.33 mL of acetic acid and 0.20 mL of concentrated hydrochloric acid was heated at reflux for 12 h. Ethyl acetate (10 mL) was added and the solution was neutralized with 6 N sodium hydroxide until the pH reached 7.The mixture was extracted with ethyl acetate (2×5 mL) and the combined organic layers were dried with anhydrous magnesium sulfate, filtered and evaporated under reduced pressure to give a greenish-brown oil. The crude product was purified via flash chromatography (1:1 hexanes EtOAc) to afford 6 mg (42%) of Compound 141, a yellow solid. $^1$H NMR (400 MHz, CDC13) δ 11.4 (broad s, 1H), 7.21 (d, J=9.2 Hz, 1H), 7.16 (s, 1H), 7.00 (d, J=9.2 Hz, 1H), 4.78 (d, AB, J=9.0, 1H), 4.29–4.38 (m, 1H), 4.05–4.11 (m, 1H), 3.90–4.05 (m, 1H), 3.83–3.93 (m, 1H).

EXAMPLE 43

(−)-2,3,4,7-Tetrahydro-4-(2,2,2-trifluoroethyl)-3,10-bis(trifluoromethyl)-8H-[1,4]oxazino[2,3-f]quinolin-8-one (Compound 142, Structure (−)-29 of Scheme V, where $R^1$, $R^3$, $R^4$, $R^6$, $R^7$, $R^8$=H, $R^2$=trifluoromethyl, $R^5$=trifluoromethyl, $R^{13}$=—CH$_2$CF$_3$)and (+)-2,3,4,7-Tetrahydro-4-(2,2,2-trifluoroethyl)-3,10-bis(trifluoromethyl)-8H-[1,4]oxazino[2,3-f]quinolin-8-one (Compound 143, Structure (+)-29 of Scheme V, where $R^1$, $R^3$, $R^4$, $R^5$, $R^7$, $R^8$=H, $R^2$=trifluoromethyl, $R^6$=trifluoromethyl, $R^{13}$=—CH$_2$CF$_3$)

Compound 141 (3 mg) was dissolved in hexanes:isopropanol was separated by chiral HPLC on a preparative Chiralpak AS column (20×250 mm) on a Beckman Gold HPLC with 14% ethanol:hexanes at a rate of 6.0 mL/min, to afford 1.2 mg each of Compound 142 and Compound 143. Data for Compound 142: HPLC (Chiralpak AS prep, 20×250 mm, 14% EtOH/hexanes, 6 mL/min) $t_R$ 22.5 min; $[\alpha]_D$=−20 (c=0.11,EtOH). Data for Compound 143:HPLC (Chiralpak AS prep, 20×250 mm, 14% EtOH/hexanes, 6 mL/min) tR 28.6 min; $[\alpha]_D$=+15 (c=0.12,EtOH).

EXAMPLE 44

(±)-2,3,4,7-Tetrahydro-3-(2,2,2-trifluoroethyl)-10-(trifluoromethyl)-8H-[1,4]oxazino[2,3-f]quinolin-8-one (Compound 144, Structure 9 of Scheme II, where $R^1$, $R^3$, $R^4$, $R^5$,=H, $R^2$=trifluoromethyl, $R^6$=2,2,2-trifluoroethyl)

(±)-6-Bromo-5-[(2'-t-butoxycarbonylamino)-(4',4', 4'-trifluoro)-1'-butoxy]-2-isopropoxy-4-(trifluoromethyl)quinoline (Structure 7 of Scheme II, where $R^1$, $R^3$, $R^4$, $R^5$, =H, $R^2$=trifluoromethyl, $R^6$=2,2,2-trifluoroethyl): This compound was prepared according to General Method 1 (EXAMPLE 1) from 6-bromo-5-hydroxy-2-isopropoxy-4-(trifluoromethyl)quinoline (0.086 g, 0.24 mmol), (±)-2-N-t-butoxycarbonylamino-4,4,4-trifluoro-1-butanol (0.12 g, 0.49 mmol), triphenylphosphine (0.13 g, 0.49 mmol), DIAD (0.1 mL, 0.49 mmol) and N-methylmorpholine (0.09 mL) in THF (4 mL) to afford 0.061 g (43%) of (±)-6-bromo-5-[(2'-t-butoxycarbonylamino)-(4',4',4'-trifluoro)-1'-butoxy]-2-isopropoxy-4-(trifluoromethyl)quinoline as a tan solid. $^1$H NMR (500 MHz, CDCl$_3$) δ 7.81 (d, J=8.8, 1H), 7.58 (d, J=9.3, 1H), 7.31 (s, 1H), 5.53 (m, 1H), 5.00 (bm, 1H), 4.41 (bm, 1H), 4.10 (bm, 2H), 2.74 (bm, 2H), 1.46 (bs, 9H), 1.42 (s, 3H), 1.41 (s, 3H).

(±)-3,4-Dihydro-8-isopropoxy-3-(2,2,2-trifluoroethyl)-10-(trifluoromethyl)-2H-[1,4]oxazino[2,3-f]quinoline (Structure 8 of Scheme II, where $R^1$, $R^3$, $R^4$, $R^5$,=H, $R^2$=trifluoromethyl, $R^6$=2,2,2-trifluoroethyl): This compound was prepared according to General Method 2 (EXAMPLE 1) from (±)-6-bromo-5-[(2'-t-butoxycarbonylamino)-(4',4',4'-trifluoro)-1'-butoxy]-2-isopropoxy-4-(trifluoromethyl)quinoline (0.061 g, 0.11 mmol) in CH$_2$Cl$_2$ (2 mL) and TFA (2 mL) to afford 0.038 g (75%) of (±)-6-bromo-5-[(2'-amino-(4',4',4'-trifluoro)-1'-butoxy]-2-isopropoxy-4-(trifluoromethyl)quinoline. $^1$H NMR (500 MHz, CDCl$_3$) δ 7.81 (d, J=9.3, 1H), 7.58 (d, J=8.8, 1H), 7.32 (s, 1H), 5.53 (m, 1H), 3.91 (m, 2H), 3.85 (m, 1H), 2.57 (m, 1H), 2.24 (m, 1H), 1.65 (bs, 2H), 1.42 (d, J=2.0, 3H), 1.41 (d, J=1.5, 3H). This material (0.038g, 0.08 mmol) was carried on according to General Method 3 (EXAMPLE 1) by treatment with Pd$_2$(dba)$_3$ (1.5 mg), BINAP (2 mg) and t-BuONa (11 mg, 0.12 mmol) in toluene (1 mL) heated at reflux to afford 0.025 g (79%) of (±)-3,4-dihydro-8-isopropoxy-3-(2,2,2-trifluoroethyl)-10-(trifluoromethyl)-2H-[1,4]oxazino[2,3-f]quinoline, a yellow solid. $^1$H NMR (500 MHz, CDCl$_3$) δ 7.41 (d, J=8.9, 1H), 7.20 (s, 1H), 7.04 (d, J=8.9, 1H), 5.48 (m, 1H), 4.30 (dd, J=10.7, 3.1, 1H), 4.11 (m, 2H), 3.95 (m, 1H), 2.41 (m, 2H), 1.39 (s, 3H), 1.38 (s, 3H).

(±)-2,3,4,7-Tetrahydro-3-(2,2,2-trifluoroethyl)-10-(trifluoromethyl)-8H-[1,4]oxazino[2,3-f]quinolin-8-one (Compound 144, Structure 9 of Scheme II. where $R^1$, $R^3$, $R^4$, $R^5$,=H, $R^2$=trifluoromethyl, $R^6$=2,2,2-trifluoroethyl): Compound 144 was prepared according to General Method 4 (EXAMPLE 1) from (±)-3-ethyl-3,4-dihydro-8-isopropoxy-3-(2,2,2-trifluoroethyl)-10-(trifluoromethyl)-2H-[1,4]oxazino[2,3-f]quinoline (8 mg, 0.02 mmol) in conc. HCl (1 mL) in AcOH (1 mL) heated at 90° C. to afford Compound 144, a yellow solid. $^1$H NMR (500 MHz, CDCl$_3$) δ 11.91 (bs, 1H), 7.14 (s, 1H), 6.94 (s, 2H), 4.31 (dd, J=10.7, 2.4, 1H), 4.08 (m, 1H), 4.05 (bs, 1H), 3.92 (m, 1H), 2.38 (m, 2H).

EXAMPLE 45

(±)-2,3,4,7-Tetrahydro-4-methyl-3-(2,2,2-trifluoroethyl)-10-(trifluoromethyl)-8H-[1.4]oxazino[2,3-f]guinolin-8-one (Compound 145, Structure 11 of Scheme II, where $R^1$, $R^3$, $R^4$, $R^5$, $R^7$, $R^8$=H, $R^2$=trifluoromethyl, $R^6$=2,2,2-trifluoroethyl, $R^{13}$=CH$_3$)

(±)-3,4-Dihydro-8-isopropoxy-4-methyl-3-(2,2,2-trifluoroethyl)-10-(trifluoromethyl)-2H-[1,4]oxazino[2,3-f]quinoline (Structure 10 of Scheme II, where $R^1$, $R^3$, $R^4$, $R^5$, $R^7$, $R^8$=H, $R^2$=trifluoromethyl, $R^6$=2,2,2-trifluoroethyl, $R^{13}$=CH$_3$). This compound was prepared by General Method 5 (EXAMPLE 1) from (±)-3,4-dihydro-8-isopropoxy-3-(2,2,2-trifluoroethyl)-10-(trifluoromethyl)-2H-[1,4] oxazino[2,3-f]quinoline (0.025 g, 0.06 mmol), paraformaldehyde (0.02 g, 0.6 mmol) and NaCNBH$_3$ (0.04 g, 0.6 mmol) in 2 mL glacial acetic acid to afford 0.017 g (65%) of (±)-3-ethyl-3,4-dihydro-8-isopropoxy-4-methyl-3-(2,2,2-trifluoroethyl)-10-(trifluoromethyl)-2H-[1,4]oxazino[2,3-f] quinoline, of sufficient purity as to be used directly in the next reaction. $^1$H NMR (500 MHz, CDCl$_3$) 7.48 (d, J=8.8, 1H), 7.22 (d, J=9.3, 1H), 7.21 (s, 1H), 5.49 (m, 1H), 4.37 (d, J=10.7, 1H), 4.08 (d, J=10.7, 1H), 3.68 (m, 1H), 3.05 (s, 3H), 2.40 (m, 2H), 1.39 (d, J=6.3, 3H), 1.38 (d, J=6.3, 3H).

(±)-2,3,4,7-Tetrahydro-4-methyl-3-(2,2,2-trifluoroethyl)-10-(trifluoromethyl-8H-[1,4]oxazino[2,3-f]quinolin-8-one (Compound 145, Structure 11 of Scheme II, where $R^1$, $R^3$, $R^4$, $R^5$, $R^7$, $R^8$=H, $R^2$=trifluoromethyl, $R^{13}$=2,2,2-trifluoroethyl, $R^3$=CH$_3$): Compound 145 was prepared according to General Method 4 (EXAMPLE 1) from (±)-3,4-dihydro-8-isopropoxy-4-methyl-3-(2,2,2-trifluoroethyl)-10-(trifluoromethyl)-2H-[1,4]oxazino[2,3-f]quinoline (0.017 g, 0.04 mmol) in conc. HCl (1.5 mL) in AcOH (1.5 mL) heated at 90° C. to afford Compound 145, a yellow solid. $^1$H NMR (500 MHz, CDCl$_3$) δ 12.52 (bs, 1H), 7.16 (s, 1H), 7.06 (d, J=9.3, 1H), 7.04 (d, J=9.3, 1H), 4.38 (dd, J=11.23, 2.0, 1H), 4.11 (d, J=5.4, 1H), 3.67 (m, 1H), 3.00 (s, 3H), 2.38 (m, 2H).

EXAMPLE 46

(±)-4-Ethyl-2,3,4,7-tetrahydro-3-(2,2,2-trifluoroethyl)-10-(trifluoromethyl)-8H-[1,4]oxazino[2,3-f] quinolin-8-one (Compound 146, Structure 11 of Scheme II, where $R^1$, $R^3$, $R^4$, $R^5$, $R^7$, $R^8$=H, $R^2$=trifluoromethyl, $R^6$=2,2,2-trifluoroethyl, $R^{13}$=Et)

(±)-4-Ethyl-3,4-Dihydro-8-isopropoxy-3-(2,2,2-trifluoroethyl)-10-(trifluoromethyl)-2H-[1,4]oxazino[2,3-f]quinoline (Structure 10 of Scheme II, where $R^1$, $R^3$, $R^4$, $R^5$, $R^7$, $R^8$=H, $R^2$=trifluoromethyl, $R^6$=2,2,2-trifluoroethyl, $R^{13}$=Et): This compound was prepared by General Method 5 (EXAMPLE 1) from (±)-3,4-dihydro-8-isopropoxy-3-(2,2,2-trifluoroethyl)-10-(trifluoromethyl)-2H-[1,4]oxazino[2,3-f]quinoline (0.019 g, 0.05 mmol) and NaBH$_4$ (0.5 pellets, >0.5 mmol) in 2 mL glacial acetic acid to afford (±)-4-ethyl-3,4-dihydro-8-isopropoxy-3-(2,2,2-trifluoroethyl)-10-(trifluoromethyl)-2H-[1,4]oxazino[2,3-f]quinoline, of sufficient purity as to be used directly in the next reaction.

(±)-3-Ethyl-2,3,4,7-Tetrahydro-3-(2,2,2-trifluoroethyl)-10-(trifluoromethyl)-8H-[1,4]oxazino[2,3-f]quinolin-8-one (Compound 146, Structure 11 of Scheme II, where $R^1$, $R^3$, $R^4$, $R^5$, $R^7$, $R^8$=H, $R^2$=trifluoromethyl, $R^{13}$=2,2,2-trifluoroethyl, $R^{13}$=Et): Compound 146 was prepared according to General Method 4 (EXAMPLE 1) from (±)-4-ethyl-3,4-dihydro-8-isopropoxy-3-(2,2,2-trifluoroethyl)-10-(trifluoromethyl)-2H-[1,4]oxazino[2,3-f]quinoline in conc. HCl (2.5 mL) in AcOH (2.5 mL) heated at 90° C. to afford Compound 146, a yellow solid. $^1$H NMR (500 MHz, CDCl$_3$) δ 11.97 (bs, 1H), 7.15 (s, 1H), 7.06 (d, J=9.3, 1H), 7.01 (d, J=8.8, 1H), 4.38 (dd, J=1.0, 10.7, 1H), 3.88 (d, J=11.2, 1H), 3.71 (m, 1H), 3.47 (m, 1H), 3.25 (m, 1H), 2.41 (m, 1H), 2.28 (m, 1H), 1.22 (t, J=7.3, 3H).

EXAMPLE 47

(±)-2,3,4,7-Tetrahydro-3,4-bis(2,2,2-trifluoroethyl)-10-(Trifluoromethyl)-8H-[1,4]oxazino[2,3-f]quinolin-8-one (Compound 147, Structure 11 of Scheme II, where $R^1$, $R^3$, $R^4$, $R^5$, $R^7$, $R^8$=H, $R^2$=trifluoromethyl, $R^6$=2,2,2-trifluoroethyl, $R^{13}$=2,2,2-trifluoroethyl)

(±)-3,4-Dihydro-8-isopropoxy-3,4-bis(2,2,2-trifluoroethyl)-10-(trifluoromethyl)-2H-[1,4]oxazino[2,3-f]quinoline (Structure 10 of Scheme II, where $R^1$, $R^3$, $R^4$, $R^5$,=H, $R^2$=trifluoromethyl, $R^6$=2,2,2-trifluoroethyl, $R^{13}$=2,2,2-trifluoroethyl): This compound was prepared by General Method 5 (EXAMPLE 1) from (±)-3,4-dihydro-8-isopropoxy-3,4-bis(2,2,2-trifluoroethyl)-10-(trifluoromethyl)-2H-[1,4]oxazino[2,3-f]quinoline (0.02 g, 0.05 mmol) and NaBH$_4$ (0.5 pellets, >0.5 mmol) in 4 mL trifluoroacetic acid to afford 0.02 g (83%) of (±)-3,4-dihydro-8-isopropoxy-4-methyl-3,4-bis(2,2,2-trifluoroethyl)-10-(trifluoromethyl)-2H-[1,4]oxazino[2,3-f]quinoline, of sufficient purity as to be used directly in the next reaction.

(±)-2,3,4,7-Tetrahydro-3,4-bis(2,2,2-trifluoroethyl)-10-(trifluoromethyl)-8H-[1,4]oxazino[2,3-f]quinolin-8-one (Compound 147, Structure 11 of Scheme II, where $R^1$, $R^3$, $R^4$, $R^5$,=H, R=trifluoromethyl, $R^6$=2,2,2-trifluoroethyl, $R^{13}$=2,2,2-trifluoroethyl): Compound 147 was prepared according to General Method 4 (EXAMPLE 1) from (±)-3,4-dihydro-8-isopropoxy-4-methyl-3-(2,2,2-trifluoroethyl)-10-(trifluoromethyl)-2H-[1,4]oxazino[2,3-f]quinoline (0.02 g, 0.04 mmol) in conc. HCl (2 mL) in AcOH (2 mL) heated at 90° C. to afford 12 mg (67%) of Compound 147, a yellow solid. $^1$H NMR (500 MHz, CDCl$_3$) 12.57 (bs, 1H), 7.18 (s, 1H), 7.17 (d, J=8.8, 1H), 7.08 (d, J=8.8, 1H), 4.44 (dd, J=10.7, 1.0, 1H), 4.06 (m, 1H), 3.96 (m, 1H), 3.79 (m, 1H), 3.73 (m, 1H), 2.38 (m, 2H).

EXAMPLE 48

(−)-2,3,4,7-Tetrahydro-3,4-bis(2,2,2-trifluoroethyl)-10-(trifluoromethyl)-8H-[1,4]oxazino[2,3-f]quinolin-8-one (Compound 148, Structure 11 of Scheme II, where $R^1$, $R^3$, $R^4$, $R^5$,=H, $R^2$=trifluoromethyl, $R^6$=2,2,2-trifluoroethyl, $R^{13}$=2,2,2-trifluoroethyl), and (+)-2,3,4,7-Tetrahydro-3,4-bis(2,2,2-trifluoroethyl)-10-(trifluoromethyl)-8H-[1,4]oxazino[2,3-f]quinolin-8-one (Compound 149, Structure 11 of Scheme II, where $R^1$, $R^3$, $R^4$, $R^5$,=H, $R^2$=trifluoromethyL, $R^6$=2,2,2-trifluoroethyl, $R^{13}$=2,2,2-trifluoroethyl)

Compound 147 (12 mg) was dissolved in hexanes:ethanol was separated by chiral HPLC on a preparative Chirapak AS column (20×250 mm) on a Beckman Gold HPLC with 86% hexanes:ethanol at a rate of 7.0 mL/min, to afford 6 mg each of Compound 148 and Compound 149. Data for Compound 148: HPLC (Chirapak AS prep, 14% EtOH/hexanes, 7 mL/min) $t_R$ 25.6;[α]$_D$=−35.9 (c=0.30,EtOH). Data for Compound 149: HPLC (Chiralpak AS prep, 20×250 mm, 14% EtOH/hexanes, 6 mL/min) $t_R$ 64.1 min; [α]$_D$=+34.6 (c=0.31, EtOH).

EXAMPLE 49

(±)-4-Cyclopropylmethyl-2,3,4,7-tetrahydro-3-(2,2,2-trifluoroethyl)-10-(trifluoromethyl)-8H-[1,4]oxazino[2,3-f]quinolin-8-one (Compound 150, Structure 11 of Scheme II, where $R^1$, $R^3$, $R^4$, $R^5$,=H, $R^2$=trifluoromethyl $R^6$=2,2,2-trifluoroethyl, $R^{13}$=cyclopropylmethyl)

Compound 150 was prepared by General Method 5 (EXAMPLE 1) Compound 144 (0.02 g, 0.06 mmol), cyclopropylmethylcarboxaldehyde (0.05 mL, 0.6 mmol) and NaCNBH$_3$ (0.036 g, 0.6 mmol) in 1 mL glacial acetic acid and 3 mL methanol to afford Compound 150. $^1$H NMR (500 MHz, CDCl$_3$) 12.55 (bs, 1H), 7.20 (s, 1H), 7.17 (d, J=8.6, 1H), 7.05 (d, J=9.2, 1H), 4.41 (dd, J=10.7, 1.2, 1H), 4.01 (d, J=9.2, 1H), 3.89 (m, 1H), 3.35 (dd, J=15.0, 6.1, 1H), 3.04 (dd, J=14.7, 6.7, 1H), 2.34 (m, 2H), 1.04 (m, 1H), 0.61 (m, 2H), 0.25 (m, 2H).

EXAMPLE 50

(3R)-4-Cyclopropylmethyl-3-ethyl-2,3,4,7-tetrahydro-10-(trifluoromethyl)-8H-[1,4]oxazino[2,3-f]quinolin-8-one (Compound 151, Structure 11 of Scheme II, where $R^1$, $R^3$, $R^4$, $R^5$,=H, $R^2$=trifluoromethyl, $R^6$=ethyl, $R^{13}$=cyclopropylmethyl)

Compound 151 was prepared by General Method 5 (EXAMPLE 1) Compound 107 (0.015 g, 0.05 mmol), cyclopropylmethylcarboxaldehyde (0.05 mL, 0.5 mmol) and NaCNBH$_3$ (0.032 g, 0.5 mmol) in 1 mL glacial acetic acid and 3 mL methanol to afford Compound 151. $^1$H NMR (500 MHz, CDCl$_3$) δ 12.23 (bs, 1H), 7.15 (d, J=8.9, 1H), 7.13 (s, 1H), 6.98 (d, J=8.9, 1H), 4.33 (dd, J=10.4, 1.8, 1H), 3.96 (dd, J=10.4, 2.4, 1H), 3.37 (dd, J=14.6, 5.8, 1H), 3.34 (m, 1H), 3.00 (dd, J=15.0, 7.0, 1H), 1.55 (m, 2H), 1.03 (m, 1H), 0.97 (t, J=7.6, 3H), 0.57 (m, 2H), 0.23 (m, 2H).

EXAMPLE 51

(3R)-4-(2-Chloroethyl)-2,3,4,7-tetrahydro-3-isopropyl-10-(trifluoromethyl)-8H-[1,4]oxazino[2,3-f]quinolin-8-one (Compound 152, Structure 11 of Scheme II, where $R^1$, $R^3$, $R^4$, $R^5$,=H, $R^2$=trifluoromethyl, $R^6$=isopropyl, $R^{13}$=2-chloroethyl)

Compound 152 was prepared according to General Method 5 (EXAMPLE 2) from (3R)-3,4-dihydro-8-isopropoxy-3-isopropyl-10-(trifluoromethyl)-2H-[1,4]oxazino[2,3-f]quinoline (16 mg, 0.05 mmol) and $NaBH_4$ pellets (>10 equiv) in 0.5 g chloroacetic acid to afford 11 mg (58%) of (3R)-4-(2-chloroethyl)-3,4-dihydro-8-isopropoxy-3-isopropyl-10-(trifluoromethyl)-2H-[1,4]oxazino[2,3-f]quinoline. This material (11 mg, 0.03 mmol) was carried on according to General Method 4 (EXAMPLE 1) by treatment with 4 mL of 1:1 acetic acid:concentrated HCl (0.02M) heated at 90° C. for 4 h to afford Compound 152. $^1$H NMR (500 MHz, $CDCl_3$) 12.06 (bs, 1H), 7.13 (s, 1H), 7.12 (d, J=8.8, 1H), 6.98 (d, J=8.8, 1H), 4.53 (dd, J=10.7, 1.5, 1H), 3.88 (dd, J=10.7, 2.4, 1H), 3.82 (m, 1H), 3.71 (m, 1H), 3.63 (m, 1H), 3.49 (m, 1H), 2.93 (m, 1H), 1.82 (m, 1H), 0.99 (d, J=10.3, 3H), 0.98 (d, J=10.3, 3H).

EXAMPLE 52

(±)-2,3,4,7-Tetrahydro-2-methyl-4-(2,2,2-trifluoroethyl)-10-(trifluoromethyl)-8H-[1,4]oxazino[2,3-f]quinolin-8-one (Compound 153, Structure 11 of Scheme II, where $R^3$, $R^4$, $R^5$, $R^6$,=H, $R^2$=trifluoromethyl, $R^3$=Me, $R^{13}$=$CH_2CF_3$)

(±)-6-Bromo-5-[(1-t-butoxycarbonylamino)-2'-propoxy]-2-isopropoxy-4-(trifluoromethyl)quinoline (Structure 7 of Scheme II, where $R^1$, $R^4$, $R^5$, $R^6$,=H, $R^2$=trifluoromethyl, $R^3$=Me): The compound was prepared according to General Method 1 (EXAMPLE 1) from 6-bromo-5-hydroxy-2-isopropoxy-4-(trifluoromethyl)quinoline (0.1 g, 0.3 mmol), (±)-1-N-t-butoxycarbonyl-2-propanol (80 mg, 0.5 mmol), triphenylphosphine (120 mg, 0.5 mmol) and diisopropyl azodicarboxylate (0.09 ml, 0.5 mmol) in 0.12 mL N-methylmorponline in 3 mL dry THF to afford 145 mg (63%) of (±)-6-bromo-5-[(1'-t-butoxycarbonylamino-2'-propoxy]-2-isopropoxy-4-(trifluoromethyl)quinoline after flash chromatography (4:1 hexanes/EtOAc). $^1$H NMR (500 MHz, $CDCl_3$) δ 7.76 (d, J=9.3, 1H), 7.51 (d, J=8.8, 1H), 7.27 (s, 1H), 5.53 (m, 1H), 5.12 (m, 2H), 3.57 (m, 1H), 3.28 (m, 1H), 1.46 (s, 9H), 1.43 (d, J=8.3, 3H), 1.42 (d, J=8.3, 3H), 0.92 (d, J=6.3, 3H).

(±)-6-Bromo-5-(1'-amino-2'-propoxy)-2-isopropoxy-4-(trifluoromethyl)quinoline: This compound was prepared according to General Method 2 (EXAMPLE 1) from (±)-6-bromo-5-[(3'-t-butoxycarbonylamino)-2'-butoxy]-2-isopropoxy-4-(trifluoromethyl)quinoline (91 mg, 0.2 mmol) in 2 mL $CH_2Cl_2$ and 2 mL TFA to afford 86 mg (100%) of (±)-6-bromo-5-(1'-amino-2'-propoxy)-2-isopropoxy-4-(trifluoromethyl)quinoline. $^1$H NMR (500 MHz, $CDCl_3$) δ 7.77 (d, J=8.8, 1H), 7.53 (d, J=8.8, 1H), 7.27 (s, 1H), 5.52 (m, 1H), 5.21 (m, 1H), 3.20 (m, 2H), 1.42 (d, J=10.3, 3H), 1.41 (d, J=10.3, 3H), 0.93 (d, J=6.3, 3H).

(±)-3,4-Dihydro-8-isopropoxy-2-methyl-10-(trifluoromethyl)-2H-[1,4]oxazino[2,3-f]quinoline (Structure 8 of Scheme II, where $R^1$ $R^4$, $R^5$, $R^6$,=H $R^2$=trifluoromethyl, $R^3$=Me): This compound was prepared according to General Method 3 (EXAMPLE 1) from (+)-6-bromo-5-(1'-amino-2'-propoxy)-2-isopropoxy-4-(trifluoromethyl)quinoline (86 mg, 0.2 mmol), (±)-2,2'-bis(diphenylphosphino)-1,1'-binaphthyl (5 mg), $Pd_2(dba)_3$ (4 mg), sodium t-butoxide (28 mg, 0.3 mmol) to afford 9 mg (14%) of (±)-3,4-dihydro-8-isopropoxy-2-methyl-10-(trifluoromethyl)-2H-[1,4]oxazino[2,3-f]quinoline, after purification by flash chromatography (4:1 hexanes:EtOAc). $^1$H NMR (500 MHz, $CDCl_3$) δ 7.35 (d, J=8.8, 1H), 7.18 (s, 1H), 7.04 (d, J=8.8, 1H), 5.48 (m, 1H), 4.23 (m, 1H), 3.82 (m, 1H), 3.47 (dd, J=11.7, 2.4, 1H), 3.22 (dd, J=11.2, 8.3, 1H), 1.44 (d, J=6.3, 3H), 1.39 (d, J=6.3, 3H), 1.38 (d, J=6.3, 3H).

(±)-3,4-Dihydro-8-isopropoxy-2-methyl-4-(2,2,2-trifluoroethyl)-10-(trifluoromethyl)-2H-[1,4]oxazino[2,3-f]quinoline (Structure 10 of Scheme II, where $R^1$, $R^4$, $R^5$, $R^6$, =H, R=trifluoromethyl, $R^3$=Me, $R^{13}$=$CH_2CF_3$): This compound was prepared according to General Method 6 (EXAMPLE 3) from (±)-3,4-dihydro-8-isopropoxy-2-methyl-10-(trifluoromethyl)-2H-[1,4]oxazino[2,3-f]quinoline (9 mg, 0.03 mmol) and $NaBH_4$ pellets (>10 equiv) in 1 mL trifluoroacetic acid to afford 8 mg (73%) of (+)-3,4-dihydro-8-isopropoxy-2-methyl-10-(trifluoromethyl)-2H-[1,4]oxazino[2,3-f]quinoline, which was carried on without purification.

(±)-2,3,4,7-Tetrahydro-2-methyl-4-(2,2,2-trifluoroethyl)-10-(trifluoromethyl)-8H-[1,4]oxazino[2,3-f]quinolin-8-one (Compound 153, Structure 11 of Scheme II, where $R^1$, $R^4$, $R^5$, $R^6$,=H, $R^2$=trifluoromethyl, $R^3$Me, $R^{13}$=$CH_2CF_3$):

Compound 153 was prepared by General Method 4 (EXAMPLE 1) from (±)-3,4-dihydro-8-isopropoxy-2-methyl-10-(trifluoromethyl)-2H-[1,4]oxazino[2,3-f]quinoline (8 mg, 0.02 mmol) in 4 mL of a 1:1 acetic acid:concentrated HCl heated at 90° C. for 4 h to afford Compound 153. $^1$H NMR (500 MHz, $CDCl_3$) 11.68 (bs, 1H), 7.14 (s, 1H), 7.08 (d, J=8.8, 1H), 6.94 (d, J=9.3, 1H), 4.24 (m, 1H), 3.88 (m, 1H), 3.78 (m, 1H), 3.44 (dd, J=11.7, 2.4, 1H), 3.29 (dd, J=11.7, 8.8, 1H), 1.45 (d, J=6.3, 3H).

EXAMPLE 53

(3R)-3-Ethyl-4-(2-hydroxy-2-methylpropyl)-2,3,4,7-tetrahydro-10-(trifluoromethyl)-8H-[1,4]oxazino[2,3-f]quinolin-8-one (Compound 154, Structure 11 of Scheme II, where $R^1$, $R^3$, $R^4$, $R^5$, $R^7$, $R^8$=H, $R^2$=trifluoromethyl, $R^6$=isopropyl, $R^{13}$=2-hydroxy-2-methylpropyl)

(3R)-3-Ethyl-4-(2-methyl-2-propenyl)-3,4-dihydro-8-isopropoxy-10-(trifluoromethyl)-2H-[1,4]oxazino[2,3-f]quinoline: This compound was prepared by treatment of (3R)-3-ethyl-3,4-dihydro-8-isopropoxy-10-(trifluoromethyl)-2H-[1,4]oxazino[2,3-f]quinoline (20 mg, 0.059 mmol), 2-methallyl bromide (40 mg, 0.30 mmol) and $K_2CO_3$ (41 mg, 0.30 mmol) in 1 mL DMF heated at 50° C. for 16 h. The reaction was treated with an additional 2-methallyl bromide (60 mg) and was heated overnight at 50° C. The mixture was extracted with ethyl acetate (2×25 mL), and the combined organic layers were washed with water (25 mL), brine (25 mL), dried over $MgSO_4$, filtered, and concentrated afford 20 mg (87%) of (3R)-3-ethyl-4-(2-methyl-2-propenyl)-3,4-dihydro-8-isopropoxy-10-(trifluoromethyl)-2H-[1,4]oxazino[2,3-f]quinoline after flash chromatography (9:1 hexanes:EtOAc). $^1$H NMR (400 MHz, $CDCl_3$) δ7.39 (d, J=9.0, 1H), 7.18 (s, 1H), 7.12 (d, J=9.0, 1H), 5.47 (septet, J=6.2, 1H), 4.91 (broad s, 2H), 4.33 (dd, J=10.7, 2.1, 1H), 3.96 (dd, J=10.7, 2.6, 1H), 3.85 (d, AB, J=17.1, 1H), 3.80 (d, AB, J=17.1, 1H), 3.20–3.26 (m, 1H), 1.79 (s, 3H), 1.58–1.68 (m, 2H), 1.38 (d, J=6.2, 3H), 1.37 (d, J=6.2, 3H), 0.96 (t, J=7.4, 3H).

(3R)-3-Ethyl-4-(2-hydroxy-2-methylpropyl)-2,3,4,7-tetrahydro-10-(trifluoromethyl)-8H-[1,4]oxazino[2,3-f]quinolin-8-one (Compound 154, Structure 11 of Scheme II, where $R^1$, $R^3$, $R^4$, $R^5$H, $R^2$=trifluoromethyl, $R^6$=isopropyl, $R^{13}$=2-hydroxy-2-methylpropyl): This compound was prepared by General Method 4 (EXAMPLE 1) with some modifications. A solution of (3R)-3-ethyl-4-(2-methyl-2-propenyl)-3,4-dihydro-8-isopropoxy-10-(trifluoromethyl)-2H-[1,4]oxazino[2,3-f]quinoline (11 mg, 0.028 mmol) was heated in 1 mL concentrated HCl at 75° C. and afforded 3 mg (30%) of Compound 154 after sequential column chromatography (9:1 $CH_2Cl_2$:MeOH) and preparative HPLC (ODS semi-prep column, 20×250 mm, 65% MeOH/water, 3 mL/min). $^1$H NMR (400 MHz, $CDCl_3$) δ 11.4 (broad s, 1H), 7.26 (d, J=8.9, 1H), 7.10 (s, 1H), 6.86 (d, J=8.9, 1H), 4.40 (d, J=10.3, 1H), 4.06 (broad d, J=10.3, 1H), 3.29 (d, AB, J=15.0, 1H), 3.20–3.30 (m, 1H), 3.10 (d, AB, J=15.0, 1H), 1.99 (s, 1H), 1.33 (s, 3H), 1.30 (s, 3H), 0.97 (t, J=7.4, 3H).

EXAMPLE 54

(3R)-2,3,4,7-Tetrahydro-3-isobutyl-4-(2,2,2-trifluoroethyl)-10-(trifluoromethyl)-8H-[1,4]oxazino[2,3-f]quinolin-8-one (Compound 155, Structure 17 of Scheme III, where $R^1$, $R^3$, $R^4$, $R^5$, $R^7$, $R^8$=H, $R^2$=trifluoromethyl, $R^6$=isobutyl, $R^{13}$=$CH_2CF_3$)

(2R)-2-(2-Fluoro-4-nitrophenyl)amino-4-methyl-1-pentanol (Structure 21 of Scheme V, where $R^3$, $R^4$, $R^5$, $R^5$, $R^7$, $R^8$=H, $R^6$=isobutyl): This compound was prepared according to the procedure described in EXAMPLE 41 (Structure 21 of Scheme V) from 3,4-difluoronitrobenzene (8.73 g, 54.9 mmol), R-2-amino-4-methyl-1-pentanol (5.00 g, 42.7 mmol) in EtOH heated at reflux for 16 h to afford 6.0 g (55%) of (2R)-2-(2-fluoro-4-nitrophenyl)amino-4-methyl-1-pentanol, a yellow solid, after flash chromatography (gradient elution, hexanes:EtOAc 9:1 to 1:1). Data for (2R)-2-(2-fluoro-4-nitrophenyl)amino-4-methyl-1-pentanol: $R_f$ 0.3 (3:1 hexanes:EtOAc); $^1$H NMR (400 MHz, $CDCl_3$) δ 8.01–7.97 (m, 1H), 7.90 (dd, 1H, J=11.7, 2.7), 6.74 (dd, 1H, J=8.6, 8.6), 4.62–4.57 (m, 1H), 3.82–3.74 (m, 1H), 3.75–3.62 (m, 2H), 1.77–1.65 (m, 1H), 1.61–1.45 (m, 2H), 0.99 (d, 3H, J=6.6), 0.93 (d, 3H, J=6.6).

(4R)-3-(2-Fluoro-4-nitrophenyl)-4-isobutyl-2-(trifluoromethyl)-1,3-oxazolidine (Structure 22 of Scheme V, where $R^1$, $R^4$, $R^5$, $R^7$, $R^8$=H, $R^6$=isobutyl, $R^4$=trifluoromethyl): This compound was prepared according to the procedure described in EXAMPLE 41 (Structure 22 of Scheme V) from (2R)-2-(2-fluoro-4-nitrophenyl)amino-4-methyl-1-pentanol (6.0 g, 23 mmol) trifluoroacetaldehyde ethyl hemiacetal (30.4 g, 211 mmol) and p-toluenesulfonic acid (0.020 g, 0.10 mmol) in 250 mL benzene to afford 5.15 g (65%) of (4R)-3-(2-fluoro-4-nitrophenyl)-4-isobutyl-2-trifluoromethyloxazolidine. Data for (4R)-3-(2-fluoro-4-nitrophenyl)-4-isobutyl-2-trifluoromethyloxazolidine as a mixture of diastereomers: $R_f$ 0.8 (3:1 hexanes:EtOAc); $^1$H NMR (400 MHz, $CDCl_3$) δ 8.03–7.94 (m, 2H), 6.96–6.88 (m, 1H), 5.81 (q, 1H, minor diast., J=4.7), 5.69 (q, 1H, major diast., J=4.7), 4.45–4.40 (m, 1H, minor diast.), 4.36–4.28 (m, 1H, major diast.), 4.11–4.01 (m, 2H), 1.82–1.74 (m, 1H), 1.66–1.52 (m, 2H), 1.02 (d, 3H, major diast., J=6.4), 0.99–0.95 (m, 3H), 0.91 (d, 3H, minor diast., J=6.6).

(2R)-2-[2-Fluoro-4-nitro(2,2,2-trifluoroethyl)anilino]-4-methyl-1-pentanol (Structure 23 of Scheme V, where $R^3$, $R^4$, $R^5$, $R^7$, $R^8$=H, $R^6$=isobutyl, $R^{13}$=$CH_2CF_3$): To a solution of (4R)-3-(2-fluoro-4-nitrophenyl)-4-isobutyl-2-trifluoromethyloxazolidine (4.8 g, 14.3 mmol) and $Et_3SiH$ (21.6 g, 186 mmol) in 60 mL chloroform was added $BF_3OEt_2$ (14.2, 60 mmol, added in portions) The reaction was heated at reflux for 1 d After cooling, the reaction was poured in water (200 mL) and extracted with chloroform (3 ×150 mL). The organic layers were combined, washed sequentially with water (200 mL) and brine (200 mL), dried ($MgSO_4$), filtered, and concentrated under reduced pressure to a brown oil. Flash chromatography (gradient elution, hexanes:ethyl acetate 95:5 to 3:1) afforded 2.1 g (44%) of (2R)-2-[2-fluoro-4-nitro(2,2,2-trifluoroethyl)anilino]-4-methyl-1-pentanol, an orange oil. Data for (2R)-2-[2-fluoro-4-nitro(2,2,2-trifluoroethyl)anilino]-4-methyl-1-pentanol: $R_f$ 0.8 (3:1 hexanes:EtOAc); $^1$H NMR (400 MHz, $CDCl_3$) δ 7.98 (dd, 1H, J=9.3, 2.4), 7.94 (dd, 1H, J=12.9, 2.5), 7.40 (dd, 1H, J=8.7, 8.7), 4.21–4.10 (m, 1H), 3.89–3.78 (m, 1H), 3.79–3.65 (m, 3H), 1.96–1.89 (m, 1H), 1.67–1.54 (m, 1H), 1.55–1.44 (m, 1H), 1.32–1.22 (m, 1H), 0.91 (d, 3H, J=6.6), 0.77 (d, 3H, J=6.6).

(3R)-3,4-Dihydro-3-isobutyl-7-nitro-4-(2,2,2-trifluoroethyl)-2H-1,4-benzoxazine (Structure 24 of Scheme V, where $R^3$, $R^4$, $R^5$, $R^7$, $R^8$=H, $R^6$=isobutyl, $R^{13}$=$CH_2CF_3$): This compound was prepared according to the procedure described in EXAMPLE 41 (Structure 24 of Scheme V) from (2R)-2-[2-fluoro-4-nitro(2,2,2-trifluoroethyl)anilino]-4-methyl-1-pentanol (1.95 g, 5.76 mmol) in 30 mL THF and NaH (1.4 g, 35 mmol) in 25 mL THF heated at reflux for 1 hr to afford 0.87 g (50%) of (3R)-3,4-dihydro-3-isobutyl-7-nitro-4-(2,2,2-trifluoroethyl)-2H-1,4-benzoxazine, a yellow oil. Data for (3R)-3,4-dihydro-3-isobutyl-7-nitro-4-(2,2,2-trifluoroethyl)-2H-1,4-benzoxazine: $R_f$ 0.6 (3:1 hexanes:EtOAc); $^1$H NMR (400 MHz, $CDCl_3$) δ 7.79 (dd, 1H, J=9.1, 2.7), 7.71 (d, 1H, J=2.5), 6.72 (d, 1H, J=9.1), 4.30 (dd, 1H, ABx, J=11.0, 1.5), 4.19–4.06 (m, 1H), 4.06–4.01 (m, 1H), 3.82–3.73 (m, 1H), 3.53–3.47 (m, 1H), 1.71–1.61 (m, 2H), 1.38–1.29 (m, 1H), 0.99 (d, 3H, J=6.5), 0.96 (d, 3H, J=6.5).

(3R)-7-Amino-3,4-dihydro-3-isobutyl-4-(2,2,2-trifluoroethyl-2H-1,4-benzoxazine (Structure 16 of Scheme III, where $R^3$, $R^4$, $R^5$, $R^7$, $R^8$=H, R=isobutyl, $R^{13}$=$CH_2CF_3$) This compound was prepared by treatment of (3R)-3,4-dihydro-3-isobutyl-7-nitro-4-(2,2,2-trifluoroethyl)-2H-1,4-benzoxazine (0.22 g, 0.69 mmol) and 10% Pd/C (0.075 g) in 5 mL ethyl acetate under an $H_2$ atmosphere for 16 h. The mixture was filtered through Celite and concentrated to an oil. Flash chromatography (3:1 hexanes:ethyl acetate) afforded 0.13 g (65%) of (3R)-7-amino-3,4-dihydro-3-isobutyl-4-trifluoroethyl-2H-1,4-benzoxazine. Data for (3R)-7-amino-3,4-dihydro-3-isobutyl-4-trifluoroethyl-2H-1,4-benzoxazine: $R_f$ 0.3 (3:1 hexanes:EtOAc); $^1$H NMR (400 MHz, $CDCl_3$) δ 6.63 (d, 1H, J=8.5), 6.27 (dd, 1H, J=8.5, 2.6), 6.23 (d, 1H, J=2.5), 4.10 (dd, 1H, ABx, J=10.6, 1.8), 3.97 (dd, 1H, ABx, J=10.6, 2.3), 3.70–3.51 (m, 2H), 3.38 (broad s, 2H), 3.19–3.13 (m, 1H), 1.75–1.63 (m, 1H), 1.47–1.25 (m, 2H), 0.93 (d, 3H, J=6.6), 0.89 (d, 3H, J=6.6).

(3R)-2,3,4,7-Tetrahydro-3-isobutyl-4-(2,2,2-trifluoroethyl)-10-(trifluoromethyl)-8H-[1,4]oxazino[2,3-f]quinolin-8-one (Compound 155, Structure 17 of Scheme III, where $R^1$, $R^3$, $R^4$, $R^5$, $R^7$, $R^8$=H, $R^2$=trifluoromethyl, $R^6$=isobutyl, R=$CH_2CF_2$), and (2R)-1,2,3,6-tetrahydro-2-isobutyl-1-(2,2,2-trifluoroethyl)-9-(trifluoromethyl)-7H-[1,4]oxazino[3,2-f]quinolin-7-one (Structure 18 of Scheme III, where $R^1$, $R^3$, $R^4$, $R^5$, $R^7$=H, R=trifluoromethyl, $R^6$=isobutyl, $R^{13}$=$CH_2CF_3$): This compound was prepared by treatment of (3R)-7-amino-3,4-dihydro-3-isobutyl-4-trifluoroethyl-2H-1,4-benzoxazine (0.13 g, 0.45 mmol) and ethyl-4,4,4-trifluoroacetoacetate (0.25 g, 1.4 mmol) in 6 mL toluene heated at reflux for 3 h, followed by removal of solvent and treatment with 3 mL concentrated $H_2SO_4$ heated to 95° C. for 1 h. The mixture was poured into water (100 mL), neutralized with 6N NaOH, and extracted with chloroform (3×50 mL). The combined organic layers were washed with brine, dried over $MgSO_4$, filtered, and concentrated. The baseline impurities and were removed and partial purification achieved by flash chromatography (95:5 $CH_2Cl_2$: MeOH). Further purification by HPLC (Kromasil, 0.5" semi-prep column, 70% MeOH/water at 3 mL/min) afforded 5.0 mg (3%) of Compound 155, and recrystallization of the other impure fractions (ethyl acetate:hexanes) afforded 17 mg (9%) of (2R)-1,2,3,6-tetrahydro-2-isobutyl-1-(2,2,2-trifluoroethyl)-9-(trifluoromethyl)-7H-[1,4]oxazino[3,2-g]
quinolin-7-one, the regioisomer of Compound 155. Data for
Compound 155: $^1$H NMR (500 MHz, CDCl$_3$) δ 12.0–12.4 (v
broad s, 1H), 7.15 (s, 1H), 7.13 (d, J=9.0, 1H), 7.01 (d,
J=9.0, 1H), 4.34 (d, J=11, 1H), 3.99 (broad d, J=10, 1H),
3.75–3.85 (m, 1H), 3.65–3.75 (m, 1H), 3.35–3.40 (m, 1H),
1.70–1.80 (m, 1H), 1.40–1.50 (m, 1H), 1.30–1.40 (m, 1H),
0.95 (d, J=6.5, 3H), 0.93 (d, J=7.0, 3H).

Biological Examples

A. Steroid Receptor Activity

Utilizing the "cis-trans" or "co-transfection" assay described by Evans et al., Science, 240:889–95 (May 13, 1988), the disclosure of which is incorporated by reference herein, the compounds of the present invention were tested and found to have strong, specific activity as agonists, partial agonists and antagonists of AR. This assay is described in further detail in U.S. Pat. Nos. 4,981,784 and 5,071,773, the disclosures of which are incorporated herein by reference.

The co-transfection assay provides a method for identifying functional agonists and partial agonists that mimic, or antagonists that inhibit, the effect of native hormones and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. , See e.g., T. Berger et al. 41 J. Steroid Biochem. Molec. Biol. 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. A partial agonist's activity can be detected in a manner similar to that of the full agonist, except that the maximum measured activity, e.g., luciferase production, is less than that of an agonist standard. For example, for AR, a partial agonist can be detected by measuring increased luciferase production, but the maximum effect at high concentration is less than the maximum effect for dihydrotestosterone. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay and in standard IR binding assays, according to the following illustrative Examples.

B. Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum (CH-FBS) then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 J. Steroid Biochem. Mol. Biol., 733 (1992) with the following plasmids: pRShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor", 266 J. Biol. Chem., 510 (1991).

The reporter plasmid, MTV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of E. coli β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11β,17β)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]-pronanamide; Schering-Plough) as an AR antagonist; estradiol (Sigma) as an ER agonist and ICI 164,384 (N-butyl-3,17-dihydroxy-N-methyl-(7-α,17-β)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-α-[acetylthio]-17-α-hydroxy-3-oxopregn-4-ene-21-carboxylic acid γ-lactone (Sigma) as an MR antagonist; and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal/β-Gal incubation time.

The mean and standard error of the mean (SEM) of the NR were calculated. Data were plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of a test compound that inhibited 50% of LUC expression induced by the reference agonist was quantified ($IC_{50}$). In addition, the efficacy of antagonists was determined as a function (%) of maximal inhibition.

TABLE 1

Agonist, partial agonist, antagonist and binding activity of androgen receptor modulator compounds of present invention and the reference agonist compound, dihydrotestosterone (DHT), a known synthetic androgen, fluoxymesterone (Fluox) and reference antagonist compounds, 2-hydroxyflutamide (Flut) and Casodex (Cas), on hAR in CV-1 cells. Efficacy (%) for AR agonist is determined by comparing activity (e.g., luciferase production) of putative agonist to that of dihydrotestosterone (DHT). Efficacy (%) for AR antagonist is determined by the percentage amount by which the luciferase production is reduced (maximum concentration of antagonist) from the luciferase production of the standard (DHT).

| Cmpd No. | AR Agonist CV-1 Cells | | AR Antagonist CV-1 Cells | |
|---|---|---|---|---|
| | Efficacy (%) | Potency (nM) | Efficacy (%) | Potency (nM) |
| 101 | na | na | 64 | 72 |
| 102 | na | na | 32 | nd |
| 103 | 37 | 304 | 24 | nd |
| 104 | 73 | 7 | na | na |
| 106 | 97 | 228 | na | na |
| 107 | 17 | 301 | 56 | 70 |
| 109 | 29 | 411 | na | na |

TABLE 1-continued

Agonist, partial agonist, antagonist and binding activity of androgen receptor modulator compounds of present invention and the reference agonist compound, dihydrotestosterone (DHT), a known synthetic androgen, fluoxymesterone (Fluox) and reference antagonist compounds, 2-hydroxyflutamide (Flut) and Casodex (Cas), on hAR in CV-1 cells. Efficacy (%) for AR agonist is determined by comparing activity (e.g., luciferase production) of putative agonist to that of dihydrotestosterone (DHT). Efficacy (%) for AR antagonist is determined by the percentage amount by which the luciferase production is reduced (maximum concentration of antagonist) from the luciferase production of the standard (DHT).

| Cmpd No. | AR Agonist CV-1 Cells | | AR Antagonist CV-1 Cells | |
|---|---|---|---|---|
| | Efficacy (%) | Potency (nM) | Efficacy (%) | Potency (nM) |
| 110 | 89 | 0.6 | na | na |
| 114 | 74 | 53 | na | na |
| 116 | na | na | 79 | 65 |
| 117 | na | na | 74 | 8 |
| 122 | 76 | 270 | na | na |
| 124 | 70 | 2 | na | na |
| 126 | 78 | 35 | na | na |
| 128 | na | na | 88 | 50 |
| 135 | 72 | 11 | na | na |
| 136 | 61 | 34 | 24 | nd |
| 138 | na | na | 90 | 613 |
| DHT | 100 | 6 | na | na |
| Fluox | 120 | 2.8 | na | na |
| Flut | na | na | 83 | 25 |
| Cas | na | na | 81 | 201 |

[1]na = not active (i.e. efficacy of <20 and potency of >10,000 nM for the cotransfection assay and $K_i$ > 1000 nM for the binding assay)
nd = not determined

TABLE 2

Overall agonist and antagonist potency of selected androgen receptor modulator compounds of present invention and the reference agonist and antagonist compounds shown in Table 1 on PR, AR, ER, GR and MR.

| Cmpd No. | PR Potency | | AR-wt Potency | | ER Potency | | GR Potency | MR Potency |
|---|---|---|---|---|---|---|---|---|
| | Agon (nM) | Antag (nM) | Agon (nM) | Antag (nM) | Agon (nM) | Antag (nM) | Antag (nM) | Antag (nM) |
| 101 | na | 3900 | na | 72 | na | na | na | na |
| 103 | na | 3150 | 304 | nd | na | na | na | na |
| 110 | na | 520 | 0.6 | na | na | na | 1510 | 1270 |
| 114 | na | 700 | 53 | na | na | na | 5900 | na |
| 124 | na | 360 | 2 | na | na | na | 2400 | na |
| 135 | na | 481 | 11 | na | na | na | 2500 | na |
| Fluox | 1210 | 224 | 2.8 | na | na | na | 263 | 193 |
| Prog | 4 | na | 1300 | na | na | na | na | nt |

TABLE 2-continued

Overall agonist and antagonist potency of selected androgen receptor modulator compounds of present invention and the reference agonist and antagonist compounds shown in Table 1 on PR, AR, ER, GR and MR.

| Cmpd No. | PR Potency | | AR-wt Potency | | ER Potency | | GR Potency | MR Potency |
|---|---|---|---|---|---|---|---|---|
| | Agon (nM) | Antag (nM) | Agon (nM) | Antag (nM) | Agon (nM) | Antag (nM) | Antag (nM) | Antag (nM) |
| RU486 | na | 0.1 | na | 12 | na | 1500 | 0.7 | 1100 |
| DHT | na | 1800 | 6 | na | 1700 | na | na | nt |
| Flut | na | 1900 | na | 26 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of >20 and potency of >10,000);
nd = not determined,
nt = not tested The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

While in accordance with the patent statutes, description of the various embodiments and processing conditions have been provided, the scope of the invention is not to be limited thereto or thereby. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

We claim:
1. A compound having the formula:

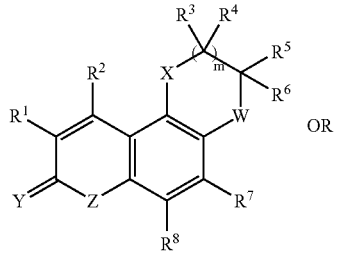

(I)

wherein:
$R^1$ is selected from the group consisting of hydrogen, F, Cl, Br, I, $NO_2$, $OR^9$, $NR^{10}R^{11}$, $S(O)_nR^9$, optionally substituted $C_1-C_8$ alkyl, optionally substituted $C_1-C_8$ haloalkyl, optionally substituted $C_1-C_8$ heteroalkyl, optionally substituted $C_3-C_8$ cycloalkyl, optionally substituted aryl, optionally substituted arylalkyl, optionally substituted heteroaryl, optionally substituted $C_2-C_8$ alkynyl and optionally substituted $C_2-C_8$ alkenyl;

$R^2$ is selected from the group consisting of hydrogen, F, Cl, Br, I, $CF_3$, $CF_2Cl$, $CF_2H$, $CFH_2$, $CF_2OR^9$, $CH_2OR^9$, $S(O)_nR^9$, $NR^{10}R^{11}$, optionally substituted $C_1-C_8$ alkyl, optionally substituted $C_1-C_8$ haloalkyl, optionally substituted $C_1-C_8$ heteroalkyl, optionally substituted $C_3-C_8$ cycloalkyl, optionally substituted aryl, optionally substituted arylalkyl, optionally substituted heteroaryl, optionally substituted $C_2-C_8$ alkynyl and optionally substituted $C_2-C_8$ alkenyl;

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, optionally substituted $C_1-C_8$alkyl, optionally substituted $C_1-C_8$ haloalkyl, optionally substituted $C_1-C_8$ heteroalkyl, optionally substituted $C_3-C_8$ cycloalkyl, optionally substituted aryl, optionally substituted arylalkyl, optionally substituted heteroaryl, optionally substituted $C_2-C_8$ alkynyl and optionally substituted $C_2-C_8$ alkenyl;

$R^5$ and $R^6$ each independently is selected from the group consisting of hydrogen, $CF_3$, $CF_2Cl$, $CF_2H$, $CFH_2$, optionally substituted $C_1-C_8$ alkyl, optionally substituted $C_1-C_8$haloalkyl, optionally substituted $C_1-C_8$ heteroalkyl, optionally substituted $C_3-C_8$ cycloalkyl, optionally substituted aryl, optionally substituted arylalkyl, optionally substituted heteroaryl, optionally substituted $C_2-C_8$ alkynyl and optionally substituted $C_2-C_8$ alkenyl;

$R^7$ is selected from the group consisting of hydrogen, F, Cl, Br, I, optionally substituted $C_1-C_8$ alkyl, optionally substituted $C_1-C_8$ haloalkyl, optionally substituted $C_1-C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1-C_8$ alkyl, optionally substituted $C_1-C_8$ haloalkyl, optionally substituted $C_1-C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1-C_8$ alkyl, optionally substituted $C_1-C_8$ haloalkyl, optionally substituted $C_1-C_8$ heteroalkyl, optionally substituted aryl, optionally substituted heteroaryl and optionally substituted arylalkyl;

$R^{10}$ is selected from the group consisting of hydrogen, optionally substituted $C_1-C_8$ alkyl, optionally substituted $C_1-C_8$ haloalkyl, optionally substituted $C_1-C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is selected from the group consisting of 0, 1 and 2;

n is selected from the group consisting of 0, 1 and 2;

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof; wherein:

the substituents of an optionally substituted group comprise one or more substituents independently selected from among alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

2. A compound according to claim 1, wherein $R^1$ is selected from the group consisting of hydrogen, F, Cl, $OR^9$, $NR^{10}R^{11}$, $S(O)_nR^9$, optionally substituted $C_1$–$C_4$ alkyl, optionally substituted $C_1$–$C_4$ haloalkyl and optionally substituted $C_1$–$C_4$ heteroalkyl.

3. A compound according to claim 2, wherein $R^1$ is selected from the group consisting of hydrogen, F, Cl, optionally substituted $C_1$–$C_4$ alkyl, optionally substituted $C_1$–$C_4$ haloalkyl and optionally substituted $C_1$–$C_4$ heteroalkyl.

4. A compound according to claim 3, wherein $R^1$ is selected from the group consisting of hydrogen, F and optionally substituted $C_1$–$C_4$ alkyl.

5. A compound according to claim 1, wherein $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, optionally substituted $C_1$–$C_6$ alkyl, optionally substituted $C_1$–$C_6$ haloalkyl, optionally substituted $C_1$–$C_6$ heteroalkyl, optionally substituted $C_2$–$C_6$ alkynyl and optionally substituted $C_2$–$C_6$ alkenyl.

6. A compound according to claim 5, wherein $R^2$ is selected from the group consisting of hydrogen, F, Cl, $CF_3$, $CF_2Cl$, $CF_2H$, $CFH_2$, optionally substituted $C_1$–$C_4$ alkyl, optionally substituted $C_1$–$C_4$ haloalkyl and optionally substituted $C_1$–$C_4$ heteroalkyl.

7. A compound according to claim 6, wherein $R^2$ is selected from the group consisting of hydrogen, optionally substituted $C_1$–$C_2$ alkyl, optionally substituted $C_1$–$C_2$ haloalkyl and optionally substituted $C_1$–$C_2$ heteroalkyl.

8. A compound according to claim 7, wherein $R^2$ is $CF_3$.

9. A compound according to claim 1, wherein $R^3$ is selected from the group consisting of hydrogen, optionally substituted $C_1$–$C_6$ alkyl, optionally substituted $C_1$–$C_6$ haloalkyl, optionally substituted $C_1$–$C_6$ heteroalkyl, $C(Y)OR^{11}$ and $C(Y)NR^{10}R^{11}$.

10. The compound of claim 1, wherein:

$R^1$ is selected from the group consisting of hydrogen, F, Cl, Br, I, $NO_2$, $OR^9$, $NR^{10}R^{11}$, $S(O)_nR^9$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^5$ and $R^6$ each independently is selected from the group consisting of hydrogen, $CF_3$, $CF_2Cl$, $CF_2H$, $CFH_2$, $C_1$–$C_8$ alkyl, $C_1$–$C_8$ haloalkyl, $C_1$–$C_8$ heteroalkyl, $C_3$–$C_8$ aryl, arylalkyl, heteroaryl, $C_2$–$C_8$ alkynyl and $C_2$–$C_8$ alkenyl;

$R^7$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, $C_1$–$C_8$ alkyl, $C_1$–$C_8$ haloalkyl, $C_1$–$C_8$ heteroalkyl, aryl, heteroaryl and arylalkyl;

$R^{10}$ is selected from the group consisting of hydrogen, $C_1$–$C_8$ alkyl, $C_1$–$C_8$ haloalkyl, $C_1$–$C_8$ heteroalkyl, aryl, heteroaryl, arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, $C_1$–$C_8$ alkyl, $C_1$–$C_8$ haloalkyl, $C_1$–$C_8$ heteroalkyl, aryl, heteroaryl and arylalkyl;

$R^{13}$ is selected from the group consisting of $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl;

m is selected from the group consisting of 0, 1 and 2;

n is selected from the group consisting of 0, 1 and 2;

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof.

11. A compound according to claim 9, wherein $R^3$ is selected from the group consisting of hydrogen, optionally substituted $C_1$–$C_4$ alkyl, optionally substituted $C_1$–$C_4$ haloalkyl and optionally substituted $C_1$–$C_4$ heteroalkyl.

12. A compound according to claim 1, wherein $R^6$ is selected from the group consisting of hydrogen, $CF_3$, $CF_2Cl$, $CF_2H$, $CFH_2$, optionally substituted $C_1$–$C_6$ alkyl, optionally substituted $C_1$–$C_6$ haloalkyl, optionally substituted $C_1$–$C_6$ heteroalkyl, optionally substituted aryl, optionally substituted arylalkyl, optionally substituted heteroaryl, optionally substituted $C_2$–$C_6$ alkynyl and optionally substituted $C_2$–$C_6$ alkenyl.

13. A compound according to claim 12, wherein $R^6$ is selected from the group consisting of hydrogen, $CF_3$, $CF_2Cl$, $CF_2H$, $CFH_2$, optionally substituted $C_1$–$C_4$ alkyl, optionally substituted $C_1$–$C_4$ haloalkyl, optionally substituted $C_1$–$C_4$ heteroalkyl, optionally substituted $C_2$–$C_4$ alkynyl and optionally substituted $C_2$–$C_4$ alkenyl.

14. A compound according to claim 13, wherein $R^6$ is selected from the group consisting of hydrogen, $CF_3$, $CF_2Cl$, $CF_2H$, $CFH_2$, optionally substituted $C_1$–$C_4$ alkyl, optionally substituted $C_1$–$C_4$ haloalkyl and optionally substituted $C_1$–$C_4$ heteroalkyl.

15. A compound according to claim 12, wherein $R^6$ is selected from the group consisting of optionally substituted aryl, optionally substituted arylalkyl and optionally substituted heteroaryl.

16. A compound according to claim 1, wherein $R^5$ is selected from the group consisting of hydrogen, $CF_3$, $CF_2Cl$, $CF_2H$, $CFH_2$, optionally substituted $C_1$–$C_6$ alkyl, optionally substituted $C_1$–$C_6$ haloalkyl, optionally substituted $C_1$–$C_6$ heteroalkyl, optionally substituted $C_2$–$C_6$ alkynyl, optionally substituted $C_2$–$C_6$ alkenyl.

17. A compound according to claim 16, wherein $R^5$ is selected from the group consisting of hydrogen, $CF_3$, $CF_2Cl$, $CF_2H$, $CFH_2$, optionally substituted $C_1$–$C_6$ alkyl, optionally substituted $C_1$–$C_6$ haloalkyl and optionally substituted $C_1$–$C_6$ heteroalkyl.

18. A compound according to claim 17, wherein $R^5$ is selected from the group consisting of hydrogen, $CF_3$, $CF_2Cl$, $CF_2H$, $CFH_2$, optionally substituted $C_1$–$C_4$ alkyl, optionally substituted $C_1$–$C_4$ haloalkyl and optionally substituted $C_1$–$C_4$ heteroalkyl.

19. A compound according to claim 18, wherein $R^5$ is hydrogen or $CF_3$.

20. A compound according to claim 1, wherein $R^7$ is selected from the group consisting of hydrogen, F, Cl, optionally substituted $C_1$–$C_4$ alkyl, optionally substituted $C_1$–$C_4$ haloalkyl and optionally substituted $C_1$–$C_4$ heteroalkyl.

21. A compound according to claim 1, wherein $R^8$ is selected from the group consisting of hydrogen, F, Cl, optionally substituted $C_1$–$C_4$ alkyl, optionally substituted $C_1$–$C_4$ haloalkyl and optionally substituted $C_1$–$C_4$ heteroalkyl.

22. A compound according to claim 21, wherein $R^7$ and $R^8$ are each hydrogen or optionally substituted $C_1$–$C_2$ alkyl.

23. A compound according to claim 1, wherein $R^9$ is selected from the group consisting of hydrogen, optionally substituted $C_1$–$C_6$ alkyl, optionally substituted $C_1$–$C_6$ haloalkyl and optionally substituted $C_1$–$C_6$ heteroalkyl.

24. A compound according to claim 23, wherein $R^9$ is selected from the group consisting of hydrogen and optionally substituted $C_3$–$C_4$ alkyl.

25. A compound according to claim 1, wherein $R^{10}$ is selected from the group consisting of hydrogen, $S(O)R^{12}$, $SO_2R^{12}$, $C(O)R^{12}$, $CO_2R^{12}$, optionally substituted $C_1$–$C_6$ alkyl, optionally substituted $C_1$–$C_6$ haloalkyl and optionally substituted $C_1$–$C_6$ heteroalkyl.

26. A compound according to claim 25, wherein $R^{10}$ is selected from the group consisting of hydrogen, $S(O)R^{12}$, $SO_2R^{12}$, $C(O)R^{12}$ and $CO_2R^{12}$.

27. A compound according to claim 1, wherein $R^4$ is selected from the group consisting of hydrogen, optionally substituted $C_1$–$C_4$ alkyl, optionally substituted $C_1$–$C_4$ haloalkyl and optionally substituted $C_1$–$C_4$ heteroalkyl.

28. A compound according to claim 27, wherein $R^4$ is selected from the group consisting of hydrogen and optionally substituted $C_1$–$C_2$ alkyl.

29. A compound according to claim 1, wherein $R^{13}$ is selected from the group consisting of $CF_3$, $CF_2Cl$, $CF_2H$, $CFH_2$, $CH_2CF_3$, $CH_2CF_2Cl$, $CH_2CCl_2F$, optionally substituted $C_1$–$C_6$ alkyl, optionally substituted $C_3$–$C_6$ cycloalkyl, optionally substituted $C_1$–$C_6$ haloalkyl, optionally substituted $C_1$–$C_6$ heteroalkyl, optionally substituted $C_2$–$C_6$ alkenyl, optionally substituted $C_2$–$C_6$ alkynyl, optionally substituted aryl, optionally substituted heteroaryl, optionally substituted arylalkyl and optionally substituted heteroarylalkyl.

30. A compound according to claim 29, wherein $R^{13}$ is selected from the group consisting of $CF_3$, $CF_2Cl$, $CF_2H$, $CFH_2$, $CH_2CF_3$, $CH_2CF_2Cl$, $CH_2CCl_2F$, optionally substituted $C_1$–$C_4$ alkyl, optionally substituted $C_1$–$C_4$ haloalkyl, optionally substituted $C_1$–$C_4$ heteroalkyl, optionally substituted $C_2$–$C_4$ alkenyl and optionally substituted aryl.

31. A compound according to claim 30, wherein $R^{13}$ is selected from the group consisting of $CF_3$, $CF_2Cl$, $CF_2H$, $CFH_2$, $CH_2CF_3$, $CH_2CF_2Cl$, $CH_2CCl_2F$, methyl, ethyl, propyl, isopropyl, isobutyl, cyclopropylmethyl, allyl.

32. A compound according to claim 1, wherein m is 0 or 1.

33. A compound according to claim 32, wherein m is 1.

34. A compound according to claim 1, wherein W is selected from the group consisting of NH, N{$R^{13}$} and N{C(Y)$R^{11}$}.

35. A compound according to claim 34, wherein W is NH or N{$R^{13}$}.

36. A compound according to claim 1, wherein Z is NH or N{$R^{11}$}.

37. A compound according to claim 1, wherein:
$R^1$ is selected from the group consisting of hydrogen, F, Cl, $OR^9$, $S(O)_nR^9$, $NR^{10}R^{11}$, optionally substituted $C_1$–$C_4$ alkyl, optionally substituted $C_1$–$C_4$ haloalkyl and optionally substituted $C_1$–$C_4$ heteroalkyl;
$R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, optionally substituted $C_1$–$C_6$ alkyl, optionally substituted $C_1$–$C_6$ haloalkyl, optionally substituted $C_1$–$C_6$ heteroalkyl, optionally substituted $C_2$–$C_6$ alkynyl and optionally substituted $C_2$–$C_6$ alkenyl;
$R^3$ is selected from the group consisting of hydrogen, optionally substituted $C_1$–$C_6$ alkyl, optionally substituted $C_1$–$C_6$ haloalkyl, optionally substituted $C_1$–$C_6$ heteroalkyl, $C(Y)OR^{11}$ and $C(Y)NR^{10}R^{11}$;
$R^5$ is selected from the group consisting of hydrogen, $CF_3$, $CF_2Cl$, $CF_2H$, $CFH_2$, optionally substituted $C_1$–$C_6$ alkyl, optionally substituted $C_1$–$C_6$ haloalkyl, optionally substituted $C_1$–$C_6$ heteroalkyl, optionally substituted $C_2$–$C_6$ alkynyl and optionally substituted $C_2$–$C_6$ alkenyl; and
$R^6$ is selected from the group consisting of hydrogen, $CF_3$, $CF_2Cl$, $CF_2H$, $CFH_2$, optionally substituted $C_1$–$C_6$ alkyl, optionally substituted $C_1$–$C_6$ haloalkyl, optionally substituted $C_1$–$C_6$ heteroalkyl, optionally substituted aryl, optionally substituted arylalkyl, optionally substituted heteroaryl, optionally substituted $C_2$–$C_6$ alkynyl and optionally substituted $C_2$–$C_6$ alkenyl.

38. A compound according to claim 37, wherein:
$R^7$ is selected from the group consisting of hydrogen, F, Cl, optionally substituted $C_1$–$C_4$ alkyl, optionally substituted $C_1$–$C_4$ haloalkyl and optionally substituted $C_1$–$C_4$ heteroalkyl;

$R^8$ is selected from the group consisting of hydrogen, F, Cl, optionally substituted $C_1$–$C_4$ alkyl, optionally substituted $C_1$–$C_4$ haloalkyl and optionally substituted $C_1$–$C_4$ heteroalkyl; and $R^{13}$ is selected from the group consisting of $CF_3$, $CF_2Cl$, $CF_2H$, $CFH_2$, $CH_2CF_3$, $CH_2CF_2Cl$, $CH_2CCl_2F$, optionally substituted $C_1$–$C_6$ alkyl, optionally substituted $C_1$–$C_6$ haloalkyl, optionally substituted $C_1$–$C_6$ heteroalkyl, optionally substituted $C_3$–$C_6$ cycloalkyl, optionally substituted $C_2$–$C_6$ alkenyl, optionally substituted $C_2$–$C_6$ alkynyl, optionally substituted aryl, optionally substituted heteroaryl, optionally substituted arylalkyl and optionally substituted heteroarylalkyl.

39. A compound according to claim 38, wherein:

m is 0 or 1;

W is selected from the group consisting of NH, $N\{R^{13}\}$, $N\{C(Y)R^{11}\}$ and $N\{SO_2R^{11}\}$;

X is O;

Z is NH or $N\{R^{11}\}$.

40. A pharmaceutical composition comprising a pharmaceutically acceptable carrier and a compound of formula:

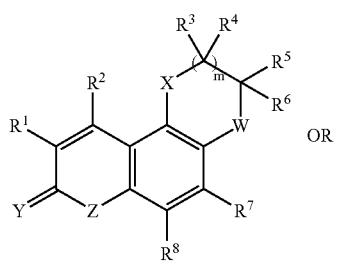

(I)

wherein:

$R^1$ is selected from the group consisting of hydrogen, F, Cl, Br, I, $NO_2$, $OR^9$, $NR^{10}R^{11}$, $S(O)_nR^9$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^5$ and $R^6$ each independently are selected from the group consisting of hydrogen, $CF_3$, $CF_2Cl$, $CF_2H$, $CFH_2$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^7$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ optionally substituted heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$,$S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{10}$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is 1;

n is selected from the group consisting of 0, 1 and 2;

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof; wherein:

the substituents of an optionally substituted group comprise one or more substituents independently selected from among alkyl, alkenyl, alkynyl, heteroalkyl, haloalkyl, haloalkenyl,. haloalkynyl. cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

41. A pharmaceutical composition according to claim 40, wherein said composition is suitable for enteral, parenteral, suppository or topical administration.

42. A pharmaceutical composition according to claim 40, wherein $R^1$ is selected from the group consisting of hydrogen, F, Cl, $OR^9$, $NR^{10}R^{11}$, $S(O)_nR^9$, optionally substituted $C_1-C_4$ alkyl, optionally substituted $C_1-C_4$ haloalkyl and optionally substituted $C_1-C_4$ heteroalkyl.

43. A pharmaceutical composition according to claim 41, wherein:
$R^1$ is selected from the group consisting of hydrogen, F and optionally substituted $C_1-C_4$ alkyl; and
$R^2$ is selected from the group consisting of hydrogen, optionally substituted $C_1-C_2$ alkyl, optionally substituted $C_1-C_2$ haloalkyl and optionally substituted $C_1-C_2$ heteroalkyl.

44. A pharmaceutical composition according to claim 40, wherein $R^3$ is selected from the group consisting of hydrogen, optionally substituted $C_1-C_6$ alkyl, optionally substituted $C_1-C_6$ haloalkyl, optionally substituted $C_1-C_6$ heteroalkyl, $C(Y)OR^{11}$ and $C(Y)NR^{10}R^{11}$.

45. A pharmaceutical composition according to claim 40, wherein $R^6$ selected from the group consisting of hydrogen, $CF_3$, $CF_2Cl$, $CF_2H$, $CFH_2$, optionally substituted $C_1-C_6$ alkyl, optionally substituted $C_1-C_6$ haloalkyl, optionally substituted $C_1-C_6$ heteroalkyl, optionally substituted aryl, optionally substituted arylalkyl, optionally substituted heteroaryl, optionally substituted $C_2-C_6$ alkynyl and optionally substituted $C_2-C_6$ alkenyl.

46. A pharmaceutical composition according to claim 45, wherein $R^6$ selected from the group consisting of hydrogen, $CF_3$, $CF_2Cl$, $CF_2H$, $CFH_2$, optionally substituted $C_1-C_4$ alkyl, optionally substituted $C_1-C_4$ haloalkyl, optionally substituted $C_1-C_4$ heteroalkyl, optionally substituted $C_2-C_4$ alkynyl and optionally substituted $C_2-C_4$ alkenyl.

47. A pharmaceutical composition according to claim 40, wherein $R^5$ is selected from the group consisting of hydrogen, $CF_3$, $CF_2Cl$, $CF_2H$, $CFH_2$, optionally substituted $C_1-C_6$ alkyl, optionally substituted $C_1-C_6$ haloalkyl, optionally substituted $C_1-C_6$ heteroalkyl, optionally substituted $C_2-C_6$ alkynyl and optionally substituted $C_2-C_6$ alkenyl.

48. A pharmaceutical composition according to claim 47, wherein $R^5$ is selected from the group consisting of hydrogen, $CF_3$, $CF_2Cl$, $CF_2H$, $CFH_2$, optionally substituted $C_1-C_4$ alkyl, optionally substituted $C_1-C_4$ haloalkyl and optionally substituted $C_1-C_4$ heteroalkyl.

49. A pharmaceutical composition according to claim 40, wherein $R^7$ and $R^8$ each independently is selected from the group consisting of hydrogen, F, Cl, optionally substituted $C_1-C_4$ alkyl, optionally substituted $C_1-C_4$ haloalkyl and optionally substituted $C_1-C_4$ heteroalkyl.

50. A pharmaceutical composition according to claim 40, wherein:
$R^9$ is selected from the group consisting of hydrogen, optionally substituted $C_1-C_6$ alkyl, optionally substituted $C_1-C_6$ haloalkyl, and optionally substituted $C_1-C_6$ heteroalkyl; and
$R^{10}$ is selected from the group consisting of hydrogen, $S(O)R^{12}$, $SO_2R^{12}$, $C(O)R^{12}$, $CO_2R^{12}$, optionally substituted $C_1-C_6$ alkyl, optionally substituted $C_1-C_6$ haloalkyl and optionally substituted $C_1-C_6$ heteroalkyl.

51. A pharmaceutical composition according to claim 40, wherein $R^4$ is selected from the group consisting of hydrogen, optionally substituted $C_1-C_4$ alkyl, optionally substituted $C_1-C_4$ haloalkyl and optionally substituted $C_1-C_4$ heteroalkyl.

52. A pharmaceutical composition according to claim 40, wherein $R^{13}$ is selected from the group consisting of $CF_3$, $CF_2Cl$, $CF_2H$, $CFH_2$, $CH_2CF_3$, $CH_2CF_2Cl$, $CH_2CCl_2F$, optionally substituted $C_1-C_6$ alkyl, optionally substituted $C_1-C_6$ haloalkyl, optionally substituted $C_1-C_6$ heteroalkyl, optionally substituted $C_2-C_6$ alkenyl, optionally substituted $C_2-C_6$ alkynyl, optionally substituted $C_3-C_6$ cycloalkyl, optionally substituted aryl, optionally substituted heteroaryl, optionally substituted arylalkyl and optionally substituted heteroarylalkyl.

53. A pharmaceutical composition according to claim 52, wherein $R^{13}$ is selected from the group consisting of $CF_3$, $CF_2Cl$, $CF_2H$, $CFH_2$, $CH_2CF_3$, $CH_2CF_2Cl$, $CH_2CCl_2F$, methyl, ethyl, propyl, isopropyl, isobutyl, cyclopropylmethyl, and allyl.

54. A pharmaceutical composition according to claim 40, wherein:
W is selected from the group consisting of NH, $N\{R^{13}\}$ and $N\{C(Y)R^{11}\}$; and
X is O.

55. A pharmaceutical composition according to claim 40, wherein Z is $N\{R^{11}\}$.

56. A pharmaceutical composition comprising a compound according to claim 1, wherein $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, optionally substituted $C_1-C_6$ alkyl, optionally substituted $C_1-C_6$ haloalkyl, optionally substituted $C_1-C_6$ heteroalkyl, optionally substituted $C_2-C_6$ alkynyl and optionally substituted $C_2-C_6$ alkenyl.

57. A compound selected from the group consisting of:
(3R)-2,3,4,7-Tetrahydro-3-methyl-10-(trifluoromethyl)-8H-[1,4]oxazino[2,3-f]-quinolin-8-one;
(3R)-2,3,4,7-Tetrahydro-3,4-dimethyl-10-(trifluoromethyl)-8H-[1,4]oxazino[2,3-f]-quinolin-8-one;
(3R)-4-Ethyl-2,3,4,7-tetrahydro-3-methyl-10-(trifluoromethyl)-8H-[1,4]oxazino[2,3-f]-quinolin-8-one;
(3R)-2,3 4,7-Tetrahydro-3-methyl-4-(2,2,2-trifluoroethyl)-10-(trifluoromethyl)-8H-[1,4]oxazino[2,3-f]quinolin-8-one;
(3R)-2,3,4,7-Tetrahydro-3-methyl-4-propyl-10-(trifluoromethyl)-8H-[1,4]oxazino[2,3-f]-quinolin-8-one;
(3R)-4-Allyl-2,3,4,7-tetrahydro-3-methyl-10-(trifluoromethyl)-8H-[1,4]oxazino[2,3-f]-quinolin-8-one;
(3R)-3-Ethyl-2,3,4,7-tetrahydro-10-(trifluoromethyl)-8H-[1,4]oxazino[2,3-f]quinolin-8-one;
(3R)-3-Ethyl-2,3,4,7-tetrahydro-4-methyl-10-(trifluoromethyl)-8H-[1,4]oxazino[2,3-f]-quinolin-8-one;
(3R)-3,4-Diethyl-2,3,4,7-tetrahydro-10-(trifluoromethyl)-8H-[1,4]oxazino[2,3-f]-quinolin-8-one;
(3R)-3-Ethyl-2,3,4,7-tetrahydro-4-(2,2,2-trifluoroethyl)-10-(trifluoromethyl)-8H-[1,4]oxazino[2,3-f]quinolin-8-one;
(3R)-4-(2-Chloro-2,2-difluoroethyl)-3-ethyl-2,3,4,7-tetrahydro-10-(trifluoromethyl)-8H-[1,4]oxazino[2,3-f]quinolin-8-one;
(3R)-4-(2,2-Difluoroethyl)-3-ethyl-2,3,4,7-tetrahydro-10-(trifluoromethyl)-8H-[1,4]oxazino[2,3-f]quinolin-8-one;
(3R)-3-Ethyl-2,3,4,7-tetrahydro-4-propyl-10-(trifluoromethyl)-8H-[1,4]oxazino[2,3-f]-quinolin-8-one;
(3R)-4-Allyl-3-ethyl-2,3,4,7-tetrahydro-10-(trifluoromethyl)-8H-[1,4]oxazino[2,3-f]-quinolin-8-one;
(3R)-3-Ethyl-2,3,4,7-tetrahydro-4-isobutyl-10-(trifluoromethyl)-8H-[1,4]oxazino[2,3-f]-quinolin-8-one;
(3R/S)-2,3,4,7-Tetrahydro-3-propyl-10-(trifluoromethyl)-8H-[1,4]oxazino[2,3-f]-quinolin-8-one;
(3R/S)-2,3,4,7-Tetrahydro-4-methyl-3-propyl-10-(trifluoromethyl)-8H-[1,4]oxazino-[2,3-f]quinolin-8-one;
(3R/S)-4-Ethyl-2,3,4,7-tetrahydro-3-propyl-4-(2,2,2-trifluoroethyl)-10-(trifluoromethyl)-8H-[1,4]oxazino[2,3-f]-quinolin-8-one;

(3R/S)-2,3,4,7-Tetrahydro-3-propyl-4-(2,2,2-trifluoroethyl)-10-(trifluoromethyl)-8H-[1,4]oxazino[2,3-f]quinolin-8-one;
(3R)-2,3,4,7-Tetrahydro-3-isopropyl-10-(trifluoromethyl)-8H-[1,4]oxazino[2,3-f]-quinolin-8-one;
(3R)-2,3,4,7-Tetrahydro-3-isopropyl-4-methyl-10-(trifluoromethyl)-8H-[1,4]oxazino-[2,3-f]quinolin-8-one;
(3R)-4-Ethyl-2,3,4,7-tetrahydro-3-isopropyl-10-(trifluoromethyl)-8H-[1,4]oxazino-[2,3-f]quinolin-8-one;
(3R)-2,3,4,7-Tetrahydro-3-isopropyl-4-(2,2,2-trifluoroethyl)-10-(trifluoromethyl)-8H-[1,4]oxazino[2,3-f]quinolin-8-one;
(3R)-4-(2-Chloro-2,2-difluoroethyl)-2,3,4,7-tetrahydro-3-isopropyl-10-(trifluoromethyl)-8H-[1,4]oxazino[2,3-f]quinolin-8-one;
(3R)-4-(2,2-Difluoroethyl)-2,3,4,7-tetrahydro-3-isopropyl-10-(trifluoromethyl)-8H-[1,4]oxazino[2,3-f]quinolin-8-one;
(3R)-4-Allyl-2,3,4,7-tetrahydro-3-isopropyl-10-(trifluoromethyl)-8H-[1,4]oxazino-[2,3-f]quinolin-8-one;
(3R)-2,3,4,7-Tetrahydro-3-phenyl-10-(trifluoromethyl)-8H-[1,4]oxazino[2,3-f]-quinolin-8-one;
(3R)-2,3,4,7-Tetrahydro-3-phenyl-4-(2,2,2-trifluoroethyl)-10-(trifluoromethyl)-8H-[1,4]oxazino[2,3-f]quinolin-8-one;
(3R)-4-Cyclopropylmethyl-2,3,4,7-tetrahydro-3-phenyl-10-(trifluoromethyl)-8H-[1,4]oxazinol[2,3-f]quinolin-8-one;
(3R)-3-Benzyl-2,3,4,7-tetrahydro-4-(2,2,2-trifluoroethyl)-10-(trifluoromethyl)-8H-[1,4]oxazino[2,3-f]quinolin-8-one;
2,3,4,7-Tetrahydro-10-(trifluoromethyl)-8H-[1,4]oxazino[2,3-f]quinolin-8-one;
2,3,4,7-tetrahydro-4-(2,2,2-trifluoroethyl)-10-(trifluoromethyl)-8H-[1,4]oxazino[2,3-f]-quinolin-8-one;
(7aR,10aS)-7,7a,8,9,10,10a-Hexahydro-1-(trifluoromethyl)-7-(2,2,2-trifluoroethyl)-4H-cyclopenta[5,6][1,4]oxazino[2,3-f]quinolin-3-one;
(7aR,10aS)-7-Ethyl-7,7a,8,9,10,10a-hexahydro-1-(trifluoromethyl)-4H-cyclopenta-[5,6][1,4]oxazino[2,3-f]quinolin-3-one;
(7aR,10aS)-7,7a,8,9,10,10a-Hexahydro-3-isopropoxy-1-(trifluoromethyl)-7-(2,2,2-trifluoroethyl)-4H-cyclopental[5,6][1,4]oxazino[2,3-f]quinolin-3-one;
(±)-(2S,3R)-2,3,4,7-Tetrahydro-2,3-dimethyl-4-(2,2,2-trifluoroethyl)-10 -(trifluoromethyl)-8H-[1,4]oxazino[2,3-f]quinolin-8-one;
(6aR)-6a,7,8,9-Tetrahydro-4-(trifluoromethyl)-1H,6H-pyrrolo[1',2':4,5][1,4]-oxazino[2,3-f]quinolin-2-one;
2,3,4,7-Tetrahydro-2,2,4-trimethyl-10-(trifluoromethyl)-8H-[1,4]oxazino[2,3-f]-quinolin-8-one;
(3R)-8-Chloro-3-ethyl-3,4-dihydro-8-isopropoxy-4-(2,2,2-trifluoroethyl)-10-(trifluoromethyl)-2H-[1,4]oxazino[2,3-f]quinoline;
(3R)-3-Ethyl-3,4-dihydro-8-isopropoxy-8-methoxy-4-(2,2,2-trifluoroethyl)-10-(trifluoromethyl)-2H-[1,4]oxazino[2,3-f]quinoline;
(±)-2,3,4,7-Tetrahydro-4-(2,2,2-trifluoroethyl)-3,10-bis(trifluoromethyl)-8H-[1,4]oxazino[2,3-f]quinolin-8-one;
(−)-2,3,4,7-Tetrahydro-4-(2,2,2-trifluoroethyl)-3,10-bis(trifluoromethyl)-8H-[1,4]oxazino[2,3-f]quinolin-8-one;
(+)-2,3,4,7-Tetrahydro-4-(2,2,2-trifluoroethyl)-3,10-bis(trifluoromethyl)-8H-[1,4]oxazino[2,3-f]quinolin-8-one;
(±)-2,3,4,7-Tetrahydro-3-(2,2,2-trifluoroethyl)-10-(trifluoromethyl)-8H-[1,4]oxazino[2,3-f]quinolin-8-one;
(±)-2,3,4,7-Tetrahydro-4-methyl-3-(2,2,2-trifluoroethyl)-10-(trifluoromethyl)-8H-[1,4]oxazino[2,3-f]quinolin-8-one;
(±)-4-Ethyl-2,3,4,7-tetrahydro-3-(2,2,2-trifluoroethyl)-10-(trifluoromethyl)-8H-[1,4]oxazino[2,3-f]quinolin-8-one;
(±)-2,3,4,7-Tetrahydro-3,4-bis(2,2,2-trifluoroethyl)-10-(trifluoromethyl)-8H-[1,4]oxazino[2,3-f]quinolin-8-one;
(−)-2,3,4,7-Tetrahydro-3,4-bis(2,2,2-trifluoroethyl)-10-(trifluoromethyl)-8H-[1,4]oxazino[2,3-f]quinolin-8-one;
(+)-2,3,4,7-Tetrahydro-3,4-bis(2,2,2-trifluoroethyl)-10-(trifluoromethyl)-8H-[1,4]oxazino[2,3-f]quinolin-8-one;
(±)-4-Cyclopropylmethyl-2,3,4,7-tetrahydro-3-(2,2,2-trifluoroethyl)-10-(trifluoromethyl)-8H-[1,4]oxazino[2,3-f]quinolin-8-one;
(3R)-4-Cyclopropylmethyl-3-ethyl-2,3,4,7-tetrahydro-10-(trifluoromethyl)-8H-[1,4]oxazino[2,3-f]quinolin-8-one;
(3R)-4-(2-Chloroethyl)-2,3,4,7-tetrahydro-3-isopropyl-10-(trifluoromethyl)-8H-[1,4]oxazino[2,3-f]quinolin-8-one;
(±)-2,3,4,7-Tetrahydro-2-methyl-4-(2,2,2-trifluoroethyl)-10-(trifluoromethyl)-8H-[1,4]oxazino[2,3-f]quinolin-8-one;
(3R)-3-Ethyl-4-(2-hydroxy-2-methylpropyl)-2,3,4,7-tetrahydro-10-(trifluoromethyl)-8H-[1,4]oxazino[2,3-f]quinolin-8-one;
(3R)-2,3,4,7-Tetrahydro-3-isobutyl-4-(2,2,2-trifluoroethyl)-10-(trifluoromethyl)-8H-[1,4]oxazino[2,3-f]quinolin-8-one; and pharmaceutically acceptable salt thereof.

58. A compound selected from the group consisting of:
(3R)-2,3,4,7-Tetrahydro-3-methyl-4-(2,2,2-trifluoroethyl)-10-(trifluoromethyl)-8H-[1,4]oxazino[2,3-f]quinolin-8-one;
(3R)-3-Ethyl-2,3,4,7-tetrahydro-4-(2,2,2-trifluoroethyl)-10-(trifluoromethyl)-8H-[1,4]oxazino[2,3-f]quinolin-8-one;
(3R)-4-(2-Chloro-2,2-difluoroethyl)-3-ethyl-2,3,4,7-tetrahydro-10-(trifluoromethyl)-8H-[1,4]oxazino[2,3-f]quinolin-8-one;
(3R)-4-(2,2-Difluoroethyl)-3-ethyl-2,3,4,7-tetrahydro-10-(trifluoromethyl)-8H-[1,4]oxazino[2,3-f]quinolin-8-one;
(3R)-2,3,4,7-Tetrahydro-3-isopropyl-4-(2,2,2-trifluoroethyl)-10-(trifluoromethyl)-8H-[1,4]oxazino[2,3-f]quinolin-8-one;
(3R)-4-(2-Chloro-2,2-difluoroethyl)-2,3,4,7-tetrahydro-3-isopropyl-10-(trifluoromethyl)-8H-[1,4]oxazino[2,3-f]quinolin-8-one;
(3R)-4-(2,2-Difluoroethyl)-2,3,4,7-tetrahydro-3-isopropyl-10-(trifluoromethyl)-8H-[1,4]oxazino[2,3-f]quinolin-8-one;
(7aR,10aS)-7-Ethyl-7,7a,8,9,10,10a-hexahydro-1-(trifluoromethyl)-4H-cyclopenta[5,6][1,4]oxazino[2,3-f]quinolin-3-one;
(7aR,10aS)-7,7a,8,9,10,10a-Hexahydro-1-(trifluoromethyl)-7-(2,2,2-trifluoroethyl)-4H-cyclopenta[5,6][1,4]oxazino[2,3-f]quinolin-3-one;
(±)-(2S,3R)-2,3,4,7-Tetrahydro-2,3-dimethyl-4-(2,2,2-trifluoroethyl)-10-(trifluoromethyl)-8H-[1,4]oxazino[2,3-f]quinolin-8-one;

(±)-2,3,4,7-Tetrahydro-4-(2,2,2-trifluoroethyl)-3,10-bis(trifluoromethyl)-8H-[1,4]oxazino[2,3-f]quinolin-8-one;

(−)-2,3,4,7-Tetrahydro-4-(2,2,2-trifluoroethyl)-3,10-bis(trifluoromethyl)-8H-[1,4]oxazino[2,3-f]quinolin-8-one;

(+)-2,3,4,7-Tetrahydro-4-(2,2,2-trifluoroethyl)-3,10-bis(trifluoromethyl)-8H-[1,4]oxazino[2,3-f]quinolin-8-one; and a pharmaceutically acceptable salts thereof.

* * * * *

UNITED STATES PATENT AND TRADEMARK OFFICE
CERTIFICATE OF CORRECTION

PATENT NO.         : 7,214,690 B2
APPLICATION NO. : 10/080503
DATED                  : May 8, 2007
INVENTOR(S)        : Higuchi et al.

It is certified that error appears in the above-identified patent and that said Letters Patent is hereby corrected as shown below:

IN THE TITLE PAGES:
In Item [56] References Cited, in OTHER PUBLICATIONS:
in Venturoli et al., please replace "Prospectiove" with --Prospective--

IN THE SPECIFICATION:
At column 5, line 20, please replace structure

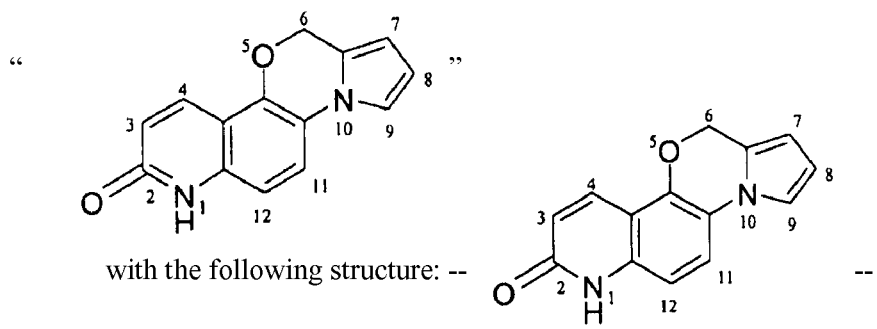

At column 9, line 34, please replace "A $R^9$" with --$R^9$--
At column 31, line 56-67, please replace structure

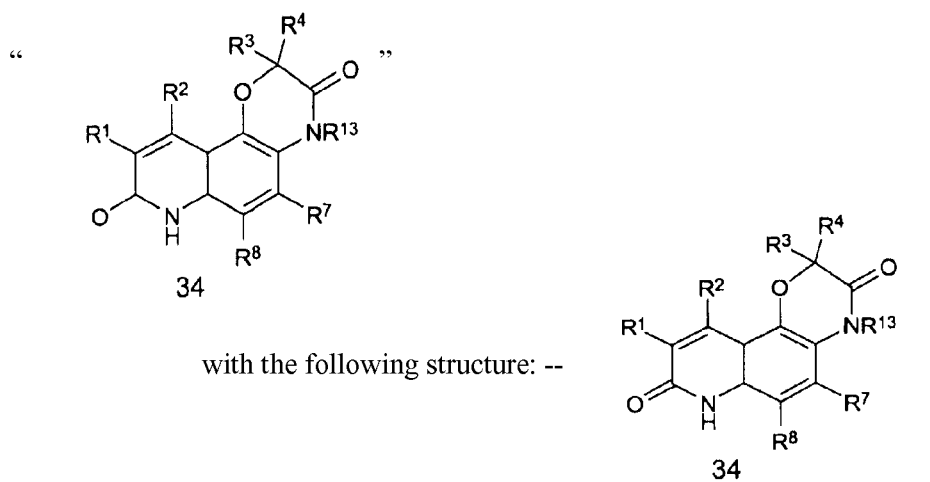

UNITED STATES PATENT AND TRADEMARK OFFICE
CERTIFICATE OF CORRECTION

PATENT NO.       : 7,214,690 B2
APPLICATION NO.  : 10/080503
DATED            : May 8, 2007
INVENTOR(S)      : Higuchi et al.

It is certified that error appears in the above-identified patent and that said Letters Patent is hereby corrected as shown below:

IN THE CLAIMS:
Please replace Claims 1, 10, 24, 40, 57, and 58 with the following Claims:
1. A compound having the formula:

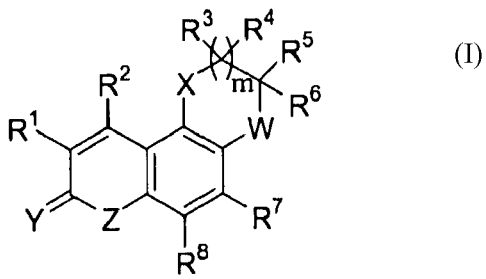

(I)

wherein:
  $R^1$ is selected from the group consisting of hydrogen, F, Cl, Br, I, $NO_2$, $OR^9$, $NR^{10}R^{11}$, $S(O)_nR^9$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
  $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
  $R^3$ and $R^4$ each independently is selected from the group consisting of hydrogen, $OR^9$, $S(O)_nR^9$, $NR^{10}R^{11}$, $C(Y)OR^{11}$, $CNR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

UNITED STATES PATENT AND TRADEMARK OFFICE
CERTIFICATE OF CORRECTION

| | | |
|---|---|---|
| PATENT NO. | : 7,214,690 B2 | |
| APPLICATION NO. | : 10/080503 | |
| DATED | : May 8, 2007 | |
| INVENTOR(S) | : Higuchi et al. | |

It is certified that error appears in the above-identified patent and that said Letters Patent is hereby corrected as shown below:

$R^5$ and $R^6$ each independently is selected from the group consisting of hydrogen, $CF_3$, $CF_2Cl$, $CF_2H$, $CFH_2$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^7$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, and optionally substituted arylalkyl;

$R^{10}$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is selected from the group consisting of 0, 1 and 2;

n is selected from the group consisting of 0, 1 and 2;

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof; wherein:

UNITED STATES PATENT AND TRADEMARK OFFICE
CERTIFICATE OF CORRECTION

| | | |
|---|---|---|
| PATENT NO. | : 7,214,690 B2 | |
| APPLICATION NO. | : 10/080503 | |
| DATED | : May 8, 2007 | |
| INVENTOR(S) | : Higuchi et al. | |

It is certified that error appears in the above-identified patent and that said Letters Patent is hereby corrected as shown below:

the substituents of an optionally substituted group comprise one or more substituents independently selected from among alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

10. The compound of claim 1, wherein:

$R^1$ is selected from the group consisting of hydrogen, F, Cl, Br, I, $NO_2$, $OR^9$, $NR^{10}R^{11}$, $S(O)_nR^9$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^5$ and $R^6$ each independently is selected from the group consisting of hydrogen, $CF_3$, $CF_2Cl$, $CF_2H$, $CFH_2$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;

$R^7$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, $C_1$–$C_8$ alkyl, $C_1$–$C_8$ haloalkyl, $C_1$–$C_8$ heteroalkyl, aryl, heteroaryl and arylalkyl;

$R^{10}$ is selected from the group consisting of hydrogen, $C_1$–$C_8$ alkyl, $C_1$–$C_8$ haloalkyl, $C_1$–$C_8$ heteroalkyl, aryl, heteroaryl, arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, $C_1$–$C_8$ alkyl, $C_1$–$C_8$ haloalkyl, $C_1$–$C_8$ heteroalkyl, aryl, heteroaryl, arylalkyl;

UNITED STATES PATENT AND TRADEMARK OFFICE
CERTIFICATE OF CORRECTION

PATENT NO.         : 7,214,690 B2
APPLICATION NO. : 10/080503
DATED                  : May 8, 2007
INVENTOR(S)        : Higuchi et al.

It is certified that error appears in the above-identified patent and that said Letters Patent is hereby corrected as shown below:

$R^{13}$ is selected from the group consisting of $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl;
    m is selected from the group consisting of 0, 1 and 2;
    n is selected from the group consisting of 0, 1 and 2;
    W is selected from the group consisting of NH, $N\{R^{13}\}$, $N\{C(Y)R^{11}\}$ and $N\{SO_2R^{11}\}$;
    X is O;
    Z is selected from the group consisting of NH, $N\{R^{11}\}$, $N\{C(Y)R^{11}\}$, $N\{SO_2R^{12}\}$ and $N\{S(O)R^{12}\}$; and
    Y is O;
    and pharmaceutically acceptable salts thereof.
    24. A compound according to claim 23, wherein $R^9$ is selected from the group consisting of hydrogen and optionally substituted $C_1$–$C_4$ alkyl.
    40. A pharmaceutical composition comprising a pharmaceutically acceptable carrier and a compound of formula:

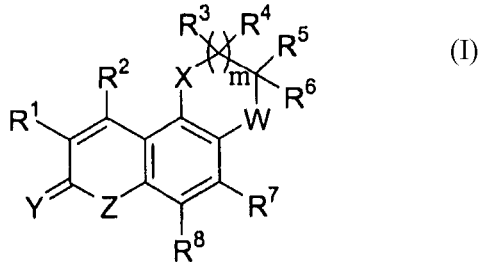

(I)

wherein:
    $R^1$ is selected from the group consisting of hydrogen, F, Cl, Br, I, $NO_2$, $OR^9$, $NR^{10}R^{11}$, $S(O)_nR^9$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
    $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

UNITED STATES PATENT AND TRADEMARK OFFICE
CERTIFICATE OF CORRECTION

| | |
|---|---|
| PATENT NO. | : 7,214,690 B2 |
| APPLICATION NO. | : 10/080503 |
| DATED | : May 8, 2007 |
| INVENTOR(S) | : Higuchi et al. |

It is certified that error appears in the above-identified patent and that said Letters Patent is hereby corrected as shown below:

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^5$ and $R^6$ each independently are selected from the group consisting of hydrogen, $CF_3$, $CF_2Cl$, $CF_2H$, $CFH_2$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^7$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{10}$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is 1;
n is selected from the group consisting of 0, 1 and 2;

UNITED STATES PATENT AND TRADEMARK OFFICE
CERTIFICATE OF CORRECTION

| | |
|---|---|
| PATENT NO. | : 7,214,690 B2 |
| APPLICATION NO. | : 10/080503 |
| DATED | : May 8, 2007 |
| INVENTOR(S) | : Higuchi et al. |

It is certified that error appears in the above-identified patent and that said Letters Patent is hereby corrected as shown below:

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof; wherein:

the substituents of an optionally substituted group comprise one or more substituents independently selected from among alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkythio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

57. A compound selected from the group consisting of:

(3$R$)-2,3,4,7-Tetrahydro-3-methyl-10-(trifluoromethyl)-8$H$-[1,4]oxazino[2,3-$f$]-quinolin-8-one;

(3$R$)-2,3,4,7-Tetrahydro-3,4-dimethyl-10-(trifluoromethyl)-8$H$-[1,4]oxazino[2,3-$f$]-quinolin-8-one;

(3$R$)-4-Ethyl-2,3,4,7-tetrahydro-3-methyl-10-(trifluoromethyl)-8$H$-[1,4]oxazino[2,3-$f$]-quinolin-8-one;

(3$R$)-2,3,4,7-Tetrahydro-3-methyl-4-(2,2,2-trifluoroethyl)-10-(trifluoromethyl)-8$H$-[1,4]oxazino[2,3-$f$]quinolin-8-one;

(3$R$)-2,3,4,7-Tetrahydro-3-methyl-4-propyl-10-(trifluoromethyl)-8$H$-[1,4]oxazino[2,3-$f$]-quinolin-8-one;

(3$R$)-4-Allyl-2,3,4,7-tetrahydro-3-methyl-10-(trifluoromethyl)-8$H$-[1,4]oxazino[2,3-$f$]-quinolin-8-one;

(3$R$)-3-Ethyl-2,3,4,7-tetrahydro-10-(trifluoromethyl)-8$H$-[1,4]oxazino[2,3-$f$]quinolin-8-one;

(3$R$)-3-Ethyl-2,3,4,7-tetrahydro-4-methyl-10-(trifluoromethyl)-8$H$-[1,4]oxazino[2,3-$f$]-quinolin-8-one;

(3$R$)-3,4-Diethyl-2,3,4,7-tetrahydro-10-(trifluoromethyl)-8$H$-[1,4]oxazino[2,3-$f$]-quinolin-8-one;

(3$R$)-3-Ethyl-2,3,4,7-tetrahydro-4-(2,2,2-trifluoroethyl)-10-(trifluoromethyl)-8$H$-[1,4]oxazino[2,3-$f$]quinolin-8-one;

(3$R$)-4-(2-Chloro-2,2-difluoroethyl)-3-ethyl-2,3,4,7-tetrahydro-10-(trifluoromethyl)-8$H$-[1,4]oxazino[2,3-$f$]quinolin-8-one;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

(3$R$)-4-(2,2-Difluoroethyl)-3-ethyl-2,3,4,7-tetrahydro-10-(trifluoromethyl)-8$H$-[1,4]oxazino[2,3-$f$]quinolin-8-one;
(3$R$)-3-Ethyl-2,3,4,7-tetrahydro-4-propyl-10-(trifluoromethyl)-8$H$-[1,4]oxazino[2,3-$f$]-quinolin-8-one;
(3$R$)-4-Allyl-3-ethyl-2,3,4,7-tetrahydro-10-(trifluoromethyl)-8$H$-[1,4]oxazino[2,3-$f$]-quinolin-8-one;
(3$R$)-3-Ethyl-2,3,4,7-tetraydro-4-isobutyl-10-(trifluoromethyl)-8$H$-[1,4]oxazino[2,3-$f$]-quinolin-8-one;
(3$R/S$)-2,3,4,7-Tetrahydro-3-propyl-10-(trifluoromethyl)-8$H$-[1,4]oxazino[2,3-$f$]-quinolin-8-one;
(3$R/S$)-2,3,4,7-Tetrahydro-4-methyl-3-propyl-10-(trifluoromethyl)-8$H$[1,4]oxazino-[2,3-$f$]quinolin-8-one;
(3$R/S$)-4-Ethyl-2,3,4,7-tetrahydro-3-propyl-4-(2,2,2-trifluoroethyl)-10-(trifluoromethyl)-8$H$-[1,4]oxazino[2,3-$f$]quinolin-8-one;
(3$R/S$)-2,3,4,7-Tetrahydro-3-propyl-4-(2,2,2-trifluoroethyl)-10-(trifluoromethyl)-8$H$-[1,4]oxazino[2,3-$f$]quinolin-8-one;
(3$R$)-2,3,4,7-Tetrahydro-3-isopropyl-10-(trifluoromethyl)-8$H$-[1,4]oxazino[2,3-$f$]-quinolin-8-one;
(3$R$)-2,3,4,7-Tetrahydro-3-isopropyl-4-methyl-10-(trifluoromethyl)-8$H$-[1,4]oxazino-[2,3-$f$]quinolin-8-one;
(3$R$)-4-Ethyl-2,3,4,7-tetrahydro-3-isopropyl-10-(trifluoromethyl)-8$H$-[1,4]oxazino-[2,3-$f$]quinolin-8-one;
(3$R$)-2,3,4,7-Tetrahydro-3-isopropyl-4-(2,2,2-trifluoroethyl)-10-(trifluoromethyl)-8$H$-[1,4]oxazino[2,3-$f$]quinolin-8-one;
(3$R$)-4-(2-Chloro-2,2-difluoroethyl)-2,3,4,7-tetrahydro-3-isopropyl-10-(trifluoromethyl)-8$H$-[1,4]oxazino[2,3-$f$]quinolin-8-one;
(3$R$)-4-(2,2-Difluoroethyl)-2,3,4,7-tetrahydro-3-isopropyl-10-(trifluoromethyl)-8$H$-[1,4]oxazino[2,3-$f$]quinolin-8-one;
(3$R$)-4-Allyl-2,3,4,7-tetrahydro-3-isopropyl-10-(trifluoromethyl)-8$H$-[1,4]oxazino-[2,3-$f$]quinolin-8-one;
(3$R$)-2,3,4,7-Tetrahydro-3-phenyl-10-(trifluoromethyl)-8$H$-[1,4]oxazino[2,3-$f$]quinolin-8-one;
(3$R$)-2,3,4,7-Tetrahydro-3-phenyl-4-(2,2,2-trifluoroethyl)-10-(trifluoromethyl)-8$H$-[1,4]oxazino[2,3-$f$]quinolin-8-one;
(3$R$)-4-Cyclopropylmethyl-2,3,4,7-tetrahydro-3-phenyl-10-(trifluoromethyl)-8$H$-[1,4]oxazino[2,3-$f$]quinolin-8-one;
(3$R$)-3-Benzyl-2,3,4,7-tetrahydro-4-(2,2,2-trifluoroethyl)-10-(trifluoromethyl)-8$H$-[1,4]oxazino[2,3-$f$]quinolin-8-one;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

2,3,4,7-Tetrahydro-10-(trifluoromethyl)-8*H*-[1,4]oxazino[2,3-*f*]quinolin-8-one;
2,3,4,7-tetrahydro-4-(2,2,2-trifluoroethyl)-10-(trifluoromethyl)-8*H*-[1,4]oxazino[2,3-*f*]quinolin-8-one;
(7a*R*,10a*S*)-7,7a,8,9,10,10a-Hexahydro-1-(trifluoromethyl)-7-(2,2,2-trifluoroethyl)-4*H*-cyclopenta[5,6][1,4]oxazino[2,3-*f*]quinolin-3-one;
(7a*R*,10a*S*)-7-Ethyl-7,7a,8,9,10,10a-hexahydro-1-(trifluoromethyl)-4*H*-cyclopenta-[5,6][1,4]oxazino[2,3-*f*]quinolin-3-one;
(7a*R*,10a*S*)-7,7a,8,9,10,10a-Hexahydro-3-isopropoxy-1-(trifluoromethyl)-7-(2,2,2-trifluoroethyl)-4*H*-cyclopenta[5,6][1,4]oxazino[2,3-*f*]quinolin-3-one;
(±)-(2*S*,3*R*)-2,3,4,7-Tetrahydro-2,3-dimethyl-4-(2,2,2-trifluoroethyl)-10-(trifluoromethyl)-8*H*-[1,4]oxazino[2,3-*f*]quinolin-8-one;
(6a*R*)-6a,7,8,9-Tetrahydro-4-(trifluoromethyl)-1*H*,6*H*-pyrrolo[1',2':4,5][1,4]-oxazino[2,3-*f*]quinolin-2-one;
2,3,4,7-Tetrahydro-2,2,4-trimethyl-10-(trifluoromethyl)-8*H*-[1,4]oxazino[2,3-*f*]-quinolin-8-one;
(3*R*)-8-Chloro-3-ethyl-3,4-dihydro-8-isopropoxy-4-(2,2,2-trifluoroethyl)-10-(trifluoromethyl)-2*H*-[1,4]oxazino[2,3-*f*]quinoline;
(3*R*)-3-Ethyl-3,4-dihydro-8-isopropoxy-8-methoxy-4-(2,2,2-trifluoroethyl)-10-(trifluoromethyl)-2*H*-[1,4]oxazino[2,3-*f*]quinoline;
(±)-2,3,4,7-Tetrahydro-4-(2,2,2-trifluoroethyl)-3,10-bis(trifluoromethyl)-8*H*-[1,4]oxazino[2,3-*f*]quinolin-8-one;
(−)-2,3,4,7-Tetrahydro-4-(2,2,2-trifluoroethyl)-3,10-bis(trifluoromethyl)-8*H*-[1,4]oxazino[2,3-*f*]quinolin-8-one;
(+)-2,3,4,7-Tetrahydro-4-(2,2,2-trifluoroethyl)-3,10-bis(trifluoromethyl)-8*H*-[1,4]oxazino[2,3-*f*]quinolin-8-one;
(±)-2,3,4,7-Tetrahydro-3-(2,2,2-trifluoroethyl)-10-(trifluoromethyl)-8*H*-[1,4]oxazino[2,3-*f*]quinolin-8-one;
(±)-2,3,4,7-Tetrahydro-4-methyl-3-(2,2,2-trifluoroethyl)-10-(trifluoromethyl)-8*H*-[1,4]oxazino[2,3-*f*]quinolin-8-one;
(±)-4-Ethyl-2,3,4,7-tetrahydro-3-(2,2,2-trifluoroethyl)-10-(trifluoromethyl)-8*H*-[1,4]oxazino[2,3-*f*]quinolin-8-one;
(±)-2,3,4,7-Tetrahydro-3,4-bis(2,2,2-trifluoroethyl)-10-(trifluoromethyl)-8*H*-[1,4]oxazino[2,3-*f*]quinolin-8-one;
(-)-2,3,4,7-Tetrahydro-3,4-bis(2,2,2-trifluoroethyl)-10-(trifluoromethyl)-8*H*-[1,4]oxazino[2,3-*f*]quinolin-8-one;
(+)-2,3,4,7-Tetrahydro-3,4-bis(2,2,2-trifluoroethyl)-10-(trifluoromethyl-8*H*-[1,4]oxazino[2,3-*f*]quinolin-8-one;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

(±)-4-Cyclopropylmethyl-2,3,4,7-tetrahydro-3-(2,2,2-trifluoroethyl)-10-(trifluoromethyl)-8$H$-[1,4]oxazino[2,3-$f$]quinolin-8-one;
  (3$R$)-4-Cyclopropylmethyl-3-ethyl-2,3,4,7-tetrahydro-10-(trifluoromethyl)-8$H$-[1,4]oxazino[2,3-$f$]quinolin-8-one;
  (3$R$)-4-(2-Chloroethyl)-2,3,4,7-tetrahydro-3-isopropyl-10-(trifluoromethyl)-8$H$-[1,4]oxazino[2,3-$f$]quinolin-8-one;
  (±)-2,3,4,7-Tetrahydro-2-methyl-4-(2,2,2-trifluoroethyl)-10-(trifluoromethyl)-8$H$-[1,4]oxazino[2,3-$f$]quinolin-8-one;
  (3$R$)-3-Ethyl-4-(2-hydroxy-2-methylpropyl)-2,3,4,7-tetrahydro-10-(trifluoromethyl)-8$H$-[1,4]oxazino[2,3-$f$]quinolin-8-one; and
  (3$R$)-2,3,4,7-Tetrahydro-3-isobutyl-4-(2,2,2-trifluoroethyl)-10-(trifluoromethyl)-8$H$-[1,4]oxazino[2,3-$f$]quinolin-8-one; and
  pharmaceutically acceptable salts thereof.
 58. A compound selected from the group consisting of:
  (3$R$)-2,3,4,7-Tetrahydro-3-methyl-4-(2,2,2-trifluoroethyl)-10-(trifluoromethyl)-8$H$-[1,4]oxazino[2,3-$f$]quinolin-8-one;
  (3$R$)-3-Ethyl-2,3,4,7-tetrahydro-4-(2,2,2-trifluoroethyl)-10-(trifluoromethyl)-8$H$-[1,4]oxazino[2,3-$f$]quinolin-8-one;
  (3$R$)-4-(2-Chloro-2,2-difluoroethyl)-3-ethyl-2,3,4,7-tetrahydro-10-(trifluoromethyl)-8$H$-[1,4]oxazino[2,3-$f$]quinolin-8-one;
  (3$R$)-4-(2,2-Difluoroethyl)-3-ethyl-2,3,4,7-tetrahydro-10-(trifluoromethyl)-8$H$-[1,4]oxazino[2,3-$f$]quinolin-8-one;
  (3$R$)-2,3,4,7-Tetrahydro-3-isopropyl-4-(2,2,2-trifluoroethyl)-10-(trifluoromethyl)-8$H$-[1,4]oxazino[2,3-$f$]quinolin-8-one;
  (3$R$)-4-(2-Chloro-2,2-difluoroethyl)-2,3,4,7-tetrahydro-3-isopropyl-10-(trifluoromethyl)-8$H$-[1,4]oxazino[2,3-$f$]quinolin-8-one;
  (3$R$)-4-(2,2-Difluoroethyl)-2,3,4,7-tetrahydro-3-isopropyl-10-(trifluoromethyl)-8$H$-[1,4]oxazino[2,3-$f$]quinolin-8-one;
  (7a$R$,10a$S$)-7-Ethyl-7,7a,8,9,10,10a-hexahydro-1-(trifluoromethyl-4$H$-cyclopenta[5,6][1,4]oxazino[2,3-$f$]quinolin-3-one;
  (7a$R$,10a$S$)-7-7a,8,9,10,10a-Hexahydro-1-(trifluoromethyl)-7-(2,2,2-trifluoroethyl)-4$H$-cyclopenta[5,6][1,4]oxazino[2,3-$f$]quinolin-3-one;
  (±)-(2$S$,3$R$)-2,3,4,7-Tetrahydro-2,3-dimethyl-4-(2,2,2-trifluoroethyl)-10-(trifluoromethyl)-8$H$-[1,4]oxazino[2,3-$f$]quinolin-8-one;
  (±)-2,3,4,7-Tetrahydro-4-(2,2,2-trifluoroethyl)-3,10-bis(trifluoromethyl)-8$H$-[1,4]oxazino[2,3-$f$]quinolin-8-one;

UNITED STATES PATENT AND TRADEMARK OFFICE
CERTIFICATE OF CORRECTION

PATENT NO.      : 7,214,690 B2
APPLICATION NO. : 10/080503
DATED           : May 8, 2007
INVENTOR(S)     : Higuchi et al.

It is certified that error appears in the above-identified patent and that said Letters Patent is hereby corrected as shown below:

(−)-2,3,4,7-Tetrahydro-4-(2,2,2-trifluoroethyl)-3,10-bis(trifluoromethyl)-8*H*-[1,4]oxazino[2,3-*f*]quinolin-8-one; and
(+)-2,3,4,7-Tetrahydro-4-(2,2,2-trifluoroethyl)-3,10-bis(trifluoromethyl)-8*H*-[1,4]oxazino[2,3-*f*]quinolin-one; and
pharmaceutically acceptable salts thereof.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.        : 7,214,690 B2                                Page 1 of 11
APPLICATION NO. : 10/080503
DATED             : May 8, 2007
INVENTOR(S)       : Higuchi et al.

It is certified that error appears in the above-identified patent and that said Letters Patent is hereby corrected as shown below:

IN THE TITLE PAGES:
In Item [56] References Cited, in OTHER PUBLICATIONS:
in Venturoli et al., please replace "Prospectiove" with --Prospective--

IN THE SPECIFICATION:
At column 5, line 20, please replace structure

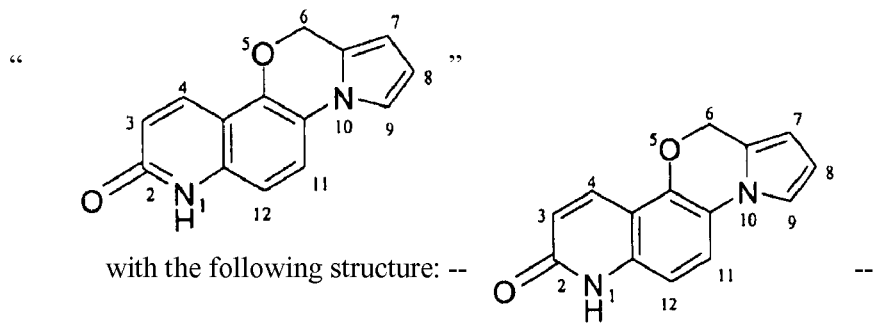

At column 9, line 34, please replace "A $R^9$" with --$R^9$--
At column 31, line 56-67, please replace structure

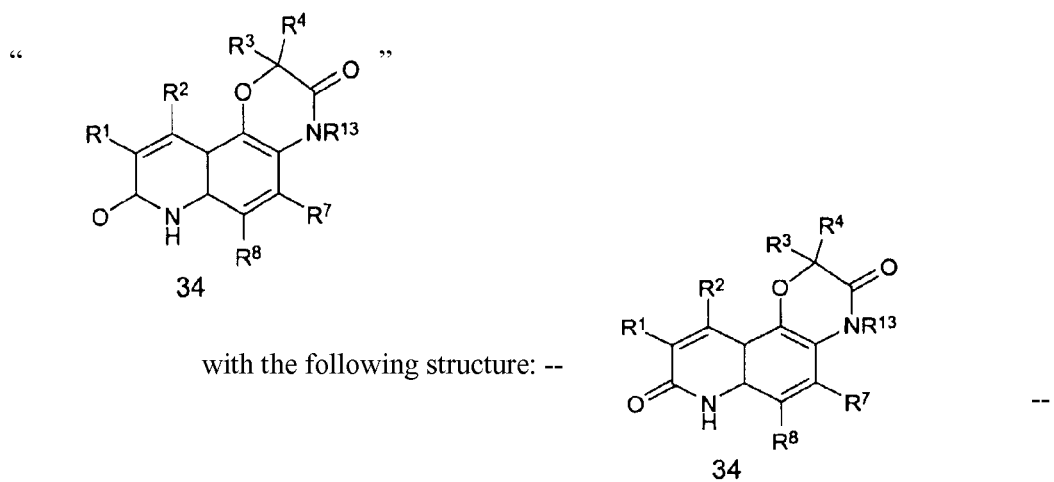

UNITED STATES PATENT AND TRADEMARK OFFICE
CERTIFICATE OF CORRECTION

PATENT NO.         : 7,214,690 B2
APPLICATION NO.    : 10/080503
DATED              : May 8, 2007
INVENTOR(S)        : Higuchi et al.

It is certified that error appears in the above-identified patent and that said Letters Patent is hereby corrected as shown below:

IN THE CLAIMS:
Column 79, line 40 thru Column 81, line 37 (Claim 1) should read
Please replace Claims 1, 10, 24, 40, 57, and 58 with the following Claims:
1.  A compound having the formula:

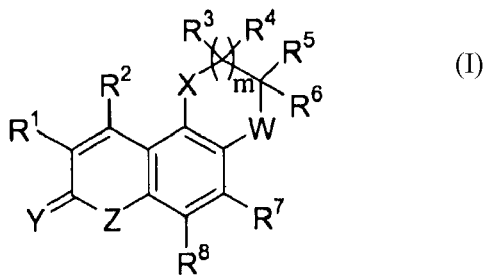

(I)

wherein:
    $R^1$ is selected from the group consisting of hydrogen, F, Cl, Br, I, $NO_2$, $OR^9$, $NR^{10}R^{11}$, $S(O)_nR^9$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
    $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
    $R^3$ and $R^4$ each independently is selected from the group consisting of hydrogen, $OR^9$, $S(O)_nR^9$, $NR^{10}R^{11}$, $C(Y)OR^{11}$, $CNR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

$R^5$ and $R^6$ each independently is selected from the group consisting of hydrogen, $CF_3$, $CF_2Cl$, $CF_2H$, $CFH_2$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^7$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, and optionally substituted arylalkyl;

$R^{10}$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is selected from the group consisting of 0, 1 and 2;

n is selected from the group consisting of 0, 1 and 2;

W is selected from the group consisting of NH, $N\{R^{13}\}$, $N\{C(Y)R^{11}\}$ and $N\{SO_2R^{11}\}$;

X is O;

Z is selected from the group consisting of NH, $N\{R^{11}\}$, $N\{C(Y)R^{11}\}$, $N\{SO_2R^{12}\}$ and $N\{S(O)R^{12}\}$; and Y is O;

and pharmaceutically acceptable salts thereof; wherein:

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

the substituents of an optionally substituted group comprise one or more substituents independently selected from among alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

Column 82, lines 6-58, Claim 10 should read
  10. The compound of claim 1, wherein:
    $R^1$ is selected from the group consisting of hydrogen, F, Cl, Br, I, $NO_2$, $OR^9$, $NR^{10}R^{11}$, $S(O)_nR^9$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;
    $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;
    $R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;
    $R^5$ and $R^6$ each independently is selected from the group consisting of hydrogen, $CF_3$, $CF_2Cl$, $CF_2H$, $CFH_2$, $C_1$–$C_8$ alkyl, $C_1$–$C_8$ haloalkyl, $C_1$–$C_8$ heteroalkyl, $C_3$–$C_8$ cycloalkyl, aryl, arylalkyl, heteroaryl, $C_2$–$C_8$ alkynyl and $C_2$–$C_8$ alkenyl;
    $R^7$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;
    $R^8$ is selected from the group consisting of hydrogen, F, Cl, Br, I, $C_1$–$C_8$ alkyl, $C_1$–$C_8$ haloalkyl, $C_1$–$C_8$ heteroalkyl, aryl, heteroaryl, $OR^9$, $S(O)_nR^9$, $NR^{10}R^{11}$, $C(Y)OR^{11}$ and $C(Y)NR^{10}R^{11}$;
    $R^9$ is selected from the group consisting of hydrogen, $C_1$–$C_8$ alkyl, $C_1$–$C_8$ haloalkyl, $C_1$–$C_8$ heteroalkyl, aryl, heteroaryl and arylalkyl;
    $R^{10}$ is selected from the group consisting of hydrogen, $C_1$–$C_8$ alkyl, $C_1$–$C_8$ haloalkyl, $C_1$–$C_8$ heteroalkyl, aryl, heteroaryl, arylalkyl, $CO_2R^{12}$, $C(O)R^{12}$, $SO_2R^{12}$ and $S(O)R^{12}$;
    $R^{11}$ and $R^{12}$ each independently is selected from the group consisting of hydrogen, $C_1$–$C_8$ alkyl, $C_1$–$C_8$ haloalkyl, $C_1$–$C_8$ heteroalkyl, aryl, heteroaryl, arylalkyl;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

$R^{13}$ is selected from the group consisting of $C_1$–$C_8$ alkyl, $C_1$–$C_8$ haloalkyl, $C_1$–$C_8$ heteroalkyl, $C_2$–$C_8$ alkenyl, $C_2$–$C_8$ alkynyl, $C_3$–$C_8$ cycloalkyl, aryl, heteroaryl, arylalkyl and heteroarylalkyl;
  m is selected from the group consisting of 0, 1 and 2;
  n is selected from the group consisting of 0, 1 and 2;
  W is selected from the group consisting of NH, $N\{R^{13}\}$, $N\{C(Y)R^{11}\}$ and $N\{SO_2R^{11}\}$;
  X is O;
  Z is selected from the group consisting of NH, $N\{R^{11}\}$, $N\{C(Y)R^{11}\}$, $N\{SO_2R^{12}\}$ and $N\{S(O)R^{12}\}$; and
  Y is O;
  and pharmaceutically acceptable salts thereof.

Column 83, lines 53-55 Claim 24 should read
  24. A compound according to claim 23, wherein $R^9$ is selected from the group consisting of hydrogen and optionally substituted $C_1$–$C_4$ alkyl.

Column 85, line 20 thru column 86, line 64 Claim 40 should read
  40. A pharmaceutical composition comprising a pharmaceutically acceptable carrier and a compound of formula:

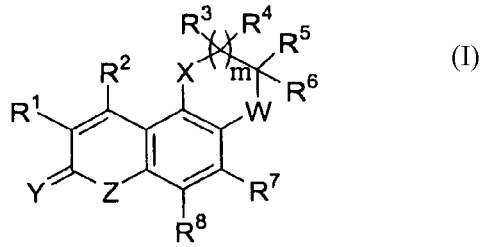

wherein:
  $R^1$ is selected from the group consisting of hydrogen, F, Cl, Br, I, $NO_2$, $OR^9$, $NR^{10}R^{11}$, $S(O)_nR^9$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;
  $R^2$ is selected from the group consisting of hydrogen, F, Cl, Br, I, $CF_3$, $CF_2Cl$, $CF_2H$, $CFH_2$, $CF_2OR^9$, $CH_2OR^9$, $OR^9$, $S(O)_nR^9$, $NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

UNITED STATES PATENT AND TRADEMARK OFFICE
CERTIFICATE OF CORRECTION

| | |
|---|---|
| PATENT NO. | : 7,214,690 B2 |
| APPLICATION NO. | : 10/080503 |
| DATED | : May 8, 2007 |
| INVENTOR(S) | : Higuchi et al. |

It is certified that error appears in the above-identified patent and that said Letters Patent is hereby corrected as shown below:

$R^3$ and $R^4$ each independently is selected from the group consisting of hydrogen, $OR^9$, $S(O)_nR^9$, $NR^{10}R^{11}$, $C(Y)OR^{11}$, $C(Y)NR^{10}R^{11}$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^5$ and $R^6$ each independently are selected from the group consisting of hydrogen, $CF_3$, $CF_2Cl$, $CF_2H$, $CFH_2$, optionally substituted $C_1$–$C_8$ alkyl, optionally substituted $C_1$–$C_8$ haloalkyl, optionally substituted $C_1$–$C_8$ heteroalkyl, optionally substituted $C_3$–$C_8$ cycloalkyl, optionally substituted aryl, optionally substituted arylalkyl, optionally substituted heteroaryl, optionally substituted $C_2$–$C_8$ alkynyl and optionally substituted $C_2$–$C_8$ alkenyl;

$R^7$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^8$ is selected from the group consisting of hydrogen, F, Cl, Br, I, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, $OR^9$, $S(O)_nR^9$, $NR^{10}R^{11}$, $C(Y)OR^{11}$ and $C(Y)NR^{10}R^{11}$;

$R^9$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{10}$ is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl, optionally substituted arylalkyl, $CO_2R^{12}$, $C(O)R^{12}$, $SO_2R^{12}$ and $S(O)R^{12}$;

$R^{11}$ and $R^{12}$ each independently is selected from the group consisting of hydrogen, optionally substituted $C_1$–$C_8$ alkyl, optionally substituted $C_1$–$C_8$ haloalkyl, optionally substituted $C_1$–$C_8$ heteroalkyl, optionally substituted aryl, optionally substituted heteroaryl and optionally substituted arylalkyl;

$R^{13}$ is selected from the group consisting of optionally substituted $C_1$–$C_8$ alkyl, optionally substituted $C_1$–$C_8$ haloalkyl, optionally substituted $C_1$–$C_8$ heteroalkyl, optionally substituted $C_2$–$C_8$ alkenyl, optionally substituted $C_2$–$C_8$ alkynyl, optionally substituted $C_3$–$C_8$ cycloalkyl, optionally substituted aryl, optionally substituted heteroaryl, optionally substituted arylalkyl and optionally substituted heteroarylalkyl;

m is 1;

n is selected from the group consisting of 0, 1 and 2;

UNITED STATES PATENT AND TRADEMARK OFFICE
CERTIFICATE OF CORRECTION

| | |
|---|---|
| PATENT NO. | : 7,214,690 B2 |
| APPLICATION NO. | : 10/080503 |
| DATED | : May 8, 2007 |
| INVENTOR(S) | : Higuchi et al. |

It is certified that error appears in the above-identified patent and that said Letters Patent is hereby corrected as shown below:

W is selected from the group consisting of NH, $N\{R^{13}\}$, $N\{C(Y)R^{11}\}$ and $N\{SO_2R^{11}\}$;
    X is O;
    Z is selected from the group consisting of NH, $N\{R^{11}\}$, $N\{C(Y)R^{11}\}$, $N\{SO_2R^{12}\}$ and $N\{S(O)R^{12}\}$; and
    Y is O;
    and pharmaceutically acceptable salts thereof; wherein:
    the substituents of an optionally substituted group comprise one or more substituents independently selected from among alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkythio, arylthio, heteroarylthio, oxo, carboxyester, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^9$, $SR^9$, $NR^{10}R^{11}$, $CF_2CF_3$, $CH_2CH_2F$ and $CH_2CF_3$.

Column 88, line 27 thru Column 90, line 35, Claim 57 should read
    57. A compound selected from the group consisting of:
    (3*R*)-2,3,4,7-Tetrahydro-3-methyl-10-(trifluoromethyl)-8*H*-[1,4]oxazino[2,3-*f*]-quinolin-8-one;
    (3*R*)-2,3,4,7-Tetrahydro-3,4-dimethyl-10-(trifluoromethyl)-8*H*-[1,4]oxazino[2,3-*f*]-quinolin-8-one;
    (3*R*)-4-Ethyl-2,3,4,7-tetrahydro-3-methyl-10-(trifluoromethyl)-8*H*-[1,4]oxazino[2,3-*f*]-quinolin-8-one;
    (3*R*)-2,3,4,7-Tetrahydro-3-methyl-4-(2,2,2-trifluoroethyl)-10-(trifluoromethyl)-8*H*-[1,4]oxazino[2,3-*f*]quinolin-8-one;
    (3*R*)-2,3,4,7-Tetrahydro-3-methyl-4-propyl-10-(trifluoromethyl)-8*H*-[1,4]oxazino[2,3-*f*]-quinolin-8-one;
    (3*R*)-4-Allyl-2,3,4,7-tetrahydro-3-methyl-10-(trifluoromethyl)-8*H*-[1,4]oxazino[2,3-*f*]-quinolin-8-one;
    (3*R*)-3-Ethyl-2,3,4,7-tetrahydro-10-(trifluoromethyl)-8*H*-[1,4]oxazino[2,3-*f*]quinolin-8-one;
    (3*R*)-3-Ethyl-2,3,4,7-tetrahydro-4-methyl-10-(trifluoromethyl)-8*H*-[1,4]oxazino[2,3-*f*]-quinolin-8-one;
    (3*R*)-3,4-Diethyl-2,3,4,7-tetrahydro-10-(trifluoromethyl)-8*H*-[1,4]oxazino[2,3-*f*]-quinolin-8-one;
    (3*R*)-3-Ethyl-2,3,4,7-tetrahydro-4-(2,2,2-trifluoroethyl)-10-(trifluoromethyl)-8*H*-[1,4]oxazino[2,3-*f*]quinolin-8-one;
    (3*R*)-4-(2-Chloro-2,2-difluoroethyl)-3-ethyl-2,3,4,7-tetrahydro-10-(trifluoromethyl)-8*H*-[1,4]oxazino[2,3-*f*]quinolin-8-one;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

(3$R$)-4-(2,2-Difluoroethyl)-3-ethyl-2,3,4,7-tetrahydro-10-(trifluoromethyl)-8$H$-[1,4]oxazino[2,3-$f$]quinolin-8-one;

(3$R$)-3-Ethyl-2,3,4,7-tetrahydro-4-propyl-10-(trifluoromethyl)-8$H$-[1,4]oxazino[2,3-$f$]-quinolin-8-one;

(3$R$)-4-Allyl-3-ethyl-2,3,4,7-tetrahydro-10-(trifluoromethyl)-8$H$-[1,4]oxazino[2,3-$f$]-quinolin-8-one;

(3$R$)-3-Ethyl-2,3,4,7-tetraydro-4-isobutyl-10-(trifluoromethyl)-8$H$-[1,4]oxazino[2,3-$f$]-quinolin-8-one;

(3$R/S$)-2,3,4,7-Tetrahydro-3-propyl-10-(trifluoromethyl)-8$H$-[1,4]oxazino[2,3-$f$]-quinolin-8-one;

(3$R/S$)-2,3,4,7-Tetrahydro-4-methyl-3-propyl-10-(trifluoromethyl)-8$H$[1,4]oxazino-[2,3-$f$]quinolin-8-one;

(3$R/S$)-4-Ethyl-2,3,4,7-tetrahydro-3-propyl-4-(2,2,2-trifluoroethyl)-10-(trifluoromethyl)-8$H$-[1,4]oxazino[2,3-$f$]quinolin-8-one;

(3$R/S$)-2,3,4,7-Tetrahydro-3-propyl-4-(2,2,2-trifluoroethyl)-10-(trifluoromethyl)-8$H$-[1,4]oxazino[2,3-$f$]quinolin-8-one;

(3$R$)-2,3,4,7-Tetrahydro-3-isopropyl-10-(trifluoromethyl)-8$H$-[1,4]oxazino[2,3-$f$]-quinolin-8-one;

(3$R$)-2,3,4,7-Tetrahydro-3-isopropyl-4-methyl-10-(trifluoromethyl)-8$H$-[1,4]oxazino-[2,3-$f$]quinolin-8-one;

(3$R$)-4-Ethyl-2,3,4,7-tetrahydro-3-isopropyl-10-(trifluoromethyl)-8$H$-[1,4]oxazino-[2,3-$f$]quinolin-8-one;

(3$R$)-2,3,4,7-Tetrahydro-3-isopropyl-4-(2,2,2-trifluoroethyl)-10-(trifluoromethyl)-8$H$-[1,4]oxazino[2,3-$f$]quinolin-8-one;

(3$R$)-4-(2-Chloro-2,2-difluoroethyl)-2,3,4,7-tetrahydro-3-isopropyl-10-(trifluoromethyl)-8$H$-[1,4]oxazino[2,3-$f$]quinolin-8-one;

(3$R$)-4-(2,2-Difluoroethyl)-2,3,4,7-tetrahydro-3-isopropyl-10-(trifluoromethyl)-8$H$-[1,4]oxazino[2,3-$f$]quinolin-8-one;

(3$R$)-4-Allyl-2,3,4,7-tetrahydro-3-isopropyl-10-(trifluoromethyl)-8$H$-[1,4]oxazino-[2,3-$f$]quinolin-8-one;

(3$R$)-2,3,4,7-Tetrahydro-3-phenyl-10-(trifluoromethyl)-8$H$-[1,4]oxazino[2,3-$f$]quinolin-8-one;

(3$R$)-2,3,4,7-Tetrahydro-3-phenyl-4-(2,2,2-trifluoroethyl)-10-(trifluoromethyl)-8$H$-[1,4]oxazino[2,3-$f$]quinolin-8-one;

(3$R$)-4-Cyclopropylmethyl-2,3,4,7-tetrahydro-3-phenyl-10-(trifluoromethyl)-8$H$-[1,4]oxazino[2,3-$f$]quinolin-8-one;

(3$R$)-3-Benzyl-2,3,4,7-tetrahydro-4-(2,2,2-trifluoroethyl)-10-(trifluoromethyl)-8$H$-[1,4]oxazino[2,3-$f$]quinolin-8-one;

UNITED STATES PATENT AND TRADEMARK OFFICE
CERTIFICATE OF CORRECTION

PATENT NO.        : 7,214,690 B2
APPLICATION NO. : 10/080503
DATED             : May 8, 2007
INVENTOR(S)       : Higuchi et al.

It is certified that error appears in the above-identified patent and that said Letters Patent is hereby corrected as shown below:

2,3,4,7-Tetrahydro-10-(trifluoromethyl)-8*H*-[1,4]oxazino[2,3-*f*]quinolin-8-one;
2,3,4,7-tetrahydro-4-(2,2,2-trifluoroethyl)-10-(trifluoromethyl)-8*H*-[1,4]oxazino[2,3-*f*]quinolin-8-one;
(7a*R*,10a*S*)-7,7a,8,9,10,10a-Hexahydro-1-(trifluoromethyl)-7-(2,2,2-trifluoroethyl)-4*H*-cyclopenta[5,6][1,4]oxazino[2,3-*f*]quinolin-3-one;
(7a*R*,10a*S*)-7-Ethyl-7,7a,8,9,10,10a-hexahydro-1-(trifluoromethyl)-4*H*-cyclopenta-[5,6][1,4]oxazino[2,3-*f*]quinolin-3-one;
(7a*R*,10a*S*)-7,7a,8,9,10,10a-Hexahydro-3-isopropoxy-1-(trifluoromethyl)-7-(2,2,2-trifluoroethyl)-4*H*-cyclopenta[5,6][1,4]oxazino[2,3-*f*]quinolin-3-one;
(±)-(2*S*,3*R*)-2,3,4,7-Tetrahydro-2,3-dimethyl-4-(2,2,2-trifluoroethyl)-10-(trifluoromethyl)-8*H*-[1,4]oxazino[2,3-*f*]quinolin-8-one;
(6a*R*)-6a,7,8,9-Tetrahydro-4-(trifluoromethyl)-1*H*,6*H*-pyrrolo[1',2':4,5][1,4]-oxazino[2,3-*f*]quinolin-2-one;
2,3,4,7-Tetrahydro-2,2,4-trimethyl-10-(trifluoromethyl)-8*H*-[1,4]oxazino[2,3-*f*]-quinolin-8-one;
(3*R*)-8-Chloro-3-ethyl-3,4-dihydro-8-isopropoxy-4-(2,2,2-trifluoroethyl)-10-(trifluoromethyl)-2*H*-[1,4]oxazino[2,3-*f*]quinoline;
(3*R*)-3-Ethyl-3,4-dihydro-8-isopropoxy-8-methoxy-4-(2,2,2-trifluoroethyl)-10-(trifluoromethyl)-2*H*-[1,4]oxazino[2,3-*f*]quinoline;
(±)-2,3,4,7-Tetrahydro-4-(2,2,2-trifluoroethyl)-3,10-bis(trifluoromethyl)-8*H*-[1,4]oxazino[2,3-*f*]quinolin-8-one;
(–)-2,3,4,7-Tetrahydro-4-(2,2,2-trifluoroethyl)-3,10-bis(trifluoromethyl)-8*H*-[1,4]oxazino[2,3-*f*]quinolin-8-one;
(+)-2,3,4,7-Tetrahydro-4-(2,2,2-trifluoroethyl)-3,10-bis(trifluoromethyl)-8*H*-[1,4]oxazino[2,3-*f*]quinolin-8-one;
(±)-2,3,4,7-Tetrahydro-3-(2,2,2-trifluoroethyl)-10-(trifluoromethyl)-8*H*-[1,4]oxazino[2,3-*f*]quinolin-8-one;
(±)-2,3,4,7-Tetrahydro-4-methyl-3-(2,2,2-trifluoroethyl)-10-(trifluoromethyl)-8*H*-[1,4]oxazino[2,3-*f*]quinolin-8-one;
(±)-4-Ethyl-2,3,4,7-tetrahydro-3-(2,2,2-trifluoroethyl)-10-(trifluoromethyl)-8*H*-[1,4]oxazino[2,3-*f*]quinolin-8-one;
(±)-2,3,4,7-Tetrahydro-3,4-bis(2,2,2-trifluoroethyl)-10-(trifluoromethyl)-8*H*-[1,4]oxazino[2,3-*f*]quinolin-8-one;
(-)-2,3,4,7-Tetrahydro-3,4-bis(2,2,2-trifluoroethyl)-10-(trifluoromethyl)-8*H*-[1,4]oxazino[2,3-*f*]quinolin-8-one;
(+)-2,3,4,7-Tetrahydro-3,4-bis(2,2,2-trifluoroethyl)-10-(trifluoromethyl-8*H*-[1,4]oxazino[2,3-*f*]quinolin-8-one;

UNITED STATES PATENT AND TRADEMARK OFFICE
CERTIFICATE OF CORRECTION

| | | |
|---|---|---|
| PATENT NO. | : 7,214,690 B2 | |
| APPLICATION NO. | : 10/080503 | |
| DATED | : May 8, 2007 | |
| INVENTOR(S) | : Higuchi et al. | |

It is certified that error appears in the above-identified patent and that said Letters Patent is hereby corrected as shown below:

(±)-4-Cyclopropylmethyl-2,3,4,7-tetrahydro-3-(2,2,2-trifluoroethyl)-10-(trifluoromethyl)-8*H*-[1,4]oxazino[2,3-*f*]quinolin-8-one;
  (3*R*)-4-Cyclopropylmethyl-3-ethyl-2,3,4,7-tetrahydro-10-(trifluoromethyl)-8*H*-[1,4]oxazino[2,3-*f*]quinolin-8-one;
  (3*R*)-4-(2-Chloroethyl)-2,3,4,7-tetrahydro-3-isopropyl-10-(trifluoromethyl)-8*H*-[1,4]oxazino[2,3-*f*]quinolin-8-one;
  (±)-2,3,4,7-Tetrahydro-2-methyl-4-(2,2,2-trifluoroethyl)-10-(trifluoromethyl)-8*H*-[1,4]oxazino[2,3-*f*]quinolin-8-one;
  (3*R*)-3-Ethyl-4-(2-hydroxy-2-methylpropyl)-2,3,4,7-tetrahydro-10-(trifluoromethyl)-8*H*-[1,4]oxazino[2,3-*f*]quinolin-8-one; and
  (3*R*)-2,3,4,7-Tetrahydro-3-isobutyl-4-(2,2,2-trifluoroethyl)-10-(trifluoromethyl)-8*H*-[1,4]oxazino[2,3-*f*]quinolin-8-one; and
  pharmaceutically acceptable salts thereof.

Column 90, line 35 thru Column 92, line 4 Claim 58 should read
  58. A compound selected from the group consisting of:
  (3*R*)-2,3,4,7-Tetrahydro-3-methyl-4-(2,2,2-trifluoroethyl)-10-(trifluoromethyl)-8*H*-[1,4]oxazino[2,3-*f*]quinolin-8-one;
  (3*R*)-3-Ethyl-2,3,4,7-tetrahydro-4-(2,2,2-trifluoroethyl)-10-(trifluoromethyl)-8*H*-[1,4]oxazino[2,3-*f*]quinolin-8-one;
  (3*R*)-4-(2-Chloro-2,2-difluoroethyl)-3-ethyl-2,3,4,7-tetrahydro-10-(trifluoromethyl)-8*H*-[1,4]oxazino[2,3-*f*]quinolin-8-one;
  (3*R*)-4-(2,2-Difluoroethyl)-3-ethyl-2,3,4,7-tetrahydro-10-(trifluoromethyl)-8*H*-[1,4]oxazino[2,3-*f*]quinolin-8-one;
  (3*R*)-2,3,4,7-Tetrahydro-3-isopropyl-4-(2,2,2-trifluoroethyl)-10-(trifluoromethyl)-8*H*-[1,4]oxazino[2,3-*f*]quinolin-8-one;
  (3*R*)-4-(2-Chloro-2,2-difluoroethyl)-2,3,4,7-tetrahydro-3-isopropyl-10-(trifluoromethyl)-8*H*-[1,4]oxazino[2,3-*f*]quinolin-8-one;
  (3*R*)-4-(2,2-Difluoroethyl)-2,3,4,7-tetrahydro-3-isopropyl-10-(trifluoromethyl)-8*H*-[1,4]oxazino[2,3-*f*]quinolin-8-one;
  (7a*R*,10a*S*)-7-Ethyl-7,7a,8,9,10,10a-hexahydro-1-(trifluoromethyl)-4*H*-cyclopenta[5,6][1,4]oxazino[2,3-*f*]quinolin-3-one;
  (7a*R*,10a*S*)-7-7a,8,9,10,10a-Hexahydro-1-(trifluoromethyl)-7-(2,2,2-trifluoroethyl)-4*H*-cyclopenta[5,6][1,4]oxazino[2,3-*f*]quinolin-3-one;
  (±)-(2*S*,3*R*)-2,3,4,7-Tetrahydro-2,3-dimethyl-4-(2,2,2-trifluoroethyl)-10-(trifluoromethyl)-8*H*-[1,4]oxazino[2,3-*f*]quinolin-8-one;
  (±)-2,3,4,7-Tetrahydro-4-(2,2,2-trifluoroethyl)-3,10-bis(trifluoromethyl)-8*H*-[1,4]oxazino[2,3-*f*]quinolin-8-one;

UNITED STATES PATENT AND TRADEMARK OFFICE
CERTIFICATE OF CORRECTION

PATENT NO. : 7,214,690 B2
APPLICATION NO. : 10/080503
DATED : May 8, 2007
INVENTOR(S) : Higuchi et al.

It is certified that error appears in the above-identified patent and that said Letters Patent is hereby corrected as shown below:

(−)-2,3,4,7-Tetrahydro-4-(2,2,2-trifluoroethyl)-3,10-bis(trifluoromethyl)-8$H$-[1,4]oxazino[2,3-$f$]quinolin-8-one; and
    (+)-2,3,4,7-Tetrahydro-4-(2,2,2-trifluoroethyl)-3,10-bis(trifluoromethyl)-8$H$-[1,4]oxazino[2,3-$f$]quinolin-one; and
    pharmaceutically acceptable salts thereof.

This certificate supersedes the Certificate of Correction issued June 17, 2008.

Signed and Sealed this

Twenty-second Day of July, 2008

JON W. DUDAS
*Director of the United States Patent and Trademark Office*